(12) United States Patent
Glenn et al.

(10) Patent No.: US 7,026,463 B2
(45) Date of Patent: Apr. 11, 2006

(54) POLYNUCLEOTIDES AND POLYPEPTIDES, MATERIALS INCORPORATING THEM AND METHODS FOR USING THEM

(76) Inventors: Matthew Glenn, Genesis Research & Development Corporation Limited, 1 Fox Street, 1001 Parnell, Auckland (NZ); Mark W. Lubbers, New Zealand Dairy Research Institute, Private Bag 11029, Palmerston North (NZ); James Dekker, New Zealand Dairy Reseach Institute, Private Bag 11029, Palmerston North (NZ)

( * ) Notice: Subject to any disclaimer, the term of this patent is extended or adjusted under 35 U.S.C. 154(b) by 358 days.

(21) Appl. No.: 10/288,930

(22) Filed: Nov. 5, 2002

(65) Prior Publication Data

US 2003/0138822 A1 Jul. 24, 2003

Related U.S. Application Data

(63) Continuation-in-part of application No. 09/724,623, filed on Nov. 28, 2000, now Pat. No. 6,476,209.

(60) Provisional application No. 60/148,801, filed on Dec. 2, 1999.

(51) Int. Cl.
*C07H 21/02* (2006.01)

(52) U.S. Cl. .......................................... 536/23.1; 435/6

(58) Field of Classification Search ................ 536/22.1, 536/23.1; 435/6, 91.1; 530/200

See application file for complete search history.

(56) References Cited

FOREIGN PATENT DOCUMENTS

| EP | 0307011 | 3/1989 |
|---|---|---|
| WO | 0212506 | 2/2002 |

OTHER PUBLICATIONS

Rijnen et al., "Genetic Characterization of the Major Lactococcal Aromatic Aminotransferase and Its Involvement in Conversion of Amino Acids to Aroma Compounds", Applied and Environmental Microbiology, (1999), vol. 65(11), pp. 4873–4880.*

Holck, Askild et al., "Cloning, sequencing and expression of the gene encoding the cell–envelope–associated proteinase from *Lactobacillus paracasei* subsp. *paracasei* NCDO 151", *Journal of General Microbiology,* vol. 138, pp. 1353–1364 (1992).

Kiwaki, M. et al., "Molecular characterization of a cell wall–associated proteinase gene from *Streptococcus lactis* NCDO763", *Molecular Microbiology,* vol. 3, No. 3, pp. 359–369 (1989).

Dossonnet, Valérie et al., "Phosphorylation of HPr by the Bifunctional HPr Kinase/P–Ser–HPr Phosphatase from *Lactobacillus casei* Controls Catabolite Repression and Inducer Exclusion but Not Inducer Expulsion", *Journal of Bacteriology,* vol. 182, No. 9, pp. 2582–2590 (2000).

Makino, Kozo et al., "Complete nucleotide sequence of the prophage VT2–Sakai carrying the verotoxin 2 genes of the enterohemorrhagic *Escherichia coli* O157:H7 derived from the Sakai outbreak", *Genes and Genetic Systems,* vol. 74, pp. 227–239 (1999).

O'Sullivan, David et al., "Novel type I restriction specificities through domain shuffling of HsdS subunits in *Lactococcus lactis*", *Molecular Microbiology,* vol. 36, No. 4, pp. 866–875 (2000).

Van Kranenburg, Richard et al., "Characterization of Multiple Regions Involved in Replication and Mobilization of Plasmid pNZ4000 Coding for Exopolysaccharide Production in *Lactococcus lactis*", *Journal of Bacteriology,* vol. 80, No. 20, pp. 5285–5290 (1998).

Van Kranenburg, Richard et al., "Exopolysaccharide Biosynthesis in *Lactococcus lactis* NIZO B40: Functional Analysis of the Glycosyltransferase Genes Involved in Synthesis of the Polysaccharide Backbone", *Journal of Bacteriolgy,* vol. 181, No. 1, pp. 338–340 (1999).

Frost, Laura S. et al., "Analysis of the Sequence and Gene Products of the Transfer Region of the F Sex Factor", *Microbiological Reviews,* vol. 58, No. 2, pp. 162–210 (1994).

Blattner, Frederick R. et al., "The Complete Genome Sequence of *Escherichia coli* K–12", *Science,* vol. 277, pp. 1453–1434 (1997).

GenPept Accession No. BAA77928, submitted May 28, 1999.

Swiss–Prot Accession No. Q47689, submitted May 30, 2000.

Gosalbes, María José et al., "Establishing a model to study the regulation of the lactose operon in *Lactobacillus casei*", *FEMS Microbiology Letters,* vol. 148, pp. 83–89 (1997).

Porter, E. Victoria et al., "Nucleotide sequence of the β–D–phosphogalactoside galactohydrolase gene of *Lactobacillus casei:* comparison to analogous pbg genes of other Gram–positive organisms", *Gene,* vol. 62, pp. 263–276 (1988).

(Continued)

*Primary Examiner*—Jeffrey Fredman
*Assistant Examiner*—Heather G. Calamita
(74) *Attorney, Agent, or Firm*—Speckman Law Group PLLC; Janet Sleath; Ann W. Speckman

(57) ABSTRACT

Novel polynucleotides isolated from *Lactobacillus rhamnosus*, as well as probes and primers, genetic constructs comprising the polynucleotides, biological materials, including plants, microorganisms and multicellular organisms incorporating the polynucleotides, polypeptides expressed by the polynucleotides, and methods for using the polynucleotides and polypeptides are disclosed.

4 Claims, No Drawings

OTHER PUBLICATIONS

Andrews, J. et al., "Nucleotide sequence of the dihydrofolate reductase gene of methotrexate–resistant *Lactobacillus casei*", *Gene*, vol. 35, No. 1–2, pp. 217–222 (1985).

Kim, Sungmin F. et al., "Cloning and Nucleotide Sequence of the *Lactobacillus casei* Lactate Dehydrogenase Gene", *Applied and Environmental Microbiology*, vol. 57, No. 8, pp. 2413–2417 (1991).

Schmidt, Gudrun et al., "Molecular Characterisation of the dnaK Operon of *Lactobacillus sakei* LTH681", *Systematic and Applied Microbiology*, vol. 22, pp. 321–328 (1999).

Griffiths, Anthony J.F. et al., "Functionsl Genomics", *Modern Genetic Analysis*, pp. 399–405 (1999).

* cited by examiner

POLYNUCLEOTIDES AND POLYPEPTIDES, MATERIALS INCORPORATING THEM AND METHODS FOR USING THEM

CROSS-REFERENCE TO RELATED APPLICATIONS

This application is a continuation in part of U.S. patent application Ser. No. 09/724,623, filed Nov. 28, 2000, now U.S. Pat. No. 6,476,209, which claims to priority under 35 U.S.C. §119(e) to U.S. Provisional Patent Application 60/148,801, filed Dec. 2, 1999.

TECHNICAL FIELD OF THE INVENTION

This invention relates to polynucleotides isolated from lactic acid bacteria, including partial and extended sequences, as well as to probes and primers specific to the polynucleotides; DNA constructs comprising the polynucleotides; biological materials, including plants, microorganisms and multicellular organisms, incorporating the polynucleotides; polypeptides expressed by the polynucleotides; and methods for using the polynucleotides and polypeptides.

BACKGROUND OF THE INVENTION

The present invention relates to polynucleotides isolated from a specific strain of lactic acid bacteria, namely *Lactobacillus rhamnosus* HN001 (*L. rhamnosus* HN001). Lactic acid bacteria, and their enzymes, are the major determinants of flavor and fermentation characteristics in fermented dairy products, such as cheese and yogurt. Flavors are produced through the action of bacteria and their enzymes on proteins, carbohydrates and lipids.

*Lactobacillus rhamnosus* strain HN001 are heterofermentative bacteria that are Gram positive, non-motile, non-spore forming, catalase negative, facultative anaerobic rods exhibiting an optimal growth temperature of 37±1° C. and an optimum pH of 6.0–6.5. Experimental studies demonstrated that dietary supplementation with *Lactobacillus rhamnosus* strain HN001 induced a sustained enhancement in several aspects of both natural and acquired immunity (See PCT International Publication No. WO 99/10476). In addition, *L. rhamnosus* HN001, and certain other Gram-positive bacteria can specifically and directly modulate human and animal health (See, for example, Tannock et al., *Applied Environ. Microbiol.* 66:2578–2588, 2000; Gill et al., *Brit. J. Nutrition* 83:167–176; Quan Shu et al., *Food and Chem. Toxicol.* 38:153–161, 2000; Quan Shu et al., *Intl. J. Food Microbiol.* 56:87–96, 2000; Quan Shu et al., *Intl. Dairy J.* 9:831–836, 1999; Prasad et al., *Intl. Dairy J.* 8:993–1002, 1998; Sanders and Huis in't Veld, *Antonie van Leeuwenhoek* 76:293–315, 1999; Salminen et al., 1998. In: Lactic Acid Bacteria, Salminen S and von Wright A (eds)., Marcel Dekker Inc, New York, Basel, Hong Kong, pp. 211–253; Delcour et al., *Antonie van Leeuwenhoek* 76:159–184, 1999; Blum et al., *Antonie van Leeuwenhoek* 76:199–205, 1999; Yasui et al., *Antonie van Leeuwenhoek* 76:383–389, 1999; Hirayama and Rafter, *Antonie van Leeuwenhoek* 76:391–394, 1999; Ouwehand, 1998. In: Lactic Acid Bacteria, Salminen S and von Wright A (eds)., Marcel Dekker Inc, New York, Basel, Hong Kong, pp. 139–159; Isolauri et al., S 1998. In: Lactic Acid Bacteria, Salminen S and von Wright A (eds)., Marcel Dekker Inc, New York, Basel, Hong Kong, pp. 255–268; Lichtenstein and Goldin, 1998. In: Lactic Acid Bacteria, Salminen S and von Wright A (eds)., Marcel Dekker Inc, New York, Basel, Hong Kong, pp. 269–277; El-Nezami and Ahokas, 1998. In: Lactic Acid Bacteria, Salminen S and von Wright A (eds)., Marcel Dekker Inc, New York, Basel, Hong Kong, pp. 629–367; Nousianen et al., 1998. In: Lactic Acid Bacteria, Salminen S and von Wright A (eds)., Marcel Dekker Inc, New York, Basel, Hong Kong, pp. 437–473; Meisel and Bockelmann, *Antonie van Leeuwenhoek* 76:207–215, 1999; Christensen et al., *Antonie van Leeuwenhoek* 76:217–246, 1999; Dunne et al., *Antonie van Leeuwenhoek* 76:279–292, 1999). Beneficial health effects attributed to these bacteria include the following:

Increased resistance to enteric pathogens and anti-infection activity, including treatment of rotavirus infection and infantile diarrhea—due to increases in antibody production caused by an adjuvant effect, increased resistance to pathogen colonization, alteration of intestinal conditions, such as pH; and the presence of specific antibacterial substances, such as bacteriocins and organic acids.

Aid in lactose digestion—due to lactose degradation by bacterial lactase enzymes (such as beta-galactosidase) that act in the small intestine.

Anti-cancer (in particular anti-colon cancer) and anti-mutagenesis activities—due to anti-mutagenic activity; alteration of procancerous enzymatic activity of colonic microbes; reduction of the carcinogenic enzymes azoreductase, beta-glucuronidase and nitroreductase in the gut and/or faeces; stimulation of immune function; positive influence on bile salt concentration; and antioxidant effects.

Liver cancer reduction—due to aflatoxin detoxification and inhibition of mould growth.

Reduction of small bowel bacterial overgrowth—due to antibacterial activity; and decrease in toxic metabolite production from overgrowth flora.

Immune system modulation and treatment of autoimmune disorders and allergies—due to enhancement of non-specific and antigen-specific defence against infection and tumors; enhanced mucosal immunity; adjuvant effect in antigen-specific immune responses; and regulation of Th1/Th2 cells and production of cytokines.

Treatment of allergic responses to foods—due to prevention of antigen translocation into blood stream and modulation of allergenic factors in food.

Reduction of blood lipids and prevention of heart disease—due to assimilation of cholesterol by bacteria; hydrolysis of bile salts; and antioxidative effects.

Antihypertensive effect—bacterial protease or peptidase action on milk peptides produces antihypertensive peptides. Cell wall components act as ACE inhibitors Prevention and treatment of urogenital infections—due to adhesion to urinary and vaginal tract cells resulting in competitive exclusion; and production of antibacterial substances (acids, hydrogen peroxide and biosurfactants).

Treatment of inflammatory bowel disorder and irritable bowel syndrome—due to immuno-modulation; increased resistance to pathogen colonization; alteration of intestinal conditions such as pH; production of specific antibacterial substances such as bacteriocins, organic acids and hydrogen peroxide and biosurfactants; and competitive exclusion.

Modulation of infective endocarditis—due to fibronectin receptor-mediated platelet aggregation associated with *Lactobacillus* sepsis.

Prevention and treatment of *Helicobacter pylori* infection—due to competitive colonization and antibacterial effect.

Prevention and treatment of hepatic encephalopathy—due to inhibition and/or exclusion of urease-producing gut flora.

Improved protein and carbohydrate utilization and conversion—due to production of beneficial products by bacterial action on proteins and carbohydrates.

Other beneficial health effects associated with *L. rhamnosus* include: improved nutrition; regulation of colonocyte proliferation and differentiation; improved lignan and isoflavone metabolism; reduced mucosal permeability; detoxification of carcinogens and other harmful compounds; relief of constipation and diarrhea; and vitamin synthesis, in particular folate.

Peptidases are enzymes that break the peptide bonds linking the amino group of one amino acid with the carboxy group (acid group) of an adjacent amino acid in a peptide chain. The bonds are broken in a hydrolytic reaction. There is a large family of peptidase enzymes that are defined by their specificity for the particular peptides bonds that they cleave (Barrett A J, Rawlings N D and Woessner J F (Eds.) 1998. *Handbook of proteolytic enzymes.* Academic Press, London, UK). The two main families are exopeptidases and endopeptidases.

Exopeptidases cleave amino acids from the N- or C-terminus of a peptide chain, releasing free amino acids or short (di- and tripeptides). Different types of exopeptidases include:

Aminopeptidases—release a free amino acid from the N-terminus of a peptide chain;

dipeptidyl-peptidase (also known as dipeptidyl-aminopeptidases)—release a dipeptide from the N-terminus of a peptide chain;

tripeptidyl-peptidases (also known as tripeptidyl-aminopeptidases)—release a tripeptide from the N-terminus of a peptide chain);

carboxypeptidases—release a free amino acid from the C-terminus of a peptide chain;

peptidyl-dipeptidase—release a dipeptide from the C-terminus of a peptide chain;

dipeptidases—release two free amino acids from a dipeptide; and tripeptidases—release a free amino acid and a dipeptide from a tripeptide.

Endopeptidases hydrolyze peptide bonds internally within a peptide and are classified on the basis of their mode of catalysis:

serine-endopeptidases—depend on serine (or threonine) as the nucleophile in the catalytic reaction;

cysteine-endopeptidases—depend on the sulphydryl group of cysteine as the nucleophile in the catalytic reaction;

aspartic-endopeptidases—contain aspartate residues that act as ligands for an activated water molecule which acts as the nucleophile in the catalytic reaction; and metallo-endopeptidases—contain one or more divalent metal ions that activate the water molecule that acts as the nucleophile in the catalytic reaction.

Peptidases are important enzymes in the process of cheese ripening and the development of cheese flavor. The hydrolysis of milk caseins in cheese results in textural changes and the development of cheese flavors. The raft of proteolytic enzymes that cause this hydrolysis come from the lactic acid bacteria that are bound up in the cheese—either starter cultures that grow up during the manufacture of the cheese, or adventitious and adjunct non-starter lactic acid bacteria that grow in the cheese as it ripens (Law Haandrikman, *Int. Dairy J.* 7:1–11, 1997).

Many other enzymes can also influence dairy product flavor, and functional and textural characteristics, as well as influencing the fermentation characteristics of the bacteria, such as speed of growth, acid production and survival (Urbach, *Int. Dairy J.* 5:877–890, 1995; Johnson and Somkuti, *Biotech. Appl. Biochem.* 13:196–204, 1991; El Soda and Pandian, *J. Dairy Sci.* 74:2317–2362, 1991; Fox et al,. In Cheese: chemistry, physics and microbiology. Volume 1, General aspects, $2^{nd}$ edition, P Fox (ed) Chapman and Hall, London; Christensen et al., *Antonie van Leeuwenhoek* 76:217–246, 1999; Stingle et al., *J. Bacteriol.* 20:6624–6360, 1999; Stingle et al., *Mol. Microbiol.* 32:1287–1295, 1999; Lemoine et al., *Appl. Environ. Microbiol.* 63:1512–6218, 1997). Enzymes influencing specific characteristics and/or functions include the following:

Lysis of cells. These enzymes are mostly cell wall hydrolases, including amidases; muramidases; lysozymes, including N-acetyl muramidase; muramidase; N-acetylglucosaminidase; and N-acetylmuramoyl-L-alanine amidase. DEAD-box helicase proteins also influence autolysis.

Carbohydrate utilization. Lactose, citrate and diacetyl metabolism, and alcohol metabolism are particularly important. The enzymes involved include beta-galactosidase, lactate dehydrogenase, citrate lyase, citrate permease, 2,3 butanediol dehydrogenase (acetoin reductase), acetolactate decaboxylase, acetolactate synthase, pyruvate decarboxylase, pyruvate formate lyase, diacetyl synthase, diacetyl reductase, alcohol decarboxylase, lactate dehydrogenase, pyruvate dehydrogenase, and aldehyde dehydrogenase.

Lipid degradation, modification or synthesis. Enzymes involved include lipases, esterases, phospholipases, serine hydrolases, desaturases, and linoleate isomerase.

Polysaccharide synthesis. Polysaccharides are important not only for potential immune enhancement and adhesion activity but are important for the texture of fermented dairy products. The enzymes involved are a series of glucosyl transferases, including beta-(1-3) glucosyl transferase, alpha-N acetylgalactosaminyl transferase, phosphogalactosyl transferase, alpha-glycosyl transferase, UDP-N-acetylglucosamine C4 epimerase and UDP-N-acetylglucosamine transferase.

Amino acid degradation. Enzymes include glutamate dehydrogenase, aminotransferases, amino acid decarboxylases, and enzymes involved in sulphur amino acid degradation including cystothione beta-lyase.

Sequencing of the genomes, or portions of the genomes, of numerous organisms, including humans, animals, microorganisms and various plant varieties, has been and is being carried out on a large scale. Polynucleotides identified using sequencing techniques may be partial or full-length genes, and may contain open reading frames, or portions of open reading frames, that encode polypeptides. Putative polypeptides may be identified based on polynucleotide sequences and further characterized. The sequencing data relating to polynucleotides thus represents valuable and useful information.

Polynucleotides and polypeptides may be analyzed for varying degrees of novelty by comparing identified sequences to sequences published in various public domain databases, such as EMBL. Newly identified polynucleotides and corresponding putative polypeptides may also be compared to polynucleotides and polypeptides contained in public domain information to ascertain homology to known polynucleotides and polypeptides. In this way, the degree of similarity, identity or homology of polynucleotides and polypeptides having an unknown function may be determined relative to polynucleotides and polypeptides having known functions.

Information relating to the sequences of isolated polynucleotides may be used in a variety of ways. Specified polynucleotides having a particular sequence may be isolated, or synthesized, for use in in vivo or in vitro experimentation as probes or primers. Alternatively, collections of sequences of isolated polynucleotides may be stored using magnetic or optical storage medium and analyzed or manipulated using computer hardware and software, as well as other types of tools.

SUMMARY OF THE INVENTION

The present invention provides isolated polynucleotides comprising a sequence selected from the group consisting of: (a) sequences identified in the attached Sequence Listing as SEQ ID NOS: 1–62; (b) variants of those sequences; (c) extended sequences comprising the sequences set out in SEQ ID NOS: 1–62, and their variants; and (d) sequences comprising at least a specified number of contiguous residues of a sequence of SEQ ID NOS: 1–62 (x-mers). Oligonucleotide probes and primers corresponding to the sequences set out in SEQ ID NOS: 1–62, and their variants are also provided. All of these polynucleotides and oligonucleotide probes and primers are collectively referred to herein, as "polynucleotides of the present invention."

The polynucleotide sequences identified as SEQ ID NOS: 1–62 were derived from a microbial source, namely from fragmented genomic DNA of Lactobacillus rhamnosus, strain HN001, described in PCT International Publication No. WO 99/10476. Lactobacillus rhamnosus strain HN001 are heterofermentative bacteria that are Gram positive, non-motile, non-spore forming, catalase negative, facultative anaerobic rods exhibiting an optimal growth temperature of 37±1° C. and an optimum pH of 6.0–6.5. Experimental studies demonstrated that dietary supplementation with Lactobacillus rhamnosus strain HN001 induced a sustained enhancement in several aspects of both natural and acquired immunity. A biologically pure culture of Lactobacillus rhamnosus strain HN001 was deposited at the Australian Government Analytical Laboratories (AGAL), The New South Wales Regional Laboratory, 1 Suakin Street, Pymble, NSW 2073, Australia, as Deposit No. NM97/09514, dated 18 Aug. 1997.

Certain of the polynucleotide sequences disclosed herein are "partial" sequences in that they do not represent a full-length gene encoding a full-length polypeptide. Such partial sequences may be extended by analyzing and sequencing various DNA libraries using primers and/or probes and well-known hybridization and/or PCR techniques. The partial sequences disclosed herein may thus be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NOS: 1–62 or a variant thereof, or a portion of one of the sequences of SEQ ID NOS: 1–62 or a variant thereof, when the extended polynucleotide comprises an identified sequence or its variant, or an identified contiguous portion (x-mer) of one of the sequences of SEQ ID NOS: 1–62 or a variant thereof.

The polynucleotides identified as SEQ ID NOS: 1–62 were isolated from Lactobacillus rhamnosus genomic DNA clones and represent sequences that are present in the cells from which the DNA was prepared. The sequence information may be used to identify and isolate, or synthesize, DNA molecules such as promoters, DNA-binding elements, open reading frames or full-length genes, that then can be used as expressible or otherwise functional DNA in transgenic organisms. Similarly, RNA sequences, reverse sequences, complementary sequences, antisense sequences and the like, corresponding to the polynucleotides of the present invention, may be routinely ascertained and obtained using the polynucleotides identified as SEQ ID NOS: 1–62.

The present invention further provides isolated polypeptides encoded, or partially encoded, by the polynucleotides disclosed herein. In certain specific embodiments, the polypeptides of the present invention comprise a sequence selected from the group consisting of sequences identified as SEQ ID NO: 63–124, and variants thereof. Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

Genetic constructs comprising the inventive polynucleotides are also provided, together with transgenic host cells comprising such constructs and transgenic organisms, such as microbes, comprising such cells.

The present invention also contemplates methods for modulating the polynucleotide and/or polypeptide content and composition of an organism, such methods involving stably incorporating into the genome of the organism a genetic construct comprising a polynucleotide of the present invention. In one embodiment, the target organism is a microbe, preferably a microbe used in fermentation, more preferably a microbe of the genus Lactobacillus, and most preferably Lactobacillus rhamnosus, or other closely microbial related species used in the dairy industry. In a related aspect, methods for producing a microbe having an altered genotype and/or phenotype is provided, such methods comprising transforming a microbial cell with a genetic construct of the present invention to provide a transgenic cell, and cultivating the transgenic cell under conditions conducive to growth and multiplication. Organisms having an altered genotype or phenotype as a result of modulation of the level or content of a polynucleotide or polypeptide of the present invention compared to a wild-type organism, as well as components and progeny of such organisms, are contemplated by and encompassed within the present invention.

The isolated polynucleotides of the present invention may be usefully employed for the detection of lactic acid bacteria, preferably L. rhamnosus, in a sample material, using techniques well known in the art, such as polymerase chain reaction (PCR) and DNA hybridization, as detailed below.

The inventive polynucleotides and polypeptides may also be employed in methods for the selection and production of more effective probiotic bacteria; as "bioactive" (health-promoting) ingredients and health supplements, for immune function enhancement; for reduction of blood lipids such as cholesterol; for production of bioactive material from genetically modified bacteria; as adjuvants; for wound healing; in vaccine development, particularly mucosal vaccines; as animal probiotics for improved animal health and productivity; in selection and production of genetically modified rumen microorganisms for improved animal nutrition and productivity, better flavor and improved milk composition; in methods for the selection and production of better natural food bacteria for improved flavor, faster flavor development, better fermentation characteristics, vitamin synthesis and improved textural characteristics; for the production of improved food bacteria through genetic modification; and for the identification of novel enzymes for the production of, for example, flavors or aroma concentrates.

The isolated polynucleotides of the present invention also have utility in genome mapping, in physical mapping, and in positional cloning of genes of more or less related microbes.

Additionally, the polynucleotide sequences identified as SEQ ID NOS: 1–62, and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells, using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix (Santa Clara, Calif.).

The polynucleotides of the present invention may also be used to tag or identify an organism or derived material or product therefrom. Such tagging may be accomplished, for example, by stably introducing a non-disruptive non-functional heterologous polynucleotide identifier into an organism, the polynucleotide comprising at least a portion of a polynucleotide of the present invention.

The polynucleotides of the present invention may additionally be used as promoters, gene regulators, origins of DNA replication, secretion signals, cell wall or membrane anchors for genetic tools (such as expression or integration vectors).

All references cited herein, including patent references and non-patent publications, are hereby incorporated by reference in their entireties.

DETAILED DESCRIPTION

The polynucleotides disclosed herein were isolated by high throughput sequencing of DNA libraries from the lactic acid bacteria *Lactobacillus rhamnosus* as described in Example 1. Cell wall, cell surface and secreted components of lactic acid bacteria are known to mediate immune modulation, cell adhesion and antibacterial activities, resulting in many beneficial effects including: resistance to enteric pathogens; modulation of cancer, including colon cancer: anti-mutagenesis effects; reduction of small bowel bacterial overgrowth; modulation of auto-immune disorders; reduction in allergic disorders; modulation of urogenital infections, inflammatory bowel disorder, irritable bowel syndrome, *Helicobacter pylori* infection and hepatic encephalopathy; reduction of infection with pathogens; regulation of colonocyte proliferation and differentiation; reduction of mucosal permeability; and relief of constipation and diarrhea. These cell components include, but are not limited to, peptidoglycans, teichoic acids, lipoteichoic acids, polysaccharides, adhesion proteins, secreted proteins, surface layer or S-layer proteins, collagen binding proteins and other cell surface proteins, and antibacterial substances such as bacteriocins and organic acids produced by these bacteria. Polynucleotides involved in the synthesis of these proteins and in the synthesis, modification, regulation, transport, synthesis and/or accumulation of precursor molecules for these proteins can be used to modulate the immune, antibacterial, cell adhesion and competitive exclusion effects of the bacteria or of components that might be produced by these bacteria.

In order to function effectively as probiotic bacteria, *L. rhamnosus* HN001 must survive environmental stress conditions in the gastrointestinal tract, as well as commercial and industrial processes. Modification of particular polynucleotides or regulatory processes have been shown to be effective against a number of stresses including oxidative stress, pH, osmotic stress, dehydration, carbon starvation, phosphate starvation, nitrogen starvation, amino acid starvation, heat or cold shock, and mutagenic stress. Polynucleotides involved in stress resistance often confer multistress resistance, i.e., when exposed to one stress, surviving cells are resistant to several non-related stresses. Bacterial genes and/or processes shown to be involved in multistress resistance include:

Intracellular phosphate pools—inorganic phosphate starvation leads to the induction of pho regulon genes, and is linked to the bacterial stringent response. Gene knockouts involving phosphate receptor genes appear to lead to multistress resistance.

Intracellular guanosine pools—purine biosynthesis and scavenger pathways involve the production of phosphate-guanosine compounds that act as signal molecules in the bacterial stringent response. Gene knockouts involving purine scavenger pathway genes appear to confer multi-stress resistance.

Osmoregulatory molecules—small choline-based molecules, such as glycine-betaine, and sugars, such as trehalose, are protective against osmotic shock and are rapidly imported and/or synthesized in response to increasing osmolarity.

Acid resistance—lactobacilli naturally acidify their environment through the excretion of lactic acid, mainly through the cit operon genes responsible for citrate uptake and utilization.

Stress response genes—a number of genes appear to be induced or repressed by heat shock, cold shock, and increasing salt through the action of specific promoters.

The isolated polynucleotides of the present invention, and genetic constructs comprising such polynucleotides, may be employed to produce bacteria having desired phenotypes, including increased resistance to stress and improved fermentation properties.

Many enzymes are known to influence dairy product flavor, functional and textural characteristics as well as general fermentation characteristics such as speed of growth, acid production and survival. These enzymes include those involved in the metabolism of lipids, polysaccharides, amino acids and carbohydrates, as well as those involved in the lysis of the bacterial cells.

The isolated polynucleotides and polypeptides of the present invention have demonstrated similarity to polynucleotides and/or polypeptides of known function. The putative identity and functions of the inventive polynucleotides based on such similarities are shown below in Table 1.

TABLE 1

| SEQ ID NO Polynucleotide | SEQ ID NO Polypeptide | Gene function or protein class |
|---|---|---|
| 1 | 63 | Transmembrane protein that participates in the adhesion of bacteria to gut cells, part of an operon containing the mapA gene encoding a mucin binding protein. This gene may be used to identify or manipulate interactions with gut cells. |
| 2 | 64 | Common 28 kDa antigen and major cell adherence molecule of *Campylobacter jejuni* and *Campylobacter coli*. Significant similarity to amino acid transport proteins in Gram-negative bacteria. This gene may be used to identify or manipulate both interactions with gut cells and amino acid metabolism. |
| 3 | 65 | Histidinol-phosphate aminotransferase, may also have tyrosine and phenylalanine aminotransferase activity. Involved in amino acid metabolism. May be used to identify or manipulate metabolism and influence growth and the production of flavor compounds. |
| 4 | 66 | Aspartate transaminase (EC 2.6.1.1). Converts L-aspartate and 2-oxoglutarate to oxaloacetate and L-glutamate, but may also be involved in aromatic amino acid, alanine, cysteine, proline, and asparagine pathways. Its role amino acid metabolism suggests impact in production of flavor compounds, and may also be involved in carbon fixation. May be used to identify or manipulate metabolism and influence growth and the production of flavor compounds. |
| 5 | 67 | Aromatic amino acid transferase. It is used to identify or manipulate metabolism and influence growth and the production of flavor compounds.. |
| 6 | 68 | Tyrosine aminotransferase (EC 2.6.1.5) (L-tyrosine: 2-oxoglutarate aminotransferase). Transfers nitrogenous groups as part of the aromatic amino acid pathway. Involved in synthesis of flavor compounds and amino acid metabolism. It is used to identify or manipulate metabolism and influence growth and the production of flavor compounds. |
| 7 | 69 | Aminotransferase B. Probable aminotransferase belonging to class-II pyridoxal-phosphate-dependent aminotransferase family. it is used to identify or manipulate metabolism and influence growth and the production of flavor compounds. |
| 8 | 70 | Cysteine desulfurase, a class-V aminotransferase that supplies inorganic sulfide for Fe—S clusters. Involved in cysteine metabolism and generation of flavor compounds. It is used to identify or manipulate metabolism and influence growth and the production of flavor compounds. |
| 9 | 71 | Lipase, breakdown of triglycerides. It is used to identify or manipulate metabolism and influence growth and the production of flavor compounds. |
| 10 | 72 | O-acetylserine sulfhydrylase involved in cysteine synthesis. Converts O-acetyl-L-serine and H2S to L-cysteine and acetate. Involved in synthesis of flavor and aroma compounds. It is used to identify or manipulate metabolism and influence growth and the production of flavor compounds. |
| 11 | 73 | Surface protein thought to be involved in a number of functions including as a collagen and/or mucin binding protein in cellular adhesion and as a cysteine transporter, part of the ABC superfamily, which affects amino acid metabolism and flavor compound synthesis. It is used to identify or manipulate metabolism, growth, the production of flavor compounds, and interactions with gut cells. |
| 12 | 74 | Group B streptococcal oligopeptidase, degrades a variety of bioactive peptides. Involved in protein breakdown and metabolism, and may impact on flavor compounds as well impact on health through the stability or production of bioactive peptides. |
| 13 | 75 | Pz-peptidase, a metalloproteinase and part of the thimet oligopeptidase family. Hydrolyses the Pz-peptide, 4-phenylazobenzyloxycarbonyl-Pro-Leu-Gly-Pro-Arg. It impacts on flavor compounds as well impact on health through the stability or production of bioactive peptides. |
| 14 | 76 | Adenosine triphosphatase clpC. ATP-dependent Clp proteinase regulatory protein, a pleiotropic regulator controlling growth at high temperatures. Involved in stress response. It is used to identify or impact on the survival or virulence of organisms. |
| 15 | 77 | Streptococcal C5a peptidase. Specifically cleaves human serum chemotaxin C5a near its C-terminus, destroying its ability to serve as a chemoattractant. It mediates interactions with host immune system and is used to identify or impact on interactions with immune systems. |

TABLE 1-continued

| SEQ ID NO Polynucleotide | SEQ ID NO Polypeptide | Gene function or protein class |
| --- | --- | --- |
| 16 | 78 | Dipeptidase from *Lactococcus lactis*. Hydrolyzes a broad range of dipeptides but no tri, tetra, or larger oligopeptides. It is used to identify or impact on protein metabolism and flavor compound synthesis. |
| 17 | 79 | Acylamino-acid-releasing enzyme (acyl-peptidehydrolase or acylaminoacyl-peptidase) BC 3.4.19.1. Catalyzes removal N alpha-acetylated amino acid residues from N alpha-acetylated peptides. It is used to identify or impact on metabolism or flavor or aroma compound production. |
| 18 | 80 | Heat shock protease regulatory subunit, the ATPase subunit of an intracellular ATP-dependent protease. It is used to identify or impact on survival or virulence. |
| 19 | 81 | O-sialoglycoprotein endopeptidase (EC 3.4.24.57). Hydrolyses O-sialoglycoproteins, but does not cleave unglycosylated proteins, desialylated glycoproteins or N-glycosylated glycoproteins. Sialogylcoproteins can act as receptors for adhesion to gut cells. It is used to identify or impact on interactions with gut cells, protein metabolism, stability or production of bioactive peptides. |
| 20 | 82 | Carboxylesterase, converts a carboxylic ester to an alcohol and a carboxylic acid anion. Esters and alcohols can be potent flavor and aroma compounds. It is used to identify or impact on metabolism or flavor or aroma compound production. |
| 21 | 83 | Glycerophosphodiester phosphodiesterase. Converts glycerophosphodiesters to an alcohol and glycerol 3-phosphate. Alcohols are potentially important flavor compounds. It is used to identify or impact on metabolism or flavor or aroma compound production. |
| 22 | 84 | Bifunctional alcohol dehydrogenase and acetaldehyde dehydrogenase. Ferments glucose to ethanol under anaerobic conditions. It is used to identify or impact on metabolism or flavor or aroma compound production. |
| 23 | 85 | Short-chain alcohol dehydrogenase. It is used to identify or impact on metabolism or flavor or aroma compound production. |
| 24 | 86 | Aryl-alcohol dehydrogenase. Converts an aromatic alcohol to an aromatic aldehyde. It is used to identify or impact on metabolism or flavor or aroma compound production. |
| 25 | 87 | Branched chain amino acid transport system II carrier protein, involved in amino acid metabolism. Amino acid metabolism is important in flavor compound production. It is used to identify or impact on metabolism or flavor compound production. |
| 26 | 88 | Human bile salt export pump. Bile tolerance is an important property of probiotic bacteria. Bile salt removal can reduce cholesterol. May be used to identify or impact on bile tolerance or cholesterol reduction. |
| 27 | 89 | Bifunctional HPr Kinase/P-Ser-HPr phosphatase from *Lactobacillus casei*. Controls catabolite repression and involved in phosphate regulation. Phosphate regulation is important in cell survival and stress tolerance. It is used to identify or impact on gene regulation and on stress tolerance. |
| 28 | 90 | Suppressor of dominant negative ftsH mutations affecting extracellular protein transport in *E. coli*. It is used to identify or impact on protein transport. |
| 29 | 91 | Malolactic enzyme. Converts between malate and lactate. Central to carbohydrate metabolism, also involved in acid tolerance. It is used to identify or impact on metabolism or flavor compound production or cell survival. |
| 30 | 92 | Magnesium transporter, also has affinity for cobalt. Metal ion transport is involved in bacterial survival as well as other aspects of metabolism. It is used to identify or impact on metabolism or cell survival. |
| 31 | 93 | Pyruvate dehydrogenase E1 (lipoamide) alpha subunit (EC 1.2.4.1). Glycolytic enzyme, also involved in branched-chain amino acid synthesis. It is used to identify or impact on metabolism or flavor or aroma compound production. |
| 32 | 94 | Adhesin involved in diffuse adherence of diarrhoeagenic *E. coli*. May be used to identify or impact on interactions with gut cells, survival and persistence in the gut. |
| 33 | 95 | dTDP-4-keto-L. rhamnose reductase involved in polysaccharide biosynthesis. Polysaccharides are important for adhesion to gut cells, immune system modulation, stress tolerance and for physical properties of fermented products. It is used to identify or impact on polysaccharide production and interaction with gut cells. |

TABLE 1-continued

| SEQ ID NO Polynucleotide | SEQ ID NO Polypeptide | Gene function or protein class |
|---|---|---|
| 34 | 96 | Glucose inhibited division protein. Involved in stress resistance, gidA mutants are UV-sensitive and exhibit decreased homologous recombination in plasmidic tests. It is used to identify or impact on cell survival and gene regulation. |
| 35 | 97 | Glucose-1-phosphate thymidylyl transferase, involved in polysaccharide biosynthesis. Polysaccharides are important for adhesion to gut cells, immune system modulation, stress tolerance and for physical properties of fermented products. It is used to identify or impact on polysaccharide production and interaction with gut cells. |
| 36 | 98 | Phosphate starvation-induced protein, may be important for survival under low phospate conditions. Phosphate levels have been shown to be important in multistress resistance. It is used to identify or impact on cell survival. |
| 37 | 99 | Formate C-acetyltransferase (or pyruvate formate lyase, EC 2.3.1.54). Converts formate to pyruvate during malate utilization. Pyruvate is central to cell metabolism. It is used to identify or impact on metabolism and the generation of flavor compounds. |
| 38 | 100 | Alpha-glycerophosphate oxidase. Oxidizes alpha-glycerophosphate to dihydroxyacetone phosphate while reducing oxygen to hydrogen peroxide. These compounds are important for metabolism as well as antimicrobial activity. It is used to identify or impact on metabolism and the generation of flavor compounds as well as antimicrobial activity. |
| 39 | 101 | 6-Phosphogluconate dehydrogenase. Converts 6-phospho-D-gluconate to D-ribulose 5-phosphate and CO2, part of the hexose monophosphate shunt pathway used for carbohydrate metabolism. It is used to identify or impact on metabolism and the generation of flavor compounds. |
| 40 | 102 | 5-methyltetrahydropteroyltriglutamate homocysteine methyltransferase. Converts 5-methyltetrahydropteroyltri-L-glutamate and L-homocysteine to Tetrahydropteroyltri-L-glutamate and L-methionine. Sulpher compounds are important in flavor development. Homocysteine is important in cardiovascular health. It is used to identify or impact on metabolism and the generation of flavor or aroma compounds as well as cardiovascular health. |
| 41 | 103 | S-methylmethionine permease. Integral membrane protein involved in S-methylmethionine uptake. Sulfur compounds are important in flavor development, and 5-methylmethionine may also be involved in cellular methylation pathways. Cellular methylation is important for gene regulation. It is used to identify or impact on metabolism and the generation of flavor compounds and for cellular methylation. |
| 42 | 104 | 6-Phospho-beta-galactosidase. Central to lactose metabolism, results in alcohol compounds that may have flavor properties. It is used to identify or impact on metabolism and the generation of flavor compounds. |
| 43 | 105 | GTP binding protein, membrane bound. Involved in the stress response. It is used to identify or impact on cell survival. |
| 44 | 106 | Gamma-glutamyl phosphate reductase (glutamate-5-semialdehyde dehydrogenase), involved in proline biosynthesis and amino acid metabolism pathways. It is used to identify or impact on metabolism and the generation of flavor compounds. |
| 45 | 107 | Dihydrofolate reductase (EC 1.5.1.3), responsible for resistance to the cytotoxic drug methotrexate and involved in vitamin synthesis. It is used to identify or impact on metabolism and the generation of vitamin compounds and for drug resistance. |
| 46 | 108 | Lactate dehydrogenase. Converts lactate to pyruvate, also has a role in acid tolerance. Lactate can have antimicrobial effects. It is used to identify or impact on metabolism and the generation of flavor compounds, for cell survival and virulence and antimicrobial effects. |
| 47 | 109 | Heat-inducible transcription repressor protein. Involved in stress resistance. It is used to identify or impact on survival and on gene regulation. |
| 48 | 110 | Daunorubicin resistance protein (DrrC) is a daunorubicin resistance protein with a strong sequence similarity to the UvrA protein that is involved in excision repair of DNA. DrrC is induced by the anticancer drug daunorubicin and behaves like an ATP-dependent, DNA binding protein in vitro. |

TABLE 1-continued

| SEQ ID NO Polynucleotide | SEQ ID NO Polypeptide | Gene function or protein class |
|---|---|---|
| 49 | 111 | Dihydrodipicolinate synthase (ec 4.2.1.52) (DHDPS) is also known as DapA or AF0910. DapA catalyzes the first step in the biosynthesis of diaminopimelate and lysine from aspartate semialdehyde. The known pathways for diaminopimelate (DAP) and lysine biosynthesis share two key enzymes, dihydrodipicolinate synthase and dihydrodipicolinate reductase, encoded by the dapA and dapB genes, respectively. Diaminopimelate (DAP) is a metabolite that is also involved in peptidoglycan formation. DapA can be used for the industrial production of L-lysine. DHDPS belongs to the DHDPS family. |
| 50 | 112 | Lysin (Lys) is one of the lytic enzymes encoded bu bacteriophages. Together with holin, lysis of bacteria used in cheese-making can be achieved to accelerate cheese ripening and to facilitated release of intracellular enzymes involvement in flavor formation. Production of holin alone leads to partial lysis of the host cells, whereas production of lysin alone does not cause significant lysis. Model cheese experiments in which an inducible holinlysin overproducing strain was used showed a fourfold increase in release of L-Lactate dehydrogenase activity into the curd relative to the control strain and the holin-overproducing strain, demonstrating the suitability of the system for cheese applications. |
| 51 | 113 | Penicillin-binding protein 1A or PDPF is penicillin-binding protein PBP 1A that is an essential murein polymerases of bacteria. The penicillin binding proteins (PBPs) synthesize and remodel peptidoglycan, the structural component of the bacterial cell wall. Resistance to beta-lactam antibiotics in bacteria is due to alteration of the penicillin-binding proteins (PBPs). PBP 1A belongs to the class A high-molecular-mass PBPs, which harbor transpeptidase (TP) and glycosyltransferase (GT) activities. The GT active site represents a target for the generation of novel non-penicillin antibiotics. |
| 52 | 114 | Virulence-associated protein BH6253 plays a role in the virulence of the pathogens. |
| 53 | 115 | Adherence and virulence protein A (Pav A) is a virulence factor that is widely distributed in bacteria and participates in adherence to host cells and soft tissue pathology. |
| 54 | 116 | Proline iminopeptidase gene (pepI) is part of an operon-like structure of three open reading frames (ORF1, ORF2 and ORF3). ORF1 was preceded by a typical prokaryotic promoter region, and a putative transcription terminator was found downstream of ORF3, identified as the pepI gene. PepI was shown to be a metal-independent serine peptidase having thiol groups at or near the active site. Kinetic studies identified proline-p-nitroanilide as substrate. PepI is a dimer of M(r) 53,000. The enzyme can be utilized to facilitate the accumulation of proline from dipeptides and oligopeptides during the ripening of cheese. |
| 55 | 117 | Sensory transduction protein regX3 forms part of a two-component regulatory system regX3/senX3 phosphorylated by senX3. The N-terminal region is similar to that of other regulatory components of sensory transduction systems. The senX3-regX3 IR contains a novel type of repetitive sequence, called mycobacterial interspersed repetitive units (MIRUs). The regX3 gene has utility in diagnostic assays to differentiate between bacterial strains. |
| 56 | 118 | Aminopeptidase pepS (ec 3.4.11.-) is part of the proteolytic system of lactic acid bacteria that is essential for bacterial growth in milk and for development of the organoleptic properties of dairy products. PepS is a monomeric metallopeptidase of approximately 45 kDa with optimal activity in the range pH 7.5–8.5 and at 55 degrees C. on Arg-paranitroanilide as substrate. PepS exhibits a high specificity towards peptides possessing arginine or aromatic amino acids at the N-terminus. PepS is part of the aminopeptidase T family. In view of its substrate specificity, PepS is involved both in bacterial growth by supplying amino acids, and in the development of dairy products' flavor, by hydrolysing bitter peptides and liberating aromatic amino acids which are important precursors of aroma compounds. |
| 57 | 119 | Phosphoribosylaminoimidazolecarboxamide formyltransferase/imp cyclohydrolase (ec 2.1.2.3) (purH) or AICARFT is biosynthetic enzyme in the de novo purine biosynthesis pathway. |

TABLE 1-continued

| SEQ ID NO Polynucleotide | SEQ ID NO Polypeptide | Gene function or protein class |
|---|---|---|
| 58 | 120 | Prolinase (pepR) is a peptidase gene expressing L-proline-beta-naphthylamide-hydrolyzing activity. PepR was shown to be the primary enzyme capable of hydrolyzing Pro-Leu in Lactobacilli. The purified enzyme hydrolyzed Pro-Met, Thr-Leu, and Ser-Phe as well as dipeptides containing neutral, nonpolar amino acid residues at the amino terminus. Purified pepR was determined to have a molecular mass of 125 kDa with subunits of 33 kDa. The isoelectric point of the enzyme was determined to be 4.5. PepR is a serine-dependent protease that can be utilized in production of dairy products where it is used to acidify milk. |
| 59 | 121 | Hexulose-6-phosphate isomerase (ec 5.-.-.-) is also known as HumpI or SGBU and is part of a sugar metabolic pathway along with sgbh where it is involved in isomerization of D-arabino-6-hexulose 3-phosphate to D-fructose 6-phosphate. SGBU belongs to the HumpI family. |
| 60 | 122 | Succinyl-diaminopimelate desuccinylase encodes the DapE that has utility as antibiotic target. |
| 61 | 123 | Transcriptional regulator (GntR family) is part of the GntR family of DNA binding proteins that has a characteristic helix-turn-helix motif. The motif interacts with DNA double helix and recognizes specific base sequences. |
| 62 | 124 | Xaa-Pro dipeptidase (ec 3.4.13.9) is also known as X-Pro dipeptidase, proline dipeptidase, prolidase, imidodipeptidase or pepQ. PepQ is involved in the hydrolysis of Xaa-|-Pro dipeptides and also acts on aminoacyl-hydroxyproline analogs. PepQ belongs to peptidase family M24b. PepQ can be utilized in the production of cheese. |

Isolated polynucleotides of the present invention include the polynucleotides identified herein as SEQ ID NOS: 1–62; isolated polynucleotides comprising a polynucleotide sequence selected from the group consisting of SEQ ID NOS: 1–62; isolated polynucleotides comprising at least a specified number of contiguous residues (x-mers) of any of the polynucleotides identified as SEQ ID NOS: 1–62; isolated polynucleotides comprising a polynucleotide sequence that is complementary to any of the above polynucleotides; isolated polynucleotides comprising a polynucleotide sequence that is a reverse sequence or a reverse complement of any of the above polynucleotides; antisense sequences corresponding to any of the above polynucleotides; and variants of any of the above polynucleotides, as that term is described in this specification.

The word "polynucleotide(s)," as used herein, means a single or double stranded polymer of deoxyribonucleotide or ribonucleotide bases and includes DNA and corresponding RNA molecules, including mRNA molecules, both sense and antisense strands of DNA and RNA molecules, and comprehends cDNA, genomic DNA and recombinant DNA, as well as wholly or partially synthesized polynucleotides. A polynucleotide of the present invention may be an entire gene, or any portion thereof. A gene is a DNA sequence which codes for a functional protein or RNA molecule. Operable antisense polynucleotides may comprise a fragment of the corresponding polynucleotide, and the definition of "polynucleotide" therefore includes all operable antisense fragments. Antisense polynucleotides and techniques involving antisense polynucleotides are well known in the art and are described, for example, in Robinson-Benion, et al., "Antisense techniques," *Methods in Enzymol.* 254(23): 363–375, 1995; and Kawasaki, et al., *Artific. Organs* 20 (8): 836–848, 1996.

The definitions of the terms "complement," "reverse complement," and "reverse sequence," as used herein, are best illustrated by the following examples. For the sequence 5' AGGACC 3', the complement, reverse complement, and reverse sequences are as follows:

```
complement              3' TCCTGG 5'
reverse complement      3' GGTCCT 5'
reverse sequence        5' CCAGGA 3'
```

Preferably, sequences that are complements of a specifically recited polynucleotide sequence are complementary over the entire length of the specific polynucleotide sequence.

Identification of genomic DNA and heterologous species DNA can be accomplished by standard DNA/DNA hybridization techniques, under appropriately stringent conditions, using all or part of a DNA sequence as a probe to screen an appropriate library. Alternatively, PCR techniques using oligonucleotide primers that are designed based on known DNA and protein sequences can be used to amplify and identify other identical or similar DNA sequences. Synthetic DNA corresponding to the identified sequences or variants thereof may be produced by conventional synthesis methods. All of the polynucleotides described herein are isolated and purified, as those terms are commonly used in the art.

The polynucleotides identified as SEQ ID NOS: 1–62 may contain open reading frames ("ORFs"), or partial open reading frames, encoding polypeptides. Polynucleotides identified as SEQ ID NOS: 1–62 may also contain non-coding sequences such as promoters and terminators that may be useful as control elements. Additionally, open reading frames encoding polypeptides may be identified in extended or full-length sequences corresponding to the sequences set out as SEQ ID NOS: 1–62. Open reading frames may be identified using techniques that are well known in the art. These techniques include, for example, analysis for the location of known start and stop codons, most likely reading frame identification based on codon frequencies, similarity to known bacterial expressed genes, etc. Suitable tools and software for ORF analysis include GeneWise (The Sanger Center, Wellcome Trust Genome Campus, Hinxton, Cambridge CB10 1 ISA, United Kingdom), Diogenes (Computational Biology Centers, University of Minnesota, Academic Health Center, UMHG Box 43 Minneapolis Minn. 55455), and GRAIL (Informatics Group, Oak Ridge National Laboratories, Oak Ridge, Tennessee, Tenn.). Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, polynucleotides and open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells. In vitro expression of polypeptides is also possible, as well known in the art.

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

As used herein, the term "x-mer," with reference to a specific value of "x," refers to a polynucleotide comprising at least a specified number ("x") of contiguous residues of any of the polynucleotides identified as SEQ ID NOS: 1–62. The value of x may be from about 20 to about 600, depending upon the specific sequence.

In another aspect, the present invention provides isolated polypeptides encoded, or partially encoded, by the above polynucleotides. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide which comprises an isolated polynucleotide sequence or variant provided herein. Polypeptides of the present invention may be naturally purified products, or may be produced partially or wholly using recombinant techniques. Such polypeptides may be glycosylated with bacterial, fungal, mammalian or other eukaryotic carbohydrates or may be non-glycosylated. In specific embodiments, polypeptides of the present invention include an amino acid sequence recited in SEQ ID NO: 63–124.

Polypeptides of the present invention may be produced recombinantly by inserting a polynucleotide that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polypeptide encoding a recombinant polypeptide. Suitable host cells include prokaryotes, yeast and higher eukaryotic cells. Preferably, the host cells employed are *Escherichia coli*, *Lactococcus lactis*, *Lactobacillus*, insect, yeast or a mammalian cell line such as COS or CHO. The polynucleotide(s) expressed in this manner may encode naturally occurring polypeptides, portions of naturally occurring polypeptides, or other variants thereof.

In a related aspect, polypeptides are provided that comprise at least a functional portion of a polypeptide having an amino acid sequence encoded by a polynucleotide of the present invention. As used herein, a "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

Portions and other variants of the inventive polypeptides may be generated by synthetic or recombinant means. Synthetic polypeptides having fewer than about 100 amino acids, and generally fewer than about 50 amino acids, may be generated using techniques that are well known to those of ordinary skill in the art. For example, such polypeptides may be synthesized using any of the commercially available solid-phase techniques, such as the Merrifield solid-phase synthesis method, where amino acids are sequentially added to a growing amino acid chain (See Merrifield, *J. Am. Chem. Soc.* 85:2149–2154, 1963). Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagensis (Kunkel, *Proc. Natl. Acad. Sci. USA* 82: 488–492, 1985). Sections of DNA sequences may also be removed using standard techniques to permit preparation of truncated polypeptides.

In general, the polypeptides disclosed herein are prepared in an isolated, substantially pure form. Preferably, the polypeptides are at least about 80% pure; more preferably at least about 90% pure; and most preferably at least about 99% pure.

As used herein, the term "variant" comprehends polynucleotide or polypeptide sequences different from the specifically identified sequences, wherein one or more nucleotides or amino acid residues is deleted, substituted, or added. Variants may be naturally occurring allelic variants, or non-naturally occurring variants. Variant polynucleotide sequences preferably exhibit at least 40%, more preferably at least 60%, more preferably yet at least 75%, and most preferably at least 90% identity to a sequence of the present invention. Variant polypeptide sequences preferably exhibit at least 50%, more preferably at least 75%, more preferably yet at least 90%, and most preferably at least 95% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and the percentage of identical residues in a specified region may be determined against another polynucleotide or polypeptide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The percentage identity of polypeptide sequences may be examined using the BLASTP algorithm. The BLASTN, BLASTX and BLASTP programs are available on the NCBI anonymous FTP server and from the National Center for Biotechnology Information (NCBI), National Library of Medicine, Building 38A, Room 8N805, Bethesda, Md. 20894, USA. The BLASTN algorithm Version 2.0.4 [Feb. 24, 1998], Version 2.0.6 [Sep. 16, 1998] and Version 2.0.11 [Jan. 20, 2000], set to the parameters described below, is preferred for use in the determination of polynucleotide variants according to the present invention. The BLASTP algorithm, set to the parameters described below, is preferred for use in the determination of polypeptide variants according to the present invention. The use of the BLAST family of algorithms, including BLASTN, BLASTP and BLASTX, is described at NCBI's website and in the publication of Altschul, et al., *Nucleic Acids Res.* 25:3389–3402, 1997.

The computer algorithm FASTA is available on the Internet and from the University of Virginia by contacting David Hudson, Vice Provost for Research, University of Virginia, P.O. Box 9025, Charlottesville, Va. 22906-9025, USA. FASTA Version 2.0u4 [February 1996], set to the default parameters described in the documentation and distributed with the algorithm, may be used in the determination of variants according to the present invention. The use of the FASTA algorithm is described in Pearson and Lipman, *Proc. Natl. Acad. Sci. USA* 85:2444–2448, 1988; and Pearson, *Methods in Enzymol.* 183: 63–98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional. The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA, and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

As noted above, the percentage identity is determined by aligning sequences using one of the BLASTN, FASTA, or BLASTP algorithms, set at the running parameters described above, and identifying the number of identical nucleic or amino acids over the aligned portions; dividing the number of identical nucleic or amino acids by the total number of nucleic or amino acids of the polynucleotide or polypeptide sequence of the present invention; and then multiplying by 100 to determine the percentage identity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm using the parameters described above. The 23 nucleotide hit includes 21 identical nucleotides, one gap and one different nucleotide. The percentage identity of the polynucleotide of the present invention to the hit in the EMBL library is thus 21/220 times 100, or 9.5%. The polynucleotide sequence in the EMBL database is thus not a variant of a polynucleotide of the present invention.

In addition to having a specified percentage identity to an inventive polynucleotide or polypeptide sequence, variant polynucleotides and polypeptides preferably have additional structure and/or functional features in common with the inventive polynucleotide or polypeptide. Polypeptides having a specified degree of identity to a polypeptide of the present invention share a high degree of similarity in their primary structure and have substantially similar functional properties. In addition to sharing a high degree of similarity in their primary structure to polynucleotides of the present invention, polynucleotides having a specified degree of identity to, or capable of hybridizing to an inventive polynucleotide preferably have at least one of the following features: (i) they contain an open reading frame or partial open reading frame encoding a polypeptide having substantially the same functional properties as the polypeptide encoded by the inventive polynucleotide; or (ii) they contain identifiable domains in common.

Alternatively, variant polynucleotides of the present invention hybridize to the polynucleotide sequences recited in SEQ ID NOS: 1–62, or complements, reverse sequences, or reverse complements of those sequences, under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NOS: 1–62, or complements, reverse sequences, or reverse complements of those sequences as a result of conservative substitutions are encompassed within the present invention. Additionally, polynucleotides comprising sequences that differ from the inventive polynucleotide sequences or complements, reverse complements, or reverse sequences as a result of deletions and/or insertions totaling less than 10% of the total sequence length are also contemplated by and encompassed within the present invention. Similarly, polypeptides comprising sequences that differ from the inventive polypeptide sequences as a result of amino acid substitutions, insertions, and/or deletions totaling less than 10% of the total sequence length are contemplated by and encompassed within the present invention, provided the variant polypeptide has similar activity to the inventive polypeptide.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5-nucleotide overhang. The next segment may then be synthesized in a similar fashion, with a 5-nucleotide overhang on the opposite strand. The "sticky" ends ensure proper ligation when the two portions are hybridized. In this way, a complete polynucleotide of the present invention may be synthesized entirely in vitro.

Certain of the polynucleotides identified as SEQ ID NOS: 1–62 are referred to as "partial" sequences, in that they do not represent the full coding portion of a gene encoding a naturally occurring polypeptide. The partial polynucleotide sequences disclosed herein may be employed to obtain the corresponding full-length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding DNA, as well as identify the corresponding mRNA and genomic DNA, including the promoter and enhancer regions, of the complete gene. The present invention thus comprehends isolated polynucleotides comprising a sequence identified in SEQ ID NOS: 1–62, or a variant of one of the specified sequences, that encode a functional polypeptide, including full length genes. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,000 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Polynucleotides of the present invention comprehend polynucleotides comprising at least a specified number of contiguous residues (x-mers) of any of the polynucleotides identified as SEQ ID NOS: 1–62 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NOS: 1–62 or a variant of one of the polynucleotides identified as SEQ ID NOS: 1–62.

Oligonucleotide probes and primers complementary to and/or corresponding to SEQ ID NOS: 1–62, and variants of those sequences, are also comprehended by the present invention. Such oligonucleotide probes and primers are substantially complementary to the polynucleotide of interest. An oligonucleotide probe or primer is described as "corresponding to" a polynucleotide of the present invention, including one of the sequences set out as SEQ ID NOS: 1–62 or a variant, if the oligonucleotide probe or primer, or its complement, is contained within one of the sequences set out as SEQ ID NOS: 1–62 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. DNA—DNA hybridization studies may performed using either genomic DNA or DNA derived by preparing cDNA from the RNA present in a sample to be tested.

In addition to DNA—DNA hybridization, DNA-RNA or RNA—RNA hybridization assays are also possible. In the first case, the mRNA from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The primers and probes may be readily selected using procedures well known in the art, taking into account DNA—DNA hybridization stringencies, annealing and melting temperatures, potential for formation of loops and other factors, which are well known in the art. Tools and software suitable for designing probes, and especially suitable for designing PCR primers, are available on the Internet. In addition, a software program suitable for designing probes, and especially for designing PCR primers, is available from Premier Biosoft International, 3786 Corina Way, Palo Alto, Calif. 94303-4504. Preferred techniques for designing PCR primers are also disclosed in Dieffenbach and Dyksler, *PCR primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–62.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

Oligonucleotide probes for use in the present invention may be constructed synthetically prior to immobilization on an array, using techniques well known in the art (See, for example, Gait, ed., *Oligonucleotide synthesis a practical approach*, IRL Press: Oxford, England, 1984). Automated equipment for the synthesis of oligonucleotides is available commercially from such companies as Perkin Elmer/Applied Biosystems Division (Foster City, Calif.) and may be operated according to the manufacturer's instructions. Alternatively, the probes may be constructed directly on the surface of the array using techniques taught, for example, in PCT Publication No. WO 95/00530.

The solid substrate and the surface thereof preferably form a rigid support and are generally formed from the same material. Examples of materials from which the solid substrate may be constructed include polymers, plastics, resins, membranes, polysaccharides, silica or silica-based materials, carbon, metals and inorganic glasses. Synthetically prepared probes may be immobilized on the surface of the solid substrate using techniques well known in the art, such as those disclosed in U.S. Pat. No. 5,412,087.

In one such technique, compounds having protected functional groups, such as thiols protected with photochemically removable protecting groups, are attached to the surface of the substrate. Selected regions of the surface are then irradiated with a light source, preferably a laser, to provide reactive thiol groups. This irradiation step is generally performed using a mask having apertures at predefined locations using photolithographic techniques well known in the art of semiconductors. The reactive thiol groups are then incubated with the oligonucleotide probe to be immobilized. The precise conditions for incubation, such as temperature, time and pH, depend on the specific probe and can be easily determined by one of skill in the art. The surface of the substrate is washed free of unbound probe and the irradiation step is repeated using a second mask having a different pattern of apertures. The surface is subsequently incubated with a second, different, probe. Each oligonucleotide probe is typically immobilized in a discrete area of less than about 1 mm$^2$. Preferably each discrete area is less than about 10,000 mm$^2$, more preferably less than about 100 mm$^2$. In this manner, a multitude of oligonucleotide probes may be immobilized at predefined locations on the array.

The resulting array may be employed to screen for differences in organisms or samples or products containing genetic material as follows. Genomic or cDNA libraries are prepared using techniques well known in the art. The resulting target DNA is then labeled with a suitable marker, such as a radiolabel, chromophore, fluorophore or chemiluminescent agent, using protocols well known for those skilled in the art. A solution of the labeled target DNA is contacted with the surface of the array and incubated for a suitable period of time.

The surface of the array is then washed free of unbound target DNA and the probes to which the target DNA hybridized are determined by identifying those regions of the array to which the markers are attached. When the marker is a radiolabel, such as $^{32}$P, autoradiography is employed as the detection method. In one embodiment, the marker is a fluorophore, such as fluorescein, and the location of bound target DNA is determined by means of fluorescence spectroscopy. Automated equipment for use in fluorescence scanning of oligonucleotide probe arrays is available from Affymetrix, Inc. (Santa Clara, Calif.) and may be operated according to the manufacturer's instructions. Such equipment may be employed to determine the intensity of fluorescence at each predefined location on the array, thereby providing a measure of the amount of target DNA bound at each location. Such an assay would be able to indicate not only the absence and presence of the marker probe in the target, but also the quantitative amount as well.

The significance of such high-throughput screening system is apparent for applications such as microbial selection and quality control operations in which there is a need to identify large numbers of samples or products for unwanted materials, to identify microbes or samples or products containing microbial material for quarantine purposes, etc., or to ascertain the true origin of samples or products containing microbes. Screening for the presence or absence of polynucleotides of the present invention used as identifiers for tagging microbes and microbial products can be valuable for later detecting the genetic composition of food, fermentation and industrial microbes or microbes in human or animal digestive system after consumption of probiotics, etc.

In this manner, oligonucleotide probe kits of the present invention may be employed to examine the presence/absence (or relative amounts in case of mixtures) of polynucleotides in different samples or products containing different materials rapidly and in a cost-effective manner. Examples of microbial species which may be examined using the present invention, include lactic acid bacteria, such as *Lactobacillus rhamnosus*, and other microbial species.

Another aspect of the present invention involves collections of a plurality of polynucleotides of the present invention. A collection of a plurality of the polynucleotides of the present invention, particularly the polynucleotides identified as SEQ ID NOS: 1–62, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–62. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–62, including variants of those polynucleotides.

Another aspect of the present invention involves a combination of polynucleotides, the combination containing at least 5, preferably at least 10, more preferably at least 20, and most preferably at least 50 different polynucleotides of the present invention, including polynucleotides selected from SEQ ID NOS: 1–62, and variants of these polynucleotides.

In another aspect, the present invention provides genetic constructs comprising, in the 5'-3' direction, a gene promoter sequence; and an open reading frame coding for at least a functional portion of a polypeptide encoded by a polynucleotide of the present invention. In certain embodiments, the genetic constructs of the present invention also comprise a gene termination sequence. The open reading frame may be oriented in either a sense or antisense direction. Genetic constructs comprising a non-coding region of a gene coding for a polypeptide encoded by the above polynucleotides or a nucleotide sequence complementary to a non-coding region, together with a gene promoter sequence, are also provided. A terminator sequence may form part of this construct. Preferably, the gene promoter and termination sequences are functional in a host organism. More preferably, the gene promoter and termination sequences are common to those of the polynucleotide being introduced. The genetic construct may further include a marker for the identification of transformed cells.

Techniques for operatively linking the components of the genetic constructs are well known in the art and include the use of synthetic linkers containing one or more restriction endonuclease sites as described, for example, by Sambrook et al., in *Molecular cloning: a laboratory manual*, Cold Spring Harbor Laboratories Press: Cold Spring Harbor, N.Y., 1989. The genetic constructs of the present invention may be linked to a vector having at least one replication system, for example, *E. coli*, whereby after each manipulation, the resulting construct can be cloned and sequenced and the correctness of the manipulation determined.

Transgenic microbial cells comprising the genetic constructs of the present invention are also provided by the present invention, together with microbes comprising such transgenic cells, products and progeny of such microbes, and materials including such microbes. Techniques for stably incorporating genetic constructs into the genome of target microbes, such as *Lactobacillus* species, *Lactococcus lactis* or *E. coli*, are well known in the art of bacterial transformation and are exemplified by the transformation of *E. coli* for sequencing in Example 1.

Transgenic, non-microbial, cells comprising the genetic constructs of the present invention are also provided, together with organisms comprising such transgenic cells, and products and progeny of such organisms. Genetic constructs of the present invention may be stably incorporated into the genomes of non-microbial target organisms, such as fungi, using techniques well known in the art.

In preferred embodiments, the genetic constructs of the present invention are employed to transform microbes used in the production of food products, ingredients, processing aids, additives or supplements and for the production of microbial products for pharmaceutical uses, particularly for modulating immune system function and immunological effects; and in the production of chemoprotectants providing beneficial effects, probiotics and health supplements. The inventive genetic constructs may also be employed to transform bacteria that are used to produce enzymes or substances such as polysaccharides, flavor compounds, and bioactive substances, and to enhance resistance to industrial processes such as drying and to adverse stimuli in the human digestive system. The genes involved in antibiotic production, and phage uptake and resistance in *Lactobacillus rhamnosus* are considered to be especially useful. The target microbe to be used for transformation with one or more polynucleotides or genetic constructs of the present invention is preferably selected from the group consisting of bacterial genera *Lactococcus, Lactobacillus, Streptococcus, Oenococcus, Lactosphaera, Trichococcus, Pediococcus* and others potentially useful in various fermentation industries selected, most preferably, from the group consisting of *Lactobacillus* species in the following list: *Lactobacillus acetotolerans, Lactobacillus acidophilus, Lactobacillus agilis, Lactobacillus alimentarius, Lactobacillus amylolyticus, Lactobacillus amylophilus, Lactobacillus amylovorus, Lactobacillus animalis, Lactobacillus*

*arizonae, Lactobacillus aviarius, Lactobacillus bavaricus, Lactobacillus bifermentans, Lactobacillus brevis, Lactobacillus buchneri, Lactobacillus bulgaricus, Lactobacillus casei, Lactobacillus collinoides, Lactobacillus coryniformis, Lactobacillus crispatus, Lactobacillus curvatus, Lactobacillus delbrueckii, Lactobacillus delbrueckii* subsp. *bulgaricus, Lactobacillus delbrueckii* subsp. *lactis, Lactobacillus farciminis, Lactobacillus fermentum, Lactobacillus fructivorans, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus hetero, Lactobacillus hilgardii, Lactobacillus homohiochii, Lactobacillus japonicus, Lactobacillus johnsonii, Lactobacillus kefiri, Lactobacillus lactis, Lactobacillus leichmannii, Lactobacillus lindneri, Lactobacillus mali, Lactobacillus maltaromicus, Lactobacillus manihotivorans, Lactobacillus mucosae, Lactobacillus murinus, Lactobacillus oris, Lactobacillus panis, Lactobacillus paracasei, Lactobacillus paracasei* subsp. *pseucloplantarum, Lactobacillus paraplantarum, Lactobacillus pentosus, Lactobacillus plantarum, Lactobacillus pontis, Lactobacillus reuteri, Lactobacillus rhamnosus, Lactobacillus ruminis, Lactobacillus sake, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus thermophilus, Lactobacillus vaginalis, Lactobacillus vermiforme, Lactobacillus zeae.*

In yet a further aspect, the present invention provides methods for modifying the concentration, composition and/or activity of a polypeptide in a host organism, such as a microbe, comprising stably incorporating a genetic construct of the present invention into the genome of the host organism by transforming the host organism with such a genetic construct. The genetic constructs of the present invention may be used to transform a variety of organisms. Organisms which may be transformed with the inventive constructs include plants, such as monocotyledonous angiosperms (e.g., grasses, corn, grains, oat, wheat and barley); dicotyledonous angiosperms (e.g., *Arabidopsis,* tobacco, legumes, alfalfa, oaks, eucalyptus, maple); gymnosperms, (e.g., Scots pine (Aronen, *Finnish Forest Res. Papers,* Vol. 595, 1996); white spruce (Ellis et al., *Biotechnology* 11:84–89, 1993); and larch (Huang, et al., *In Vitro Cell* 27:201–207, 1991); and any kind of plant amenable to genetic engineering.

Thus, in yet another aspect, transgenic plant cells comprising the genetic constructs of the present invention are provided, together with plants comprising such transgenic cells, and fruits, seeds, products and progeny of such plants. Techniques for stably incorporating genetic constructs into the genome of target organisms, such as plants, are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acids Res.* 12:8711–8721, 1984. Targets for the introduction of the genetic constructs include tissues, such as leaf tissue, disseminated cells, protoplasts, seeds, embryos, meristematic regions; cotyledons, hypocotyls, and the like.

Once the cells are transformed, cells having the genetic construct incorporated in their genome are selected. Transgenic cells may then be cultured in an appropriate medium, using techniques well known in the art. In the case of protoplasts, the cell wall is allowed to reform under appropriate osmotic conditions. In the case of seeds or embryos, an appropriate germination or callus initiation medium is employed.

The polynucleotides of the present invention may be further employed as non-disruptive tags for marking organisms, particularly microbes. Other organisms may, however, be tagged with the polynucleotides of the present invention, including commercially valuable plants, animals, fish, fungi and yeasts. Genetic constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material. Detection of the tag(s) may be accomplished using a variety of conventional techniques, and will generally involve the use of nucleic acid probes. Sensitivity in assaying the presence of probe can be usefully increased by using branched oligonucleotides, as described by Horn el al., *Nucleic Acids Res.* 25(23):4842–4849, 1997, enabling detection of as few as 50 DNA molecules in the sample.

Polynucleotides of the present invention may also be used to specifically suppress gene expression by methods that operate post-transcriptionally to block the synthesis of products of targeted genes, such as RNA interference (RNAi), and quelling. For a review of techniques of gene suppression see *Science,* 288:1370–1372, 2000. Exemplary gene silencing methods are also provided in WO 99/49029 and WO 99/53050. Posttranscriptional gene silencing is brought about by a sequence-specific RNA degradation process which results in the rapid degradation of transcripts of sequence-related genes. Studies have provided evidence that double-stranded RNA may act as a mediator of sequence-specific gene silencing (see, e.g., review by Montgomery and Fire, *Trends in Genetics,* 14: 255–258, 1998). Gene constructs that produce transcripts with self-complementary regions are particularly efficient at gene silencing. A unique feature of this posttranscriptional gene silencing pathway is that silencing is not limited to the cells where it is initiated. The gene-silencing effects may be disseminated to other parts of an organism and even transmitted through the germ line to several generations.

The polynucleotides of the present invention may be employed to generate gene silencing constructs and or gene-specific self-complementary RNA sequences that can be delivered by conventional art-known methods to cells and tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. Gene silencing RNA sequences comprising the polynucleotides of the present invention are useful for creating genetically modified organisms with desired phenotypes as well as for characterizing genes (e.g., in high-throughput screening of sequences), and studying their functions in intact organisms.

In another aspect, the present invention provides methods for using one or more of the inventive polypeptides or polynucleotides to treat disorders in a mammal, such as a human.

In this aspect, the polypeptide or polynucleotide is generally present within a composition, such as a pharmaceutical or immunogenic composition. Pharmaceutical compositions may comprise one or more polypeptides, each of which may contain one or more of the above sequences (or variants thereof), and a physiologically acceptable carrier. Immunogenic compositions may comprise one or more of the above polypeptides and an immunostimulant, such as an adjuvant or a liposome, into which the polypeptide is incorporated.

Alternatively, a composition of the present invention may contain DNA encoding one or more polypeptides described herein, such that the polypeptide is generated in situ. In such compositions, the DNA may be present within any of a variety of delivery systems known to those of ordinary skill in the art, including nucleic acid expression systems, and bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the immunogenic compositions of the present invention to non-specifically enhance an immune response. Most adjuvants contain a substance designed to protect the antigen from rapid catabolism, such as aluminum hydroxide or mineral oil, and a non-specific stimulator of immune responses, such as lipid A, *Bordetella pertussis* or *M. tuberculosis*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

Routes and frequency of administration, as well as dosage, vary from individual to individual. In general, the inventive compositions may be administered by injection (e.g., intradermal, intramuscular, intravenous or subcutaneous), intranasally (e.g., by aspiration) or orally. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 µg per kg of host. Suitable dose sizes will vary with the size of the patient, but will typically range from about 0.1 ml to about 2 ml.

The following examples are offered by way of illustration and not by way of limitation.

EXAMPLE 1

Isolation and Characterization of DNA Sequences from *Lactobacillus rhamnosus* Strain HN001

*Lactobacillus rhamnosus* strain HN001 DNA libraries were constructed and screened as follows.

DNA was prepared in large scale by cultivating the bacteria in 2×100 ml cultures with 100 ml MRS broth (Difco Laboratories, Detroit Mich.) and 1 ml *Lactobacillus* glycerol stock as inoculum, placed into 500 ml culture flasks and incubated at 37° C. for approx. 16 hours with shaking (220 rpm).

The cultures were centrifuged at 6200 rpm for 10 min to pellet the cells. The supernatant was removed and the cell pellet resuspended in 40 ml fresh MRS broth and transferred to clean 500 ml culture flasks. Fresh MRS broth (60 ml) was added to bring the volume back to 100 ml and flasks were incubated for a further 2 hrs at 37° C. with shaking (220 rpm). The cells were pelleted by centrifugation (6200 rpm for 10 min) and supernatant removed. Cell pellets were washed twice in 20 ml buffer A (50 mM NaCl, 30 mM Tris pH 8.0, 0.5 mM EDTA).

Cells were resuspended in 2.5 ml buffer B (25% sucrose (w/v), 50 mM Tris pH 8.0, 1 mM EDTA, 20 mg/ml lysozyme, 20 µg/ml mutanolysin) and incubated at 37° C. for 45 min. Equal volumes of EDTA (0.25 M) was added to each tube and allowed to incubate at room temperature for 5 min. 20% SDS (1 ml) solution was added, mixed and incubated at 65° C. for 90 min. 50 µl Proteinase K (Gibco BRL, Gaithersburg, Md.) from a stock solution of 20 mg/ml was added and tubes incubated at 65° C. for 15 min.

DNA was extracted with equal volumes of phenol:chloroform:isoamylalcohol (25:24:1). Tubes were centrifuged at 6200 rpm for 40 min. The aqueous phase was removed to clean sterile Oak Ridge centrifuge tubes (30 ml). Crude DNA was precipitated with an equal volume of cold isopropanol and incubated at −20° C. overnight.

After resuspension in 500 µl TE buffer, DNase-free RNase was added to a final concentraion of 100 µg/ml and incubated at 37° C. for 30 min. The incubation was extended for a further 30 min after adding 100 µl Proteinase K from a stock solution of 20 mg/ml. DNA was precipitated with ethanol after a phenol:chloroform:isoamylalcohol (25:24:1) and a chloroform:isoamylalcohol (24:1) extraction and dissolved in 250 µl TE buffer.

DNA was digested with Sau3AI at a concentration of 0.004 U/μg in a total volume of 1480 μl, with 996 μl DNA, 138.75 μl 10× REACT 4 buffer and 252.75 μl H$_2$O. Following incubation for 1 hour at 37° C., DNA was divided into two tubes. 31 μl 0.5 M EDTA was added to stop the digestion and 17 μl samples were taken for agarose gel analysis. Samples were put into 15 ml Falcon tubes and diluted to 3 ml for loading onto sucrose gradient tubes.

Sucrose gradient size fractionation was conducted as follows. 100 ml of 50% sucrose (w/v) was made in TEN buffer (1M NaCl, 20 mM Tris pH 8.0, 5 mM EDTA) and sterile filtered. Dilutions of 5, 10, 15, 20, 25, 30, 62 and 40% sucrose were prepared and overlaid carefully in Beckman Polyallomer tubes, and kept overnight at 4° C. TEN buffer (4 ml) was loaded onto the gradient, with 3 ml of DNA solution on top. The gradients were centrifuged at 26K for 18 hours at 4° C. in a Centricon T-2060 centrifuge using a Kontron TST 28-38 rotor. After deceleration without braking (approx. 1 hour), the gradients were removed and fractions collected using an auto Densi-Flow (Haake-Buchler Instruments). Agarose gel was used to analyse the fractions. The best two pairs of fractions were pooled and diluted to contain less than 10% sucrose. TEN buffer (4 ml) was added and DNA precipitated with 2 volumes of 100% ice cold ethanol and an overnight incubation at −20° C.

DNA pellets were resuspended in 300 μl TE buffer and re-precipitated for approx. 6 hours at −20° C. after adding 1/10 volume 3 M NaOAC pH 5.2 and 2 volumes of ethanol. DNA was pelleted at top speed in a microcentrifuge for 15 min, washed with 70% ethanol and pelleted again, dried and resuspended in 10 μl TE buffer.

DNA was ligated into dephosphorylated BamHI-digested pBluescript SK II$^+$ and dephosphorylated BamHI-digested lambda ZAP Express using standard protocols. Packaging of the DNA was done using Gigapack III Gold packaging extract (Stratagene, La Jolla, Calif.) following the manufacturer's protocols. Packaged libraries were stored at 4° C.

Mass excision from the primary packaged phage library was done using XL1-Blue MRF' cells and ExAssist Helper Phage (Stratagene). The excised phagemids were diluted with NZY broth (Gibco BRL, Gaithersburg, Md.) and plated out onto LB-kanamycin agar plates containing 5-bromo-4-chloro-3-indolyl-β-D-galactoside (X-gal) and isopropylthio-beta-galactoside (IPTG). After incubation, single colonies were picked for PCR size determination before the most suitable libraries were selected for sequencing.

Of the colonies picked for DNA minipreps and subsequent sequencing, the large majority contained an insert suitable for sequencing. Positive colonies were cultured in LB broth with kanamycin or ampicillin depending on the vector used, and DNA was purified by means of rapid alkaline lysis minipreps (solutions: Qiagen, Venlo, The Netherlands; clearing plates, Millipore, Bedford, Mass.). Agarose gels at 1% were used to screen sequencing templates for chromosomal contamination and concentration. Dye terminator sequencing reactions were prepared using a Biomek 2000 robot (Beckman Coulter, Inc., Fullerton, Calif.) and Hydra 96 (Robbins Scientific, Sunnyvale, Calif.) for liquid handling. DNA amplification was done in a 9700 PCR machine (Perkin Elmer/Applied Biosystems, Foster City, Calif.) according to the manufacturer's protocol.

The sequence of the genomic DNA fragments were determined using a Perkin Elmer/Applied Biosystems Division Prism 377 sequencer.

To extend the sequences of the inserts from these clones, primers were designed from the determined nucleotide sequences so that the primer sequences are located approximately 100 bp downstream of the 5' end and 100 bp upstream of the 3' end of the determined nucleotide sequence. Selection of primers were done with the Gap4 Genome Assembly Program (Bonfield et al., *Nucleic Acids Res.* 24:4992–4999, 1995 using the following parameters: No. of bases ahead: 40; No. of bases back: 40; Minimum melting temperature: 55° C.; maximum melting temperature: 60° C.; minimum length: 17 bp; maximum length: 20 bp; minimum GC-content: 40%; maximum GC-content: 60%. Sequencing of clones was done as described above. The determined nucleotide sequences are identified as SEQ ID NOS: 1–62 disclosed herein.

This example not only shows how the sequences were obtained, but also that a bacterium (*E. coli*) can be stably transformed with any desired DNA fragment of the present invention for permanent marking for stable inheritance.

The determined DNA sequences were compared to and aligned with known sequences in the public databases. Specifically, the polynucleotides identified in SEQ ID NO: 1–62 were compared to polynucleotides in the EMBL database as of the end of July 2000, using BLASTN algorithm Version 2.0.11 [Jan. 20, 2000], set to the following running parameters: Unix running command: blastall -p blastn -d embldb -e 10 -G 0 -E 0 -r 1 -v 30 -b 30 -i querseuq -o results. Multiple alignments of redundant sequences were used to build up reliable consensus sequences. Based on similarity to known sequences, the isolated polynucleotides of the present invention identified as SEQ ID NOS: 1–62 were putatively identified as encoding polypeptides having similarity to the polypeptides shown above in Table 1. The amino acid sequences encoded by the DNA sequences of SEQ ID NO: 1–62 are provided in SEQ ID NO: 63–124, respectively.

Several of the sequences provided in SEQ ID NO: 1–62 were found to be full-length and to contain open reading frames (ORFs). Specifically, SEQ ID NOS: 1, 2, 4–12, 14, 20, 21, 24, 26, 34, 36, 42, 44, 45, 54, 55, 59 and 61 were found to be full-length. The location of ORFs (by nucleotide position) contained within SEQ ID NOS: 1–62, and the corresponding amino acid sequences are provided in Table 2 below.

TABLE 2

| Polynucleotide SEQ ID NO: | Open reading frame | Polypeptide SEQ ID NO: |
|---|---|---|
| 1 | 1-672 | 63 |
| 2 | 1-1,419 | 64 |
| 3 | 1-1,104 | 65 |
| 4 | 1-1,107 | 66 |
| 5 | 1-1,170 | 67 |
| 6 | 1-891 | 68 |
| 7 | 1-1,170 | 69 |
| 8 | 1-1,158 | 70 |
| 9 | 1-786 | 71 |
| 10 | 1-927 | 72 |
| 11 | 1-810 | 73 |
| 12 | 1-1,422 | 74 |
| 13 | 1-768 | 75 |
| 14 | 1-1,923 | 76 |
| 15 | 1-1,443 | 77 |
| 16 | 1-993 | 78 |
| 17 | 1-1,032 | 79 |
| 18 | 1-1,674 | 80 |
| 19 | 1-876 | 81 |
| 20 | 1-732 | 82 |
| 21 | 1-1,299 | 83 |
| 22 | 1-1,344 | 84 |
| 23 | 1-474 | 85 |
| 24 | 1-1,002 | 86 |

TABLE 2-continued

| Polynucleotide SEQ ID NO: | Open reading frame | Polypeptide SEQ ID NO: |
|---|---|---|
| 25 | 1-1,239 | 87 |
| 26 | 1-1,881 | 88 |
| 27 | 1-606 | 89 |
| 28 | 1-1,023 | 90 |
| 29 | 1-1,227 | 91 |
| 30 | 1-1,158 | 92 |
| 31 | 1-1,071 | 93 |
| 32 | 1-1,308 | 94 |
| 33 | 1-645 | 95 |
| 34 | 1-1,920 | 96 |
| 35 | 1-762 | 97 |
| 36 | 1-936 | 98 |
| 37 | 1-840 | 99 |
| 38 | 1-1,341 | 100 |
| 39 | 1-726 | 101 |
| 40 | 1-972 | 102 |
| 41 | 1-888 | 103 |
| 42 | 1-1,422 | 104 |
| 43 | 1-774 | 105 |
| 44 | 1-1,254 | 106 |
| 45 | 1-489 | 107 |
| 46 | 1-285 | 108 |
| 47 | 1-969 | 109 |
| 48 | 417-1,336 | 110 |
| 49 | 1-760 | 111 |
| 50 | 193-846 | 112 |
| 51 | 463-1,310 | 113 |
| 52 | 628-1,662 | 114 |
| 53 | 1-887 | 115 |

TABLE 2-continued

| Polynucleotide SEQ ID NO: | Open reading frame | Polypeptide SEQ ID NO: |
|---|---|---|
| 54 | 251-946 | 116 |
| 55 | 66-743 | 117 |
| 56 | 1-780 | 118 |
| 57 | 256-1,569 | 119 |
| 58 | 274-1,112 | 120 |
| 59 | 8-954 | 121 |
| 60 | 17-948 | 122 |
| 61 | 206-1,006 | 123 |
| 62 | 1-1,563 | 124 |

SEQ ID NOS: 1–124 are set out in the attached Sequence Listing. The codes for nucleotide sequences used in the attached Sequence Listing, including the symbol "n," conform to WIPO Standard ST.25 (1998), Appendix 2, Table 1.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:
1. An isolated polypeptide encoded by SEQ ID NO: 20.
2. An isolated polypeptide comprising SEQ ID NO: 82.
3. An isolated polypeptide comprising an amino acid sequence having at least 95% identity to SEQ ID NO: 82, wherein the polypeptide possesses carboxylesterase activity.

4. A composition comprising a polypeptide according any one of claims 2 and 3 and at least one component selected from the group consisting of; physiologically acceptable carriers and immunostimulants.

* * * * *

SEQUENCE LISTING

```
<160> NUMBER OF SEQ ID NOS: 124

<210> SEQ ID NO 1
<211> LENGTH: 711
<212> TYPE: DNA
<213> ORGANISM: Lactobacillus rhamnosus

<400> SEQUENCE: 1
atgtggaaag ttattaccga tgcagttccg caaatgatag cagccggcat taaatacacc      60
attccaattg cactcgtgtc atttgcgatc ggcctgatca tcgcacttgt aaccgcattg     120
acgcgcatat cggttcgtaa aggtattttg atccgaatcg caaaaggaat cgccgttttt     180
tacgtttggc tctttcgctc aacgcctttg ctggtgcagt tattcatcgt tttcttcggc     240
ttacccagcc tcatcatccc gggtattttc ccgcatggca tcaagttaga tcccgcggcc     300
gcgggaatta taacattctc acttaacacg ggggcgtatt gtgccgaaac gacccgcgcc     360
tcgctgttgt cgattgattc cgggcaatgg gaagcggctt atgcaattgg attgccgcgg     420
cgactggtgc tgcgcgaaat cattattcct caagcactac gaacggccat cccgccactg     480
tcaaatagtt tcatcagcct gatcaaagac acatcccttg ctgcctcgat caccattgtc     540
gaaatgtttc aagtcagcca acaaatcgcg gcggaaaatt accaaccatt actgatgtac     600
tcaatcgttg cgcttctgta tgccattgtc tgcactttct tagcttgggg tcagcggtat     660
ctcgaaaaat tcacatcacg ctacaatgcc aatgcacaaa ccacgcaatt a              711

<210> SEQ ID NO 2
<211> LENGTH: 1425
<212> TYPE: DNA
<213> ORGANISM: Lactobacillus rhamnosus
```

-continued

<400> SEQUENCE: 2

```
ctgatttgca aaggtcgaag cttgaagcca ttcggacatt ttattgatgc catcacggta      60
aatcgagaac acgtcttgac aaccgctgcc gaggccttga ttgcaagtgc gggcgatgcc     120
ttaaatgcca gtcacgcgac cttcaatgta ttaaacaact ctgatctgca attcgggttt     180
gttgaaaatg aagatggcga aaccgtccag cttagtaacg gtttgtacgg tcagttgatt     240
cgctcgacta accgtaaatt acgcaaggag gctttcgagg cccttctgcg tgcttacgaa     300
agtttaaaaa atacgttttgc gcaaacgtta agtggtcaag tgaaagccca taatttcaac     360
gcgacagcgc atcattacaa aaatgcgcgt gctgccgcta tggcaagtaa tcacattccg     420
gaaagtgtgt acacgacgct tatcgaccag gttaacaccc acctgccgct tttacatcgt     480
tatgtcgcct tgcgtaaaaa ggtgttggca gtcgatcagt tacacatgta tgacatttac     540
acaccactga ctggccagcc gccgttgact tatacgcttg aacaagccaa agcagaggcc     600
ttaaaagctt tagccccact aggcgatgat tatcttgagc atgttcgcga aatttttgac     660
aatcgctata ttgatgttgt cgaaaataaa ggcaaacgtt caggtgccta ttccggtggt     720
gcttatgata ccaatccgtt catcttattg aactggcacg atgccgttga tgaactctat     780
acgttggttc acgaaaccgg ccacagcgtc cacagttggt acacgcgtca caatcagccg     840
tatgtctatg gtgattatcc gatctttgtt gccgaaattg cttcaacaac caacgaaaac     900
ctgttaactg attatttcct gacacattcg gatgatccca aagtacgagc ctacattttg     960
aattactatc tcgatggttt taaaggaact gtttttccgtc agacacaatt tgccgagttc    1020
gagcactgga ttcaccaaca ggatcagcaa ggcgaaccgt tgacggccac cagcatgtca    1080
caatattacg ccgatctcaa cgcccggtat tatggaccgg aagttgcacg cgatccggaa    1140
attgcctttg aatgggcccg cattccgcac ttctattaca attactatgt ttaccagtat    1200
gcaaccggct ttgctgctgc ctcaaccctta gcagcgggca tcagtagcgg tgaacctgac    1260
gcggctgccc attacttaga ctatttgaag tcagggagtt ctaagtatgc cattgacacc    1320
atgaaaacag ctggcgttga tatgaccaaa cccgattatc ttgaagccgc cttttcagta    1380
tttgaacagc gcttgacgga attggaaaaa atcttgcaga aagga                    1425
```

<210> SEQ ID NO 3
<211> LENGTH: 1104
<212> TYPE: DNA
<213> ORGANISM: Lactobacillus rhamnosus

<400> SEQUENCE: 3

```
atgtttaaac ccaccattca tcaacttcat ccctatacgc cagaaaagcc tcttgccgta      60
ttaaaagaag aacttggctt gccacagctg gtgcggatgt cagcaaacga aaacccattc     120
ggtaccagcg tcaaagttca gcaggccgtg accaactgga atttttacgca aagtcgtgat     180
taccccgatg gctatgccag tcaactacgc accgcggtgg caaaacattt agacgttgcc     240
gcagagcagt tggtttttgg caatggtctg atgaagtca ttgccttaat tgcccgcact     300
ttttttgagcc cggggggatga agtcattgaa ccatggccaa catttttccga gtaccgcttg     360
catgcccaaa ttgaagggggc caccgtgatt gatgtgcccg tcactgaaac tggcaatttt     420
gatttatctg caatggcgca ggcgctaacc gcgaaaacga aactgatttg ggtgtgcaac     480
ccaaataacc ccacgggcac gctgctgtca attgcgacac tgaccgaatg gctgcgacag     540
ataccaaaag acgtgctggt tttaatggat gaggcttata ttgagttcac tgatgactat     600
```

```
ccagccacga gcgctatcag cttattatca aagtttccaa acctcgtcgt gctgcgaaca    660
ttttcaaaaa tctatggact ggcgaatttc cgggtcggct tcggtgtttt tcctaaacaa    720
cttgttaact acttgcaaac cgttcggctg ccttacaatt taagcagcat tgcccaagtt    780
agcgcacagg cggccttggc tgatcaagat tttgtcgcga tgacacgcaa gcgagtgcag    840
caagcgcgcg atagttggga acgcttttta acccaaactg gactgccaca cacccggagc    900
caaaccaact ttcaattctt tcaggcccca aaaatgcagg catcggcttt aaaaaagcgc    960
ctgctacaac aaggtttttct tgtccgtgat ggcttaaaac ccggctggct gcgcgtcacg   1020
tttggcactg aggtacaaaa cacggcggta cagcgcatca ttgaaacttt tcaggcagaa   1080
ctcactgggc caaatgcgct gaag                                          1104

<210> SEQ ID NO 4
<211> LENGTH: 1107
<212> TYPE: DNA
<213> ORGANISM: Lactobacillus rhamnosus

<400> SEQUENCE: 4
gtgcatttag caaaagaat cctcaacgtc gcaccgtcag cgacattggc cttaagtaat      60
cagacgaaag acttaaaggc aaaaggtgcc gacgtcattg atttgtctat ggccaaccca    120 gattttcaa ccctaaggc gattgatgac gcagctattg cggcgattca ggctggtaat     180
gccagtttct atacggcagc aaccggtatt ccggaattaa agcaggcgat tagtgaccgg    240
atatttgccc aagacggtat tcgttatgat catcgtcaaa tcgttgcaac caccggcgct    300
aagtttgctt tgtatgcctt atttcaggtt ttcttaaacc caggcgatga ggtgctgatt    360
cctgttccat actgggtttc ctacgaggaa cagattaaat tggcgagcgg cgtgccacat    420
ctggtcatgc cggcagtcgg acataaagtc agtgtcgatg atcttgaggc ggctcggacc    480
gataaaaccc gggcattgat tatcaattcg ccacaaaacc caagtggcgt tgtctatgat    540
cgcacggaac tgaccttaat tggcaattgg gcgctgaagc atcatatttt ggtagtgact    600
gacgatattt accgagatct gatttataac ggtacgactt acacctcaat gattagtatc    660
gatcccgata tcgcagcgaa tactgtttta atttccggcg tctccaagtc atatgcgatg    720
acgggttggc ggattggtta tgcggccggt ccggaaaagc tgattcaggc catggcgacc    780
tttattagcc acacgacctc taatccggca gcagtttccg aatacgccgc ggtggcagct    840
ttaactggcg atcagcaggt tgttgaaaag atgcgccgtg cttttgaaga acggctgaat    900
cttttctatg atcttctggc agatattccc ggtttcgata tgggagataa accgcaaggc    960
gccttctatc ttttcccgaa tattaagcgt gccgctcaat tgagtcatta tggtacggtt   1020
gatgatttta tcagtgcact gttgaccgaa accggggttg ccattgttcc tggacgggcg   1080
tttgggcatg ccggatcatg cgcggat                                       1107

<210> SEQ ID NO 5
<211> LENGTH: 1170
<212> TYPE: DNA
<213> ORGANISM: Lactobacillus rhamnosus

<400> SEQUENCE: 5
atgacattgc aacctttaaa cgaacaacta cctgccatcg aggttagtga gattcgacaa     60
tttgacgaaa gtgtcagtga tattcccggt attttgaaac tgacgctagg cgaacctgat    120
ttcaacaccc cggaacatgt taagcaagcc gggatcaaag ccattcagga aaattactcg    180
cattataccg ggatggttgg tgatccggag ttacgcgaag ccgcacaaca ttttttttaaa   240
```

```
acgaaatatg ccactgacta tcgggctaca gatgaaattc tggtgacagt cggggccact      300
gaagcactgg caaccgccat tacgacgatc agtgatccgg gtgatgccat gctggttccg      360
tcaccaattt atccgggcta cattccgctt ctgacgctga atcacgttac gccgctttat      420
atggatacga gtaaaaccga cttttgtcttg accccccgaac tcattgaggc caccatcact    480
gcaaatcctg acgctaaaat caaaggcatt atccttaact atccaagtaa tcccaccggt      540
gtcacgtatc gggcggcaga agttaaagcc attgcggaca tcgccgctaa acataacctc     600
tacattatct gtgacgaaat ttattctgaa ctgacttatg gtgagccgca tgtttccatg      660
ggacaatttg cctacgatcg tacatttatt gtcaacggtc tgtctaaatc acatgcaatg      720
accggctggc gaatcggctt tttgatgggt ccccagcagt taatcgcgca agccaaaaag     780
gtgcaccaat atcttgtgac tgccgcaacg accattgccc agcgcgctgg tattgaagct     840
ctgacgaacg gtgcagacga tgctcaggtg atgaaagcag cttacgttaa cgccgtgat      900 tttgtttatg ccgccctcat cgacatgggc tttagcgtgg ctcgtcctga tggtgccttt     960 tatcttttg caaaaattcc gacccaactg catctaagct cacgcgaatt tacgcacgcc     1020
ttggcacatg aacagaagtt agctctgatt tcaggtaccg cttttggccc cggcggcgaa    1080
ggttatatcc gaatcagtta cgcggcatca atgaccgatc ttcaagaagc cgttaagcga    1140
ttgcgcgcgt tcatggccag ccacatcggc                                      1170

<210> SEQ ID NO 6
<211> LENGTH: 891
<212> TYPE: DNA
<213> ORGANISM: Lactobacillus rhamnosus

<400> SEQUENCE: 6
gtggcgcgcc tcatgcttga tcccggcgat ggcctagttg ttgaagcgcc aacgtatctc       60
ggtgccttag ccgcctttaa tgcttatcag ccaacttatt atgaaatccc gatgcaagac      120
gatgggatgg acattaatgc cttacagcgc gttttaatga gtcacaaagt caagttcatc     180
tatacggtac ctgattttca aaatccaacc ggcgtcgtaa tgtctgtggc taagcgtcag     240
gcgctgattc gactcgccaa ccaatatgac gttatgatcc tcgaagacaa cccctaccgc    300
gatcttcgct atgatggtaa accgctgcca accattaagt catttgacac gcaaggccgc    360
gtcgtttatc tcggcagctt cagcaagatc ctctcaccaa gtctacggat gggctggctc     420
gttgctgcac cggacctttt gcaggaatta ctagcgttaa aaggcggaag cgacttggaa    480
tccagcaacc tgaccatgca cggcattgat gcctacatgg cggaaaatga cttagacgcc    540
cacatcaccg aaatccagaa ttgttgccgc gaaaagaaga atgccatggt cgcagcgatg    600
aatcgttacc ttcctgatga agcgcacttc accaaccctg atggcggctt cttcctgtgg    660
ctcaccatgc cagccggctt cgacatgggt gccttcatga gcaacatct gttaccggaa     720 agcaacattt cctatgtgcc ttccgccaac ctatatgcaa cttcggctca ggtcaacggc    780
gcacggctaa acttcaccgg tccgacactt gaacagatcg acactggtat caaagcatta    840
ggcgatgcgc tcaaaaccgc gctgcagcat cacctagtag ccgaacaagc t              891

<210> SEQ ID NO 7
<211> LENGTH: 1170
<212> TYPE: DNA
<213> ORGANISM: Lactobacillus rhamnosus

<400> SEQUENCE: 7
```

-continued

```
atgaaattga caatttatga ctttgatcat gttatcgatc gccggggtac gtttagcact      60
caatgggatt atattgctga taggtttggc cgtaacgata tcctgccctt ttcgatctcc     120
gatacagatt ttccagtacc agttgaagtg caagatgcgc taaaagaacg gttaacacat     180
ccaatttatg gctatacacg atggaatcat gctacttaca aagacagtat tgttcactgg     240
ttcgagcgtg atggtcatac aaagataaac ccggattgga ttgttttatag ccctagcgtt     300 gtttttacga ttgctacact cattcgaatg aagagcgatc ccggggacgg agtggctgtg     360
tttacgccta tgtatgatgc cttctatggt acgattaaac agaacgatcg agtgttgatc     420
ccgattcgat tagcagctgc agatgaaggc tatgtgattg attgggatag tttggcaacg     480
gtacttgctg aaaagcagac aaaaatattc ttactaacaa atccgcataa cccgacagga     540
catgttttta caaaatcgga attagcacgc ctttatgact tgtgtcaggc agcccatgtt     600
ttcttgatct ctgatgatat tcaccgcgat attgtttatc cgggtcattc gtacgaacca     660
atgacaaatg tcggcacaag tgatgttgca ctctgctgct cagggtcaaa gacatttaac     720
acaccaggcc tgattggctc atatgccttc ttaccagatc atgatgtaag ggcacaattt     780
ttgacggaat taaagcagaa aaatgctctg tcttctgtaa gcatctttgg catgctggcg     840
caaattgcgg cttataacgg ttcagaggat tacgtggaac aactgactgc ctatacaaaa     900
aataatatgg agttggttgc tagttatttta gaggaaaatt tgccggaatt gcagttttcg     960
ttaccggatg ccacgtactt agcctggata aatgtgtcta aactgagatt aacgtcagag    1020
gaacttcaac atcggttagt aaacggcggc catgttggca ttatggcggg caaaacttat    1080
ggtgatacca gatatctaag gatgaatatt gcctgtccaa agaagaagtt agtgatgggg    1140
ctagaacgtt taaagaaggg aattagggga                                      1170
```

<210> SEQ ID NO 8
<211> LENGTH: 1158
<212> TYPE: DNA
<213> ORGANISM: Lactobacillus rhamnosus
<220> FEATURE:
<221> NAME/KEY: misc_feature
<222> LOCATION: (1)...(1158)
<223> OTHER INFORMATION: n = A,T,C or G

<400> SEQUENCE: 8

```
atgatttatt ttgataatag tgcaacgacg aagatttcgc ctgatgcgtt ggcgacttat      60
aacaaggtca gcacggattt ttttgggaat cccagcagtt tgcatgctct aggaactaaa     120
gcaaatgagg ttttgcagag ttcgcgagcc cagattgcta aattaatcgg tgctaagccg     180
gacgagattt attttacgag cgggggaact gaaagggata actgggtgan nttaaagggc     240
actgcatggc ttaacgcgaa tttggcccgc attctgatta cgaccagtat cgagcctccg     300
gctgtgatca atacgatgaa acagctagag aaactgggat ttgaagtgac ttatttgccg     360
gttgatcggc gcggttttat tcatattgac gatttgaaag cggctattcg caaagatacg     420
attttggtgt cgattatggc ggttaataat gaaattggca gtatgcagcc gattgttcag     480
gccgcgcggg tgttggataa ttatccgaat attcattttc atgtcgatgc tgtacaagcc     540
gttggtaagg ggttggatgc agcgttgcag gatccgcgga ttgattttct cagttttttcc     600 ggccataagt ttcatgctcc ccgcggtacc ggctttatct atgccaaaga gggtcgcatg     660
cttgatccgt tgctaaccgg tggcggtcag gaacatgatt ggcgctcagg cacggaaaat     720
gttccggcga ttgcggcgat ggccaagtcg ctgcgcttac ttttggctaa tgaagatgct     780
aatgtggccc ggcagcaagc agttcgcaag cggattttt aacatgtcag ccaaaagccc     840
```

```
aaggtgacga tgtttagtca gttaacaccg gattttgccc cacatgtttt atgttttgcc      900
attgctggtg tccgcggcga acgattgtt catgcgtttg aggatcatca gatttacatt       960
tccacaacca gtgcctgctc gagtaagaaa ggcacgaaaa gcagtacctt ggccgccatg     1020
catacggacc cgaaaattgc tacttccgcg attcggtga gtttggatga agctaatact     1080
ttggatgaag cggatgcgtt taatgcagcg tttgatacga tttatgcaaa gtttgccaag     1140
cttgataaag cgaccgtc                                                   1158

<210> SEQ ID NO 9
<211> LENGTH: 786
<212> TYPE: DNA
<213> ORGANISM: Lactobacillus rhamnosus

<400> SEQUENCE: 9
atgccaacta aaataggcct tcactacaac aaaattggag ttgggaaaac catctacttt       60
ttacatggca tggggttaga cggacacagc atggcagctt tttatgagcc acgttttacc      120
agcgaagagc ggcattttgc ccgcctctat ccggatttac cgggaatggg aaattcaccg      180
gccacgtcag cattgcaatc tgctgatgat gtgttggcac aggttcatgc tttcattcag      240
gcgaccagcg aagggccatg ttatcttgtc ggccattctt acggtggcta tctagcatta      300
ggcctgcttg cacgatttcc tgacgagttt tccggtgctt ttttaaccgc tccggttgta      360
ctcgcggaga aaacagcacg tacggttgca cactaaagc atcttattag tgcgccagtg       420
accagtcagt caccggaatt taccgactat caacacatga atgttgttat caatccttca      480
acctggcgac aatatcagga acttatcctg ccagggctta aaacttttaa ccgcgatttc      540
tgggttgcca tgaagaaccg ccatgctat cgtctgtcga ttgaatcacg cttaaccagc       600
ctgattaagt caccagttac gcttgtgtta ggtgaaaatg acaatgaagt tggctatcag      660
gatcaagtgg tctttgccca taaaggcgca cacatgacca caaccgtaat cccaaacgcc      720
ggtcataatc tgatgatcga tgcgcctgag gctgtcatga ccgcgtttca tcagtttcta      780
cacaaa                                                                786

<210> SEQ ID NO 10
<211> LENGTH: 927
<212> TYPE: DNA
<213> ORGANISM: Lactobacillus rhamnosus

<400> SEQUENCE: 10
atggtaacag cagcagataa tattacaggt ttaattggca atacgccgct actcaagctc       60
aatcgcgttg tacctgaagg cgccgcggat gtttatgtca agctggaatt ctttaatccc      120
ggcggctcag tcaaggaccg gattgccttg gcgatgattg aagacgctga atataaaggg      180
gtcttgaagc aggcggcac cattgttgag ccaacgtccg gcaacaccgg cattggactg      240
gcactggttg cggcggcaaa aggttatcac ctcatcatca ccatgccgga aacgatgagt      300
gttgagcggc gtgctttgat gcgtggttac ggagccgaac tcattttgac gccgggtgcc      360
gatggaatgc cgggagcaat taaaaaagca gaagcattaa gcaaggaaaa tggctacttc      420
ttgccaatgc aattccagaa ccccgccaat ccagacgtcc acgagcgcac gaccggacaa      480
gaaatcatcc gttcatttga tggtggcacc ccagatgcct ttgtagccgg cgtcggcaca      540
ggcggaacac tcaccggggt tggtcgggct ctgcgtaaga tcaatccaga tgtacaaatc      600
tatgcgttgg aagcagcgga gtcgccaatg ctaaaagaag gccatggcgg caagcacaag      660
```

-continued

| attcaaggga tctcagccgg ttttattcca gacgtcttag atacgaacct ctatcaagac | 720 |
| atcattgaag tcaccagcga tcaagctatc gacatggctc gccacgtcag ccatgaagaa | 780 |
| ggcttcctac caggcatttc cgctggcgct aacattttg gcgcgattga atcgccaag | 840 |
| aaactcggca aggcaagag tgtcgccact gtagcaccgg ataatggtga acggtatttg | 900 |
| tcgacggatt tgtttaagtt tgatgat | 927 |

<210> SEQ ID NO 11
<211> LENGTH: 810
<212> TYPE: DNA
<213> ORGANISM: Lactobacillus rhamnosus

<400> SEQUENCE: 11

| atgttaaaga aaaagttgtg gttcctgttg ccgcttgtgg ccttggtaac cttcacgctc | 60 |
| accgcttgca ccagcgcatc atctgacacg tcaaaaaaca gcgacgtcac cgccgaactc | 120 |
| atcaacaaaa atgagcttac catcggcctt gaaggtactt atgcgccatt tccttatcgc | 180 |
| aaagatggca aacttgaagg cttcgaagtg aactgggga agccttagc caagaaaatc | 240 |
| ggggttaagg caaaattcgt gcccacccaa tgggattcgc tgattgcagg attaggcagc | 300 |
| cagaaatttg atctcgtact gaatgatatt agtgaaacgc ccgcacgcaa aaaggtctac | 360 |
| aacttcacca ctccgtacat gtactcgcgt tatgccttaa taccccgcag cgataacacc | 420 |
| accatcaaat cgcttgccga tattaaaggc aaaacatttg tcgaaggcac cggtacaccc | 480 |
| aatgccgctt tagccaaaaa atacggcgct aagatcaccc cgtctggcga ctttaccgta | 540 |
| tcgcttagcc ttgtgaaaga aaaacgcgca gacggaacca tcaacgcctc ggctgcatgg | 600 |
| tatgccttg ccaagaataa ctcaaccgcg ggcttaaaga gtcaaaccct caaagatagt | 660 |
| gtcgttaaac ccgatgaagt agctggcatg gtcagcaaaa aatcgcctaa actacaagcc | 720 |
| gcactttcaa agggcattca agaactacgc aaagacggca cgttgaaaaa actgtcgcaa | 780 |
| aaatattttg gcaccgattt aaccaccaag | 810 |

<210> SEQ ID NO 12
<211> LENGTH: 1425
<212> TYPE: DNA
<213> ORGANISM: Lactobacillus rhamnosus

<400> SEQUENCE: 12

| ctgatttgca aggtcgaag cttgaagcca ttcggacatt ttattgatgc catcacggta | 60 |
| aatcgagaac acgtcttgac aaccgctgcc gaggccttga ttgcaagtgc gggcgatgcc | 120 |
| ttaaatgcca gtcacgcgac cttcaatgta ttaaacaact ctgatctgca attcgggttt | 180 |
| gttgaaaatg aagatggcga aaccgtccag cttagtaacg gtttgtacgg tcagttgatt | 240 |
| cgctcgacta accgtaaatt acgcaaggag gctttcgagg cccttctgcg tgcttacgaa | 300 |
| agtttaaaaa atacgtttgc gcaaacgtta agtggtcaag tgaaagccca aatttcaac | 360 |
| gcgacagcgc atcattacaa aaatgcgcgt gctgccgcta tggcaagtaa tcacattccg | 420 |
| gaaagtgtgt acacgacgct tatcgaccag gttaacaccc acctgccgct tttacatcgt | 480 |
| tatgtcgcct tgcgtaaaaa ggtgttggca gtcgatcagt tacacatgta tgacatttac | 540 |
| acaccactga ctggccagcc gccgttgact tatacgcttg aacaagccaa agcagaggcc | 600 |
| ttaaaagctt tagccccact aggcgatgat tatcttgagc atgttcgcga aatttttgac | 660 |
| aatcgctata ttgatgttgt cgaaaataaa ggcaaacgtt caggtgccta ttccggtggt | 720 |
| gcttatgata ccaatccgtt catcttattg aactggcacg atgccgttga tgaactctat | 780 |

```
acgttggttc acgaaaccgg ccacagcgtc cacagttggt acacgcgtca caatcagccg      840
tatgtctatg gtgattatcc gatctttgtt gccgaaattg cttcaacaac caacgaaaac      900
ctgttaactg attatttcct gacacattcg gatgatccca agtacgagc ctacattttg       960 aattactatc tcgatggttt taaaggaact gttttccgtc agacacaatt tgccgagttc     1020
gagcactgga ttcaccaaca ggatcagcaa ggcgaaccgt tgacggccac cagcatgtca     1080
caatattacg ccgatctcaa cgcccggtat tatggaccgg aagttgcacg cgatccggaa     1140
attgcctttg aatgggcccg cattccgcac ttctattaca attactatgt ttaccagtat     1200
gcaaccggct tgctgctgc ctcaaccta gcagcgggca tcagtagcgg tgaacctgac      1260
gcggctgccc attacttaga ctatttgaag tcagggagtt ctaagtatgc cattgacacc     1320
atgaaaacag ctggcgttga tatgaccaaa cccgattatc ttgaagccgc cttttcagta     1380
tttgaacagc gcttgacgga attggaaaaa atcttgcaga aagga                     1425
```

<210> SEQ ID NO 13
<211> LENGTH: 768
<212> TYPE: DNA
<213> ORGANISM: Lactobacillus rhamnosus

<400> SEQUENCE: 13

```
agttatgcgc caaccatcac actagaacaa gccaaagaag atattaaaaa tgccaccgca       60
ctcatgggtc aagattacca ggcacagatg atgcaggcct tttcagagcg gtggatcgat      120
tttcctgcta atcaaggcaa ggattccgga gcttacactg ctggaccgta tggtgtgcac      180
ccttatgtcg aaatgacttg gagtaatacg ctgcctgctg tttacacctt gattcacgaa      240
ttaggccata ccgctcagat ggttcgttca caagaagccc acaatgtgtt ggatgcggac      300
tttaatgcct atttggtcga aagtccttcc accttcaacg aactgttgct gactcactat      360
ctcgaagaaa acgctaaaga tccgcgaatg aagcgctttg ccttgtcacg gttattaaat      420
gatacctatt tccacaactt tgtcacccat ctgctcgaag ctgcgtttca acgggaagtc      480
tataacttga tcgataacgg cgaaactttt gatgctgctc ggttgaacgc cattacgcgt      540
aaagtcctga ccgatttttg gggatcggca gtagaacttg agccaggtgc cgagctaact      600
tggatgcggc aaagccatta ctacatgggc ttatattcgt actcctattc ggccggcttg      660
acggttgcta cccaagcgtt tcaggccatc gaacaacaag gtcaaccagc cgttgatcgg      720
tggttgcgtt atctcagcct aggcgactca cttgatccag tcgaagca                   768
```

<210> SEQ ID NO 14
<211> LENGTH: 1923
<212> TYPE: DNA
<213> ORGANISM: Lactobacillus rhamnosus

<400> SEQUENCE: 14

```
ttgttaggtc agtttggtgt tgatctcact gaacaggcac gcaaaggtca aattgatcca       60
gtcatcggtc gtgataagga aatttcacgc gtgattgaaa ttctgaatcg ccggaccaag      120
aataatccag ttttaatcgg tgaagccggg gtcggcaaaa ccgcggttgt tgagggactg      180
gccttaaaga ttgctaatgg cgacgttcca gccaagttgc aggatcgcca tgtgattcgc      240
cttgatgtcg tttcactcgt tcaaggcaca ggcattcgcg tcaattcga gcagcgcatg      300 caacaattga ttgacgaact gaagcaaaat aagaatatta tcctatttat tgatgaaatc      360
cacgaaattg tgggtgccgg caatgctgaa ggcgggatgg acgccggcaa cgttttgaaa      420
```

-continued

| | |
|---|---|
| cccgcattgg ctcgtggcga attacaacta gtcggcgcaa cgaccagcaa cgaataccgt | 480 |
| cagattgaaa aggattctgc cctcgctcgg cgccttcagc cggtgatggt tgaagagcct | 540 |
| agcgttgatg aaaccattaa aattctgaaa ggtctgcaac cgcgctacca agacttccac | 600 |
| catgtgaaat acacggaagg cgcaattgaa gctgcggcaa ccctcagcaa tcgttacatt | 660 |
| caggatcgtt tcctccctga taaagccatt gacttgttag acgaagccgg ttcacgcaag | 720 |
| aacctaacga ttgccaccgt ggatcctgaa accattaaag ctaagattgc tgatgccgaa | 780 |
| aagcaaaagc aagccgcact caagcaggaa gactatgaaa agccgccctt ctatcgtgat | 840 |
| caggtcacca gttagaaga catggccaaa agcaatcca acctgccaga taatgaaatc | 900 |
| ccaacagtta ccgaaaaaga catggaaaaa attgttgaag aaagacaaa cattccagtc | 960 |
| ggtgaactca aagctcagga acaggcgcaa ctgaagaatc tcgccagtga ccttgagcaa | 1020 |
| cacgtcattg gtcaaaatga agcagttgat aaagttgctc gggcaattcg gcgcaatcgt | 1080 |
| atcggcttca ataaaccgg gcggccaatt ggctcattcc tctttgtcgg accaaccggt | 1140 |
| gtcggcaaaa cggaactggc aaaacagctc gctaaagaac tattcggttc tgaagatgcc | 1200 |
| atgattcggt ttgacatgtc ggaatacatg agaagttca gcgtctctaa gctcatcggg | 1260 |
| tcaccgccag gctatgtcgg ctatgaagaa gccggccagc taactgaaaa agttcggcgc | 1320 |
| aatccataca gtttgatttt gcttgatgaa attgaaaaag cccacccgga tgtcatgaac | 1380 |
| atgttcctgc agattctgga tgacggccgc ctaaccgatt cacaaggtcg aactgtttcc | 1440 |
| ttcaaagata ctatcatcat catgacttct aacgccggat caactgatgc ggaagctaac | 1500 |
| gtaggctttg gtgcaacgtt aagcggtaaa acccacagtg tgctggatca gctgggtaac | 1560 |
| tacttcaaac cagaattcct gaatcgcttt gatgacattg ttgaattcaa gccgctttct | 1620 |
| aaagacgacc ttttgaagat tgtgtcactg atgattaatg acactaacaa caatctcaag | 1680 |
| agtcagggat taacgattca cgtcaccgat cccgtcaaag aaaagcttgt cactctgggt | 1740 |
| tacaatccat ccatgggggc acggccattg cgtcgggtta tccaggaaca gattgaagac | 1800 |
| cgtgtggctg actttacct cgaccatcct aatgccaagg aacttgaagc aaggatcagc | 1860 |
| aacggagaaa tcacagttgg cgaaccagcc aaggcagaag cctcttcaaa aacagccaag | 1920 |
| aaa | 1923 |

<210> SEQ ID NO 15
<211> LENGTH: 1443
<212> TYPE: DNA
<213> ORGANISM: Lactobacillus rhamnosus

<400> SEQUENCE: 15

| | |
|---|---|
| accaagtcag ttgtcggtgt agcgccagaa tcacaattat tagcgatgaa ggtgtttacc | 60 |
| aattcagaca catcagcgac gactggttcg tcaacgcttg tttctgcgat tgaagattca | 120 |
| gccaaactgg gcgcggatgt tttgaatatg tcccttgggc tgtttccgg caatcaaaca | 180 |
| ctggaagatc ctgaaattgc agccgttcaa aacgccaatg aatccgggac cgcagcggtt | 240 |
| atttcagcag gaaattcggg tacatccggg tcaggtacag aagggggtcaa caagagattat | 300 |
| tatggcctgc aggataatga gacggttggc acaccgggga catcacgcgg ggcaacaact | 360 |
| gtcgcatcgg ccgagaatac agatgtcatc aaccaagctg ttacgattac tgacggcagt | 420 |
| gggttaaaac tcgggcctga aaccgtacag ctttcaagca atgactttgt tgacagtttt | 480 |
| gatcagaaga aattctacgt tgtcaaagac gcaagcggta agttaagtac aggtgatgct | 540 |
| ggcgactata cggcggatgc caaagggaaa attgcgattg tcaaacgtgg cagtctgact | 600 |

-continued

```
ttcactgaca agcagaaata tgccgaggcc gctggtgcag caggcttaat cattgttaat        660
aatgatggca catccacacc tttgacttcg atttctctaa cggctacttt tcctactttt        720
ggtctttcca atacgactgg ccaaaaactg gttgattggg taactgcgca tccaaatgac        780
agtctgggcg taaaaattgc cttggcattg ttgccaaatc aaaattataa agcagatcgg        840
atgtcaagtt tcacttcata tggccctgta tctgatcttt cctttaagcc tgatattaca        900
gcgccgggtg gtaatatttg gtcaacgcaa acaacaatg gttatacgaa tatgtcgggg         960
acctcaatgg catctccatt tatcgccggc tcccaggcac ttctaaaaca agcgctaaat       1020
aataaagaca atgagttcta tgccgattac aagcaactta aaggcacagc attaaccgat       1080
tttctcaaaa cagttgaaat gaatactgca agccgattac atgatattaa ctatgataat       1140
gtcatcgtct ctccacgccg acagggagca gggttggtgg atgtcaaagc cgcgattgat       1200
gctttggaga agaatccatc aacgttgtt tcggaaaacg gctatcctgc tgttgaattg        1260
aaagatttca caagcactac caaaacgttt aagttgacgt ttaccaaccg caccaaacat       1320
cagctgacgt atcaaatgac tagcaatgaa gataccaatg cggtttatac ttcggctacc       1380
gatctagaat cgtttataca aagcagtaaa atggctaaac taattcatga aaggggcgcg       1440
gca                                                                    1443
```

<210> SEQ ID NO 16
<211> LENGTH: 993
<212> TYPE: DNA
<213> ORGANISM: Lactobacillus rhamnosus

<400> SEQUENCE: 16

```
atgaccatta attggcagca agaagttgaa aaattggaac cccaacttct ctcagatcta         60
accacacttt tgaagatcaa ttcggaacgt gatactgatc atcaaaccga tgagtatcca        120
ctcggaccgg gaccggccaa agcgcttgaa gcattttttgg cgattgcaca gcgggacggt        180
ttcaaaacat taaatgtcga ccatgttgcc ggccgcatcg aattaggcga tggcgatgaa        240
atctttgggc ttttttggcca tgttgatgtc gtgcccgcgg gaccaggctg gcaaaaccgat       300
ccatttgacc ccgttattcg cgatggcaag atttatggcc gcggaacaag cgatgacaaa        360
ggcccaagta tcgctgctta ctatgcctta aagcttattc gcgatctcaa gttgccgatt        420
aataaaaaga ttcacttcat tcttggtacc gatgaagagt ctgactgggt cggtattcac        480
cgctatctcg aaactgaacc tgctcccgac ttcggatttt caccagacgc ggaatttcct        540
atcatcaatg gcgaaaaagg gattgctagt tttgaaatcg ttcaaaaacc aatcgccgct        600
gcaaccgctg atctaacgtt gaatcatttt tccgccggta ttcggccaaa catggtgcca        660
caagaagcaa aggctgtcct cagcgggcca ttaccggaag catttgtgac gcaagccgag        720
aaatgggcag cggagcaaga agtcaccctc actctgacac taggcaaccc gacaacgatt        780
gaattgattg gaaaggcgc ccatgcccaa gaaccaaaag atggcaaaaa cgccgcaacc         840
tatttagcaa cgcttttggc cgacttacca tttgatccag ccgggaaagc ctatctgacc        900
atgattgcca accaccttca tctggactca cgtggtcacc atttagggat taattatacc        960
gataaactaa tgggtgacct gaccgcaagt ccg                                    993
```

<210> SEQ ID NO 17
<211> LENGTH: 1032
<212> TYPE: DNA
<213> ORGANISM: Lactobacillus rhamnosus

```
<400> SEQUENCE: 17
ggcaaaatga gtctgtatgc tggcgggcct gacgagcggt tgacgccttt gattgatggt      60
cggcgtcatg tgacggactt tgcattgaca ccagatcatc gtggggtggt tttcactgag     120
agtacgatga ccattccgag tcggctggtt tattttgatt tggcatcgga agaagagcag     180
gttttgtatg acccgaatcg tcaggtaaca cgtcacttgg gcttagttac ccctcaaacg     240
tttaattttc aacgagacgg ttttgagatt gagggctggt attttccacc gcaacaggcg     300
tcatcatcgc atccggcaat tttgtatgtc catggcggcc cagcagtcgg atatggctat     360
acctttttcc atgaaatgca gtatctggca gcaaaaggct atggcgtgat tgtcgaaat      420 ccgcgtggag ggttaggtta ccgcgaggca tttacgggcg ctgtcattaa acattaaccg     480
gcaggcgatt atgaagattg cttggcttcg ggtgaagaag cgctaaagct cgatacaaca     540
attgatccgc aacgtctatt tgtcactggc ggttcttatg cgggtttat gactaactgg      600 attgtgaccc atacgcatcg ttttaaagca gcggtaaccc agcgttcgat ttccaattgg     660
ctgagtatgt atggtaccag tgacatcggt tattacttta caccgtggga actagaagga     720
aagtggactg gcgatttgtc agatgtgcaa gggctttggg atttttcacc attagctcac     780
attgatcatg ccagaacacc gacgcttgtg atgcacagtg aaaatgatga acgctgcccc     840
atcggcccaa gtagaaaagt tgatcatcgg tctcaaactg catggtgttg aaaccaagtt     900
catgcgtttc ccaaagtcaa atcatgattt gtccccgcag cggggttgcc gaatttgcga     960
gtggcacgat tgcaggcaat tgtggattgg tttgacgccc atcaagcaca accgcagatg    1020
gctaaaggag aa                                                         1032

<210> SEQ ID NO 18
<211> LENGTH: 1674
<212> TYPE: DNA
<213> ORGANISM: Lactobacillus rhamnosus

<400> SEQUENCE: 18
catttaatcg gtgcgacgac gctggacgaa tatcgcgaaa atattgaaaa agataaagca      60
ttagagcgcc gattccaacg ggtgctggta caagagccaa ctgtggaaga tacgatcagt     120
attttacgtg gcttgaagga acggtttgaa attttttcaca aagtgcgcat tcatgattcg     180
gcgttggtgg ctgccgcgac attatccaat cgctatatca cggatcggtt tttaccggat     240
aaggcgattg atttagtcga tgaagcctgt gccacgatta atgttgaaat gaactcgcgc     300
ccaactgaac tggacgtggc cgagcgtaag cagatgcagc ttgaaatcga gcagcaggcg     360
ttaaagaatg aaagtgatcc cgcaagtaag aaacgcctgg aaaatgcaaa cgccgaattg     420
gcaaatttaa agaaaaaac caataaactc aaagcacagt gggaagctga aaagaaggac     480
attcgccagc ttaacgagaa gaagtcagcg atcgacaaag ctaaacacga actggaagat     540
gcccagagcc gttacgattt ggaacggct gctcgtctgc aacacggaac gattccacaa      600
cttgaaaaag aattgcaggc aatggagcac agtgatcggc cgcagtcttg gctggtccaa     660
gaaagtgtca cggctaatga gattgctgct gttatttcac gagaaaccgg tattcccgtg     720
gcaaaactgg ttgaaggcga tcgtcaaaaa ttgctgcatc ttgccggtaa tctgcatcag     780
cgtgtcattg gtcaggatga agccgtcacg gcagtttcag atgcggtatt gcgttcgcgc     840
gccggactgc aagacccaag ccggccatta gggagttttc ttttccttgg tccgaccggg     900
gtggggaaga ccgaactcgc aaaagcgctg gccgaggatc tgtttgattc tgaaaaacac     960
atggttcgaa ttgatatgtc cgaatatatg gagaaggcga gtgtttcacg gttggtcggt    1020
```

```
gcggctccgg gttatgtcgg ttatgaacaa ggcggtcaat taaccgaagc agttcgccgc   1080
aatccgtata cgattgtcct attagacgaa atcgaaaaag ccaatccgga tgtcttcaac   1140
attcttttgc aagtgttaga cgatgggcgg ttaacggacg ggcaaggacg caccgttgac   1200
tttaagaaca cgatcatcat tatgacctct aacctcggct ctgaatattt gctggatggc   1260
gtgcaaaaag acggaactgt cagtcagcaa gctaaggatc aggttcgtca gttgatcggt   1320
aaagctttta aaccggaatt tctcaatcgc attgacgata tcatcatgtt ccatccactt   1380
tcactagatg atgttaagaa gattgccgtt aaggatctgc atgagctggg aacacgcttg   1440
gcagaccagc aaattagttt ggacatcacg ccagaagctc agacctggtt ggcggataag   1500
ggctatgacc cggcatttgg tgcgcgtccg ttgcagcgtc taattaccag tgccgttgaa   1560
acgccgttag ccaaagagct cattcgcgga acgattcagc ccggtcagga agtggtcata   1620
accgttgcgg atgatcagct gcaattcaaa gcaaaacaag tagtagcgaa ggca          1674

<210> SEQ ID NO 19
<211> LENGTH: 876
<212> TYPE: DNA
<213> ORGANISM: Lactobacillus rhamnosus

<400> SEQUENCE: 19
atttcggcga tcatcgtgat tgtagaggag aataatgtgg cagcaagaga attaatttta    60
gcattcgaaa gcagctgcga tgaaaccagc gtggccgttg tcgaaaatgg gaccaaaatc   120
ctatcgaaca tcatcgccac gcaaatcaag agtcatcagc ggtttggcgg cgttgtaccg   180
gaagttgcca gtcgtcacca tgtggaacag attacgttgg tgaccgatgc ggcattaaaa   240
gaggcaggtg tgacttatac tgacctgacc gcagttgccg tgacgtatgg accgggactg   300
gtaggtgcct tgttgatcgg ggtacgggct gccaaaccca ttgcgtatgc ccatcactta   360
ccacttattc cggtcaatca tatggcaggc catatttatg cagctagatt tgttaagcca   420
ttggtctatc cattgttggc attagcggtt tccggcgggc acacggaact ggtctatatg   480
cgcgctgccg tgaatttga atcatcggt gataccgtg acgatgcggc cggtgaagcg   540
tatgacaaag tcggccggat attgggtatc ccttacccag ccggaaaaga agtcgataga   600
ttggcgcatc ttggtcatga taccttcat ttccgcgag ccatggataa agaagacaat   660
ctcgatttta gtttcagcgg tttgaagtca gctgtcatta atacggtaca tcatgccgat   720
caaattgggg aatcactcag ccgtgaagat ctgtctgcga gttctcaagc gtcagtggtg   780
cacgtgatgg ttctcaaatc ccaatcagcg atagccgaat atccggttat acaggtggtg   840
atcgccgggg gcgttgccga taatcaaggg ctgaaa                              876

<210> SEQ ID NO 20
<211> LENGTH: 732
<212> TYPE: DNA
<213> ORGANISM: Lactobacillus rhamnosus

<400> SEQUENCE: 20
atgattttcc gcaaaccaca accattcgaa tatgaaggta ccgatactgg cgtggtattg    60
ttacatgcat acacgggtag ccccaatgat atgaatttta tggcgcgggc cttgcagcga   120
tccggttatg gggtttatgt tccgcttttt tccgggcatg ggacagtgga gccgttagat   180
attttgacaa aaggcaaccc ggatatttgg tgggcagaaa gtagtgccgc ggttgcgcat   240
atgaccgcaa aatacgccaa ggtgtttgtt tttggcttat cactgggagg tattttgcg    300
```

```
atgaaggcgc tagaaacctt gccagggatt acagcaggcg gtgtttttc atccccgatt      360 ttgccgggca acatcactt agtaccgggt tttttaaagt atgccgagta tatgaatcgg       420
ttagcaggca atcagatga aagcacacag attctggcat atttgccggg acagttggcc      480
gcaatcgatc agtttgccac gacggttgct gctgatttaa atttagtcaa acagccgact     540
tttattggac aagccggtca ggatgaatta gttgatggtc gattagcgta tcaattacgc     600
gatgccttaa tcaatgctgc acgcgttgat tttcattggt atgatgatgc caagcatgtc    660
attaccgtta actcggccca tcacgcatta aagaagacg taatcgcatt tatgcaacaa     720
gaaaacgagg ga                                                          732
```

<210> SEQ ID NO 21
<211> LENGTH: 1299
<212> TYPE: DNA
<213> ORGANISM: Lactobacillus rhamnosus

<400> SEQUENCE: 21

```
ctgggtatat ttttctttaa acgcttcagg aagttgcact tgttcgatcc tttaaattat    60
ccggaagaga cttttcaaag tttcgacagc gcttttaaca acggagctga ttacgttgag    120
cttgacgtac atgaaagtgc agatggtgtg attgtgattc aacatgacac cacgattcag   180
cgaacgactg gtgccaactt ggcgatcgcg aaaacaaact tcgcacaact tcagcaatat  240
cataccaaaa atggcgaacc gattcacagc ctagaggaac tcttcgccca tgagcaacaa   300
acaaagcata aattcctgat tgaaactaaa attgtaaaag gtgaaccgca tccgcatcta    360
gaagacaaag ttgcggccct gatcaagcaa tatcacatgg aaaatcgcgt gatgtttcat   420
tcattctcag cagctagcct caaacgcttg caagcagctc tgccaaatat tccgcgaatt    480
ttgatcgttg gctcgcttaa gcggatcaac tttgacgtct tgacgtacgt ggacggtatt     540
aatctaagtt ccgatttagt gacgccgcaa cttgtcaccc aactgcatga tctaggtaag    600
aaagtttatg tttgggatga aatgaacgag gatcgggcga atggacttg gctcgtcaat    660 ctcaacattg atggcgtcgt cactaattac accagcctcg gccacgaatt tcaaacgctt    720
aaggcagctg ctgtcaccac cagcatcaat gatcttggcg caaactcaag ccttgctgca   780
ctgccagttt atgaaaatcc ttatcagcca ttgttgcgct ctgaacggct ggcaccgcaa     840
accccgatca tgatttccag catggtttcc ctcgctggca gcacgtacta ccaaattggc    900
gataatgcat ttgtccctgc cgaaaccatt aaccttgccc ctgaagccgg ttgggcaagt    960
ctttttctcc atcagcgcat cgtcatcacc agccggcact taaggtacc cgtgcacgct    1020 gatcccttac atcagcaagc cattaccggc catgttggca atcacaaatg ctaccgggta    1080
ttagcagccc gttatcaaag cggccagctg tatttaaaaa caaaaatcgg ttggttaaac    1140
gccaaagatt tacaggtgct gccaaccgcc gagaatatgc gcatctggct cacgctctat     1200
cgcagcatcc ccgaaaacca aaaccgctc cttcactggg cacttggcga cacggccttc    1260
gatacaccgc ttctcaatgc cagtgtcctg aacatcggt                           1299
```

<210> SEQ ID NO 22
<211> LENGTH: 1344
<212> TYPE: DNA
<213> ORGANISM: Lactobacillus rhamnosus

<400> SEQUENCE: 22

```
atggaattag cgaaactcgc tgttgacgaa accggccgtg gtgtttggga agataaagcc    60
attaaaaata tgtttgccac tgaagaaatc tggcattcga ttaagaacaa caagaccgtt    120
```

-continued

```
ggcgttatca atgaagataa acaacgcggc ttggtatcca tcgccgaacc aatcggggtt    180
attgccgggg taacgccggt gaccaacccg acatcaacca cgatctttaa atccgaaatt    240
tccatcaaga cccgtaatcc gattatcttt gctttccacc cgggtgcaca aaagtcttca    300
gcgcgtgcgt tggaggtcat tcgggaggaa gctgaaaagg ccggattgcc aaaaggggcc    360
ttgcagtata ttccggttcc aagcatggaa gcaactaaga cactgatgga tcatcccggc    420
attgccacga tcttggcaac cggtggccct ggcatggtta agtcagctta tcatccggc    480 aaaccggcct tgggtgttgg cgcagggaat gcaccggcat acatcgaagc aagtgccaat    540
attaagcaag ccgttaatga tttggtcttg tccaagagtt ttgataacgg tatgatctgt    600
gcttccgaac aaggggccat cgttgattcc agcatttacg atgccgcgaa gaaagaattt    660
gaagcccaag gtgcctattt tgtcaaacct aaggacatga agaagttcga gagcacggtt    720
attaaccttg agaagcaaag tgttaatcct cgaattgttg ccaaagtcc taagcaaatt    780 gctgaatggg cagggattcg aattcctgat gacacgacca tcctgattgc cgaactaaaa    840
gacgttggca agaaatatcc gctttctcgg gaaaaactga gcccggtttt ggcgatggtt    900
aaagccgatg gtcatgaaga tgccttcaag aaatgtgaaa ccatgttgga tatcggcggc    960
ttgggacaca ccgcggtgat tcacacagct gacgacgaat ggcattgaa atttgctgat   1020 accatgcagg cttgccgaat cctgatcaat acaccttctt ctgttggcgg tatcggggat   1080
ctctacaacg aaatgattcc tagttttgacg ctgggctgcg gctcctatgg cggcaactcg   1140
atttcgcaca atgtggggac ggttgacttg ttgaatatca agaccatggc aaaacggcgc   1200
aacaacatgc aatggatgaa attgccgcca agatttatt tcgaaaaaaa ctcggttcgc   1260
tatctggaac acatggaaag catcaagcgc gccttcatcg ttgctgatcg ttcaatggaa   1320
aaagctgggt tcgtcaaga tcat                                          1344
```

<210> SEQ ID NO 23
<211> LENGTH: 474
<212> TYPE: DNA
<213> ORGANISM: Lactobacillus rhamnosus

<400> SEQUENCE: 23

```
gtgttggtca ataatgccgg cattaccgac gatatgttgg cgatgcgcat gaaacccgct    60
tcttttgcca aggtcgttca ggttaacttg gatggcacct tttatgttac ccaaccggcc   120
ttcaagaaaa tgctaaaggc ccgcgctggc gtcatcatca atctggccag tgtggtcggt   180
ttgaccggta atatcggcca agccaattat gcggcaagta agcaggcat catcgggctg   240 actaagacgc tagctcgtga aggggctatg cgtggcgtgc gcgttaatgc cattgccca   300 gggatgatcg ccaccgatat gaccgctgcc ttgagccaat ccagtcagga ccagattctg   360
gcggaaattc cgttgaagcg gttcggtcaa cctgaagaaa ttgcccacac ggcccgtttt   420
ctggtcgaaa atgcctacat aaccggtcag acagtgactg tcgccggcgg atta        474
```

<210> SEQ ID NO 24
<211> LENGTH: 1002
<212> TYPE: DNA
<213> ORGANISM: Lactobacillus rhamnosus

<400> SEQUENCE: 24

```
atgtatcatg cagcagctga tcgttatgag aaaatgccgg tcgccatgc tggtaagaca    60 gggttgatgt tgccggttat ttcgttggga ttgtggcagc attatggcaa cttggatcca   120
```

```
tttggcccgc gacgctcggt gattttggat gcgtttgatc gtggcgtttt tcattttgat    180
gtcgctaatc attatggtaa tggtgatcgt gaaccgggat ttggctctag tgaaaggtta    240
ctcgggcaga ttctggccac ggatttaaaa ccgtatcgag acgaattggt gattagtacc    300
aaggtgggtt atgagattca ccctggtcca tacggtgtcg ggacgtcgcg taaagcagtt    360
attcaaggct tgaatgattc actcaagcgc ttgcagttgg attatgtcga tatttactat    420
gcccaccgat ttgacgatac cgtggccttg aagagacgg ttaatgcgct ggatcaaacg     480
gtgcgtgacg gtaaggcgtt gtatattggt atttccaact atgatacgaa gcagaccaaa    540
gaagcaattg cgatgtttaa agatctgcac acgcctttg tactgaatca atacagttac     600
aacatgttta atcgcaccgc tgaaacgtcc ggcttgatcg atgcattaaa agctgatggt    660
gccgggttga ttgcatacgg accgttatca gaaggcttgt tatcagatcg ctacctaaag    720
ggaattccgg atactttcaa atccatcca accaacaagg ccacttttgc taagggcaaa     780
gaggctgtgg ttaagcaact aaatgcgctt aatgaaattg cgcatgatcg tgaccaaacc    840
ctgagtcaaa tggccttggc gtggttgtta cgggatccgg ttgtcacaag tgtgatcatt    900
gggacgacct cagttgaaca ccttcaggat aaccttaaag caacggaaca tctgaccttt    960
actgctgaag agattcaaca aattgatgat attttaaatg ct                      1002

<210> SEQ ID NO 25
<211> LENGTH: 1239
<212> TYPE: DNA
<213> ORGANISM: Lactobacillus rhamnosus

<400> SEQUENCE: 25
gccgttgcat taccgttact tggcgttttg gctatcgccg caacgcatgc tgaaggtgtt     60
tatgatattg gccgtccact tggccgcttc ttcgccttag cgttcatggt gctcattcat    120
gccacgatcg ggccaatgtt cggcacgccg cggactgcca ccgtttcctt caccaccggc    180
gtcttaccga tgttaccaaa agcctggcaa caaggcggct tgcttgtctt ttcggctttA    240
ttctttgggg ctgctttttt cctgtcatac aaggaacgca aaattaccac agctgttggt    300
aaagtcttaa atcccgtctt cttgctattg ttattcttcg tcttcttcat tggtttctta    360
cacccaatgg ggaatccggc tgctcaaaca gtaacggctg cgtacaaaaa tggcggcagt    420
ttcatgagcg gcttcctgca aggttacaat accatggacg cgcttgctgc cttagccttt    480
ggtgtgactg tcgtaacggc ggttcgcggt ttaggcttga aaaacgatga tcatgtcgcc    540 aaaagcaacgg ctaaagctgg ggtcatggct acagttgga tcgcgttaat ctacgttgcc    600
ttgatcgtct taggaagtat gtccctggcc cactttaagc ttagtgctga agggggaact    660
gcttttaatc aagtgggtac gttctacttt ggtactgttg gccaccctgc ttggcaacct    720
tgcttaaccc tgacctgttt gaacaccccg gttggtttg tcagggcatt cccgcacgac    780
ttccaccggc atttccctaa agtcagctat caggtctggc ttggattgac aagttttctg    840
tcattcttaa ccgccaactt cggacttgaa caaatcattg catggtccgt tccaatgctg    900
atgttcctat atcctttctc aatggttctc atcttactat cggtctttgg caaagcgttc    960
catcacgatc cactagttta ccgaatcgtt gtagcattca ccatcgttcc ggctgtgctc   1020
gacatgtttg cagcttttccc cgccgttgtt agtcaaagtt cgttaggctt ggcattgcat   1080
agcttccagc ttcattttct accattttcc gcaatgggtc tcggctggct cgtgccggct   1140
ggtgtgggtc tcgtccttgg cctcgtcgca catgccgtca agttcgcaa agcagtcgca     1200 gcaactcatc tcgaagctga acaaaactcag ctagtacac                         1239
```

<210> SEQ ID NO 26
<211> LENGTH: 1881
<212> TYPE: DNA
<213> ORGANISM: Lactobacillus rhamnosus

<400> SEQUENCE: 26

| | | | | | |
|---|---|---|---|---|---|
| atggcagaca | atcacaaagc | ccaaacgacc | aagcagccat | ctggcccacg | gatgggtcct | 60 |
| ggccgtggtg | gtctcgttga | aaagccgaag | aacttctggg | gcacaacagc | gcggttattt | 120 |
| ggttacatgc | gcaaccgtct | gattggtatt | attgcggtgc | tagtcttggc | cattgcttcg | 180 |
| accgtctttc | aaattcgcac | gccaaaaatc | ctaggggaag | ctacaaccga | gattttaaa | 240 |
| ggggttatga | aggccaagc | ggagcaaaag | gccggtatcg | ctgttggcaa | ctatccaatt | 300 |
| gattttgata | agatcaaaca | gattatttta | atcgtcttgg | tgctgtattt | gggtagcgca | 360 |
| ctgtttagtt | tcttgcagca | gttcatcatg | actcggatct | cgcagaatac | ggtttaccag | 420 |
| ttgcgtaaag | atctcaagca | aagatgaag | actgtgccga | tcaagtatta | tgacacgcat | 480 |
| agtaatggcg | atattatgtc | acgggcgatt | aacgatatgg | ataacatcgc | ctcgacactg | 540 |
| caacaaagtc | tgacgcagat | ggtgaccagt | gcggttatgt | tcgtgggaac | catttggatg | 600 |
| atgcttacga | tttcctggaa | gttaacgctg | attgcgctgg | taacgattcc | gctgggctta | 660 |
| attgttgtcg | ggattgtcgc | gccaaaatcg | caacggttct | tgccgccca | gcaaaaagct | 720 |
| ttaggtctct | tgaataatca | agttgaagaa | acttatggcg | gtcaggtgat | catcaagagc | 780 |
| tttaatcgtg | aagatgatga | agttgaggca | tttgaaggcc | agaaccaggc | attttatgat | 840 |
| gcagcgtgga | aagcgcagtt | tgtttccggg | atcatcatgc | cgcttatgat | tttcctaaac | 900 |
| aacattggtt | acgtgtttgt | tgcgattatg | ggtggcattg | aagtttccaa | tggcacgatc | 960 |
| acccttggga | atgttcaggc | gttcctccag | tatatgcagc | aattttccca | gccgatttcc | 1020 |
| cagcttgcta | acctagccaa | tacgattcaa | tccactattg | ccagtgccga | gcggatcttt | 1080 |
| gcggtgttgg | acgaagaaga | tatgcaggat | gagccgtctg | gtgtgccggc | agtggccaat | 1140 |
| gatcctaaca | aactggtcat | ggatcatgtt | cagtttggtt | ataccccgga | tgccttgttg | 1200 |
| ctcaaggact | ataacctgca | agtcaaaccg | ggtgagatgg | tcgcgattgt | cgggccgacc | 1260 |
| ggtgcaggga | aaacaacgat | catcaacctg | ctagagcgtt | tttatgatat | tagcggcgga | 1320 |
| tcgattcgct | tgaatggtac | cgataccgc | gatatgaagc | gagaagatgt | tcgcgcgcat | 1380 |
| tttgcgatgg | tgcttcagga | tacttggctg | tttaccggca | cgatttggga | taacttgaaa | 1440 |
| tatggccgcg | aagacgcaac | tgacgacgaa | gtattggccg | cagccaaagc | agcccatgtt | 1500 |
| gacaactttg | tgcggcagtt | gccggatggc | tacaacacga | ttctgaacga | agaagcctcg | 1560 |
| aatatttcgc | aaggtcagcg | acagttgttg | acgatcgctc | gggccttcgt | ggcagatccg | 1620 |
| gaaattctta | ttctggacga | ggccaccagc | tcggttgata | cgcggacgga | aattcatatt | 1680 |
| caacacgcca | tgaaccgttt | gctgaccgat | cgtacgagct | tcgtagtcgc | ccaccggctg | 1740 |
| tcaacgattc | gtgatgccga | caagattatc | gtgatgaatc | acggctccat | tgttgaaacc | 1800 |
| gggaatcatg | acgaactaat | ggctaaaaac | ggcttttatg | ctgatctgta | caacagtcag | 1860 |
| ttcagtggca | atgtcgcgat | t | | | | 1881 |

<210> SEQ ID NO 27
<211> LENGTH: 606
<212> TYPE: DNA
<213> ORGANISM: Lactobacillus rhamnosus -continued

```
<400> SEQUENCE: 27
accaccaggc tgtcaagttt gatcaccgaa tacttagaca gccaactagc tgaacgtcgc      60
agcatgcatg gcgtcttggt tgatatttac ggtctgggcg tgctcattac tggcgattcc     120
ggggtgggaa aatccgaaac tgccttggaa ttggttcagc gtggtcatcg gcttattgct     180
gatgatcggg tggatgttta tcagcaagat gaacaaacgg ttgtcggagc tgcaccgccg     240
attttatccc acttgttgga gattcgcgga ttgggtatca ttgatgtcat gaatctcttt     300
ggtgccgggg cggttcgtga agacaccacc atttcgctga ttgtgcactt ggagaattgg     360
acaccagaca aaaccttcga tcgcttgggc tctggcgaac agacgcaaat gatctttgac     420
gtgccggttc ccaaaattac gattccggtc aaggtcggtc gtaacttagc cattatcatc     480
gaagtggccg cgatgaattt ccgcgccaaa tcgatgggct atgatgccac taaaacattt     540
gaaaagaatt taaatcatct gatcgaacat aacgaagcga acgaccagaa gagttcggag     600
gaaaaa                                                                606

<210> SEQ ID NO 28
<211> LENGTH: 1023
<212> TYPE: DNA
<213> ORGANISM: Lactobacillus rhamnosus
<220> FEATURE:
<221> NAME/KEY: misc_feature
<222> LOCATION: (1)...(1023)
<223> OTHER INFORMATION: n = A,T,C or G

<400> SEQUENCE: 28
atgtctatct ccacgcgtgc aaataaactc gacggcgtcg agcaggcatn tgtggcgatg      60
gcgaccgaaa tgaataaagg cgtgctgaag aatttaggac tgctgacgcc ggagctggag     120
caggcgaaaa acggcgacct gatgattgtc atcaatggta aatcgggtgc ggacaacgag     180
cagttactgg tggagattga agaactgttc aacaccaaag cgcaaagcgg ctcgcacgag     240
gcgcgttacg ccactattgg cagcgccaaa aagcatatcc cggaaagtaa cctggcggtg     300
atttcggtca acggtctgtt tgccgctcgc gaagcgcgtc aggcgctgca aaacgatctc     360
aacgtgatgc tgttttccga taacgtctca gttgaagatg aactggcgct caagcaactg     420
gcccacgaaa aagggctgct gatgatgggg ccagactgtg gcacggcgat tatcaacggc     480
gcggcgctct gttttggtaa cgccgtgcgt cgcggcaaca tcggtattgt tggcgcatcc     540
ggcaccggca gtcaggagtt gagcgtccgc attcatgaat ttggcggcgg cgtttcgcaa     600
ctgattggca ccggcgggcg cgacctgagc gagaaaatcg gcggcctgat gatgctcgac     660
gccatcggga tgctgaaaaa cgatccgcaa actgaaatca ttgcgcttat ctccaaaccg     720
cctgcgcctg cggtggcccg caaagtgctg gaacgtgcgc gcgcctgccg caagccggtg     780
gtcgtctgct tcctcgatcg tggcgaaacg ccagtggatg agcaggggct acagtttgcc     840
cgcggcacca aagaggcagc gctaaaagcg gtgatgctct ccggcgtgaa acaggaaaat     900
ctcgacctgc atacgcttaa ccagccgttg attgcggatg tgcgtgcgcg tctgcaaccg     960
cagcagaaat acattcgtgg cctttctgcg gcggcacgct gtgcgacgaa accatgttcg    1020
cgg                                                                  1023

<210> SEQ ID NO 29
<211> LENGTH: 1227
<212> TYPE: DNA
<213> ORGANISM: Lactobacillus rhamnosus

<400> SEQUENCE: 29
```

-continued

```
cagatcctga ataacccatt tttaaataaa gggactgctt ttacgcagga ggaacggaac      60
caatatggct tgaatggttt gctgccacca gctgtacaaa cacttgatca gcaggttaag     120
caagcttatg cccagttgca gaccaagcca actgatttgg ctaagcgtca atttttgatg     180
accttgttca atgagaatca tgttttgttc tataagcttt tctccgagca tatcaacgaa     240
ttcatgccaa ttgtttacga tccgactatt gccgacacga ttgaaaacta cagtgcgctt     300
tttgttaatc cacaaaatgc cacgtatctt tcaatcgatg atccggacca tatcgaaagc     360
gcactgaagc atagcgcaga tggccgcgat attcggttgc tggttgtaag cgatgctgaa     420
ggcattcttg gcattggcga ttggggcaca caaggtgttg acatctcagt cggtaaatta     480
atggtttata cggctgctgc cggcattgat ccgagccagg tcttgccagt ggtcttggat     540
gtcgggacta acaatgaagg tttgttgaac gacgaccttt atttaggcaa tcgtcacaag     600
cgcgtatacg gtgaaaagta tcaccacttt gtcgataaat ttgtcgccgc agcagaaaag     660
ctgttcccga acctgtattt gcattttgaa gactttggac gcagtaatgc tgcagatatt     720
ttgaatcaat ataaagacaa gatcactact ttcaatgatg acattcaagg caccgggatc     780
attgtcttgg ctgggctatt aggcgccatg aatatttcca agcaaaaatt gaccgaccaa     840
gtttatttga gctttggtgc cggaactgcc ggtgctggca ttgcttcgcg agtttacgag     900
gcctttgttg aagaaggatt gagcccggaa gaagccaaga agcatttcta cttggtggac     960
aaacaaggct tgctctttga tgacatgacg gatttgacgc cagaacaaaa gccgtttgcc    1020
cgttctcgca gcgagtttgc taatgcagac gagctgacaa cgcttgaagc tgtcgttaag    1080
gcagttcatc caacagtctt ggttgggacg tcaaccgttc cgggtacgtt tacagagagt    1140
atcgtcaagg aaatggctgc ccacaccgat cgaccgatta tcttcccatt gtccaatccg    1200
acgaagctgg ctgaagctaa agcagat                                        1227
```

<210> SEQ ID NO 30
<211> LENGTH: 1158
<212> TYPE: DNA
<213> ORGANISM: Lactobacillus rhamnosus
<220> FEATURE:
<221> NAME/KEY: misc_feature
<222> LOCATION: (1)...(1158)
<223> OTHER INFORMATION: n = A,T,C or G

<400> SEQUENCE: 30

```
atgatcaaac ccgaaaagac aatcaatgga accaaatgga ttgaaacgat tcaaatcaat      60
gccgaagaac gggcaaccct cgaagatcag tatggcgtcg atgaagatat tattgagtac     120
gtcactgata atgatgaaag tactaattat gtttatgata tcaatgagga cgaccaatta     180
ttcatctttc tggcgccgta tgccctcgac aaagatgcgc tgagatacat tacccagcca     240
tttggcatgt tgctccataa gggcgttttta ttcacgtttta atcaaagcca catacctgaa     300
gtcaacacgg cactttactc ggcattggat aatcccgagg ttaagagcgt cgatgcattt     360
attctggaaa cactgtttac agttgttgac agctttatcc caatttctcg cggcattacc     420
aagaaacgca actatttgga taaaatgttg aaccggaaga cgaagaacag tgacttggtt     480
tcactttcat atcttcaaca gacgttgacc ttttgtcca gcgcggtcca aaccaatctc     540
agtgaactcg atctcaacgg cagtgacgcc cttcagcaga ttatcgaatt gctcaatcag     600 catccccctcg actntgcgcc agatgaaaaa ggtgcctatt ccaatagtaa ctactatctc     660
ctaggacaca ttattacgca ggttgcgaat atgccgctga gtgattttct caaccaacac     720
```

```
ttctttgaac cattggcaat gacgaaaact caactgggta cgcaacatgc tgatgccaat    780
agttacgatg atttggactt tactaacggc aaaccagtcg cccttggccg cggccactac    840
caaggtggag atggcgcggt ggtgagttca ctcgcagact tggccatctg ggcgcgagcc    900
gttttacagc gccgcatttt gccggaatcc gcgtgggatg aggcactgac gctgacccac    960
gacttttacg gcatggggttg gatgaaatcc cgaacacagc actggttaag tcacaatggt   1020
catattttcg gttactgggc gttttttgat gtttcatttg aaaagcaatt agcacagatt   1080
acgctgacca acatgtcgcc tggtgttgag acactcaaaa aatggcaaga ggagatggct   1140
aactggcgcg catcgtta                                                  1158

<210> SEQ ID NO 31
<211> LENGTH: 1071
<212> TYPE: DNA
<213> ORGANISM: Lactobacillus rhamnosus

<400> SEQUENCE: 31
ttggacaatc aagatgccga ttttaagccc acaatccaaa ttctggatga agttggcaaa     60
gtcgtcaatc ctgatattat gcccgatttg agtgatgatc agctggtcga tttgatgtca    120
aaaatggttt ggcaacgcgt gctggatcaa agggcgacag cgttgaatcg gcagggacga    180
ttaggctttt atgccccaag tgcaggcgaa gaggccagca tgatcggtag tcacgctgct    240
atgaagtcat cagattggct gcttccagct taccgtgatt taccgcaatt gattcaacac    300
gggttaccgc ttgacaaagc ttttctctgg tcgcgcggtc acgttgccgg caatgagtat    360
ccggaagatt ttcacgcatt accgccgcaa atcattattg gtgcgcagta tgttcaaact    420
gcgggtgttg cgctcggttt gaagaaaaat ggcagtgatg aggtggcctt cacctatacg    480
ggtgatggcg gtacttcaca aggtgacttt tatgaaggcg ttaactttgc tgggcatttc    540
aaagcgccgg cactgtttat tgttcaggac aacggctttg ctatttccgt gccgcgggcg    600
agtcaaacgg cagccaaaac gcttgcgcaa aaggcggttg cagccggtgt tcccggcgtg    660
caggttgacg ggatggacgc tttggcagtc tatgaagtca ccaaggaagc gcgtgcatgg    720
gcggctgctg gcaatggacc ggttttaatc gagacgttga catatcggta tggcccacac    780
acgctatcag gtgatgaccc aactcgttat cgctccaaag agaccgatga gttatggcaa    840
aaacgagatc cgttaattcg aatgcgcaac tatttgaccg ataaaggctt gtggagcaaa    900
gacaaagaag atgccttgat tgaaaaggtc aaagatgaaa ttaaagatgc tatcaataag    960
gccgataaag cgccgcagca gacggtatcg cgcttcttga agacacccta tgaagttgcc   1020
ccgcaaaatg ttgctgaaca attggcagaa tttcaaggaa aggagtcgaa g            1071

<210> SEQ ID NO 32
<211> LENGTH: 1310
<212> TYPE: DNA
<213> ORGANISM: Lactobacillus rhamnosus

<400> SEQUENCE: 32
tctgtactga acatcaatgg cgggaatttg accctgactg atgatggcgt atctgccggt     60
actctgactg gaggtggctt cctgaatatc agcggcggcg tcctcgatat tacaggaggc    120
aaccacactt ttgctgtcag caccataata gcaaaagatg caactgtccg aatgaacgat    180
gtttccggac tgggtactgg taacatcagt aacgctggga cattatctct tactcatgcc    240
tcaggcttgc taagtaataa tctgagtggt tctggtacag tatctttgat caatagtgat    300
acccagattt caggaaataa cagtaactac tcagggctgt tgtagtagaa taccagctct    360
```

```
cagttgactg ccactggagc gcagaatctt gggattgctt ccgtgagtaa ccgtggaatc      420
ttgcagctga acaacacaac agactggcaa cttataaata atgttactgg aaccggtaat      480
gtccgtaaaa ccggttccgg ttcactgact gtccgaagca atgctgcctg gagcggacag      540
acagatattg atgacggctc tctgattctt ggcaatctg atgcacctgt catgctcgcc       600
agtagcctgg tcaatattgc aaagaacggt aaacttaccg gatttggtgg cgtagtaggg      660
aacgtaacca atagtggaag ccttgacctg cgatcggcgg ctccgggaaa tattctgacg      720
attggaggta actacaccgg taataatggc acgctgctca ttaacacagt gctggatgat      780
agctcttctg caaccgacaa actggtaatt aaaggcgatg cgtccggtaa gacccgagtg      840
gctgttacga atgttggtgg ttcaggcgct aatacgctga atagtattga agttattcat      900
gttgatggta atgcagctaa cgctgaattt attcaggccg gacgtatagc ggccggcgct      960
tatgactaca ctcttggacg tgggccggga agcaactatg gaaactggta tctgagcagt     1020
agtaaaaata ctccagaacc aaggcctgat cctgaaccca ctccggaagg gcatgataac     1080
aacctgcgcc cggaagccag ctcctatacc gcgaatatag ctgcggcaaa caccatgttt     1140
gtgacccgcc ttcatgaacg tctggggcag acgcaatacg tcgatgcaat taccggagaa     1200
ccgaaagcaa ccagtatgtg gatgcgccat gaaggaggac ataaccgctg gcgcgacggt     1260
tctggtcaac tgaaaactca agtaatcgt tatgtgattc aactgggtgg                 1310

<210> SEQ ID NO 33
<211> LENGTH: 645
<212> TYPE: DNA
<213> ORGANISM: Lactobacillus rhamnosus

<400> SEQUENCE: 33
atgaagattt tgattaccgg cgcacaaggc caactaggca ccgaactacg ccacttattg       60
gatgcacgcg gcattactta tcgggcaact gatgccaaag acttagatat taccgatgaa      120
gccgccgtta atcagtactt tgcggactat cagccagacg tggtgtatca ctgtgctgcc      180
tatacagccg ttgataaagc cgaagacgaa gcaaagcgc tcaatcaatt ggtgaacgtt       240
gacggtacgc gtaacttggc taaagcagcg gccaaagttg atgcaacctt ggtttacatc      300
agcaccgatt acgtgtttga tggcgatagt aaggagattt acaccgttga cgatcagccg      360
gcgccacgca atgaatatgg gcgggctaaa tacgaaggcg aacagcaggt gcaaaagtac      420
cttaagaagt actacatcat tcggacttct tgggtctttg gtgaatatgg tcacaacttt      480
gtctacacga tgttgaacct cgccaaaacg cataaggaac tgaccgtggt ggacgatcat      540
caagaatctt tttccgtctc atcatcacgg acatttgtga aatatcaaca cgaacacctg      600
atttattccc gacctgtgcc atatcggccc caccttcctg gcata                     645

<210> SEQ ID NO 34
<211> LENGTH: 1920
<212> TYPE: DNA
<213> ORGANISM: Lactobacillus rhamnosus
<220> FEATURE:
<221> NAME/KEY: misc_feature
<222> LOCATION: (1)...(1920)
<223> OTHER INFORMATION: n = A,T,C or G

<400> SEQUENCE: 34
atgcttggag gaaacagat gcctgaagta aagaaatttg aagccggcac ttatgatgtc        60
atcgttgtcg gtgctggtca cgctggnntt gtgaagccgg ccttggctgc agcacgcatg      120
```

-continued

```
ggcgaaaaga cattattact gacgatcagc ctggaaatgt tggcatttat gccatgtaat      180
cccagcttag gcggtccggc caaaggaatt gtggtccgtg aaattgatgc cctcggcggt      240
gaaatgggga agaatattga tcggacctac atccagatgc gcatgctcaa cacgggtaaa      300
ggtccggcag tgcgcgcatt acgtgcccaa gcagataaag cggcctatca ccgcagtatg      360
aaacacgtca ttgaagatac gccgcatttg gacttacggc agggactcgc taccgaagtg      420
ctggtcgaag atggtaaggc agtcggcatc gtggctgcta ccggggccat ttatcgcgcc      480
aagagtattg tgctaacagc tggcaccagt tcccgcggta aaattattat cggcgaactc      540
atgtatagtt ccgccctaa caatagtctg ccaagcatta agctctctga aaatctggag       600
cagctgggct ttaagctgcg ccgcttcaaa accggaactc cgccgcgtgt taatggcaat      660
acgattgact tttccaaaac cgaagaacaa ccaggcgata aaacaccgaa tcattttagt      720
tttacaacgc cggattcggt ttatctcaaa gatcagttga gttgttggat gacgtacacc      780
aacgcgacga ctcatcagat tattcgggag aatctggatc gcgcgccgat gttttccggc      840
gtgattaagg gagtcgggcc gcgttactgt ccatccattg aagataaaat tgttcgcttt      900
gctgataagc cgcggcatca attattcttg gaacctgaag gccgcgacac ctcggaatat      960
tatgtggggg acttttcaac gtccatgcct gaggaaatcc agttgaaaat gctgcacagt     1020
gtcgcgggat tggaacatgc cgaactcatg cgcgccggtt atgccatcga gtatgacgtc     1080
atcgagccat ggcagttgaa agcaacgttg gaaactaagg ttgtggagaa tttgtatacc     1140 gccgacaaa tgaacggtac cagtggttat gaagaagctg ccggtcaggg aattgtggcc      1200
gggattaatg ctgcccgccg cgctcaaggc aaaggaccct tcacgttgaa gcgttcagat     1260
gcttatattg gcgtgatgat agatgatctc gtgacaaaag gaacgaatga accgtatcgt     1320
ttgttaacca gccgcgccga gtatcggttg ttactgcgtc atgacaatgc ggatctgcgc     1380
ttaacgccaa tgggacatga acttggcctg attagtgatc aacgctatgc tgtcttttg     1440 gctaagcgtc aagccattac cgatgaatta gcgcgccttg agcacacccg cctgaagccc      1500
aaggatgtca acccgtggct tgaagctcat cattttgcct cccttaaaga tgggtctta      1560 gccagtgact tcttgaagcg tccggaaatc aattatcaga cgctagaaca gttcttaccg     1620
gaaaacccaa ccttggatca tcgggtgatt gaacaggttg agatccaaat caaatacgcc     1680
ggctacattg ccaaagaaga agccagtgt gccaagttga agcggcttga aggcaaaaag      1740
attccggcac gtatcaacta cgaagcaatc aatggcttag caaccgaggc acggcaaaag     1800
ctggttaaga ttcaaccgga aaccattgcc caagcaagcc gaatcagtgg cgttaatccg     1860
gctgatgtcg ctattttgtc cgtgtatatt gaacagggac gaattagtaa ggtggcacag     1920
```

```
<210> SEQ ID NO 35
<211> LENGTH: 762
<212> TYPE: DNA
<213> ORGANISM: Lactobacillus rhamnosus

<400> SEQUENCE: 35
```

```
cccctgtcaa ccatgatgtt ggctgggatt cgcgatatct tggtcatttc aacgccgaga       60
gatattgatc gttttcagga tctgttaaaa gacggtaaac aactgggact caatattagt      120
tacaaaatac aggaaaagcc aaatggcctg gcggaagctt tcattgtcgg ggctgacttc      180
attggcgatg attctgtgtg cttgattctc ggcgacaata tcttttatgg cagcggcttg      240
tccaagctgg tgcagcgctc ggcggctaaa acaaccgggg caacggtgtt cggctatcaa      300
gtcaatgacc ctgagcgttt tggcgtagta gcctttgacg agcagcatca tgtgcaatcg      360
```

```
attgtcgaaa agccagagca tccggagagt aactttgcgg ttaccggcat gtatttctat      420
gacaaccaag tggtggacat tgctaagaac cttaaaccgt caccacgagg cgaactagag      480
attacggatg tgaacaaagc gtatctcgaa cgtggccaac ttgatgttga gctgttgggt      540
cgaggatttg cttggttaga tactggcacc catgaatcct tacatgaggc ggctagtttt      600
attgagaccg ttcagaagcg gcagaatctt aaaattgcct gtcttgaaga agtagcctac      660
cggatgggtt acattgatcg cgatcaatta cgcaaactgg cgcagccgct taagaagaat      720
gattacggtc agtacatttt gcgcttagca gacgaagaag ac                        762

<210> SEQ ID NO 36
<211> LENGTH: 936
<212> TYPE: DNA
<213> ORGANISM: Lactobacillus rhamnosus

<400> SEQUENCE: 36
atggcaatta acctagttgg gattaatgac gcgaatttaa cgttaattga agaaggcctg       60
aacgtccgga tttcgccgtt tggggacgaa ttacgcatca gcggcgaaac cgaagcggtc      120
agcttgacac tacagctgct tgaggcggca actaagttat tagcacaagg catcaaactg      180
tcacctcagg atattgctag tgcggttgca atggcaaaac ggggtacact cgaatatttt      240
gcggatatgt atagtgagac cttgttacgc gacgccaagg ggcaaccgat tcggattaag      300
aattttggcc agcgtcaata tgttgatgcc atcaaacaca acgatattac ttttggcatt      360
ggcccagccg gtaccgggaa acttttctc gccgtggtga tggcagttgc agccatgaag      420
gccggccaag tcgagcggat tattttgacg cgtccggccg tggaagcagg cgaaagtctt      480
ggctttctcc ctggtgatct caaggaaaag gttgatcctt atttgcgtcc ggtttatgac      540
gctttatatg ccgttttggg gaaagaacac accgatcgcc taatggatcg cggcgtcatc      600
gaaattgcgc cattagcgta tatgcgtggt cgtacgttgg acaatgcgtt tgcgattttg      660
gatgaagccc agaatacgac tcaggcccag atgaaaatgt ttctgacgcg cctgggcttt      720
ggctcgaaaa tgattgtcaa tggtgatgtg acgcaaattg acttgccgca taatgccaaa      780
agtggcttat tgcaagcgga acagttatta aaagggatta gtcatattgc cttcacgcaa      840
ttttccgcac aggatgttgt gcgccaccca gttgtcgcca agattatcga agcttatggc      900
aaacatgatt tacagctgca aaagcaaacg aaggag                               936

<210> SEQ ID NO 37
<211> LENGTH: 840
<212> TYPE: DNA
<213> ORGANISM: Lactobacillus rhamnosus

<400> SEQUENCE: 37
atgaagaagt tcgacaagat gatggactgg ttagcagatg tctatgtcaa tgccctgaat       60
gttattcact acatgcacga caagtactac tatgaagctg cgcagttggc attgaaggat      120
acacgtctga atcggacgtt tgctaccggg atttccggtt tgtcacatgc ggttgattcc      180
atcagtgcca tcaagtatgg ccacgtgaag gcaattcggg atgaaaatgg cgttgcaatc      240
gactttgttg ctgacaatga tgactatccg cgttatggta acaatgatga ccgggcagac      300
aacattgcta agtggttggt taagaccttc tacaacaaga tgaatacaca tcatctgtat      360
cgcggtgcta agctcagtac cagtgttctg accattacat caaatgtggt ttatggtaag      420
aataccggga caacaccaaa cggccgtcag aagggcgaac cattctcacc tggagccaac      480
```

```
ccagcgtatg cgcctgaaaa gaacggtgct ttagcttcct tgatgtcaac cgccaagatc    540
ccatatcact atgcaacaga cgggatcagc aatacctttg gggtaacacc gaacaccttc    600
ggccatgacg atgaaactcg taaggacacc ttggttcaca tggttgacgg ctacatggaa    660
aatagcggca tgcaccttaa catcaacgtc ttcaataaag aaacgttgat tgatgcccag    720
aagcacccag aagaatatcc aactttgact gttcgagttt ccggttactg cgtctacttt    780
gcagacctga ccaaagaaca gcaagacgat gttatcgctc ggaccttctt cgacgaaatg    840
```

<210> SEQ ID NO 38
<211> LENGTH: 1341
<212> TYPE: DNA
<213> ORGANISM: Lactobacillus rhamnosus

<400> SEQUENCE: 38

```
atggcatttt caaaagaaac ccgcacccag acgattgatc aattgaagca gaccgaactc     60
gacttactca ttgttggcgg tggtattacc ggtgccggcg tagcaattca ggcagcagca    120
agcggtttaa aaaccggctt gattgaaatg caggatttcg cggaaggaac cagttcccgc    180
tcgaccaaat tggttcatgg cggcattcgt tacctcaaga cgtttgatgt cggcgttgtc    240
gccgataccg ttaaagaacg tgccgtagtt caaggaattg cgcctcacat tccgcgacca    300
ttcccgatgt tgttgccgat ttatcaggaa gccggcagta cttttgacat gttcagtatc    360
aaaatcgcca tggatctcta tgatcgtctg gcaaacgttg aaggttccca atacgccaac    420
tacaccgtca ccaaagatga aattctgcaa cgtgaaccgc atttagcctc tgatggcctc    480
caaggcggcg gcgtgtacct cgattttgtc aacaacgatg cccggcttgt tattgaaaac    540
atcaaagaag cagcagaatt aggcggactg atggctagtc gggttcaagc cattggcgtt    600
ttgcatgatg atgcaggtca ggttaatggc ttacaggtta aggatctttt ggatggcagc    660 gttttttgaca ttcatgccaa actcgtgatc aatacgaccg gaccttggtc tgacaagttc    720
aaggcgttgg atcaagccga agatcaaacg ccaacattgc ggccaacgaa aggggttcac    780
ttggttgtcg atggttctcg actgccggta ccacagccaa cgtatatgga tactggcttg    840
aacgacggcc ggatgttctt cgtggtgcca cgggaaggca agacttactt cggcaccacc    900
gataccgatt accatggcga tttcaaccat ccgcaagtcg aacaagccga tgtcgattat    960
ctcttgaaag tcatcaacaa gcgctatccg caaagccata tcacgcttga cgatatcgaa    1020
gcgagctggg caggattgcg accgctgatt gccaacaacg gcagctccga ttacaacggc    1080
ggcggtgcga acaccggtaa agtttcggat gattcctttg aagcgttaat ccgtgtcgtt    1140
gatgattacg aagacaacca ggctaccccgc gctgacgttg aacatgcgat ctccaaacta    1200
gaaacagccc acgccgaagc tgctttgagc ccatcacagg tttcccgcgg cagctcactt    1260
cgccaagccg atgatggcat gatcaccttg tccggcggga aaatcacgga ttatcggaaa    1320
atggcagcgg gcgcgcttgc t                                              1341
```

<210> SEQ ID NO 39
<211> LENGTH: 726
<212> TYPE: DNA
<213> ORGANISM: Lactobacillus rhamnosus

<400> SEQUENCE: 39

```
gatctcttct gcccagatat cacggcagat attctgactc gtaaagacga tcttggtagt     60
gacaagccga tcgttgatgt gattttggac cgcgctggca acaaagggac cggcaaatgg    120
tcttcacaat ctgctcttga gctaggtgtt ccgcaaagtg tgattaccga atccgtctat    180
```

```
gcgcgttaca ttagtgcgat gaagcaggag cgggttgcgg caagtaaagt tctgccaaag      240
ccggtcggaa atgtcacgat tgacaaaaaa gaagctatcg agatgattcg taaggcgtta      300
tacttcagca agctgatgtc ctatgctcaa ggctttgaac aaatgcgcgt tgcatcggat      360
aactacgact ggaacctgca gtacggtgaa ttggccaaga tttggcgtgc aggttgcatc      420
attcgcgcac gtttcttgca aaatatcacc gatgcctacg ataagaagcc agatttacag      480
aacttgttgt tagacgatta cttcctgaat attgctaaga actatcagga aagtgttcgt      540
gacttggtcg gcttggcagt taaagccggt gttccggtgc cgggcttctc agcggcgatc      600
agttactacg actcttatcg cgcccctgtt ctgccggcca acctgactca ggctcaacgc      660
gactactttg gtgcccacac atatgaacgt actgatcgtg atggcatttt ccattacacc      720
tggtac                                                                 726

<210> SEQ ID NO 40
<211> LENGTH: 972
<212> TYPE: DNA
<213> ORGANISM: Lactobacillus rhamnosus

<400> SEQUENCE: 40
gaagatttct ttatacagat aagcgctacc cagcatcact gaatccccga ctgctgtgat       60
cagattccga ccggtgactt ttcattcttc gataacactt tggacgttgc aaatcttttta     120 aacattgtac ccaagcgcta ccaagacctg aacttatcac cgcttgacac ctactttgcc     180
caagcgcgtg gctatcaagg agaggccggc gatgttaaag ctctggcgat gaaaaagtgg     240
ttcaacacca actatcatta cttggtacct gaattcgatc gcgataccaa gatccaagta     300
acggattggc agcttttcgt gcaatttgaa gaagctaaag cgctaggcat taacggacgt     360
ccgactttga ttggaccgta tacgttactg aaaattgtctc gcttcattga tgttgtgcct     420
gatgactttg tagccgacct gatttctgcg tacacgacca tcattgatcg cttgcatgac     480
gccggagcag actgggtaca acttgacgaa ccggcgctgg tttatgatca aaccgatgcc     540
gacctcgcct tattcgagcg gctttatacc ccgattttga cccaaaaaaa agctgccaaa     600
atcctggttc agacttattt tggtgattta accgattcgt ttgaccgtat tcaaaagttg     660
ccatttgacg gcttcgggct ggattttgtc gaaggatatg ccaatcttga tctgctcaaa     720
caacacggct tcccagcgca cgctacctta tttgccggaa tcgtgaatgg taagaacatt     780
tggcggacac attatgccga tgccttggca acgatcaaac aactggcaac cattacggac     840
aagctggtat taagcacctc gacctcactc ttgcatgtcc catatacact tcgcaatgaa     900
acccatctga aacctgaaga aaagcaatat ttggcctttg ccgaagaaaa actcaacgaa     960
ttgcatgagt ta                                                          972

<210> SEQ ID NO 41
<211> LENGTH: 888
<212> TYPE: DNA
<213> ORGANISM: Lactobacillus rhamnosus

<400> SEQUENCE: 41
gggccggcga ttttcggctt tattccgatg caggatggct cgcccgcgcc ggggctgagt       60
aatatcacgg cagaaggctg gttcccgcac ggtggcttac cgattttgat gactatggtg     120
gcagtgaact ttgcttttttc gggtaccgag cttatcggca ttgccgccgg tgaaacggaa     180
aacccgcgca agttatccc ggtagcgatt cgtactacca tcgcgcgact gattattttc     240
```

```
tttatcggca ccgtgtttgt gctggcagcg ctgatcccga tgcagcaggt gggcgtggag    300
aaaagcccgt tgtgctggt atttgagaaa gtagggatcc cgtacgccgc tgatattttt    360
aacttcgtga tcctgacggc tattctttgt gcagcgaact ccgggttata tgcctccggg    420
cgcatgctgt ggtcgttgtc gaatgaacgt acgctaccgg cctgttttgc gcgagtaacg    480
aaaaacggcg tgccactgac ggcgctgtcg gtcagtatgc tcggtggtgt gctggcgctg    540
ttttccagcg tggtggcccc gaacacggta tttgttgcgc tgtcggcaat ctccgggttt    600
gcggtggtag cggtgtggct gagtatctgc gcctcgcatt tgttttttcg tcgccgtcat    660
ctgcaacaag gtaaggcatt gagtgaatta cattatcgcg cgccgtggta tccgctggtg    720
ccagtattag gttttgtgct gtgcctggtg gcctgtgttg ggctggcatt cgatccagcg    780
cagagaattg cgttgtggtg cgggttaccg tttgttgcgt gtgctatgg tgcttatttc     840 cttactcaac cccgaaacgc aaaacaggag ccagaacatg tcgcagaa                 888
```

<210> SEQ ID NO 42
<211> LENGTH: 1422
<212> TYPE: DNA
<213> ORGANISM: Lactobacillus rhamnosus

<400> SEQUENCE: 42

```
atgcgtaaac aattacccaa ggactttgta atcggtggcg caactgctgc ttaccaagtt     60 gaagggcaa ccaagaaga cggaaaaggt cgagttcttt gggatgattt tctggaaaaa       120
caagggcggt ttagtcctga ccccgccgct gattttatc atcgctatga tgaggatttg      180
gcgttagcag aagcatatgg tcatcaagta atacggcttt caattgcctg gtcgcgaatt    240 tttcggatg gtgccggggc ggtggaatct cgtggcgttg cttctatca tcggctcttt      300 gctgcctgtg ccaagcatca tcttatcccg tttgtaacgt tgcatcattt tgatacacca    360
gaacggttac acgagattgg tgactggctg agtcaagaaa tgctggaaga ttttgtcgag    420
tacgcgcggt tttgcttcga agaatttccg gaaatcaaac actggattac gatcaatgaa    480
ccaacgtcca tggcagtgca acaatatacg agcggtactt ttccaccagc ggaaaccggt    540
cattttgata aacatttca agccgaacat aatcaaatcg ttgcccatgc gcgtattgtt      600
aatttgtaca agtcaatggg gctagacggt gaaatcggta tcgtgcatgc cttgcagaca    660
ccttatccat atagtgattc gtcggaagat cagcatgccg ctgatttaca ggatgcgttg    720
gaaaatcggc tgtatttaga tggcacactg gcaggagatt atgcccctaa gaccttggct    780
ttgatcaaag aaattctggc agccaatcaa caaccgatgt ttaagtacac tgatgaagag   840
atggcggcta ttaagaaggc ggcgcaccag cttgattttg ttggcgttaa taattacttc    900
agcaaatggc tgcgcgctta tcacggcaag tcggaaacga ttcataatgg tgatggctca    960
aagggatcgt cagttgcccg ccttcacggt atcggcgagg agaagaagcc agccgggatt   1020
gagacaacgg attgggactg gtccatctat ccgcgtggta tgtatgacat gttgatgcgg   1080
attcaccaag attatccgtt agtaccagcc atctatgtca ccgaaaacgg tattggattg   1140
aaagaatcct taccagcaga agtgacgcca aatacggtca tcgcggatcc caaacgcatt   1200
gattatttga aaaatatttt aagtgccatt gccgatgcga ttcaggctgg cgcgaatgta   1260
aaaggctact ttgtctggtc actgcaggat cagttttcct ggacaaatgg ttatagcaaa   1320
cggtacggat tgttttcgt cgactttccg acgcaaaaac gttatgtcaa gcaaagtgcc    1380
gaatggttaa acaggttag ccaaacgcat gtgattcccg aa                        1422
```

<210> SEQ ID NO 43
<211> LENGTH: 774
<212> TYPE: DNA
<213> ORGANISM: Lactobacillus rhamnosus

<400> SEQUENCE: 43

| | | |
|---|---|---|
| atgacgacct tgaaatcatt ccgggtgatc aataaggttg acttgcctag tgcccagcct | 60 |
| gatgttgtta agaagagat tgaagagatg atcggcttag acgcttctga cgccattttg | 120 |
| gccagtggta aaccggctt gggagttcct gaaattcttg agcgcatcgt ctcagacatt | 180 |
| ccggctcctt ctggcgatgt taacgcgccg ttgcaagcgt tgatctttga ttccgtttat | 240 |
| gatgattatc gcggtgttgt ccttgatgtt cgggttaaag aaggacaagt taaggtcggc | 300 |
| gatacgatcc agctgatgag caatggcaag cagtttcagg ttactgaagt cggcgtgatg | 360 |
| tcacctaaag cagtgaaacg cgatttttcta atggtcgggg atgtcggtta tatcacggcc | 420 |
| tcaattaaga cgattcagga tacgcgcgtg ggggacacgg tgacgctggc agaccgcccg | 480 |
| gcagcagccc cgctgaaagg gtatcgtaaa atcacgccaa tggtctattc aggcctgttt | 540 |
| ccagtagata cgcgaaatt caatgacttg cgcgaggcat ggaaaagtt gcaactcaac | 600 |
| gatgctgcgc ttgaatttga gccggaaacg tcccaggcac tcgggtttgg gttccgttgt | 660 |
| gggttcttgg gcctcttgca tatggatgtg gttcaggaac ggctggaacg cgattacggt | 720 |
| ctcgatttga tcatgaccgc accgagcgtg gactatcagg tagcgttaac agat | 774 |

<210> SEQ ID NO 44
<211> LENGTH: 1254
<212> TYPE: DNA
<213> ORGANISM: Lactobacillus rhamnosus

<400> SEQUENCE: 44

| | | |
|---|---|---|
| atggatgtca ccacgattga tctggaacaa atgggccgag cagcaaaggc cgcggcgact | 60 |
| gtcttgagcc agttgacgac cgcacagaaa atgccgggt tgttggccat ggttacggct | 120 |
| cttgaaacgc atactgaaac aattttggga gctaatcatg aagatctaaa agcggcagca | 180 |
| agcttgccgg ctaagttcac ggatcgattg gtactgacag ccgagcggat tgctgacatg | 240 |
| gcagcagggg ttcgccaagt tgccgcctta cctgatccaa ccgcccagac ggataaggcc | 300 |
| tgggtgaatc acgcaggact gaatattgcg caaaaacggg taccttaggg ggtggtcggg | 360 |
| atgatttatg aggcccggcc aaatgtaacc gttgatgctg ctgcgttaac ttttaaaagt | 420 |
| ggcaatgcgg tcattctccg tggcggtaaa gaggcgctgc acagcaattt ggccttggcg | 480 |
| accgttttac aggctgcatt gaccgcacaa ggattgccaa agacgcgat tcaattaatc | 540 |
| acggacccga gcgagaagt cgcgaatcag atgatgcacc tgaatggcta cattgatgtg | 600 |
| ctgattccgc gtggtggccg agggttgatt aaagcagtcg ttgaacaggc taccgtaccg | 660 |
| gtcattgaaa ccggggcggg caattgtcac atttatgttg atgcgtatgc gcaagcccag | 720 |
| atggcaatcg acattgttgt caacgccaaa gttcagcggc cgtctgtttg caatgcggcc | 780 |
| gagaaacttt taatccacgc tgatgttgca acgcgcagc tgcctttaat tgctgcggca | 840 |
| ctgcaagcgc atggtgtcga attgcgcggt gatgaacggg cgcgggcaat tgtgccgaac | 900 |
| atgcagatcg ccacggaaga agactgggat accgaatata tgacttaat tatgcggtc | 960 |
| aaggtggtgg attccgagga agaagcgatt gcgcatatca acgcacacaa cacgaagcac | 1020 |
| agcgaggcca tcattacgga taactaccaa aatagtcagc aattcctcca acaggtagat | 1080 |
| gcggctgttg tctatgtgaa tgcctcaact cggtttacag acggcttcga gttcggtttc | 1140 |

| | |
|---|---|
| ggcgcagaga tcggtattag tacgcaaaaa ttacacgcac gcggaccgat ggggttagcg | 1200 |
| gcgttgacga cgattaagta tcaggtgctg ggtaacggac aggtacgcga aggt | 1254 |

<210> SEQ ID NO 45
<211> LENGTH: 489
<212> TYPE: DNA
<213> ORGANISM: Lactobacillus rhamnosus

<400> SEQUENCE: 45

| | |
|---|---|
| atgaccgcat ttttatgggc acaggatcgc gatggcttaa ttggcaaaga tggtcatttg | 60 |
| ccatggcatt taccggatga tttacattat tccgggcgc agacagttgg taagatcatg | 120 |
| gtcgttggcc ggcgcaccta tgaaagtttt cctaaacgtc ctttacctga gcgaaccaat | 180 |
| gttgttttga cccatcagga agactatcaa gcgccaggtg ccgtggtcgt gcatgatgtt | 240 |
| gcggcggttt ttgcttatgc taagcagcat cccgatcagg aactggtcat tgctggcggt | 300 |
| gcgcaggtct ttacagcgtt taagatgat gtcgatacgt tattggtgac acggttggct | 360 |
| ggcagttttg aaggcgacac gaaaatgatt ccattaaact gggatgattt taccaaagtc | 420 |
| tccagccgca ccgttgaaga taccaatccg gcgctgacgc acacttatga ggtttggcaa | 480 |
| aagaaggct | 489 |

<210> SEQ ID NO 46
<211> LENGTH: 285
<212> TYPE: DNA
<213> ORGANISM: Lactobacillus rhamnosus

<400> SEQUENCE: 46

| | |
|---|---|
| caagggtgca acctttacgg tatcgcaact gctttggcac ggatttccaa agcaattctt | 60 |
| aacgatgaaa atgcggtact cccattgtcc gtttacatgg acggccaata tggcttgaac | 120 |
| gacatctaca ttggtacacc tgctgtgatc aaccgcaatg gtattcagaa cattctggaa | 180 |
| atcccattga ccgaccacga agaagaatcc atgcagaagt cggcttcaca attgaagaaa | 240 |
| gttctgaccg atgcgtttgc taagaacgac atcgaaacac gtcag | 285 |

<210> SEQ ID NO 47
<211> LENGTH: 969
<212> TYPE: DNA
<213> ORGANISM: Lactobacillus rhamnosus

<400> SEQUENCE: 47

| | |
|---|---|
| atgttgacga acggcaatt gctcgtctta aaagaaatca tccgcctgtt tactgaaagt | 60 |
| gggcagccgg tcggttccaa gacgttaatg caggaactgc cggttcatgt cagttccgcc | 120 |
| acgatccgca atgatatggc atcgctggaa gacgccggtt tgatcaccaa gactcatagc | 180 |
| agttccggtc gagtaccctc gactcaaggc tatcgctact atcttgatca tctggtcgag | 240 |
| ccagtgcgtg tttcccaccg tgaactagcc acgatcaagc aagcattcgg tcaacgctac | 300 |
| aataagatgg atgaaattgt ggcgcaaagt gcgcagattt tatccaatct gaccagttac | 360 |
| acggcgatca gcttagggcc agaagtgaat aacattaaat tgaccggatt tcgccttgta | 420 |
| ccgttgggca atcaccaggt tatggcgatt ttagtgacga caacggcaa tgttgaaaat | 480 |
| caggttttca ccgttcctga agcatctca tctgacgagc tggaaaaggc gattcgcatt | 540 |
| gtcaatgatc agctggtcgg tttgccgctt attcaagttg ctcagcggct aaagactgat | 600 |
| gttccgtcga tgctgatgca gtatctgacc agtcctgaag gcttcctgga tatcttcggt | 660 |
| aatgtcttaa agtccgccgc ttcagagcgt ttctatgtgg gtggccgctt aaatttaatg | 720 |

```
gactatctcg gcgactcgga tattcacgag ttgaaaaaga ttatgtcctt gattgatgct      780
gatcatggtg atcttactga actgcttggc ggaccggttc gccaaacgcc ggttacggtt      840
cgtctaggcc cggagttaaa gccaattgat ctggccaatc tcaagctgat taccgccagt      900
tatgatgtcg gtgaccacgg cacgggaatg attgccctat tagggccaac ccaaatgccg      960
ttttccaag                                                              969
```

<210> SEQ ID NO 48
<211> LENGTH: 1336
<212> TYPE: DNA
<213> ORGANISM: Lactobacillus rhamnosus

<400> SEQUENCE: 48

```
ctaattcacc gtatacagcg gcgaataaac tgaagatgac ggtggctaag acgctggaca       60
agtttcagct ggatgtgacc acaggcaacg ggcttaaggc gattaacatt ttcatgaatg      120
acagcacgaa ggaaaatgtt gaacaatatg aatattggat taacaatttc attgaacgcg      180
gcgtgcttga gccaaaataa gtctctttga aaatcacggt aactctcctt tcgaacaagc      240
ggagattacc gtgcttttttt gttgtatgaa tcacggatta aagcgttacg actggtaaag      300
catgagctac atcacggatg cgtggtttaa gtgaggcaaa tgtcgtgacc gccaaatcga      360
gcggccaaaa gtggtaagct ggaaacattg aaatttttgat atgaaggagg cttgtatgt       420 ttgaacatgg gtttattgag gtacacgatg ccaaccagaa caacttgcaa catgtgaatg      480
tgaagatacc taaggatgcc attacggttt ttgtgggtcg gtctgggtca ggcaaatcat      540
cgttagtgtt cgatacgatt gctgcggagt cacggcggga gttgaacgaa acttttccga      600
gctttaccca gcaatattta ccaaagtatg gccagcctga tgtcggctcg attgatcact      660
tgccggttgc cattgtggtg gagcaaaaac gtatcgggaa aaacgctcgc tcaactttag      720
caacttacac gggcatttac tcactgttac ggctgttgtt ttcgcgtgcc ggcaagccat      780
tcatcggcta ttcggacaca ttttcgttta atttacctca agggatgtgc cccacctgcc      840
aaggcttagg ttacgtagat gatattgacg tcagtaagtt gattgatccc aataaatcgc      900
ttaaccaaga ggcgatcacc tttgtcagtt ttggaccgga tacttggcgt tggcggcgtt      960
atgcttacag cggggttgttt gataatgaca aaccccttacg tgactatacg cccgaagaaa     1020
tgaaactgtt actttatgca ccgcaacaga cactgaagca tgcaccggct aaatggccaa     1080
gaacagcgct atatgaaggt gtcgtgcctc gcattaaacg atccattatt ggtaaaaaag     1140
aagcagaaca tcataaggcc gcactggcag aaatcgtaac gcgcaagcct tgtccggatt     1200
gccaagggac acgcctacgt ccggaagtgt taacctgttt gattaatcaa accaatattg     1260
cccaagtgct gcaaatggac ttggtaaacg tacggcattt tctaaaaaac attcaagtgc     1320
cgctggttca ggatgt                                                    1336
```

<210> SEQ ID NO 49
<211> LENGTH: 760
<212> TYPE: DNA
<213> ORGANISM: Lactobacillus rhamnosus

<400> SEQUENCE: 49

```
aatgacacaa tcggccgatc cccacgcgcc gccattgctt gcaaagtggc ggcaatggga       60
tactgaccgc cataagtcat cgccatttga acatcccaat ccggaagtgc ctggcgcaag      120
cgatcgttta ttaactgaag agattgcggg cattttcatt ttaggaacaa atggcgagtc      180
```

```
ttacgtctta gcggaagatg aaaagttggc atttgtagaa catgttatcg actatgtcca      240
tggtcgaacc aaagtactgg taggaacagg tttgaacgga acagcggaaa ccattcgctt      300
cagtcaaaag gtagcgtctt taaaaccaga cgcaattacc ttagttgctc cttcatttgt      360
tgctccctcg caacaggaac ttgttgatca cgttgctgcc ataattcacg cggacgatat      420
acctgttcta ctgtacaata tgccagcaaa acgggcatt aacattgagc cagcttcatt       480
aaaacagttg tcaaatatg agaacttaat cggtataaaa gatagctcgg gaaagtggga      540
gaattttgac ggttatctag ccaatcgccc cgaacgacca ttctcagtta ttatgggctc      600
tgacggtcgc attcttgaaa gctttcagca cggtggtaat gcggctattg caagtacagc      660
caatctcctg acggctaaca atgtagcgtt gtatcaagca tttgttaatg acaatattga      720
aaaagcccag aaatttcagg atcggattca gccccttaga                           760

<210> SEQ ID NO 50
<211> LENGTH: 1056
<212> TYPE: DNA
<213> ORGANISM: Lactobacillus rhamnosus

<400> SEQUENCE: 50
aagacagttg ccaaaacccc aatcacgaga ctgacaagaa cggctaatac agcagccagc       60
gtacccgtag ttggccaata aggcgcaatc cccgtttcaa tcagaatgac caccgccgcg      120
gcgacaatgc cacaaaccgc gtaataaacc tcaacctcaa aatgttttag taaataaccc      180
attagtttgg caatggcaat gagcccgatc aacgcaccta ccataaaagg taccagtaag      240
gcgacagatc aaggtgtcga ctggagccgg taccaaggag ataacggtgt ctttggttac      300
tccactgaca agttcggcat ctctcaaatc ggtggctata cggctacgg cacgtacgag       360 caaaccacgt ataagacaca ggttgcatcg ttgattgccg ctggcaagcg agcacacacc      420
tatatctggt ggcagaatat cgacaacacc aattttgcca agcaagtact agatcatttc      480
ttgccagaga ttcaaacacc aaaagggtcg attgttgcgc ttgattacga ggccggttca      540
acaaatacgg caactttgct gtgggcactc gactatatcc gtgatgctgg ttacacgcca      600
atgctgtacg gctataagag cttcttgatg agtcacattg acttgtcaca gattgccagt      660
cgctaccagc tatggcttgc ggaatatcct gattacaatg tcactactgt tccgaattat      720
ggctacttcc cgagttttga taatgtaggt atcttccagt tcacttccac ctatcgcgct      780
ggcggccttg atggcaacgt tgatcggtct ccgcgaacgc tcacaaaacc tcgctgttgt      840
caatgaagct atcgagaaca cagtttcccg tccagcttac gtaaccttg acgacaataa       900 gaaggaaggt tcccttgttc gcttaccaga acgtggcgaa ctcgaaccag aagttgacga      960
atcactggtt gttgaatact ataaccagaa actttaatac ttcacagcta cagccaactc     1020
tttgcggagt tggctgtttt tatttggaat cagatc                              1056

<210> SEQ ID NO 51
<211> LENGTH: 1310
<212> TYPE: DNA
<213> ORGANISM: Lactobacillus rhamnosus

<400> SEQUENCE: 51
cgccggtgaa cgcgtttcag accagagcgt gaacaggagc gcttagaaat cggagtgtaa       60
gtggcctcag acgtgatgac ccgggctttg gccattgcgt tccaggtctt tacacgcaga      120
cccatgcgcc ggtgaacgcg ttttagaacg tgaaccggcg cgcacacgta accccccta       180 aaaaaccacc accccaaacc taacgctcct tagattcaaa cctccaaaca cctcacttgg      240
```

-continued

| | |
|---|---|
| cactccccat ttacagcatt agaatccgcc ctgtttttaa ggtatactaa ggcgtactag | 300 |
| accaaaattt aaggtgggac aagcacttga aaaagttcgt caatcgggtc aagacgcttg | 360 |
| ggactcgatt ttgtcgctgg ttcacgcaat tcgtgacccg gcatcccgat tccaaatcag | 420 |
| ataccaatca acaactaacg ggtaaagctg ccgttgtcta ttatggcaac gtcacacttc | 480 |
| aaagcatcaa acaactgtg ttactattta ttaggcgttt taggcattgc tgtcgtgttt | 540 |
| ggccttggct tgtttggcgg ctattttgtg tcgattattg acgcaacgcc aattccaact | 600 |
| gaaaccgcta tgaaagcaac gttgtccaat accagccgca cttccagcat gtattttgcc | 660 |
| cacaacgtca agcttagcga tgttaaaagc gacctgtact caaccaaagt caacctcaat | 720 |
| gagatgtcgc catggctcac caaggcgatt atcgccactg aagatgaaga cttctatcgc | 780 |
| cacaacggca tcgttcctaa ggcggttatc cgtgcgttct tctccgactt aaccggtatg | 840 |
| gggagtcaga cgggggggtc aactttaacg cagcaagtgg tcaaaatgat gtttttaaat | 900 |
| tcggagacaa cctttaaacg taaggctgct gaaattatgc tggcccggcg cttgaacaat | 960 |
| cacttcagta aaacaccat tctggcaact tatctcaatg ttgctacgct tggtcgtaat | 1020 |
| aacaaaggcc aaaatattgc cggagttgaa gcagcggctc aaggactgtt tggggtttcg | 1080 |
| gctaaggaag ttaacctgcc ggaagcggct ttcatcgctg gcctgccgca aagtccatt | 1140 |
| gtctataccc cttacacggc cgatggtaaa ttgaaaacca gtctcaaagc cggtatcaat | 1200 |
| cgccaacaaa ccgtcctgtt ccgcatgtat cgggctggcg ttatcagcca tcgtcaatat | 1260 |
| gttgctgcca aatcatttga tccactagtg tcgacctgca ggcgcgcgag | 1310 |

<210> SEQ ID NO 52
<211> LENGTH: 1859
<212> TYPE: DNA
<213> ORGANISM: Lactobacillus rhamnosus

<400> SEQUENCE: 52

| | |
|---|---|
| ccttgcagcg atccggttat ggggtttatg ttccgctttt ttccgggcat gggacagtgg | 60 |
| agccgttaga tattttgaca aaaggcaacc cggatatttg tgggcagaa agtagtgccg | 120 |
| cggttgcgca tatgaccgca aaatacgcca aggtgtttgt ttttggctta tcactgggag | 180 |
| gtatttttgc gatgaaggcg ctagaaacct tgccagggat tacagcaggc ggtgtttttt | 240 |
| catccccgat tttgccgggc aaacatcact tagtaccggg ttttttaaag tatgccgagt | 300 |
| atatgaatcg gttagcaggc aaatcagatg aaagcacaca gattctggca tatttgccgg | 360 |
| gacagttggc cgcaatcgat cagtttgcca cgacggttgc tgctgattta aatttagtca | 420 |
| aacagccgac ttttattgga caagccggtc aggatgaatt agttgatggt cgattagcgt | 480 |
| atcaattacg cgatgcctta atcaatgctg cacgcgttga ttttcattgg tatgatgatg | 540 |
| ccaagcatgt cattaccgtt aactcggccc atcacgcatt agaagaagac gtaatcgcat | 600 |
| ttatgcaaca agaaaacgag ggatagcatg accacagttg gccatattcg taatgaacta | 660 |
| ttagcaacat ttcgtaagaa tccgaacatt gattattcgg ttcaaacact cagtcgcgca | 720 |
| cttaagttaa gtgaaggcgg cgattttaaa gtactcgtcc aggcgttaaa cggtatggaa | 780 |
| aatgataacc tgattcacgc caatcacgaa ggacgttatg cattgggcgg cgcgcctaaa | 840 |
| gtcttgaccg gcactttccg cggcaacgaa aaaggctttg gcttcgtggc agttgagggc | 900 |
| ttggacaatg atgtttatgt accggcgatg aacaccgatt ttgcgcttga tggcgatacc | 960 |
| gttgaagtgc ggatcgttcg tgaagcccgt cccaatgata gtcgcggacc tgaaggcgaa | 1020 |

```
atcactaaga ttgtgcagcg cagtttaacc acactggttg gtgaattcaa accatttttcc      1080 gataaagatc gggctaagtc tggatttatc ggaatggtgg ttagtcatga aaagaaactg      1140
aagaattttc cggtttatgt taaagatacc ggtaatattc cgcaactcgg cgatatgacc      1200
gtgacggaga ttactgaatt tccaaccgaa tatcatccca agttgatgta tgggatcgtt      1260
gtcgagacgt taggcaacaa gaatgatcct ggcgttgata ttatgtcgct ggtcatgcaa      1320
aaccatatca aaacggaatt tccggatgaa gtgatggatc agaccaatgc cattcccgat      1380
cacgttacgc cagaagaacg agttggtcgc aaagatatta ccgatcaggc tgttgtcacg      1440
attgacgggg atgacagtaa agactttgac gatgccgtgg tggtttggaa attaccaaat      1500
ggaaacttcc atcttggggt tcacattgcc gatgtttcgc attatgtgac ggaaggctct      1560
gcgttggatc aagaagcatt tgatcgtggt accagtacgt acttggttga tcgcgtcatt      1620
caatgctgcc atttcgacta tccaatggca tttgttcgtt aaatccaggt gtagatcgat      1680
tggcaatgtc atgtgatatg gaaatcgatc atgatggtca tgtcgtaaac cacgagattt      1740
atcaaagtgt gatcaagagt catgcccgga tgacctacaa caatgtgaat aaaatcgtga      1800
ccgatcacga cccggaagtc atggccgaat atcaagaact ggtacccatg tttgaagac       1859

<210> SEQ ID NO 53
<211> LENGTH: 887
<212> TYPE: DNA
<213> ORGANISM: Lactobacillus rhamnosus

<400> SEQUENCE: 53
cttatgaaaa tgaaattatc atcacgattc gagctggacg caagaaccat cccttgttgc       60
tctcagctaa tccacagtat gcgcgggtgc aaattaccca cattccattt acaaatccag      120
acgttcctgc aaccttcacg atgacgttgc ggaagtattt taacgcggct acgttaacag      180
agattcacca agtgcaaaac gatcgggtac tacactttga attctccacg cgggatgaat      240
tgggggatga actggggctg cgcttgatca ttgaaatgat gggtcggcac agtaacatct      300
ttttagtcag caagcgcacc ggcaaaatta ttgatctcat tcgccacgtt tctgcggatc      360
aaaatcgcta tcgtccgttg atgcccggtg ccccgtatgt cgagccgcct aagcaagata      420
aagtggatcc gtttcatgat tcggagcgga tttatcacga acttgaacgt caggtaacac      480
cttcattgag tcgcgccgcc ttgctccagc aacattacca aggacttgcc aaggattctg      540
cagctgaatt ggccctgcga ctcaatcaag gcgatgccgg ctgggatagc tttttttgcag      600 cgctggcaac ccctgaaccg actattacaa cccaagggaa aaaagccgtt tttaccgcga      660
tcccgtatca gtctctgacc ggcgagcagc aacattttcc aaccttaagc gcgatgctgg      720
atgcctatta tgcgcaaaaa gcggaacatg atcgggtttt gcaacaaggc gggaacctga      780
ttcatgtgat caaaaatgtg attgataaag atcgcaaaaa gcagcgcaaa ttaaagcgaa      840
cgctggaaga aaccgaaaaa gccgatgatt atcgaattcg attcaag                    887

<210> SEQ ID NO 54
<211> LENGTH: 999
<212> TYPE: DNA
<213> ORGANISM: Lactobacillus rhamnosus

<400> SEQUENCE: 54
gcctatttgg gattgacaga aaaacaaacc ggcagcctgt atcacctgag cgaaggccag       60
aaaaaaatgg tgcagctgat cgcaatgtta agtctggagc gaactttttt gctgttggat      120
gaaccgttta gcggcttaga tgaacgtgcc tgtgcattct ttgccgcgtg gatcaaggaa      180
```

```
aaagcagcta agcaggcgtt tttgattgtg acgcaccgac tggctccgct agctggcatc      240
agtcaccagc atgtggcact tgccgatcac cggttacaca ttctacagga gtgacatgat      300
gccagtaaaa aagaccaatg cagtgaatct gagtttattt attctactgc tgacacttga      360
aatatctttc agccatgcgg tgagtcttaa tgtagcgttg atcggactgg caagcggttt      420
tttaatatgg cggcgggcgt ttaaaagtct cgtcgttttg gccttgttac cgttgatccc      480
ggctgccagc acgtactggg caattccct gcatggtacg atacgactt acgctttgct       540 gctgtgggtt cgcacctatg ctttcaccgc gttgggattg tgtttctta cggagttga       600 cttagagacc ttgctgttat ggctggagca gcataaatta tcccctaatt ttgtttacgg      660
attactggtt gtgatccatg ccttgccgca aatcatgcat gaagtggctg ctattcgtga      720
agcgagtctg ttacgtggcc aaaagttgca cgcgtggtcg ccgatgattt atgtgaaggt      780
gatttttgtt gccatgtcgt ggcaggacca gtacgtcaaa gctatgtatg cccatggtta      840
taccgaagga gcagcgcgaa cggttcacca aaccatccgt agttcatggc gcggcttgat      900
cgccatggtg gggggatttg tccttttaaa tctaattgac cgttagtttg aggatcaaaa      960
agaggtggtc gcgcggtgtt taagcgattg tgcagggac                             999

<210> SEQ ID NO 55
<211> LENGTH: 846
<212> TYPE: DNA
<213> ORGANISM: Lactobacillus rhamnosus

<400> SEQUENCE: 55
tttgctttac aaaaaccagc atagcgatca ttccttaatt accagcataa tcaatcctta       60
attaatccta aattgtgaaa aggtgcatta atagcttaca ctatcattgg aggaaaggag      120
tgacgatgat ggcgaagata ttaattgttg aagatcatag gatatccagg cacttattga      180
aagatgtact aaccccgact tatacggtca ctcaggctta tgacggcatt caggctttaa      240
cggcctttca tcgagaacaa ccggacttga tcattctcga tttaatgctg cccaacgtga      300
ctggtgaaag tgttttaaca accattcgta aaacatccca agttcccgtg ctggtgttaa      360
cggcgattca ggaaaaagcc aaaaccgttg ccctgctgca gcaaggcgca acgattatt      420 tgaccaaacc gtttgacatt gacgaattac tagcacgcat tcaagtccaa ctgcgccaag      480
tcagcggcca accaataacg acgaacgatc aactaaaagt cggcgaaatt caattagacc      540
ctaagcgtca tgtggtgacc gttaatcagc aaacccctaac gctgcctaaa aaagaatatg      600
acatgttggc gttaatgatg cgtgatcccc atcaagtctt tgataaaagc caactttatg      660
aacatgtatg gggggagccg tttttaaatg ccgataatac cctaaacgtt cacatcagca      720
acttacggac aaaaatcaat gaacttgccc atgatcccaa atacatcatt tcaatctggg      780
gcatcggtgt acgtttgatt tagcaaggag aaatcattat gcttggcttc cttatttac       840 ttatcg                                                                846

<210> SEQ ID NO 56
<211> LENGTH: 780
<212> TYPE: DNA
<213> ORGANISM: Lactobacillus rhamnosus

<400> SEQUENCE: 56
tacgatttgc ttcagttcct caagatccgg ataacttggc aggaattgat tccaaccgca       60
ttgccaagta tcaagaagcg ttcgcaaaag cctacaaacg actcatggaa gcaatcagtt      120
```

-continued

```
ccatgagcat tagctggacg attatcggtg ctgcaagtcc gcgctgggct caaaaagttt    180
tccctgatgc cgccacccct gaagaagcaa ctgagctact ctgggaggca attttcaaaa    240
ctacccgaat cgatcaaccc gatccggaag ctgcctggaa agcccacgat caaaagctgc    300
gggaaaaagc ggcctggtta acaacgaac aatttgatca gctgcattac atggctccgg     360
gaacggattt ggtagtcggt ttaccaaaga accacatttg ggaaggcgcc ggcgctttta    420
acccgcgtgg tgaggaattt atggctaaca tgccaaccga ggaagtcttc accgccctg     480 attttcggcg catcgacggg accgttgctt ccaccaaacc gcttagttat ggcggcaaca    540
tcctcgaaga tatgcacttt actttcaaag acgggcaaat cgtggaagcc cacgccaaac    600
aaggcgatga cgtcttacaa aacctgctaa aaacgccggg tgctcgttca ttaggcgaag    660
tgtcgttggt tccggatcct tcttccatct cacaatcggg ccttattttc ttcaatacgc    720
tggttgacga aaatgcttcc gatcatatgg cactcggtca agcctatccg ttctcagtca    780
```

<210> SEQ ID NO 57
<211> LENGTH: 1569
<212> TYPE: DNA
<213> ORGANISM: Lactobacillus rhamnosus

<400> SEQUENCE: 57

```
ttgcatcccg ctctgctgcc tagttttccc ggacggcagg gcattaaaga tgcgtttgat     60
tatggcgtca agtgaccggg cgtgacggtt cattacgtag atgccggaat cgacaccggc    120
gaaatcatcg cacaggatcc ggtccgcgta agcccgggga tgacgctggc acaattagaa    180
gcagccattc accatcagga acatcaaact tttcccgcaa ctgtcaagca actcattgaa    240
gaaggagcga tttaagtgaa gcgtgcatta ttaagtgtct ctgataaaac tggtttggta    300
ccttttgcaa aaggtctggt tgaacgcggt tttgaactga tttcgaccgg tggtacccat    360
cgcgcactgg ctgaagctgg ggttgcggtg accggcgtag aagcagtaac cggttttcca    420
gaaatgctcg atggtcgagt taagacactg catcctaaga tccatgccgg catcttggcg    480
cggcgggatg atcctgccca tatgcaggca ttggcagatc atgatattca gccaattgat    540
gtggtttgtg tcaatctta tccgtttgcc gcgaccattc agcgtgcggg tgtgacgcgt    600
gccgaggcga ttgaacaaat tgatattggt ggcccgtctg cgttacgtgc ggcagctaaa    660
aatagtgaca gcgtctgggc cgtggttgat ccggcagatt atgcggatgt tttagccgga    720
ctcgatcaaa atgatgctga tttacggcaa cggttggcag ccaaagtctt ttccgccact    780
gccgcttacg atgctcaaat cgcccattac ttagatccga gccttttccc agagcagttc    840
acgccaactt atcacaaacg gcaggacttg cgttacgggg aaaacagcca ccaacaagct    900
gccttttatg ttgagccgaa tcctgatcca accagtcttg ccgctgctaa gcaattacac    960
ggtaaagagc tttcttataa caatatcaag gatgcggatg cagcattggc aatgttgcgg   1020
gaattcaaac aaccggcagc cgtggccgtt aaacatatga acccatgcgg tattggcttg   1080
ggcgatacgc ttgaagccgc ttgggacaag gcatatgccg ccgatccgat gtccattttt   1140
ggcggcatca ttgctttgaa tcggcgggtt gatcttgcca ctgccgagaa aatgcataaa   1200
cttttccttg agatcatcat ggcaccggca tttgatgatg atgcttatga gattctggcg   1260
aagaagaaaa atgtgcgctt attgacgatt aataccgccg atacgccaga gaattggga   1320 acagaaacaa cttcaattta tggtgggttg ttgattcaaa cacgtgacga caaagctgag   1380
acaccagccg atatgacggt ggtgacggag gtcaagccga ctgaagctca actcaaggca   1440
ttggcatttg ctcagacggt ggtcaaacat gttaagagta atgcgattgt cgtggctcag   1500
```

-continued

| gctgatcaga cgttagggat tggcgccggt caaatgaatc ggattggctc ggttgaattg | 1560 |
| gcgttaacc | 1569 |

<210> SEQ ID NO 58
<211> LENGTH: 1112
<212> TYPE: DNA
<213> ORGANISM: Lactobacillus rhamnosus

<400> SEQUENCE: 58

| gatcgtgtca gtggctttag tggcaggttg tgttggcctg catcgattcg ttgctgaact | 60 |
| tgttcttccg ataaccctttg atcaggtgaa atcttttgct ctgccatcgc atgccctcca | 120 |
| gtacttttca tccattttac caatccagac aacaagatgc ccgaatatca cacttgtttt | 180 |
| tacaaaactt tgaagttgtt ggcgtggttg ggttatggtt agggagtcat gaaaccgtca | 240 |
| taatgagatg aaagttatag aaagaagtgc tctcatggta aaacgaaacc caaatggaac | 300 |
| ccgatttatc acattaccta tggctacca cttgtggacc cagacattag cagcggccga | 360 |
| ttcattactg acgttgcacg gcggaccagg cggcacgaat gaagtgtttg aaaatttcgc | 420 |
| tactgaactg gcatcttttg gtgtccgtgt ctcacggtac gaccaactgg gttcattttt | 480 |
| ctctgatcaa ccggactttt ccgatccggc taatcaaaag cgttttctca atatcgccta | 540 |
| ttatgttgac gaagtggaaa atgttcggca acagctgggc cttgatcatt tttacctatt | 600 |
| aggtcagtcc tggggcggtg tgttggcgat tgaatatggc ttgaaatatt cgcagcatct | 660 |
| taagggactt attttgagct cgatgattga taatttggat gagtatttgg ttaacattaa | 720 |
| caagattcgg gagaccatgt tttctagtga tgacgtggca tacatgcaac ggattgaagc | 780 |
| ccagcacgcg tttacggatg ccaaatacca gcaattggtg cgtgagttag gggagcaata | 840 |
| tcttcatcat gccaaagatc cccagccgcg ccatttaatt agcacgttgg cgaccccgt | 900 |
| gtatcatcat tttcaaggtg ataatgaatt tgtgatggta ggcgcactta gggactggga | 960 |
| tcgacgggct gatatacacc gtctgacaat gccgacttat ctgacattcg gtggacatga | 1020 |
| aaccatgccg ttatcagctg ccaagcgaat ggctcggaca ataccaaatg ccactttgca | 1080 |
| tgtcacacct aatgccggtc atggtcagat gt | 1112 |

<210> SEQ ID NO 59
<211> LENGTH: 1570
<212> TYPE: DNA
<213> ORGANISM: Lactobacillus rhamnosus

<400> SEQUENCE: 59

| atagggggatg agtaggcgat ataggcagtt tgatgctaac cgcgccggct cgcgctcacg | 60 |
| aggaggatta aatttgattt cactaggaat ttacgaaaaa gcactgccca ggaccgaatc | 120 |
| ttgggttgaa cggttgaaaa tggttcggga tttgggtttc aacttttttgg agttatcgt | 180 |
| tgatgaaagt gacgaacggt tggcccggtt ggattggacg gcagcgaaac gggcgaaggt | 240 |
| gcgtgatgct tgttggcaaa caggggtgcg gatccataca ttgatgttaa gcggccatcg | 300 |
| tcggtttcca ttaggctcgg cagacccggc gatccgtgaa aaaagtctga cgatgttatg | 360 |
| taaggcgatt gatttggcta gtgatctggg cgttcgcaat gttcaactag ccggttatga | 420 |
| cgtttactat gagccgaaaa ccttagcttc acgagaatat ttcatcgaga atttgaagcg | 480 |
| cggtgtggcc tatgctgcgg ctaaagaagt gatgctggca attgagacga tggacgatcc | 540 |
| gtttttgaat tcactttcca agatcaagac gattaaagat gagattccga gtccgtggtt | 600 |

-continued

```
gcaagcatat ccggatctgg gcaacttgtc agcctggccg gaaaacaatg tcggtcgcga      660
gcttgaactg ggaattgcaa acatcgtctc ggttcatttg aaggataccc aagcggtgac      720
ggtaaaaagc aaagggcaat tccgcgatgt cccgtttggc gctggcgtgg tggacttttc      780
cggctgcctg cgtacgctca aacgccttga ctacagcggt gcctttacga tcgagatgtg      840
gacggaaaag gccgctgatc caatccaaga agtgaagcag gccaaggact ttttcgatcc      900
gctgtttgtg caggccggtt tgttcagga gccagtggca aaaaccaatg tcccatcatg       960
aagcgcctgc tgacctgcac acgaaaaaag tcgccaattg cttgccggct ttagacgatt     1020
catttaacta taggcgaatg gcagtggggc tgatctggaa gtaatcgatt aaatagttag     1080
caaccccgtc atcatcattt gagcccacgg taatgtccgc aatttgtttg atttcaggaa     1140
tcgcgttacc catggccacc ccgatgccgg catactccag catgtctttg tcattttcct     1200
catcgccaaa tgcggccagt tgttcgcgcg ggatgcggta aaagttgagt gcggctttta     1260
aaccgttcat cttattgaca tttggcggca ggatttcaag cagtgtgcgc cgggatcgcg     1320
tgacggtcag ctgcttgagt gactgggcag cgtctgatgc ggcatcgatc taagtgcaac     1380
gcgattggca aatcagtatg atttgccgca tcaataactt gtgccacaaa actgtcgcgg     1440
agaaattcta attctgtggg atgaatcgcc ataataaatg gtgcctgcag ttcttccgcc     1500
ttttccaacg tggcagtgaa gagttgtcct gagcctgcgt tgaaagcagg aatggcaaaa     1560
tggtgttcct                                                            1570
```

<210> SEQ ID NO 60
<211> LENGTH: 948
<212> TYPE: DNA
<213> ORGANISM: Lactobacillus rhamnosus

<400> SEQUENCE: 60

```
aactagtgga tcaaacatga cagatcccat tgcgtttttg caaaaactaa tccaaattga       60
ctctgcaaat ggaaacgaac ttgcagtagc ccgcgttttg caagctgaac tcgaagcggc      120
cgatattcca accaaattga tcccatacaa agatgatcgg gtcaatttag tcgcccagct      180
caatcacggt gaccgcgtat taggcttcac cggccatgaa gacgtggtga gtcccggcga      240
tgagaacgcc tggacctatc cgccttttc cggaaagatc gtgaacaaca ccatgtacgg      300
tcgcggcacc gatgatatga aaagtgggct agcagccatg accttggcac tgatccacct      360
taagcaaagc ggctttgccc atccgctgcg tttcatggcc acggtcggtg aagagtttgg      420
tgcaatggga gcgcgccaac tcaccgaaca aggttatgcc gatgacttaa ccggactcgt      480
ggtaggcgaa ccaacgaaca aattgctaaa atacgcacac ggcggaacgg ttaactacga      540
aattgacagc gaaggcgttt ccgtccacag ctcccggccg gaaaaaggcg ttaacgcaat      600
tgaagggttg gtggcatttt ctactcccga accgcacgcc tttgatcagg ccctgatga      660
tcctgacctt ggtccattcc gccactccat taccgtgatc aaaggcggcg atcaagtcaa      720
caccattcct gcccatgcat acttacgcgg caacttgcgc ccgactcctg cagcaaatat      780
cgaattagtc gtcgggttat tggaaaaatt agtcgatcag gcaaataaag ccaccgccgc      840
taacttgacg ttgaacgttt tacatcgttt tttgccggta cactctgaca aaaacgggca      900
tctcgtgaca accgctaacg aagccattgc cgctgtgact ggtaagcc                   948
```

<210> SEQ ID NO 61
<211> LENGTH: 1188
<212> TYPE: DNA
<213> ORGANISM: Lactobacillus rhamnosus

<400> SEQUENCE: 61

```
ggttagaagg aattggcgag tttgcgcagt gaatgctttt gtattccaat atcatcgcca         60
aagcctgatt aataaatcga ttttgtatct taaataataa atatgtacac gttttcatga        120
atatgagaac gtgtttttta tttaaaaaag ataaagcgct tgcataagag ataaatggct        180
tttatattta acttgttcac agaggtaccc tgtgatacac ggttgttcta tgatgttcgt        240
aaactaatag aaagatggcg ggaaaatgaa aattgatatt gacaaaacgt ctatgattcc        300
agtttacgaa caaattgcaa atagtttgcg agacatgatg tatggcggaa gtctacagga        360
tggagaccgt ttagactctg agcagaagat gtgtcgcaac cttaatgtca gccgtggaac        420
tgttagaaaa gctattgata ttctactgaa ggagggtatg gtcaaaaaga ttcatgggaa        480
aggaaccttt gtcagtaacc caaacgttga gtactcgttg aatgatcagt taatgtcatt        540
cgctgagtcg ctcgataatc aacacttaag ttacacaaca caagttattc agcaggaact        600
acgacccgcg accgcgaaaa ttgctgatat gctcaagatc cctattgata gtcagtactt        660
gtatttagaa cgattgcgat cagttgccga tgataagtta atgttaatcg aaaatcgcat        720
taatattacg ctctgtccgg gaattgagaa ggtcaatttt aacaacatta gccttttaa         780
tgagattgaa gaactagcaa aagaaagat tagctttgcc cgcagtacct atgaagcact         840
tacgattggc acggaacgtg ggaaactttt agagcttcct tcttccacgc cggctttaaa        900
aatgcaacag acagtgtatc tttctgaaaa agaaccagtc gaatacggtt ccgtctggtt        960
aaaaggaaat aagtactttc tcacaacaac tttgcaaaga cgataggagg aattgaacca       1020
atgccattag taaatggatt cgatttgatc aaaattatta aggatcggca cgttgtcgca       1080
ggagctttca acacaactaa tctggagaca accatgggta tacttcgagc ggttgaaaaa       1140
agcggcatac catctttcat tcaaattgcc ccgacaaaca tccccgtt                    1188
```

<210> SEQ ID NO 62
<211> LENGTH: 1637
<212> TYPE: DNA
<213> ORGANISM: Lactobacillus rhamnosus

<400> SEQUENCE: 62

```
ctagtggatc ccttcttatt tacaccgcaa ctgaccatcg aagaagtcaa aaagccggc          60
tgggcctacc cggtattcgg ttatcttgat cacgaggacc cgtttgcaaa actggcgagt        120
catattaaaa ccgtcaaccc taatccgaca aaatgggcaa tcgaaaaaga taatctcgcc        180
gttttcaaat tgaagcgat tatgaagcag ttcccggacg ctaccttccc gattgatgct         240
tctcgtttta ttgaaaaaca gcgcctgatc aaaaccgctt cagagatcaa acagatggaa       300
gccgctggtg ctcaagccga tcgggcattt caggcaggat tcaatgccat taaagccgga       360
gcaaccgaac aagaagtcgc cgctgaaatc gattatgcca tgatgaaaga aggcgtcatg       420
cacatgagct tcggcaccat tgtccaagct ggtgtcgatg ctgccaaccc gcatggcgaa       480
ccgatgggaa caaactcgc acctaacgaa ttggttttgt tcgatctggg caccgacaat        540
catgggtata tgtccgatgc gacccgcaca gttgcttttg gtcaagtcac tggtaagcca      600
cgggaaattt ttgacatctg tcttgaggct aatttaaccg cgatggacgc tgttaagcca      660
ggacttaaag catccgaact ggacaaaatt gcgcgtgata tcattactaa agcgggctat      720
ggcgagtact tcaatcatcg gctcggccac ggcatcggta tgtcgacgca cgaattcccg      780
tccatcatgg aaggcaatga tatgatcgtg ggcgaagatt ttgggatgcg tgtcagtgtc      840
```

```
cttgccagca gcagctctgg taacgcaacc tatattgaaa cgcctggtca aaggtgtta     900
gtggatgccg gtttatcagg caagaaaatt gaagcgctga tgaagagcat cggcagagat    960
ctaaccgatg ttgacagtgt ttttatcacg catgaacata gcgatcatgt gcgtggtgta   1020
ggcgtgttgg cgcgacgtta tccgcagctc aacgtttatg cgaatgccaa acgtttgca    1080
gctttaccaa aagtgtggg caaaattcct gaagcacagc tgcggttgtt tgatatgggg    1140
acaactttga cgttaggtga tttagatgtg aaagttttg cgtttcgca tgatgctgcc     1200
gcgcctcagt tttaccaatt tcatcatgac ggcaaggcct tcactatcct aaccgacacg   1260
ggctacgttt cagatcgggt tgccgggacg attcgcgatg ccgatgcgta tgtgatggaa   1320
tgcaatcacg accttgaaat gttgcggaca ggtccgtatc cgtggccgtt gaagcaacgg   1380
attttaagcg atcaagggca cctgtccaat gaggatggtg cggatgcttt gatggatgtc   1440
atcggtttgc ggacgaagcg gatttatttg gggcatttat caccgcataa caacaataaa   1500
gccactggcg catttaaccg tggcgtcgtt gttggcacaa aaggtctgg cggtggatca     1560
tgactttcat atttatgaca ctgacccggc agttgccgac ccattgtttg ttgtgtgaag   1620
cggtttgaaa gcagttt                                                  1637
```

<210> SEQ ID NO 63
<211> LENGTH: 224
<212> TYPE: PRT
<213> ORGANISM: Lactobacillus rhamnosus

<400> SEQUENCE: 63

```
Leu Arg Gly Leu Cys Ile Gly Ile Val Ala Cys Glu Phe Phe Glu Ile
 1               5                  10                  15

Pro Leu Thr Pro Ser Glu Ser Ala Asp Asn Gly Ile Gln Lys Arg Asn
            20                  25                  30

Asp Val His Gln Trp Leu Val Ile Phe Arg Arg Asp Leu Leu Ala Asp
        35                  40                  45

Leu Lys His Phe Asp Asn Gly Asp Arg Gly Ser Lys Gly Cys Val Phe
    50                  55                  60

Asp Gln Ala Asp Glu Thr Ile Gln Trp Arg Asp Gly Arg Ser Cys Leu
65                  70                  75                  80

Arg Asn Asn Asp Phe Ala Gln His Gln Ser Pro Arg Gln Ser Asn Cys
                85                  90                  95

Ile Ser Arg Phe Pro Leu Pro Gly Ile Asn Arg Gln Gln Arg Gly Ala
            100                 105                 110

Gly Arg Phe Gly Thr Ile Arg Pro Arg Val Lys Glu Cys Tyr Asn Ser
        115                 120                 125

Arg Gly Arg Gly Ile Leu Asp Ala Met Arg Glu Asn Thr Arg Asp Asp
    130                 135                 140

Glu Ala Gly Ala Glu Glu Asn Asp Glu Leu His Gln Gln Arg Arg Ala
145                 150                 155                 160

Lys Glu Pro Asn Val Lys Asn Gly Asp Ser Phe Cys Asp Ser Asp Gln
                165                 170                 175

Asn Thr Phe Thr Asn Arg Tyr Ala Arg Gln Cys Gly Tyr Lys Cys Asp
            180                 185                 190

Asp Gln Ala Asp Arg Lys His Glu Cys Asn Trp Asn Gly Val Phe Asn
        195                 200                 205

Ala Gly Cys Tyr His Leu Arg Asn Cys Ile Gly Asn Asn Phe Pro His
    210                 215                 220
```

<210> SEQ ID NO 64
<211> LENGTH: 475
<212> TYPE: PRT
<213> ORGANISM: Lactobacillus rhamnosus

<400> SEQUENCE: 64

```
Leu Ile Cys Lys Gly Arg Ser Leu Lys Pro Phe Gly His Phe Ile Asp
 1               5                  10                  15

Ala Ile Thr Val Asn Arg Glu His Val Leu Thr Thr Ala Ala Glu Ala
            20                  25                  30

Leu Ile Ala Ser Ala Gly Asp Ala Leu Asn Ala Ser His Ala Thr Phe
        35                  40                  45

Asn Val Leu Asn Asn Ser Asp Leu Gln Phe Gly Phe Val Glu Asn Glu
    50                  55                  60

Asp Gly Glu Thr Val Gln Leu Ser Asn Gly Leu Tyr Gly Gln Leu Ile
 65                  70                  75                  80

Arg Ser Thr Asn Arg Lys Leu Arg Lys Glu Ala Phe Glu Ala Leu Leu
                85                  90                  95

Arg Ala Tyr Glu Ser Leu Lys Asn Thr Phe Ala Gln Thr Leu Ser Gly
            100                 105                 110

Gln Val Lys Ala His Asn Phe Asn Ala Thr Ala His His Tyr Lys Asn
        115                 120                 125

Ala Arg Ala Ala Met Ala Ser Asn His Ile Pro Glu Ser Val Tyr
    130                 135                 140

Thr Thr Leu Ile Asp Gln Val Asn Thr His Leu Pro Leu Leu His Arg
145                 150                 155                 160

Tyr Val Ala Leu Arg Lys Lys Val Leu Ala Val Asp Gln Leu His Met
                165                 170                 175

Tyr Asp Ile Tyr Thr Pro Leu Thr Gly Gln Pro Pro Leu Thr Tyr Thr
            180                 185                 190

Leu Glu Gln Ala Lys Ala Glu Ala Leu Lys Ala Leu Ala Pro Leu Gly
        195                 200                 205

Asp Asp Tyr Leu Glu His Val Arg Glu Ile Phe Asp Asn Arg Tyr Ile
    210                 215                 220

Asp Val Val Glu Asn Lys Gly Lys Arg Ser Gly Ala Tyr Ser Gly Gly
225                 230                 235                 240

Ala Tyr Asp Thr Asn Pro Phe Ile Leu Leu Asn Trp His Asp Ala Val
                245                 250                 255

Asp Glu Leu Tyr Thr Leu Val His Glu Thr Gly His Ser Val His Ser
            260                 265                 270

Trp Tyr Thr Arg His Asn Gln Pro Tyr Val Tyr Gly Asp Tyr Pro Ile
        275                 280                 285

Phe Val Ala Glu Ile Ala Ser Thr Thr Asn Glu Asn Leu Leu Thr Asp
    290                 295                 300

Tyr Phe Leu Thr His Ser Asp Asp Pro Lys Val Arg Ala Tyr Ile Leu
305                 310                 315                 320

Asn Tyr Tyr Leu Asp Gly Phe Lys Gly Thr Val Phe Arg Gln Thr Gln
                325                 330                 335

Phe Ala Glu Phe Glu His Trp Ile His Gln Gln Asp Gln Gln Gly Glu
            340                 345                 350

Pro Leu Thr Ala Thr Ser Met Ser Gln Tyr Tyr Ala Asp Leu Asn Ala
        355                 360                 365

Arg Tyr Tyr Gly Pro Glu Val Ala Arg Asp Pro Glu Ile Ala Phe Glu
    370                 375                 380
```

-continued

```
Trp Ala Arg Ile Pro His Phe Tyr Tyr Asn Tyr Tyr Val Tyr Gln Tyr
385                 390                 395                 400

Ala Thr Gly Phe Ala Ala Ser Thr Leu Ala Ala Gly Ile Ser Ser
            405                 410                 415

Gly Glu Pro Asp Ala Ala His Tyr Leu Asp Tyr Leu Lys Ser Gly
            420                 425                 430

Ser Ser Lys Tyr Ala Ile Asp Thr Met Lys Thr Ala Gly Val Asp Met
        435                 440                 445

Thr Lys Pro Asp Tyr Leu Glu Ala Ala Phe Ser Val Phe Glu Gln Arg
    450                 455                 460

Leu Thr Glu Leu Glu Lys Ile Leu Gln Lys Gly
465                 470                 475

<210> SEQ ID NO 65
<211> LENGTH: 345
<212> TYPE: PRT
<213> ORGANISM: Lactobacillus rhamnosus

<400> SEQUENCE: 65

Glu Glu Leu Gly Leu Pro Gln Leu Val Arg Met Ser Ala Asn Glu Asn
1               5                   10                  15

Pro Phe Gly Thr Ser Val Lys Val Gln Gln Ala Val Thr Asn Trp Asn
            20                  25                  30

Phe Thr Gln Ser Arg Asp Tyr Pro Asp Gly Tyr Ala Ser Gln Leu Arg
        35                  40                  45

Thr Ala Val Ala Lys His Leu Asp Val Ala Ala Glu Gln Leu Val Phe
    50                  55                  60

Gly Asn Gly Leu Asp Glu Val Ile Ala Leu Ile Ala Arg Thr Phe Leu
65                  70                  75                  80

Ser Pro Gly Asp Glu Val Ile Glu Pro Trp Pro Thr Phe Ser Glu Tyr
                85                  90                  95

Arg Leu His Ala Gln Ile Glu Gly Ala Thr Val Ile Asp Val Pro Val
            100                 105                 110

Thr Glu Thr Gly Asn Phe Asp Leu Ser Ala Met Ala Gln Ala Leu Thr
        115                 120                 125

Ala Lys Thr Lys Leu Ile Trp Val Cys Asn Pro Asn Asn Pro Thr Gly
130                 135                 140

Thr Leu Leu Ser Ile Ala Thr Leu Thr Glu Trp Leu Arg Gln Ile Pro
145                 150                 155                 160

Lys Asp Val Leu Val Leu Met Asp Glu Ala Tyr Ile Glu Phe Thr Asp
                165                 170                 175

Asp Tyr Pro Ala Thr Ser Ala Ile Ser Leu Leu Ser Lys Phe Pro Asn
            180                 185                 190

Leu Val Val Leu Arg Thr Phe Ser Lys Ile Tyr Gly Leu Ala Asn Phe
        195                 200                 205

Arg Val Gly Phe Gly Val Phe Pro Lys Gln Leu Val Asn Tyr Leu Gln
    210                 215                 220

Thr Val Arg Leu Pro Tyr Asn Leu Ser Ser Ile Ala Gln Val Ser Ala
225                 230                 235                 240

Gln Ala Ala Leu Ala Asp Gln Asp Phe Val Ala Met Thr Arg Lys Arg
                245                 250                 255

Val Gln Gln Ala Arg Asp Ser Trp Glu Arg Phe Leu Thr Gln Thr Gly
            260                 265                 270

Leu Pro His Thr Arg Ser Gln Thr Asn Phe Gln Phe Phe Gln Ala Pro
        275                 280                 285
```

```
Lys Met Gln Ala Ser Ala Leu Lys Lys Arg Leu Leu Gln Gln Gly Phe
    290                 295                 300

Leu Val Arg Asp Gly Leu Lys Pro Gly Trp Leu Arg Val Thr Phe Gly
305                 310                 315                 320

Thr Glu Val Gln Asn Thr Ala Val Gln Arg Ile Ile Glu Thr Phe Gln
                325                 330                 335

Ala Glu Leu Thr Gly Pro Asn Ala Leu
            340                 345

<210> SEQ ID NO 66
<211> LENGTH: 369
<212> TYPE: PRT
<213> ORGANISM: Lactobacillus rhamnosus

<400> SEQUENCE: 66

Val His Leu Ala Lys Arg Ile Leu Asn Val Ala Pro Ser Ala Thr Leu
 1               5                  10                  15

Ala Leu Ser Asn Gln Thr Lys Asp Leu Lys Ala Lys Gly Ala Asp Val
                20                  25                  30

Ile Asp Leu Ser Ile Gly Gln Pro Asp Phe Ser Thr Pro Lys Ala Ile
            35                  40                  45

Asp Asp Ala Ala Ile Ala Ala Ile Gln Ala Gly Asn Ala Ser Phe Tyr
50                  55                  60

Thr Ala Ala Thr Gly Ile Pro Glu Leu Lys Gln Ala Ile Ser Asp Arg
65                  70                  75                  80

Ile Phe Ala Gln Asp Gly Ile Arg Tyr Asp His Arg Gln Ile Val Ala
                85                  90                  95

Thr Thr Gly Ala Lys Phe Ala Leu Tyr Ala Leu Phe Gln Val Phe Leu
            100                 105                 110

Asn Pro Gly Asp Glu Val Leu Ile Pro Val Pro Tyr Trp Val Ser Tyr
        115                 120                 125

Glu Glu Gln Ile Lys Leu Ala Ser Gly Val Pro His Leu Val Met Pro
    130                 135                 140

Ala Val Gly His Lys Val Ser Val Asp Asp Leu Glu Ala Ala Arg Thr
145                 150                 155                 160

Asp Lys Thr Arg Ala Leu Ile Ile Asn Ser Pro Gln Asn Pro Ser Gly
                165                 170                 175

Val Val Tyr Asp Arg Thr Glu Leu Thr Leu Ile Gly Asn Trp Ala Leu
            180                 185                 190

Lys His His Ile Leu Val Val Thr Asp Asp Ile Tyr Arg Asp Leu Ile
        195                 200                 205

Tyr Asn Gly Thr Thr Tyr Thr Ser Met Ile Ser Ile Asp Pro Asp Ile
    210                 215                 220

Ala Ala Asn Thr Val Leu Ile Ser Gly Val Ser Lys Ser Tyr Ala Met
225                 230                 235                 240

Thr Gly Trp Arg Ile Gly Tyr Ala Ala Gly Pro Glu Lys Leu Ile Gln
                245                 250                 255

Ala Met Ala Thr Phe Ile Ser His Thr Thr Ser Asn Pro Ala Ala Val
            260                 265                 270

Ser Glu Tyr Ala Ala Val Ala Ala Leu Thr Gly Asp Gln Gln Val Val
        275                 280                 285

Glu Lys Met Arg Arg Ala Phe Glu Glu Arg Leu Asn Leu Phe Tyr Asp
    290                 295                 300

Leu Leu Ala Asp Ile Pro Gly Phe Asp Met Gly Asp Lys Pro Gln Gly
```

```
                305                 310                 315                 320
Ala Phe Tyr Leu Phe Pro Asn Ile Lys Arg Ala Ala Gln Leu Ser His
                    325                 330                 335

Tyr Gly Thr Val Asp Asp Phe Ile Ser Ala Leu Leu Thr Glu Thr Gly
                340                 345                 350

Val Ala Ile Val Pro Gly Arg Ala Phe Gly His Ala Gly Ser Cys Ala
            355                 360                 365

Asp

<210> SEQ ID NO 67
<211> LENGTH: 390
<212> TYPE: PRT
<213> ORGANISM: Lactobacillus rhamnosus

<400> SEQUENCE: 67

Met Thr Leu Gln Pro Leu Asn Glu Gln Leu Pro Ala Ile Glu Val Ser
  1               5                  10                  15

Glu Ile Arg Gln Phe Asp Glu Ser Val Ser Asp Ile Pro Gly Ile Leu
                 20                  25                  30

Lys Leu Thr Leu Gly Glu Pro Asp Phe Asn Thr Pro Glu His Val Lys
             35                  40                  45

Gln Ala Gly Ile Lys Ala Ile Gln Glu Asn Tyr Ser His Tyr Thr Gly
         50                  55                  60

Met Val Gly Asp Pro Glu Leu Arg Glu Ala Ala Gln His Phe Phe Lys
 65                  70                  75                  80

Thr Lys Tyr Ala Thr Asp Tyr Arg Ala Thr Asp Glu Ile Leu Val Thr
                 85                  90                  95

Val Gly Ala Thr Glu Ala Leu Ala Thr Ala Ile Thr Thr Ile Ser Asp
            100                 105                 110

Pro Gly Asp Ala Met Leu Val Pro Ser Pro Ile Tyr Pro Gly Tyr Ile
        115                 120                 125

Pro Leu Leu Thr Leu Asn His Val Thr Pro Leu Tyr Met Asp Thr Ser
    130                 135                 140

Lys Thr Asp Phe Val Leu Thr Pro Glu Leu Ile Glu Ala Thr Ile Thr
145                 150                 155                 160

Ala Asn Pro Asp Ala Lys Ile Lys Gly Ile Ile Leu Asn Tyr Pro Ser
                165                 170                 175

Asn Pro Thr Gly Val Thr Tyr Arg Ala Ala Glu Val Lys Ala Ile Ala
            180                 185                 190

Asp Ile Ala Ala Lys His Asn Leu Tyr Ile Ile Cys Asp Glu Ile Tyr
        195                 200                 205

Ser Glu Leu Thr Tyr Gly Glu Pro His Val Ser Met Gly Gln Phe Ala
    210                 215                 220

Tyr Asp Arg Thr Phe Ile Val Asn Gly Leu Ser Lys Ser His Ala Met
225                 230                 235                 240

Thr Gly Trp Arg Ile Gly Phe Leu Met Gly Pro Gln Gln Leu Ile Ala
                245                 250                 255

Gln Ala Lys Lys Val His Gln Tyr Leu Val Thr Ala Ala Thr Thr Ile
            260                 265                 270

Ala Gln Arg Ala Gly Ile Glu Ala Leu Thr Asn Gly Ala Asp Asp Ala
        275                 280                 285

Gln Val Met Lys Ala Ala Tyr Val Lys Arg Arg Asp Phe Val Tyr Ala
    290                 295                 300

Ala Leu Ile Asp Met Gly Phe Ser Val Ala Arg Pro Asp Gly Ala Phe
```

```
                305                 310                 315                 320
Tyr Leu Phe Ala Lys Ile Pro Thr Gln Leu His Leu Ser Ser Arg Glu
                    325                 330                 335

Phe Thr His Ala Leu Ala His Glu Gln Lys Leu Ala Leu Ile Ser Gly
                340                 345                 350

Thr Ala Phe Gly Pro Gly Gly Glu Gly Tyr Ile Arg Ile Ser Tyr Ala
                355                 360                 365

Ala Ser Met Thr Asp Leu Gln Glu Ala Val Lys Arg Leu Arg Ala Phe
370                 375                 380

Met Ala Ser His Ile Gly
385                 390

<210> SEQ ID NO 68
<211> LENGTH: 297
<212> TYPE: PRT
<213> ORGANISM: Lactobacillus rhamnosus

<400> SEQUENCE: 68

Val Ala Arg Leu Met Leu Asp Pro Gly Asp Gly Leu Val Val Glu Ala
1               5                   10                  15

Pro Thr Tyr Leu Gly Ala Leu Ala Ala Phe Asn Ala Tyr Gln Pro Thr
                20                  25                  30

Tyr Tyr Glu Ile Pro Met Gln Asp Asp Gly Met Asp Ile Asn Ala Leu
            35                  40                  45

Gln Arg Val Leu Met Ser His Lys Val Lys Phe Ile Tyr Thr Val Pro
        50                  55                  60

Asp Phe Gln Asn Pro Thr Gly Val Val Met Ser Val Ala Lys Arg Gln
65                  70                  75                  80

Ala Leu Ile Arg Leu Ala Asn Gln Tyr Asp Val Met Ile Leu Glu Asp
                85                  90                  95

Asn Pro Tyr Arg Asp Leu Arg Tyr Asp Gly Lys Pro Leu Pro Thr Ile
            100                 105                 110

Lys Ser Phe Asp Thr Gln Gly Arg Val Val Tyr Leu Gly Ser Phe Ser
        115                 120                 125

Lys Ile Leu Ser Pro Ser Leu Arg Met Gly Trp Leu Val Ala Ala Pro
    130                 135                 140

Asp Leu Leu Gln Glu Leu Leu Ala Leu Lys Gly Gly Ser Asp Leu Glu
145                 150                 155                 160

Ser Ser Asn Leu Thr Met His Gly Ile Asp Ala Tyr Met Ala Glu Asn
                165                 170                 175

Asp Leu Asp Ala His Ile Thr Glu Ile Gln Asn Cys Cys Arg Glu Lys
            180                 185                 190

Lys Asn Ala Met Val Ala Ala Met Asn Arg Tyr Leu Pro Asp Glu Ala
        195                 200                 205

His Phe Thr Asn Pro Asp Gly Gly Phe Phe Leu Trp Leu Thr Met Pro
    210                 215                 220

Ala Gly Phe Asp Met Gly Ala Phe Met Lys Gln His Leu Leu Pro Glu
225                 230                 235                 240

Ser Asn Ile Ser Tyr Val Pro Ser Ala Asn Leu Tyr Ala Thr Ser Ala
                245                 250                 255

Gln Val Asn Gly Ala Arg Leu Asn Phe Thr Gly Pro Thr Leu Glu Gln
            260                 265                 270

Ile Asp Thr Gly Ile Lys Ala Leu Gly Asp Ala Leu Lys Thr Ala Leu
        275                 280                 285
```

```
Gln His His Leu Val Ala Glu Gln Ala
    290                 295

<210> SEQ ID NO 69
<211> LENGTH: 390
<212> TYPE: PRT
<213> ORGANISM: Lactobacillus rhamnosus

<400> SEQUENCE: 69

Met Lys Leu Thr Ile Tyr Asp Phe Asp His Val Ile Asp Arg Arg Gly
  1               5                  10                  15

Thr Phe Ser Thr Gln Trp Asp Tyr Ile Ala Asp Arg Phe Gly Arg Asn
             20                  25                  30

Asp Ile Leu Pro Phe Ser Ile Ser Asp Thr Asp Phe Pro Val Pro Val
         35                  40                  45

Glu Val Gln Asp Ala Leu Lys Glu Arg Leu Thr His Pro Ile Tyr Gly
 50                  55                  60

Tyr Thr Arg Trp Asn His Ala Thr Tyr Lys Asp Ser Ile Val His Trp
 65                  70                  75                  80

Phe Glu Arg Asp Gly His Thr Lys Ile Asn Pro Asp Trp Ile Val Tyr
                 85                  90                  95

Ser Pro Ser Val Val Phe Thr Ile Ala Thr Leu Ile Arg Met Lys Ser
            100                 105                 110

Asp Pro Gly Asp Gly Val Ala Val Phe Thr Pro Met Tyr Asp Ala Phe
        115                 120                 125

Tyr Gly Thr Ile Lys Gln Asn Asp Arg Val Leu Ile Pro Ile Arg Leu
130                 135                 140

Ala Ala Ala Asp Glu Gly Tyr Val Ile Asp Trp Asp Ser Leu Ala Thr
145                 150                 155                 160

Val Leu Ala Glu Lys Gln Thr Lys Ile Phe Leu Leu Thr Asn Pro His
                165                 170                 175

Asn Pro Thr Gly His Val Phe Thr Lys Ser Glu Leu Ala Arg Leu Tyr
            180                 185                 190

Asp Leu Cys Gln Ala Ala His Val Phe Leu Ile Ser Asp Asp Ile His
        195                 200                 205

Arg Asp Ile Val Tyr Pro Gly His Ser Tyr Glu Pro Met Thr Asn Val
210                 215                 220

Gly Thr Ser Asp Val Ala Leu Cys Cys Ser Gly Ser Lys Thr Phe Asn
225                 230                 235                 240

Thr Pro Gly Leu Ile Gly Ser Tyr Ala Phe Leu Pro Asp His Asp Val
                245                 250                 255

Arg Ala Gln Phe Leu Thr Glu Leu Lys Gln Lys Asn Ala Leu Ser Ser
            260                 265                 270

Val Ser Ile Phe Gly Met Leu Ala Gln Ile Ala Ala Tyr Asn Gly Ser
        275                 280                 285

Glu Asp Tyr Val Glu Gln Leu Thr Ala Tyr Thr Lys Asn Asn Met Glu
290                 295                 300

Leu Val Ala Ser Tyr Leu Glu Glu Asn Leu Pro Glu Leu Gln Phe Ser
305                 310                 315                 320

Leu Pro Asp Ala Thr Tyr Leu Ala Trp Ile Asn Val Ser Lys Leu Arg
                325                 330                 335

Leu Thr Ser Glu Glu Leu Gln His Arg Leu Val Asn Gly His Val
            340                 345                 350

Gly Ile Met Ala Gly Lys Thr Tyr Gly Asp Thr Arg Tyr Leu Arg Met
        355                 360                 365
```

-continued

```
Asn Ile Ala Cys Pro Lys Lys Leu Val Met Gly Leu Glu Arg Leu
    370                 375                 380
Lys Lys Gly Ile Arg Gly
385             390

<210> SEQ ID NO 70
<211> LENGTH: 386
<212> TYPE: PRT
<213> ORGANISM: Lactobacillus rhamnosus
<220> FEATURE:
<221> NAME/KEY: VARIANT
<222> LOCATION: (1)...(386)
<223> OTHER INFORMATION: Xaa = Any Amino Acid

<400> SEQUENCE: 70

Met Ile Tyr Phe Asp Asn Ser Ala Thr Thr Lys Ile Ser Pro Asp Ala
 1               5                  10                  15

Leu Ala Thr Tyr Asn Lys Val Ser Thr Asp Phe Phe Gly Asn Pro Ser
            20                  25                  30

Ser Leu His Ala Leu Gly Thr Lys Ala Asn Glu Val Leu Gln Ser Ser
        35                  40                  45

Arg Ala Gln Ile Ala Lys Leu Ile Gly Ala Lys Pro Asp Glu Ile Tyr
    50                  55                  60

Phe Thr Ser Gly Gly Thr Glu Arg Asp Asn Trp Val Xaa Leu Lys Gly
65                  70                  75                  80

Thr Ala Trp Leu Asn Ala Asn Leu Ala Arg Ile Leu Ile Thr Thr Ser
                85                  90                  95

Ile Glu Pro Pro Ala Val Ile Asn Thr Met Lys Gln Leu Glu Lys Leu
            100                 105                 110

Gly Phe Glu Val Thr Tyr Leu Pro Val Asp Arg Arg Gly Phe Ile His
        115                 120                 125

Ile Asp Asp Leu Lys Ala Ala Ile Arg Lys Asp Thr Ile Leu Val Ser
    130                 135                 140

Ile Met Ala Val Asn Asn Glu Ile Gly Ser Met Gln Pro Ile Val Gln
145                 150                 155                 160

Ala Ala Arg Val Leu Asp Asn Tyr Pro Asn Ile His Phe His Val Asp
                165                 170                 175

Ala Val Gln Ala Val Gly Lys Gly Leu Asp Ala Ala Leu Gln Asp Pro
            180                 185                 190

Arg Ile Asp Phe Leu Ser Phe Ser Gly His Lys Phe His Ala Pro Arg
        195                 200                 205

Gly Thr Gly Phe Ile Tyr Ala Lys Glu Gly Arg Met Leu Asp Pro Leu
    210                 215                 220

Leu Thr Gly Gly Gly Gln Glu His Asp Trp Arg Ser Gly Thr Glu Asn
225                 230                 235                 240

Val Pro Ala Ile Ala Ala Met Ala Lys Ser Leu Arg Leu Leu Leu Ala
                245                 250                 255

Asn Glu Asp Ala Asn Val Ala Arg Gln Gln Ala Val Arg Lys Arg Ile
            260                 265                 270

Phe Glu His Val Ser Gln Lys Pro Lys Val Thr Met Phe Ser Gln Leu
        275                 280                 285

Thr Pro Asp Phe Ala Pro His Val Leu Cys Phe Ala Ile Ala Gly Val
    290                 295                 300

Arg Gly Glu Thr Ile Val His Ala Phe Glu Asp His Gln Ile Tyr Ile
305                 310                 315                 320
```

```
Ser Thr Thr Ser Ala Cys Ser Ser Lys Lys Gly Thr Glu Ser Ser Thr
            325                 330                 335

Leu Ala Ala Met His Thr Asp Pro Lys Ile Ala Thr Ser Ala Ile Arg
            340                 345                 350

Val Ser Leu Asp Glu Ala Asn Thr Leu Asp Glu Ala Asp Ala Phe Asn
            355                 360                 365

Ala Ala Phe Asp Thr Ile Tyr Ala Lys Phe Ala Lys Leu Asp Lys Ala
            370                 375                 380

Thr Val
385

<210> SEQ ID NO 71
<211> LENGTH: 262
<212> TYPE: PRT
<213> ORGANISM: Lactobacillus rhamnosus

<400> SEQUENCE: 71

Met Pro Thr Lys Ile Gly Leu His Tyr Asn Lys Ile Gly Val Gly Lys
 1               5                  10                  15

Thr Ile Tyr Phe Leu His Gly Met Gly Leu Asp Gly His Ser Met Ala
            20                  25                  30

Ala Phe Tyr Glu Pro Arg Phe Thr Ser Glu Glu Arg His Phe Ala Arg
        35                  40                  45

Leu Tyr Pro Asp Leu Pro Gly Met Gly Asn Ser Pro Ala Thr Ser Ala
    50                  55                  60

Leu Gln Ser Ala Asp Asp Val Leu Ala Gln Val His Ala Phe Ile Gln
65                  70                  75                  80

Ala Thr Ser Glu Gly Pro Cys Tyr Leu Val Gly His Ser Tyr Gly Gly
                85                  90                  95

Tyr Leu Ala Leu Gly Leu Leu Ala Arg Phe Pro Asp Glu Phe Ser Gly
            100                 105                 110

Ala Phe Leu Thr Ala Pro Val Leu Ala Glu Lys Thr Ala Arg Thr
            115                 120                 125

Val Ala Thr Leu Lys His Leu Ile Ser Ala Pro Val Thr Ser Gln Ser
    130                 135                 140

Pro Glu Phe Thr Asp Tyr Gln His Met Asn Val Val Ile Asn Pro Ser
145                 150                 155                 160

Thr Trp Arg Gln Tyr Gln Glu Leu Ile Leu Pro Gly Leu Lys Thr Phe
                165                 170                 175

Asn Arg Asp Phe Trp Val Ala Met Lys Asn Arg His Ala Tyr Arg Leu
            180                 185                 190

Ser Ile Glu Ser Arg Leu Thr Ser Leu Ile Lys Ser Pro Val Thr Leu
        195                 200                 205

Val Leu Gly Glu Asn Asp Asn Glu Val Gly Tyr Gln Asp Gln Val Val
    210                 215                 220

Phe Ala His Lys Gly Ala His Met Thr Thr Thr Val Ile Pro Asn Ala
225                 230                 235                 240

Gly His Asn Leu Met Ile Asp Ala Pro Glu Ala Val Met Thr Ala Phe
                245                 250                 255

His Gln Phe Leu His Lys
            260

<210> SEQ ID NO 72
<211> LENGTH: 309
<212> TYPE: PRT
<213> ORGANISM: Lactobacillus rhamnosus
```

```
<400> SEQUENCE: 72

Met Val Thr Ala Ala Asp Asn Ile Thr Gly Leu Ile Gly Asn Thr Pro
 1               5                  10                  15

Leu Leu Lys Leu Asn Arg Val Val Pro Glu Gly Ala Ala Asp Val Tyr
            20                  25                  30

Val Lys Leu Glu Phe Phe Asn Pro Gly Gly Ser Val Lys Asp Arg Ile
        35                  40                  45

Ala Leu Ala Met Ile Glu Asp Ala Glu Tyr Lys Gly Val Leu Lys Pro
    50                  55                  60

Gly Gly Thr Ile Val Glu Pro Thr Ser Gly Asn Thr Gly Ile Gly Leu
65                  70                  75                  80

Ala Leu Val Ala Ala Lys Gly Tyr His Leu Ile Ile Thr Met Pro
                85                  90                  95

Glu Thr Met Ser Val Glu Arg Arg Ala Leu Met Arg Gly Tyr Gly Ala
            100                 105                 110

Glu Leu Ile Leu Thr Pro Gly Ala Asp Gly Met Pro Gly Ala Ile Lys
        115                 120                 125

Lys Ala Glu Ala Leu Ser Lys Glu Asn Gly Tyr Phe Leu Pro Met Gln
    130                 135                 140

Phe Gln Asn Pro Ala Asn Pro Asp Val His Glu Arg Thr Thr Gly Gln
145                 150                 155                 160

Glu Ile Ile Arg Ser Phe Asp Gly Gly Thr Pro Asp Ala Phe Val Ala
                165                 170                 175

Gly Val Gly Thr Gly Gly Thr Leu Thr Gly Val Gly Arg Ala Leu Arg
            180                 185                 190

Lys Ile Asn Pro Asp Val Gln Ile Tyr Ala Leu Glu Ala Ala Glu Ser
        195                 200                 205

Pro Met Leu Lys Glu Gly His Gly Gly Lys His Lys Ile Gln Gly Ile
    210                 215                 220

Ser Ala Gly Phe Ile Pro Asp Val Leu Asp Thr Asn Leu Tyr Gln Asp
225                 230                 235                 240

Ile Ile Glu Val Thr Ser Asp Gln Ala Ile Asp Met Ala Arg His Val
                245                 250                 255

Ser His Glu Glu Gly Phe Leu Pro Gly Ile Ser Ala Gly Ala Asn Ile
            260                 265                 270

Phe Gly Ala Ile Glu Ile Ala Lys Lys Leu Gly Lys Gly Lys Ser Val
        275                 280                 285

Ala Thr Val Ala Pro Asp Asn Gly Glu Arg Tyr Leu Ser Thr Asp Leu
    290                 295                 300

Phe Lys Phe Asp Asp
305

<210> SEQ ID NO 73
<211> LENGTH: 270
<212> TYPE: PRT
<213> ORGANISM: Lactobacillus rhamnosus

<400> SEQUENCE: 73

Met Leu Lys Lys Lys Leu Trp Phe Leu Leu Pro Leu Val Ala Leu Val
 1               5                  10                  15

Thr Phe Thr Leu Thr Ala Cys Thr Ser Ala Ser Ser Asp Thr Ser Lys
            20                  25                  30

Asn Ser Asp Val Thr Ala Glu Leu Ile Asn Lys Asn Glu Leu Thr Ile
        35                  40                  45
```

```
Gly Leu Glu Gly Thr Tyr Ala Pro Phe Ser Tyr Arg Lys Asp Gly Lys
    50                  55                  60

Leu Glu Gly Phe Glu Val Glu Leu Gly Lys Ala Leu Ala Lys Lys Ile
65                  70                  75                  80

Gly Val Lys Ala Lys Phe Val Pro Thr Gln Trp Asp Ser Leu Ile Ala
                85                  90                  95

Gly Leu Gly Ser Gln Lys Phe Asp Leu Val Leu Asn Asp Ile Ser Glu
            100                 105                 110

Thr Pro Ala Arg Lys Lys Val Tyr Asn Phe Thr Thr Pro Tyr Met Tyr
            115                 120                 125

Ser Arg Tyr Ala Leu Ile Thr Arg Ser Asp Asn Thr Thr Ile Lys Ser
    130                 135                 140

Leu Ala Asp Ile Lys Gly Lys Thr Phe Val Glu Gly Thr Gly Thr Pro
145                 150                 155                 160

Asn Ala Ala Leu Ala Lys Lys Tyr Gly Ala Lys Ile Thr Pro Ser Gly
                165                 170                 175

Asp Phe Thr Val Ser Leu Ser Leu Val Lys Glu Lys Arg Ala Asp Gly
            180                 185                 190

Thr Ile Asn Ala Ser Ala Ala Trp Tyr Ala Phe Ala Lys Asn Asn Ser
            195                 200                 205

Thr Ala Gly Leu Lys Ser Gln Thr Leu Lys Asp Ser Val Val Lys Pro
    210                 215                 220

Asp Glu Val Ala Gly Met Val Ser Lys Lys Ser Pro Lys Leu Gln Ala
225                 230                 235                 240

Ala Leu Ser Lys Gly Ile Gln Glu Leu Arg Lys Asp Gly Thr Leu Lys
                245                 250                 255

Lys Leu Ser Gln Lys Tyr Phe Gly Thr Asp Leu Thr Thr Lys
            260                 265                 270

<210> SEQ ID NO 74
<211> LENGTH: 474
<212> TYPE: PRT
<213> ORGANISM: Lactobacillus rhamnosus

<400> SEQUENCE: 74

Ile Cys Lys Gly Arg Ser Leu Lys Pro Phe Gly His Phe Ile Asp Ala
1               5                   10                  15

Ile Thr Val Asn Arg Glu His Val Leu Thr Thr Ala Ala Glu Ala Leu
            20                  25                  30

Ile Ala Ser Ala Gly Asp Ala Leu Asn Ala Ser His Ala Thr Phe Asn
        35                  40                  45

Val Leu Asn Asn Ser Asp Leu Gln Phe Gly Phe Val Glu Asn Glu Asp
    50                  55                  60

Gly Glu Thr Val Gln Leu Ser Asn Gly Leu Tyr Gly Gln Leu Ile Arg
65                  70                  75                  80

Ser Thr Asn Arg Lys Leu Arg Lys Glu Ala Phe Glu Ala Leu Leu Arg
                85                  90                  95

Ala Tyr Glu Ser Leu Lys Asn Thr Phe Ala Gln Thr Leu Ser Gly Gln
            100                 105                 110

Val Lys Ala His Asn Phe Asn Ala Thr Ala His Tyr Lys Asn Ala
            115                 120                 125

Arg Ala Ala Ala Met Ala Ser Asn His Ile Pro Glu Ser Val Tyr Thr
    130                 135                 140

Thr Leu Ile Asp Gln Val Asn Thr His Leu Pro Leu Leu His Arg Tyr
```

```
            145                 150                 155                 160
Val Ala Leu Arg Lys Lys Val Leu Ala Val Asp Gln Leu His Met Tyr
                165                 170                 175

Asp Ile Tyr Thr Pro Leu Thr Gly Gln Pro Pro Leu Thr Tyr Thr Leu
            180                 185                 190

Glu Gln Ala Lys Ala Glu Ala Leu Lys Ala Leu Ala Pro Leu Gly Asp
        195                 200                 205

Asp Tyr Leu Glu His Val Arg Glu Ile Phe Asp Asn Arg Tyr Ile Asp
    210                 215                 220

Val Val Glu Asn Lys Gly Lys Arg Ser Gly Ala Tyr Ser Gly Gly Ala
225                 230                 235                 240

Tyr Asp Thr Asn Pro Phe Ile Leu Leu Asn Trp His Asp Ala Val Asp
                245                 250                 255

Glu Leu Tyr Thr Leu Val His Glu Thr Gly His Ser Val His Ser Trp
            260                 265                 270

Tyr Thr Arg His Asn Gln Pro Tyr Val Tyr Gly Asp Tyr Pro Ile Phe
        275                 280                 285

Val Ala Glu Ile Ala Ser Thr Thr Asn Glu Asn Leu Leu Thr Asp Tyr
    290                 295                 300

Phe Leu Thr His Ser Asp Asp Pro Lys Val Arg Ala Tyr Ile Leu Asn
305                 310                 315                 320

Tyr Tyr Leu Asp Gly Phe Lys Gly Thr Val Phe Arg Gln Thr Gln Phe
                325                 330                 335

Ala Glu Phe Glu His Trp Ile His Gln Gln Asp Gln Gln Gly Glu Pro
            340                 345                 350

Leu Thr Ala Thr Ser Met Ser Gln Tyr Tyr Ala Asp Leu Asn Ala Arg
        355                 360                 365

Tyr Tyr Gly Pro Glu Val Ala Arg Asp Pro Glu Ile Ala Phe Glu Trp
    370                 375                 380

Ala Arg Ile Pro His Phe Tyr Tyr Asn Tyr Val Tyr Gln Tyr Ala
385                 390                 395                 400

Thr Gly Phe Ala Ala Ala Ser Thr Leu Ala Ala Gly Ile Ser Ser Gly
                405                 410                 415

Glu Pro Asp Ala Ala Ala His Tyr Leu Asp Tyr Leu Lys Ser Gly Ser
            420                 425                 430

Ser Lys Tyr Ala Ile Asp Thr Met Lys Thr Ala Gly Val Asp Met Thr
        435                 440                 445

Lys Pro Asp Tyr Leu Glu Ala Ala Phe Ser Val Phe Glu Gln Arg Leu
    450                 455                 460

Thr Glu Leu Glu Lys Ile Leu Gln Lys Gly
465                 470

<210> SEQ ID NO 75
<211> LENGTH: 256
<212> TYPE: PRT
<213> ORGANISM: Lactobacillus rhamnosus

<400> SEQUENCE: 75

Ser Tyr Ala Pro Thr Ile Thr Leu Glu Gln Ala Lys Glu Asp Ile Lys
1               5                   10                  15

Asn Ala Thr Ala Leu Met Gly Gln Asp Tyr Gln Ala Gln Met Met Gln
            20                  25                  30

Ala Phe Ser Glu Arg Trp Ile Asp Phe Pro Ala Asn Gln Gly Lys Asp
        35                  40                  45
```

-continued

```
Ser Gly Ala Tyr Thr Ala Gly Pro Tyr Gly Val His Pro Tyr Val Glu
         50                  55                  60

Met Thr Trp Ser Asn Thr Leu Pro Ala Val Tyr Thr Leu Ile His Glu
 65                  70                  75                  80

Leu Gly His Thr Ala Gln Met Val Arg Ser Gln Glu Ala His Asn Val
                 85                  90                  95

Leu Asp Ala Asp Phe Asn Ala Tyr Leu Val Glu Ser Pro Ser Thr Phe
                100                 105                 110

Asn Glu Leu Leu Leu Thr His Tyr Leu Glu Glu Asn Ala Lys Asp Pro
            115                 120                 125

Arg Met Lys Arg Phe Ala Leu Ser Arg Leu Leu Asn Asp Thr Tyr Phe
        130                 135                 140

His Asn Phe Val Thr His Leu Leu Glu Ala Ala Phe Gln Arg Glu Val
145                 150                 155                 160

Tyr Asn Leu Ile Asp Asn Gly Glu Thr Phe Asp Ala Ala Arg Leu Asn
                165                 170                 175

Ala Ile Thr Arg Lys Val Leu Thr Asp Phe Trp Gly Ser Ala Val Glu
            180                 185                 190

Leu Glu Pro Gly Ala Glu Leu Thr Trp Met Arg Gln Ser His Tyr Tyr
        195                 200                 205

Met Gly Leu Tyr Ser Tyr Ser Tyr Ser Ala Gly Leu Thr Val Ala Thr
    210                 215                 220

Gln Ala Phe Gln Ala Ile Glu Gln Gln Gly Gln Pro Ala Val Asp Arg
225                 230                 235                 240

Trp Leu Arg Tyr Leu Ser Leu Gly Asp Ser Leu Asp Pro Val Glu Ala
                245                 250                 255

<210> SEQ ID NO 76
<211> LENGTH: 641
<212> TYPE: PRT
<213> ORGANISM: Lactobacillus rhamnosus

<400> SEQUENCE: 76

Leu Leu Gly Gln Phe Gly Val Asp Leu Thr Glu Gln Ala Arg Lys Gly
  1               5                  10                  15

Gln Ile Asp Pro Val Ile Gly Arg Asp Lys Glu Ile Ser Arg Val Ile
             20                  25                  30

Glu Ile Leu Asn Arg Arg Thr Lys Asn Asn Pro Val Leu Ile Gly Glu
         35                  40                  45

Ala Gly Val Gly Lys Thr Ala Val Val Glu Gly Leu Ala Leu Lys Ile
     50                  55                  60

Ala Asn Gly Asp Val Pro Ala Lys Leu Gln Asp Arg His Val Ile Arg
 65                  70                  75                  80

Leu Asp Val Val Ser Leu Val Gln Gly Thr Gly Ile Arg Gly Gln Phe
                 85                  90                  95

Glu Gln Arg Met Gln Gln Leu Ile Asp Glu Leu Lys Gln Asn Lys Asn
                100                 105                 110

Ile Ile Leu Phe Ile Asp Glu Ile His Glu Ile Val Gly Ala Gly Asn
            115                 120                 125

Ala Glu Gly Gly Met Asp Ala Gly Asn Val Leu Lys Pro Ala Leu Ala
        130                 135                 140

Arg Gly Glu Leu Gln Leu Val Gly Ala Thr Thr Ser Asn Glu Tyr Arg
145                 150                 155                 160

Gln Ile Glu Lys Asp Ser Ala Leu Ala Arg Arg Leu Gln Pro Val Met
                165                 170                 175
```

```
Val Glu Glu Pro Ser Val Asp Glu Thr Ile Lys Ile Leu Lys Gly Leu
            180                 185                 190

Gln Pro Arg Tyr Gln Asp Phe His His Val Lys Tyr Thr Glu Gly Ala
        195                 200                 205

Ile Glu Ala Ala Ala Thr Leu Ser Asn Arg Tyr Ile Gln Asp Arg Phe
    210                 215                 220

Leu Pro Asp Lys Ala Ile Asp Leu Leu Asp Glu Ala Gly Ser Arg Lys
225                 230                 235                 240

Asn Leu Thr Ile Ala Thr Val Asp Pro Glu Thr Ile Lys Ala Lys Ile
                245                 250                 255

Ala Asp Ala Glu Lys Gln Lys Gln Ala Ala Leu Lys Gln Glu Asp Tyr
            260                 265                 270

Glu Lys Ala Ala Phe Tyr Arg Asp Gln Val Thr Lys Leu Glu Asp Met
        275                 280                 285

Ala Lys Lys Gln Ser Asn Leu Pro Asp Asn Glu Ile Pro Thr Val Thr
    290                 295                 300

Glu Lys Asp Met Glu Lys Ile Val Glu Glu Lys Thr Asn Ile Pro Val
305                 310                 315                 320

Gly Glu Leu Lys Ala Gln Glu Gln Ala Gln Leu Lys Asn Leu Ala Ser
                325                 330                 335

Asp Leu Glu Gln His Val Ile Gly Gln Asn Glu Ala Val Asp Lys Val
            340                 345                 350

Ala Arg Ala Ile Arg Arg Asn Arg Ile Gly Phe Asn Lys Thr Gly Arg
        355                 360                 365

Pro Ile Gly Ser Phe Leu Phe Val Gly Pro Thr Gly Val Gly Lys Thr
    370                 375                 380

Glu Leu Ala Lys Gln Leu Ala Lys Glu Leu Phe Gly Ser Glu Asp Ala
385                 390                 395                 400

Met Ile Arg Phe Asp Met Ser Glu Tyr Met Glu Lys Phe Ser Val Ser
                405                 410                 415

Lys Leu Ile Gly Ser Pro Pro Gly Tyr Val Gly Tyr Glu Glu Ala Gly
            420                 425                 430

Gln Leu Thr Glu Lys Val Arg Arg Asn Pro Tyr Ser Leu Ile Leu Leu
        435                 440                 445

Asp Glu Ile Glu Lys Ala His Pro Asp Val Met Asn Met Phe Leu Gln
    450                 455                 460

Ile Leu Asp Asp Gly Arg Leu Thr Asp Ser Gln Gly Arg Thr Val Ser
465                 470                 475                 480

Phe Lys Asp Thr Ile Ile Ile Met Thr Ser Asn Ala Gly Ser Thr Asp
                485                 490                 495

Ala Glu Ala Asn Val Gly Phe Gly Ala Thr Leu Ser Gly Lys Thr His
            500                 505                 510

Ser Val Leu Asp Gln Leu Gly Asn Tyr Phe Lys Pro Glu Phe Leu Asn
        515                 520                 525

Arg Phe Asp Asp Ile Val Glu Phe Lys Pro Leu Ser Lys Asp Asp Leu
    530                 535                 540

Leu Lys Ile Val Ser Leu Met Ile Asn Asp Thr Asn Asn Leu Lys
545                 550                 555                 560

Ser Gln Gly Leu Thr Ile His Val Thr Asp Pro Val Lys Glu Lys Leu
                565                 570                 575

Val Thr Leu Gly Tyr Asn Pro Ser Met Gly Ala Arg Pro Leu Arg Arg
            580                 585                 590
```

-continued

```
Val Ile Gln Glu Gln Ile Glu Asp Arg Val Ala Asp Phe Tyr Leu Asp
            595                 600                 605
His Pro Asn Ala Lys Glu Leu Glu Ala Arg Ile Ser Asn Gly Glu Ile
        610                 615                 620
Thr Val Gly Glu Pro Ala Lys Ala Glu Ala Ser Ser Lys Thr Ala Lys
625                 630                 635                 640
Lys

<210> SEQ ID NO 77
<211> LENGTH: 481
<212> TYPE: PRT
<213> ORGANISM: Lactobacillus rhamnosus

<400> SEQUENCE: 77

Thr Lys Ser Val Val Gly Val Ala Pro Glu Ser Gln Leu Leu Ala Met
  1               5                  10                  15
Lys Val Phe Thr Asn Ser Asp Thr Ser Ala Thr Thr Gly Ser Ser Thr
             20                  25                  30
Leu Val Ser Ala Ile Glu Asp Ser Ala Lys Leu Gly Ala Asp Val Leu
         35                  40                  45
Asn Met Ser Leu Gly Ser Val Ser Gly Asn Gln Thr Leu Glu Asp Pro
     50                  55                  60
Glu Ile Ala Ala Val Gln Asn Ala Asn Glu Ser Gly Thr Ala Ala Val
 65                  70                  75                  80
Ile Ser Ala Gly Asn Ser Gly Thr Ser Gly Ser Gly Thr Glu Gly Val
                 85                  90                  95
Asn Lys Asp Tyr Tyr Gly Leu Gln Asp Asn Glu Thr Val Gly Thr Pro
            100                 105                 110
Gly Thr Ser Arg Gly Ala Thr Thr Val Ala Ser Ala Glu Asn Thr Asp
        115                 120                 125
Val Ile Asn Gln Ala Val Thr Ile Thr Asp Gly Ser Gly Leu Lys Leu
    130                 135                 140
Gly Pro Glu Thr Val Gln Leu Ser Ser Asn Asp Phe Val Asp Ser Phe
145                 150                 155                 160
Asp Gln Lys Lys Phe Tyr Val Val Lys Asp Ala Ser Gly Lys Leu Ser
                165                 170                 175
Thr Gly Asp Ala Gly Asp Tyr Thr Ala Asp Ala Lys Gly Lys Ile Ala
            180                 185                 190
Ile Val Lys Arg Gly Ser Leu Thr Phe Thr Asp Lys Gln Lys Tyr Ala
        195                 200                 205
Glu Ala Ala Gly Ala Ala Gly Leu Ile Ile Val Asn Asn Asp Gly Thr
    210                 215                 220
Ser Thr Pro Leu Thr Ser Ile Ser Leu Thr Ala Thr Phe Pro Thr Phe
225                 230                 235                 240
Gly Leu Ser Asn Thr Thr Gly Gln Lys Leu Val Asp Trp Val Thr Ala
                245                 250                 255
His Pro Asn Asp Ser Leu Gly Val Lys Ile Ala Leu Ala Leu Leu Pro
            260                 265                 270
Asn Gln Asn Tyr Lys Ala Asp Arg Met Ser Ser Phe Thr Ser Tyr Gly
        275                 280                 285
Pro Val Ser Asp Leu Ser Phe Lys Pro Asp Ile Thr Ala Pro Gly Gly
    290                 295                 300
Asn Ile Trp Ser Thr Gln Asn Asn Gly Tyr Thr Asn Met Ser Gly
305                 310                 315                 320
```

```
Thr Ser Met Ala Ser Pro Phe Ile Ala Gly Ser Gln Ala Leu Leu Lys
            325                 330                 335

Gln Ala Leu Asn Asn Lys Asp Asn Glu Phe Tyr Ala Asp Tyr Lys Gln
            340                 345                 350

Leu Lys Gly Thr Ala Leu Thr Asp Phe Leu Lys Thr Val Glu Met Asn
            355                 360                 365

Thr Ala Lys Pro Ile Asn Asp Ile Asn Tyr Asp Asn Val Ile Val Ser
            370                 375                 380

Pro Arg Arg Gln Gly Ala Gly Leu Val Asp Val Lys Ala Ala Ile Asp
385                 390                 395                 400

Ala Leu Glu Lys Asn Pro Ser Thr Val Val Ser Glu Asn Gly Tyr Pro
            405                 410                 415

Ala Val Glu Leu Lys Asp Phe Thr Ser Thr Thr Lys Thr Phe Lys Leu
            420                 425                 430

Thr Phe Thr Asn Arg Thr Lys His Gln Leu Thr Tyr Gln Met Thr Ser
            435                 440                 445

Asn Glu Asp Thr Asn Ala Val Tyr Thr Ser Ala Thr Asp Leu Glu Ser
            450                 455                 460

Phe Ile Gln Ser Ser Lys Met Ala Lys Leu Ile His Glu Arg Gly Ala
465                 470                 475                 480

Ala

<210> SEQ ID NO 78
<211> LENGTH: 331
<212> TYPE: PRT
<213> ORGANISM: Lactobacillus rhamnosus

<400> SEQUENCE: 78

Met Thr Ile Asn Trp Gln Gln Glu Val Glu Lys Leu Glu Pro Gln Leu
1               5                   10                  15

Leu Ser Asp Leu Thr Thr Leu Leu Lys Ile Asn Ser Glu Arg Asp Thr
            20                  25                  30

Asp His Gln Thr Asp Glu Tyr Pro Leu Gly Pro Gly Pro Ala Lys Ala
        35                  40                  45

Leu Glu Ala Phe Leu Ala Ile Ala Gln Arg Asp Gly Phe Lys Thr Leu
    50                  55                  60

Asn Val Asp His Val Ala Gly Arg Ile Glu Leu Gly Asp Gly Asp Glu
65                  70                  75                  80

Ile Phe Gly Leu Phe Gly His Val Asp Val Val Pro Ala Gly Pro Gly
                85                  90                  95

Trp Gln Thr Asp Pro Phe Asp Pro Val Ile Arg Asp Gly Lys Ile Tyr
            100                 105                 110

Gly Arg Gly Thr Ser Asp Asp Lys Gly Pro Ser Ile Ala Ala Tyr Tyr
        115                 120                 125

Ala Leu Lys Leu Ile Arg Asp Leu Lys Leu Pro Ile Asn Lys Lys Ile
    130                 135                 140

His Phe Ile Leu Gly Thr Asp Glu Glu Ser Asp Trp Val Gly Ile His
145                 150                 155                 160

Arg Tyr Leu Glu Thr Glu Pro Ala Pro Asp Phe Gly Phe Ser Pro Asp
                165                 170                 175

Ala Glu Phe Pro Ile Ile Asn Gly Glu Lys Gly Ile Ala Ser Phe Glu
            180                 185                 190

Ile Val Gln Lys Pro Ile Ala Ala Ala Thr Ala Asp Leu Thr Leu Asn
        195                 200                 205
```

-continued

```
His Phe Ser Ala Gly Ile Arg Pro Asn Met Val Pro Gln Glu Ala Lys
    210                 215                 220

Ala Val Leu Ser Gly Pro Leu Pro Glu Ala Phe Val Thr Gln Ala Glu
225                 230                 235                 240

Lys Trp Ala Ala Glu Gln Glu Val Thr Leu Thr Leu Thr Leu Gly Asn
                245                 250                 255

Pro Thr Thr Ile Glu Leu Ile Gly Lys Gly Ala His Ala Gln Glu Pro
                260                 265                 270

Lys Asp Gly Lys Asn Ala Ala Thr Tyr Leu Ala Thr Leu Leu Ala Asp
    275                 280                 285

Leu Pro Phe Asp Pro Ala Gly Lys Ala Tyr Leu Thr Met Ile Ala Asn
    290                 295                 300

His Leu His Leu Asp Ser Arg Gly His His Leu Gly Ile Asn Tyr Thr
305                 310                 315                 320

Asp Lys Leu Met Gly Asp Leu Thr Ala Ser Pro
                325                 330

<210> SEQ ID NO 79
<211> LENGTH: 344
<212> TYPE: PRT
<213> ORGANISM: Lactobacillus rhamnosus
<220> FEATURE:
<221> NAME/KEY: VARIANT
<222> LOCATION: (1)...(344)
<223> OTHER INFORMATION: Xaa = Any Amino Acid

<400> SEQUENCE: 79

Gly Lys Met Ser Leu Tyr Ala Gly Gly Pro Asp Glu Arg Leu Thr Pro
1               5                   10                  15

Leu Ile Asp Gly Arg Arg His Val Thr Asp Phe Ala Leu Thr Pro Asp
                20                  25                  30

His Arg Gly Val Val Phe Thr Glu Ser Thr Met Thr Ile Pro Ser Arg
            35                  40                  45

Leu Val Tyr Phe Asp Leu Ala Ser Glu Glu Gln Val Leu Tyr Asp
50                  55                  60

Pro Asn Arg Gln Val Thr Arg His Leu Gly Leu Val Thr Pro Gln Thr
65                  70                  75                  80

Phe Asn Phe Gln Arg Asp Gly Phe Glu Ile Glu Gly Trp Tyr Phe Pro
                85                  90                  95

Pro Gln Gln Ala Ser Ser Ser His Pro Ala Ile Leu Tyr Val His Gly
            100                 105                 110

Gly Pro Ala Val Gly Tyr Gly Tyr Thr Phe Phe His Glu Met Gln Tyr
        115                 120                 125

Leu Ala Ala Lys Gly Tyr Gly Val Ile Cys Arg Asn Pro Arg Gly Gly
    130                 135                 140

Leu Gly Tyr Arg Glu Ala Phe Thr Gly Ala Val Ile Lys His Xaa Pro
145                 150                 155                 160

Ala Gly Asp Tyr Glu Asp Cys Leu Ala Ser Gly Glu Ala Leu Lys
                165                 170                 175

Leu Asp Thr Thr Ile Asp Pro Gln Arg Leu Phe Val Thr Gly Gly Ser
                180                 185                 190

Tyr Gly Gly Phe Met Thr Asn Trp Ile Val Thr His Thr His Arg Phe
        195                 200                 205

Lys Ala Ala Val Thr Gln Arg Ser Ile Ser Asn Trp Leu Ser Met Tyr
    210                 215                 220

Gly Thr Ser Asp Ile Gly Tyr Tyr Phe Thr Pro Trp Glu Leu Glu Gly
```

-continued

```
                225                 230                 235                 240
Lys Trp Thr Gly Asp Leu Ser Asp Val Gln Gly Leu Trp Asp Phe Ser
                245                 250                 255
Pro Leu Ala His Ile Asp His Ala Arg Thr Pro Thr Leu Val Met His
            260                 265                 270
Ser Glu Asn Asp Glu Arg Cys Pro Ile Gly Pro Ser Arg Lys Val Asp
        275                 280                 285
His Arg Ser Gln Thr Ala Trp Cys Xaa Asn Gln Val His Ala Phe Pro
    290                 295                 300
Lys Val Lys Ser Xaa Phe Val Pro Ala Gly Leu Pro Asn Leu Arg
305                 310                 315                 320
Val Ala Arg Leu Gln Ala Ile Val Asp Trp Phe Asp Ala His Gln Ala
                325                 330                 335
Gln Pro Gln Met Ala Lys Gly Glu
                340

<210> SEQ ID NO 80
<211> LENGTH: 558
<212> TYPE: PRT
<213> ORGANISM: Lactobacillus rhamnosus

<400> SEQUENCE: 80

His Leu Ile Gly Ala Thr Thr Leu Asp Glu Tyr Arg Glu Asn Ile Glu
1               5                  10                  15
Lys Asp Lys Ala Leu Glu Arg Arg Phe Gln Arg Val Leu Val Gln Glu
            20                  25                  30
Pro Thr Val Glu Asp Thr Ile Ser Ile Leu Arg Gly Leu Lys Glu Arg
        35                  40                  45
Phe Glu Ile Phe His Lys Val Arg Ile His Asp Ser Ala Leu Val Ala
    50                  55                  60
Ala Ala Thr Leu Ser Asn Arg Tyr Ile Thr Asp Arg Phe Leu Pro Asp
65                  70                  75                  80
Lys Ala Ile Asp Leu Val Asp Glu Ala Cys Ala Thr Ile Asn Val Glu
                85                  90                  95
Met Asn Ser Arg Pro Thr Glu Leu Asp Val Ala Glu Arg Lys Gln Met
            100                 105                 110
Gln Leu Glu Ile Glu Gln Ala Leu Lys Asn Glu Ser Asp Pro Ala
        115                 120                 125
Ser Lys Lys Arg Leu Glu Asn Ala Asn Ala Glu Leu Ala Asn Leu Lys
    130                 135                 140
Glu Lys Thr Asn Lys Leu Lys Ala Gln Trp Glu Ala Glu Lys Lys Asp
145                 150                 155                 160
Ile Arg Gln Leu Asn Glu Lys Lys Ser Ala Ile Asp Lys Ala Lys His
                165                 170                 175
Glu Leu Glu Asp Ala Gln Ser Arg Tyr Asp Leu Glu Thr Ala Ala Arg
            180                 185                 190
Leu Gln His Gly Thr Ile Pro Gln Leu Glu Lys Glu Leu Gln Ala Met
        195                 200                 205
Glu His Ser Asp Arg Pro Gln Ser Trp Leu Val Gln Glu Ser Val Thr
    210                 215                 220
Ala Asn Glu Ile Ala Ala Val Ile Ser Arg Glu Thr Gly Ile Pro Val
225                 230                 235                 240
Ala Lys Leu Val Glu Gly Asp Arg Gln Lys Leu Leu His Leu Ala Gly
                245                 250                 255
```

-continued

```
Asn Leu His Gln Arg Val Ile Gly Gln Asp Glu Ala Val Thr Ala Val
                260                 265                 270

Ser Asp Ala Val Leu Arg Ser Arg Ala Gly Leu Gln Asp Pro Ser Arg
            275                 280                 285

Pro Leu Gly Ser Phe Leu Phe Leu Gly Pro Thr Gly Val Gly Lys Thr
        290                 295                 300

Glu Leu Ala Lys Ala Leu Ala Glu Asp Leu Phe Asp Ser Glu Lys His
305                 310                 315                 320

Met Val Arg Ile Asp Met Ser Glu Tyr Met Glu Lys Ala Ser Val Ser
                325                 330                 335

Arg Leu Val Gly Ala Ala Pro Gly Tyr Val Gly Tyr Glu Gln Gly Gly
            340                 345                 350

Gln Leu Thr Glu Ala Val Arg Arg Asn Pro Tyr Thr Ile Val Leu Leu
        355                 360                 365

Asp Glu Ile Glu Lys Ala Asn Pro Asp Val Phe Asn Ile Leu Leu Gln
    370                 375                 380

Val Leu Asp Asp Gly Arg Leu Thr Asp Gly Gln Gly Arg Thr Val Asp
385                 390                 395                 400

Phe Lys Asn Thr Ile Ile Ile Met Thr Ser Asn Leu Gly Ser Glu Tyr
                405                 410                 415

Leu Leu Asp Gly Val Gln Lys Asp Gly Thr Val Ser Gln Gln Ala Lys
            420                 425                 430

Asp Gln Val Arg Gln Leu Ile Gly Lys Ala Phe Lys Pro Glu Phe Leu
        435                 440                 445

Asn Arg Ile Asp Asp Ile Ile Met Phe His Pro Leu Ser Leu Asp Asp
    450                 455                 460

Val Lys Lys Ile Ala Val Lys Asp Leu His Glu Leu Gly Thr Arg Leu
465                 470                 475                 480

Ala Asp Gln Gln Ile Ser Leu Asp Ile Thr Pro Glu Ala Gln Thr Trp
                485                 490                 495

Leu Ala Asp Lys Gly Tyr Asp Pro Ala Phe Gly Ala Arg Pro Leu Gln
            500                 505                 510

Arg Leu Ile Thr Ser Ala Val Glu Thr Pro Leu Ala Lys Glu Leu Ile
        515                 520                 525

Arg Gly Thr Ile Gln Pro Gly Gln Glu Val Val Ile Thr Val Ala Asp
    530                 535                 540

Asp Gln Leu Gln Phe Lys Ala Lys Gln Val Val Ala Lys Ala
545                 550                 555

<210> SEQ ID NO 81
<211> LENGTH: 292
<212> TYPE: PRT
<213> ORGANISM: Lactobacillus rhamnosus

<400> SEQUENCE: 81

Ile Ser Ala Ile Ile Val Ile Val Glu Glu Asn Asn Val Ala Ala Arg
  1               5                  10                  15

Glu Leu Ile Leu Ala Phe Glu Ser Ser Cys Asp Glu Thr Ser Val Ala
             20                  25                  30

Val Val Glu Asn Gly Thr Lys Ile Leu Ser Asn Ile Ile Ala Thr Gln
         35                  40                  45

Ile Lys Ser His Gln Arg Phe Gly Gly Val Val Pro Glu Val Ala Ser
     50                  55                  60

Arg His His Val Glu Gln Ile Thr Leu Val Thr Asp Ala Ala Leu Lys
 65                  70                  75                  80
```

```
Glu Ala Gly Val Thr Tyr Thr Asp Leu Thr Ala Val Ala Val Thr Tyr
                85                  90                  95

Gly Pro Gly Leu Val Gly Ala Leu Leu Ile Gly Val Arg Ala Ala Lys
            100                 105                 110

Pro Ile Ala Tyr Ala His His Leu Pro Leu Ile Pro Val Asn His Met
            115                 120                 125

Ala Gly His Ile Tyr Ala Ala Arg Phe Val Lys Pro Leu Val Tyr Pro
    130                 135                 140

Leu Leu Ala Leu Ala Val Ser Gly Gly His Thr Glu Leu Val Tyr Met
145                 150                 155                 160

Arg Ala Ala Gly Glu Phe Glu Ile Ile Gly Asp Thr Arg Asp Asp Ala
                165                 170                 175

Ala Gly Glu Ala Tyr Asp Lys Val Gly Arg Ile Leu Gly Ile Pro Tyr
            180                 185                 190

Pro Ala Gly Lys Glu Val Asp Arg Leu Ala His Leu Gly His Asp Thr
            195                 200                 205

Phe His Phe Pro Arg Ala Met Asp Lys Glu Asp Asn Leu Asp Phe Ser
    210                 215                 220

Phe Ser Gly Leu Lys Ser Ala Val Ile Asn Thr Val His Ala Asp
225                 230                 235                 240

Gln Ile Gly Glu Ser Leu Ser Arg Glu Asp Leu Ser Ala Ser Ser Gln
                245                 250                 255

Ala Ser Val Val His Val Met Val Leu Lys Ser Gln Ser Ala Ile Ala
            260                 265                 270

Glu Tyr Pro Val Ile Gln Val Ile Ala Gly Gly Val Ala Asp Asn
            275                 280                 285

Gln Gly Leu Lys
    290

<210> SEQ ID NO 82
<211> LENGTH: 244
<212> TYPE: PRT
<213> ORGANISM: Lactobacillus rhamnosus

<400> SEQUENCE: 82

Met Ile Phe Arg Lys Pro Gln Pro Phe Glu Tyr Glu Gly Thr Asp Thr
1               5                   10                  15

Gly Val Val Leu Leu His Ala Tyr Thr Gly Ser Pro Asn Asp Met Asn
            20                  25                  30

Phe Met Ala Arg Ala Leu Gln Arg Ser Gly Tyr Gly Val Tyr Val Pro
            35                  40                  45

Leu Phe Ser Gly His Gly Thr Val Glu Pro Leu Asp Ile Leu Thr Lys
    50                  55                  60

Gly Asn Pro Asp Ile Trp Trp Ala Glu Ser Ser Ala Ala Val Ala His
65                  70                  75                  80

Met Thr Ala Lys Tyr Ala Lys Val Phe Val Phe Gly Leu Ser Leu Gly
                85                  90                  95

Gly Ile Phe Ala Met Lys Ala Leu Glu Thr Leu Pro Gly Ile Thr Ala
            100                 105                 110

Gly Gly Val Phe Ser Ser Pro Ile Leu Pro Gly Lys His His Leu Val
            115                 120                 125

Pro Gly Phe Leu Lys Tyr Ala Glu Tyr Met Asn Arg Leu Ala Gly Lys
    130                 135                 140

Ser Asp Glu Ser Thr Gln Ile Leu Ala Tyr Leu Pro Gly Gln Leu Ala
```

-continued

```
                145                 150                 155                 160
Ala Ile Asp Gln Phe Ala Thr Thr Val Ala Ala Asp Leu Asn Leu Val
                    165                 170                 175

Lys Gln Pro Thr Phe Ile Gly Gln Ala Gly Gln Asp Glu Leu Val Asp
                180                 185                 190

Gly Arg Leu Ala Tyr Gln Leu Arg Asp Ala Leu Ile Asn Ala Ala Arg
            195                 200                 205

Val Asp Phe His Trp Tyr Asp Asp Ala Lys His Val Ile Thr Val Asn
    210                 215                 220

Ser Ala His His Ala Leu Glu Glu Asp Val Ile Ala Phe Met Gln Gln
225                 230                 235                 240

Glu Asn Glu Gly

<210> SEQ ID NO 83
<211> LENGTH: 433
<212> TYPE: PRT
<213> ORGANISM: Lactobacillus rhamnosus

<400> SEQUENCE: 83

Leu Gly Ile Phe Phe Lys Arg Phe Arg Lys Leu His Leu Phe Asp
  1               5                  10                  15

Pro Leu Asn Tyr Pro Glu Glu Thr Phe Gln Ser Phe Asp Ser Ala Phe
                20                  25                  30

Asn Asn Gly Ala Asp Tyr Val Glu Leu Asp Val His Glu Ser Ala Asp
            35                  40                  45

Gly Val Ile Val Ile Gln His Asp Thr Thr Ile Gln Arg Thr Thr Gly
        50                  55                  60

Ala Asn Leu Ala Ile Ala Lys Thr Asn Phe Ala Gln Leu Gln Gln Tyr
65                  70                  75                  80

His Thr Lys Asn Gly Glu Pro Ile His Ser Leu Glu Glu Leu Phe Ala
                85                  90                  95

His Glu Gln Gln Thr Lys His Lys Phe Leu Ile Glu Thr Lys Ile Val
                100                 105                 110

Lys Gly Glu Pro His Pro His Leu Glu Asp Lys Val Ala Ala Leu Ile
            115                 120                 125

Lys Gln Tyr His Met Glu Asn Arg Val Met Phe His Ser Phe Ser Ala
        130                 135                 140

Ala Ser Leu Lys Arg Leu Gln Ala Ala Leu Pro Asn Ile Pro Arg Ile
145                 150                 155                 160

Leu Ile Val Gly Ser Leu Lys Arg Ile Asn Phe Asp Val Leu Thr Tyr
                165                 170                 175

Val Asp Gly Ile Asn Leu Ser Ser Asp Leu Val Thr Pro Gln Leu Val
            180                 185                 190

Thr Gln Leu His Asp Leu Gly Lys Lys Val Tyr Val Trp Asp Glu Met
        195                 200                 205

Asn Glu Asp Arg Ala Lys Trp Thr Trp Leu Val Asn Leu Asn Ile Asp
    210                 215                 220

Gly Val Val Thr Asn Tyr Thr Ser Leu Gly His Glu Phe Gln Thr Leu
225                 230                 235                 240

Lys Ala Ala Ala Val Thr Thr Ser Ile Asn Asp Leu Gly Ala Asn Ser
                245                 250                 255

Ser Leu Ala Ala Leu Pro Val Tyr Glu Asn Pro Tyr Gln Pro Leu Leu
            260                 265                 270

Arg Ser Glu Arg Leu Ala Pro Gln Thr Pro Ile Met Ile Ser Ser Met
```

-continued

```
                275                 280                 285
Val Ser Leu Ala Gly Ser Thr Tyr Tyr Gln Ile Gly Asp Asn Ala Phe
    290                 295                 300
Val Pro Ala Glu Thr Ile Asn Leu Ala Pro Glu Ala Gly Trp Ala Ser
305                 310                 315                 320
Leu Phe Leu His Gln Arg Ile Val Ile Thr Ser Arg His Phe Lys Val
                325                 330                 335
Pro Val His Ala Asp Pro Leu His Gln Gln Ala Ile Thr Gly His Val
                340                 345                 350
Gly Asn His Lys Cys Tyr Arg Val Leu Ala Ala Arg Tyr Gln Ser Gly
                355                 360                 365
Gln Leu Tyr Leu Lys Thr Lys Ile Gly Trp Leu Asn Ala Lys Asp Leu
    370                 375                 380
Gln Val Leu Pro Thr Ala Glu Asn Met Arg Ile Trp Leu Thr Leu Tyr
385                 390                 395                 400
Arg Ser Ile Pro Glu Asn Gln Lys Pro Leu Leu His Trp Ala Leu Gly
                405                 410                 415
Asp Thr Ala Phe Asp Thr Pro Leu Leu Asn Ala Ser Val Leu Asn Ile
                420                 425                 430
Gly
```

<210> SEQ ID NO 84
<211> LENGTH: 448
<212> TYPE: PRT
<213> ORGANISM: Lactobacillus rhamnosus

<400> SEQUENCE: 84

```
Met Glu Leu Ala Lys Leu Ala Val Asp Glu Thr Gly Arg Gly Val Trp
1               5                   10                  15
Glu Asp Lys Ala Ile Lys Asn Met Phe Ala Thr Glu Ile Trp His
            20                  25                  30
Ser Ile Lys Asn Asn Lys Thr Val Gly Val Ile Asn Glu Asp Lys Gln
        35                  40                  45
Arg Gly Leu Val Ser Ile Ala Glu Pro Ile Gly Val Ile Ala Gly Val
    50                  55                  60
Thr Pro Val Thr Asn Pro Thr Ser Thr Thr Ile Phe Lys Ser Glu Ile
65                  70                  75                  80
Ser Ile Lys Thr Arg Asn Pro Ile Ile Phe Ala Phe His Pro Gly Ala
                85                  90                  95
Gln Lys Ser Ser Ala Arg Ala Leu Glu Val Ile Arg Glu Glu Ala Glu
                100                 105                 110
Lys Ala Gly Leu Pro Lys Gly Ala Leu Gln Tyr Ile Pro Val Pro Ser
                115                 120                 125
Met Glu Ala Thr Lys Thr Leu Met Asp His Pro Gly Ile Ala Thr Ile
                130                 135                 140
Leu Ala Thr Gly Gly Pro Gly Met Val Lys Ser Ala Tyr Ser Ser Gly
145                 150                 155                 160
Lys Pro Ala Leu Gly Val Gly Ala Gly Asn Ala Pro Ala Tyr Ile Glu
                165                 170                 175
Ala Ser Ala Asn Ile Lys Gln Ala Val Asn Asp Leu Val Leu Ser Lys
                180                 185                 190
Ser Phe Asp Asn Gly Met Ile Cys Ala Ser Glu Gln Gly Ala Ile Val
                195                 200                 205
Asp Ser Ser Ile Tyr Asp Ala Ala Lys Lys Glu Phe Glu Ala Gln Gly
```

```
            210                 215                 220
Ala Tyr Phe Val Lys Pro Lys Asp Met Lys Lys Phe Glu Ser Thr Val
225                 230                 235                 240

Ile Asn Leu Glu Lys Gln Ser Val Asn Pro Arg Ile Val Gly Gln Ser
                245                 250                 255

Pro Lys Gln Ile Ala Glu Trp Ala Gly Ile Arg Ile Pro Asp Asp Thr
                260                 265                 270

Thr Ile Leu Ile Ala Glu Leu Lys Asp Val Gly Lys Lys Tyr Pro Leu
            275                 280                 285

Ser Arg Glu Lys Leu Ser Pro Val Leu Ala Met Val Lys Ala Asp Gly
        290                 295                 300

His Glu Asp Ala Phe Lys Lys Cys Glu Thr Met Leu Asp Ile Gly Gly
305                 310                 315                 320

Leu Gly His Thr Ala Val Ile His Thr Ala Asp Asp Glu Leu Ala Leu
                325                 330                 335

Lys Phe Ala Asp Thr Met Gln Ala Cys Arg Ile Leu Ile Asn Thr Pro
                340                 345                 350

Ser Ser Val Gly Gly Ile Gly Asp Leu Tyr Asn Glu Met Ile Pro Ser
            355                 360                 365

Leu Thr Leu Gly Cys Gly Ser Tyr Gly Gly Asn Ser Ile Ser His Asn
        370                 375                 380

Val Gly Thr Val Asp Leu Leu Asn Ile Lys Thr Met Ala Lys Arg Arg
385                 390                 395                 400

Asn Asn Met Gln Trp Met Lys Leu Pro Pro Lys Ile Tyr Phe Glu Lys
                405                 410                 415

Asn Ser Val Arg Tyr Leu Glu His Met Glu Ser Ile Lys Arg Ala Phe
                420                 425                 430

Ile Val Ala Asp Arg Ser Met Glu Lys Ala Gly Phe Arg Gln Asp His
            435                 440                 445

<210> SEQ ID NO 85
<211> LENGTH: 158
<212> TYPE: PRT
<213> ORGANISM: Lactobacillus rhamnosus

<400> SEQUENCE: 85

Val Leu Val Asn Asn Ala Gly Ile Thr Asp Asp Met Leu Ala Met Arg
1               5                   10                  15

Met Lys Pro Ala Ser Phe Ala Lys Val Val Gln Val Asn Leu Asp Gly
                20                  25                  30

Thr Phe Tyr Val Thr Gln Pro Ala Phe Lys Lys Met Leu Lys Ala Arg
            35                  40                  45

Ala Gly Val Ile Ile Asn Leu Ala Ser Val Val Gly Leu Thr Gly Asn
        50                  55                  60

Ile Gly Gln Ala Asn Tyr Ala Ala Ser Lys Ala Gly Ile Ile Gly Leu
65                  70                  75                  80

Thr Lys Thr Leu Ala Arg Glu Gly Ala Met Arg Gly Val Arg Val Asn
                85                  90                  95

Ala Ile Ala Pro Gly Met Ile Ala Thr Asp Met Thr Ala Ala Leu Ser
                100                 105                 110

Gln Ser Ser Gln Asp Gln Ile Leu Ala Glu Ile Pro Leu Lys Arg Phe
            115                 120                 125

Gly Gln Pro Glu Glu Ile Ala His Thr Ala Arg Phe Leu Val Glu Asn
        130                 135                 140
```

```
Ala Tyr Ile Thr Gly Gln Thr Val Thr Val Ala Gly Gly Leu
145                 150                 155
```

<210> SEQ ID NO 86
<211> LENGTH: 334
<212> TYPE: PRT
<213> ORGANISM: Lactobacillus rhamnosus

<400> SEQUENCE: 86

```
Met Tyr His Ala Ala Asp Arg Tyr Glu Lys Met Pro Val Arg His
 1               5                  10                  15

Ala Gly Lys Thr Gly Leu Met Leu Pro Val Ile Ser Leu Gly Leu Trp
                20                  25                  30

Gln His Tyr Gly Asn Leu Asp Pro Phe Gly Pro Arg Arg Ser Val Ile
            35                  40                  45

Leu Asp Ala Phe Asp Arg Gly Val Phe His Phe Asp Val Ala Asn His
        50                  55                  60

Tyr Gly Asn Gly Asp Arg Glu Pro Gly Phe Ser Ser Glu Arg Leu
65                  70                  75                  80

Leu Gly Gln Ile Leu Ala Thr Asp Leu Lys Pro Tyr Arg Asp Glu Leu
                85                  90                  95

Val Ile Ser Thr Lys Val Gly Tyr Glu Ile His Pro Gly Pro Tyr Gly
                100                 105                 110

Val Gly Thr Ser Arg Lys Ala Val Ile Gln Gly Leu Asn Asp Ser Leu
            115                 120                 125

Lys Arg Leu Gln Leu Asp Tyr Val Asp Ile Tyr Tyr Ala His Arg Phe
130                 135                 140

Asp Asp Thr Val Ala Leu Glu Glu Thr Val Asn Ala Leu Asp Gln Thr
145                 150                 155                 160

Val Arg Asp Gly Lys Ala Leu Tyr Ile Gly Ile Ser Asn Tyr Asp Thr
                165                 170                 175

Lys Gln Thr Lys Glu Ala Ile Ala Met Phe Lys Asp Leu His Thr Pro
            180                 185                 190

Phe Val Leu Asn Gln Tyr Ser Tyr Asn Met Phe Asn Arg Thr Ala Glu
        195                 200                 205

Thr Ser Gly Leu Ile Asp Ala Leu Lys Ala Asp Gly Ala Gly Leu Ile
210                 215                 220

Ala Tyr Gly Pro Leu Ser Glu Gly Leu Leu Ser Asp Arg Tyr Leu Lys
225                 230                 235                 240

Gly Ile Pro Asp Thr Phe Lys Ile His Pro Thr Asn Lys Ala Thr Phe
                245                 250                 255

Ala Lys Gly Lys Glu Ala Val Val Lys Gln Leu Asn Ala Leu Asn Glu
            260                 265                 270

Ile Ala His Asp Arg Asp Gln Thr Leu Ser Gln Met Ala Leu Ala Trp
        275                 280                 285

Leu Leu Arg Asp Pro Val Val Thr Ser Val Ile Ile Gly Thr Thr Ser
    290                 295                 300

Val Glu His Leu Gln Asp Asn Leu Lys Ala Thr Glu His Leu Thr Phe
305                 310                 315                 320

Thr Ala Glu Glu Ile Gln Gln Ile Asp Asp Ile Leu Asn Ala
                325                 330
```

<210> SEQ ID NO 87
<211> LENGTH: 413
<212> TYPE: PRT
<213> ORGANISM: Lactobacillus rhamnosus

```
<400> SEQUENCE: 87

Ala Val Ala Leu Pro Leu Leu Gly Val Leu Ala Ile Ala Ala Thr His
1               5                   10                  15

Ala Glu Gly Val Tyr Asp Ile Gly Arg Pro Leu Gly Arg Phe Phe Ala
            20                  25                  30

Leu Ala Phe Met Val Leu Ile His Ala Thr Ile Gly Pro Met Phe Gly
            35                  40                  45

Thr Pro Arg Thr Ala Thr Val Ser Phe Thr Thr Gly Val Leu Pro Met
        50                  55                  60

Leu Pro Lys Ala Trp Gln Gln Gly Leu Leu Val Phe Ser Ala Leu
65                  70                  75                  80

Phe Phe Gly Ala Ala Phe Phe Leu Ser Tyr Lys Glu Arg Lys Ile Thr
                85                  90                  95

Thr Ala Val Gly Lys Val Leu Asn Pro Val Phe Leu Leu Leu Phe
            100                 105                 110

Phe Val Phe Phe Ile Gly Phe Leu His Pro Met Gly Asn Pro Ala Ala
        115                 120                 125

Gln Thr Val Thr Ala Ala Tyr Lys Asn Gly Ser Phe Met Ser Gly
    130                 135                 140

Phe Leu Gln Gly Tyr Asn Thr Met Asp Ala Leu Ala Ala Leu Ala Phe
145                 150                 155                 160

Gly Val Thr Val Val Thr Ala Val Arg Gly Leu Gly Leu Lys Asn Asp
                165                 170                 175

Asp His Val Ala Lys Ala Thr Ala Lys Ala Gly Val Met Ala Thr Ser
            180                 185                 190

Trp Ile Ala Leu Ile Tyr Val Ala Leu Ile Val Leu Gly Ser Met Ser
        195                 200                 205

Leu Ala His Phe Lys Leu Ser Ala Glu Gly Gly Thr Ala Phe Asn Gln
    210                 215                 220

Val Gly Thr Phe Tyr Phe Gly Thr Val Gly His Pro Ala Trp Gln Pro
225                 230                 235                 240

Cys Leu Thr Leu Thr Cys Leu Asn Thr Pro Val Gly Phe Val Arg Ala
                245                 250                 255

Phe Pro His Asp Phe His Arg His Phe Pro Lys Val Ser Tyr Gln Val
            260                 265                 270

Trp Leu Gly Leu Thr Ser Phe Leu Ser Phe Leu Thr Ala Asn Phe Gly
        275                 280                 285

Leu Glu Gln Ile Ile Ala Trp Ser Val Pro Met Leu Met Phe Leu Tyr
    290                 295                 300

Pro Phe Ser Met Val Leu Ile Leu Ser Val Phe Gly Lys Ala Phe
305                 310                 315                 320

His His Asp Pro Leu Val Tyr Arg Ile Val Ala Phe Thr Ile Val
            325                 330                 335

Pro Ala Val Leu Asp Met Phe Ala Ala Phe Pro Ala Val Val Ser Gln
        340                 345                 350

Ser Ser Leu Gly Leu Ala Leu His Ser Phe Gln Leu His Phe Leu Pro
    355                 360                 365

Phe Ser Ala Met Gly Leu Gly Trp Leu Val Pro Ala Gly Val Gly Leu
370                 375                 380

Val Leu Gly Leu Val Ala His Ala Val Lys Val Arg Lys Ala Val Ala
385                 390                 395                 400

Ala Thr His Leu Glu Ala Glu Gln Thr Gln Leu Val His
```

-continued

```
                405                 410
```

<210> SEQ ID NO 88
<211> LENGTH: 627
<212> TYPE: PRT
<213> ORGANISM: Lactobacillus rhamnosus

<400> SEQUENCE: 88

```
Met Ala Asp Asn His Lys Ala Gln Thr Thr Lys Gln Pro Ser Gly Pro
1               5                   10                  15

Arg Met Gly Pro Gly Arg Gly Gly Leu Val Glu Lys Pro Lys Asn Phe
            20                  25                  30

Trp Gly Thr Thr Ala Arg Leu Phe Gly Tyr Met Arg Asn Arg Leu Ile
        35                  40                  45

Gly Ile Ile Ala Val Leu Val Leu Ala Ile Ala Ser Thr Val Phe Gln
    50                  55                  60

Ile Arg Thr Pro Lys Ile Leu Gly Glu Ala Thr Thr Glu Ile Phe Lys
65                  70                  75                  80

Gly Val Met Lys Gly Gln Ala Glu Gln Lys Ala Gly Ile Ala Val Gly
                85                  90                  95

Asn Tyr Pro Ile Asp Phe Asp Lys Ile Lys Gln Ile Ile Leu Ile Val
            100                 105                 110

Leu Val Leu Tyr Leu Gly Ser Ala Leu Phe Ser Phe Leu Gln Gln Phe
        115                 120                 125

Ile Met Thr Arg Ile Ser Gln Asn Thr Val Tyr Gln Leu Arg Lys Asp
    130                 135                 140

Leu Lys His Lys Met Lys Thr Val Pro Ile Lys Tyr Tyr Asp Thr His
145                 150                 155                 160

Ser Asn Gly Asp Ile Met Ser Arg Ala Ile Asn Asp Met Asp Asn Ile
                165                 170                 175

Ala Ser Thr Leu Gln Gln Ser Leu Thr Gln Met Val Thr Ser Ala Val
            180                 185                 190

Met Phe Val Gly Thr Ile Trp Met Met Leu Thr Ile Ser Trp Lys Leu
        195                 200                 205

Thr Leu Ile Ala Leu Val Thr Ile Pro Leu Gly Leu Ile Val Val Gly
    210                 215                 220

Ile Val Ala Pro Lys Ser Gln Arg Phe Phe Ala Ala Gln Gln Lys Ala
225                 230                 235                 240

Leu Gly Leu Leu Asn Asn Gln Val Glu Glu Thr Tyr Gly Gly Gln Val
                245                 250                 255

Ile Ile Lys Ser Phe Asn Arg Glu Asp Asp Glu Val Glu Ala Phe Glu
            260                 265                 270

Gly Gln Asn Gln Ala Phe Tyr Asp Ala Ala Trp Lys Ala Gln Phe Val
        275                 280                 285

Ser Gly Ile Ile Met Pro Leu Met Ile Phe Leu Asn Asn Ile Gly Tyr
    290                 295                 300

Val Phe Val Ala Ile Met Gly Gly Ile Glu Val Ser Asn Gly Thr Ile
305                 310                 315                 320

Thr Leu Gly Asn Val Gln Ala Phe Leu Gln Tyr Met Gln Gln Phe Ser
                325                 330                 335

Gln Pro Ile Ser Gln Leu Ala Asn Leu Ala Asn Thr Ile Gln Ser Thr
            340                 345                 350

Ile Ala Ser Ala Glu Arg Ile Phe Ala Val Leu Asp Glu Glu Asp Met
        355                 360                 365
```

-continued

Gln Asp Glu Pro Ser Gly Val Pro Ala Val Ala Asn Asp Pro Asn Lys
    370                 375                 380

Leu Val Met Asp His Val Gln Phe Gly Tyr Thr Pro Asp Ala Leu Leu
385                 390                 395                 400

Leu Lys Asp Tyr Asn Leu Gln Val Lys Pro Gly Glu Met Val Ala Ile
                405                 410                 415

Val Gly Pro Thr Gly Ala Gly Lys Thr Thr Ile Ile Asn Leu Leu Glu
            420                 425                 430

Arg Phe Tyr Asp Ile Ser Gly Gly Ser Ile Arg Leu Asn Gly Thr Asp
        435                 440                 445

Thr Arg Asp Met Lys Arg Glu Asp Val Arg Ala His Phe Ala Met Val
    450                 455                 460

Leu Gln Asp Thr Trp Leu Phe Thr Gly Thr Ile Trp Asp Asn Leu Lys
465                 470                 475                 480

Tyr Gly Arg Glu Asp Ala Thr Asp Glu Val Leu Ala Ala Ala Lys
                485                 490                 495

Ala Ala His Val Asp Asn Phe Val Arg Gln Leu Pro Asp Gly Tyr Asn
            500                 505                 510

Thr Ile Leu Asn Glu Glu Ala Ser Asn Ile Ser Gln Gly Gln Arg Gln
        515                 520                 525

Leu Leu Thr Ile Ala Arg Ala Phe Val Ala Asp Pro Glu Ile Leu Ile
    530                 535                 540

Leu Asp Glu Ala Thr Ser Ser Val Asp Thr Arg Thr Glu Ile His Ile
545                 550                 555                 560

Gln His Ala Met Asn Arg Leu Leu Thr Asp Arg Thr Ser Phe Val Val
                565                 570                 575

Ala His Arg Leu Ser Thr Ile Arg Asp Ala Asp Lys Ile Ile Val Met
            580                 585                 590

Asn His Gly Ser Ile Val Glu Thr Gly Asn His Asp Glu Leu Met Ala
        595                 600                 605

Lys Asn Gly Phe Tyr Ala Asp Leu Tyr Asn Ser Gln Phe Ser Gly Asn
    610                 615                 620

Val Ala Ile
625

<210> SEQ ID NO 89
<211> LENGTH: 202
<212> TYPE: PRT
<213> ORGANISM: Lactobacillus rhamnosus

<400> SEQUENCE: 89

Thr Thr Arg Leu Ser Ser Leu Ile Thr Glu Tyr Leu Asp Ser Gln Leu
1               5                   10                  15

Ala Glu Arg Arg Ser Met His Gly Val Leu Val Asp Ile Tyr Gly Leu
                20                  25                  30

Gly Val Leu Ile Thr Gly Asp Ser Gly Val Gly Lys Ser Glu Thr Ala
            35                  40                  45

Leu Glu Leu Val Gln Arg Gly His Arg Leu Ile Ala Asp Asp Arg Val
    50                  55                  60

Asp Val Tyr Gln Gln Asp Glu Gln Thr Val Val Gly Ala Ala Pro Pro
65                  70                  75                  80

Ile Leu Ser His Leu Leu Glu Ile Arg Gly Leu Gly Ile Ile Asp Val
                85                  90                  95

Met Asn Leu Phe Gly Ala Gly Ala Val Arg Glu Asp Thr Thr Ile Ser
            100                 105                 110

```
Leu Ile Val His Leu Glu Asn Trp Thr Pro Asp Lys Thr Phe Asp Arg
        115                 120                 125

Leu Gly Ser Gly Glu Gln Thr Gln Met Ile Phe Asp Val Pro Val Pro
    130                 135                 140

Lys Ile Thr Ile Pro Val Lys Val Gly Arg Asn Leu Ala Ile Ile Ile
145                 150                 155                 160

Glu Val Ala Ala Met Asn Phe Arg Ala Lys Ser Met Gly Tyr Asp Ala
                165                 170                 175

Thr Lys Thr Phe Glu Lys Asn Leu Asn His Leu Ile Glu His Asn Glu
            180                 185                 190

Ala Asn Asp Gln Lys Ser Ser Glu Glu Lys
        195                 200

<210> SEQ ID NO 90
<211> LENGTH: 341
<212> TYPE: PRT
<213> ORGANISM: Lactobacillus rhamnosus
<220> FEATURE:
<221> NAME/KEY: VARIANT
<222> LOCATION: (1)...(341)
<223> OTHER INFORMATION: Xaa = Any Amino Acid

<400> SEQUENCE: 90

Met Ser Ile Ser Thr Arg Ala Asn Lys Leu Asp Gly Val Glu Gln Ala
1               5                   10                  15

Xaa Val Ala Met Ala Thr Glu Met Asn Lys Gly Val Leu Lys Asn Leu
            20                  25                  30

Gly Leu Leu Thr Pro Glu Leu Glu Gln Ala Lys Asn Gly Asp Leu Met
        35                  40                  45

Ile Val Ile Asn Gly Lys Ser Gly Ala Asp Asn Glu Gln Leu Leu Val
    50                  55                  60

Glu Ile Glu Glu Leu Phe Asn Thr Lys Ala Gln Ser Gly Ser His Glu
65                  70                  75                  80

Ala Arg Tyr Ala Thr Ile Gly Ser Ala Lys Lys His Ile Pro Glu Ser
                85                  90                  95

Asn Leu Ala Val Ile Ser Val Asn Gly Leu Phe Ala Ala Arg Glu Ala
            100                 105                 110

Arg Gln Ala Leu Gln Asn Asp Leu Asn Val Met Leu Phe Ser Asp Asn
        115                 120                 125

Val Ser Val Glu Asp Glu Leu Ala Leu Lys Gln Leu Ala His Glu Lys
    130                 135                 140

Gly Leu Leu Met Met Gly Pro Asp Cys Gly Thr Ala Ile Ile Asn Gly
145                 150                 155                 160

Ala Ala Leu Cys Phe Gly Asn Ala Val Arg Arg Gly Asn Ile Gly Ile
                165                 170                 175

Val Gly Ala Ser Gly Thr Gly Ser Gln Glu Leu Ser Val Arg Ile His
            180                 185                 190

Glu Phe Gly Gly Gly Val Ser Gln Leu Ile Gly Thr Gly Gly Arg Asp
        195                 200                 205

Leu Ser Glu Lys Ile Gly Gly Leu Met Met Leu Asp Ala Ile Gly Met
    210                 215                 220

Leu Glu Asn Asp Pro Gln Thr Glu Ile Ile Ala Leu Ile Ser Lys Pro
225                 230                 235                 240

Pro Ala Pro Ala Val Ala Arg Lys Val Leu Glu Arg Ala Arg Ala Cys
                245                 250                 255
```

-continued

Arg Lys Pro Val Val Cys Phe Leu Asp Arg Gly Glu Thr Pro Val
        260             265             270

Asp Glu Gln Gly Leu Gln Phe Ala Arg Gly Thr Lys Glu Ala Ala Leu
        275             280             285

Lys Ala Val Met Leu Ser Gly Val Lys Gln Glu Asn Leu Asp Leu His
    290             295             300

Thr Leu Asn Gln Pro Leu Ile Ala Asp Val Arg Ala Arg Leu Gln Pro
305             310             315             320

Gln Gln Lys Tyr Ile Arg Gly Leu Ser Ala Ala Arg Cys Ala Thr
                325             330             335

Lys Pro Cys Ser Arg
        340

<210> SEQ ID NO 91
<211> LENGTH: 409
<212> TYPE: PRT
<213> ORGANISM: Lactobacillus rhamnosus

<400> SEQUENCE: 91

Gln Ile Leu Asn Asn Pro Phe Leu Asn Lys Gly Thr Ala Phe Thr Gln
1               5                   10                  15

Glu Glu Arg Asn Gln Tyr Gly Leu Asn Gly Leu Leu Pro Pro Ala Val
            20                  25                  30

Gln Thr Leu Asp Gln Val Lys Gln Ala Tyr Ala Gln Leu Gln Thr
        35                  40                  45

Lys Pro Thr Asp Leu Ala Lys Arg Gln Phe Leu Met Thr Leu Phe Asn
    50                  55                  60

Glu Asn His Val Leu Phe Tyr Lys Leu Phe Ser Glu His Ile Asn Glu
65                  70                  75                  80

Phe Met Pro Ile Val Tyr Asp Pro Thr Ile Ala Asp Thr Ile Glu Asn
                85                  90                  95

Tyr Ser Ala Leu Phe Val Asn Pro Gln Asn Ala Thr Tyr Leu Ser Ile
            100                 105                 110

Asp Asp Pro Asp His Ile Glu Ser Ala Leu Lys His Ser Ala Asp Gly
        115                 120                 125

Arg Asp Ile Arg Leu Leu Val Val Ser Asp Ala Glu Gly Ile Leu Gly
    130                 135                 140

Ile Gly Asp Trp Gly Thr Gln Gly Val Asp Ile Ser Val Gly Lys Leu
145                 150                 155                 160

Met Val Tyr Thr Ala Ala Gly Ile Asp Pro Ser Gln Val Leu Pro
                165                 170                 175

Val Val Leu Asp Val Gly Thr Asn Asn Glu Gly Leu Leu Asn Asp Asp
            180                 185                 190

Leu Tyr Leu Gly Asn Arg His Lys Arg Val Tyr Gly Glu Lys Tyr His
        195                 200                 205

His Phe Val Asp Lys Phe Val Ala Ala Glu Lys Leu Phe Pro Asn
    210                 215                 220

Leu Tyr Leu His Phe Glu Asp Phe Gly Arg Ser Asn Ala Ala Asp Ile
225                 230                 235                 240

Leu Asn Gln Tyr Lys Asp Lys Ile Thr Thr Phe Asn Asp Asp Ile Gln
                245                 250                 255

Gly Thr Gly Ile Ile Val Leu Ala Gly Leu Leu Gly Ala Met Asn Ile
            260                 265                 270

Ser Lys Gln Lys Leu Thr Asp Gln Val Tyr Leu Ser Phe Gly Ala Gly
        275                 280                 285

```
Thr Ala Gly Ala Gly Ile Ala Ser Arg Val Tyr Glu Ala Phe Val Glu
        290                 295                 300

Glu Gly Leu Ser Pro Glu Ala Lys Lys His Phe Tyr Leu Val Asp
305                 310                 315                 320

Lys Gln Gly Leu Leu Phe Asp Asp Met Thr Asp Leu Thr Pro Glu Gln
                325                 330                 335

Lys Pro Phe Ala Arg Ser Arg Ser Glu Phe Ala Asn Ala Asp Glu Leu
                340                 345                 350

Thr Thr Leu Glu Ala Val Val Lys Ala Val His Pro Thr Val Leu Val
            355                 360                 365

Gly Thr Ser Thr Val Pro Gly Thr Phe Thr Glu Ser Ile Val Lys Glu
        370                 375                 380

Met Ala Ala His Thr Asp Arg Pro Ile Ile Phe Pro Leu Ser Asn Pro
385                 390                 395                 400

Thr Lys Leu Ala Glu Ala Lys Ala Asp
                405
```

<210> SEQ ID NO 92
<211> LENGTH: 386
<212> TYPE: PRT
<213> ORGANISM: Lactobacillus rhamnosus
<220> FEATURE:
<221> NAME/KEY: VARIANT
<222> LOCATION: (1)...(386)
<223> OTHER INFORMATION: Xaa = Any Amino Acid

<400> SEQUENCE: 92

```
Met Ile Lys Pro Glu Lys Thr Ile Asn Gly Thr Lys Trp Ile Glu Thr
 1               5                  10                  15

Ile Gln Ile Asn Ala Glu Glu Arg Ala Thr Leu Glu Asp Gln Tyr Gly
                20                  25                  30

Val Asp Glu Asp Ile Ile Glu Tyr Val Thr Asp Asn Asp Glu Ser Thr
            35                  40                  45

Asn Tyr Val Tyr Asp Ile Asn Glu Asp Asp Gln Leu Phe Ile Phe Leu
        50                  55                  60

Ala Pro Tyr Ala Leu Asp Lys Asp Ala Leu Arg Tyr Ile Thr Gln Pro
65                  70                  75                  80

Phe Gly Met Leu Leu His Lys Gly Val Leu Phe Thr Phe Asn Gln Ser
                85                  90                  95

His Ile Pro Glu Val Asn Thr Ala Leu Tyr Ser Ala Leu Asp Asn Pro
                100                 105                 110

Glu Val Lys Ser Val Asp Ala Phe Ile Leu Glu Thr Leu Phe Thr Val
            115                 120                 125

Val Asp Ser Phe Ile Pro Ile Ser Arg Gly Ile Thr Lys Lys Arg Asn
        130                 135                 140

Tyr Leu Asp Lys Met Leu Asn Arg Lys Thr Lys Asn Ser Asp Leu Val
145                 150                 155                 160

Ser Leu Ser Tyr Leu Gln Gln Thr Leu Thr Phe Leu Ser Ser Ala Val
                165                 170                 175

Gln Thr Asn Leu Ser Glu Leu Asp Leu Asn Gly Ser Asp Ala Leu Gln
            180                 185                 190

Gln Ile Ile Glu Leu Leu Asn Gln His Pro Leu Asp Xaa Ala Pro Asp
        195                 200                 205

Glu Lys Gly Ala Tyr Ser Asn Ser Asn Tyr Tyr Leu Leu Gly His Ile
    210                 215                 220
```

-continued

```
Ile Thr Gln Val Ala Asn Met Pro Leu Ser Asp Phe Leu Asn Gln His
225                 230                 235                 240

Phe Phe Glu Pro Leu Ala Met Thr Lys Thr Gln Leu Gly Thr Gln His
            245                 250                 255

Ala Asp Ala Asn Ser Tyr Asp Asp Leu Asp Phe Thr Asn Gly Lys Pro
        260                 265                 270

Val Ala Leu Gly Arg Gly His Tyr Gln Gly Gly Asp Gly Ala Val Val
    275                 280                 285

Ser Ser Leu Ala Asp Leu Ala Ile Trp Ala Arg Ala Val Leu Gln Arg
290                 295                 300

Arg Ile Leu Pro Glu Ser Ala Trp Asp Glu Ala Leu Thr Leu Thr His
305                 310                 315                 320

Asp Phe Tyr Gly Met Gly Trp Met Lys Ser Arg Thr Gln His Trp Leu
                325                 330                 335

Ser His Asn Gly His Ile Phe Gly Tyr Trp Ala Phe Phe Asp Val Ser
            340                 345                 350

Phe Glu Lys Gln Leu Ala Gln Ile Thr Leu Thr Asn Met Ser Pro Gly
        355                 360                 365

Val Glu Thr Leu Lys Lys Trp Gln Glu Met Ala Asn Trp Arg Ala
    370                 375                 380

Ser Leu
385

<210> SEQ ID NO 93
<211> LENGTH: 357
<212> TYPE: PRT
<213> ORGANISM: Lactobacillus rhamnosus

<400> SEQUENCE: 93

Leu Asp Asn Gln Asp Ala Asp Phe Lys Pro Thr Ile Gln Ile Leu Asp
  1               5                  10                  15

Glu Val Gly Lys Val Val Asn Pro Asp Ile Met Pro Asp Leu Ser Asp
             20                  25                  30

Asp Gln Leu Val Asp Leu Met Ser Lys Met Val Trp Gln Arg Val Leu
         35                  40                  45

Asp Gln Arg Ala Thr Ala Leu Asn Arg Gln Gly Arg Leu Gly Phe Tyr
     50                  55                  60

Ala Pro Ser Ala Gly Glu Glu Ala Ser Met Ile Gly Ser His Ala Ala
 65                  70                  75                  80

Met Lys Ser Ser Asp Trp Leu Leu Pro Ala Tyr Arg Asp Leu Pro Gln
                 85                  90                  95

Leu Ile Gln His Gly Leu Pro Leu Asp Lys Ala Phe Leu Trp Ser Arg
            100                 105                 110

Gly His Val Ala Gly Asn Glu Tyr Pro Glu Asp Phe His Ala Leu Pro
        115                 120                 125

Pro Gln Ile Ile Gly Ala Gln Tyr Val Gln Thr Ala Gly Val Ala
    130                 135                 140

Leu Gly Leu Lys Lys Asn Gly Ser Asp Glu Val Ala Phe Thr Tyr Thr
145                 150                 155                 160

Gly Asp Gly Gly Thr Ser Gln Gly Asp Phe Tyr Glu Gly Val Asn Phe
                165                 170                 175

Ala Gly His Phe Lys Ala Pro Ala Leu Phe Ile Val Gln Asp Asn Gly
            180                 185                 190

Phe Ala Ile Ser Val Pro Arg Ala Ser Gln Thr Ala Ala Lys Thr Leu
        195                 200                 205
```

-continued

```
Ala Gln Lys Ala Val Ala Ala Gly Val Pro Gly Val Gln Val Asp Gly
        210                 215                 220

Met Asp Ala Leu Ala Val Tyr Glu Val Thr Lys Glu Ala Arg Ala Trp
225                 230                 235                 240

Ala Ala Ala Gly Asn Gly Pro Val Leu Ile Glu Thr Leu Thr Tyr Arg
                245                 250                 255

Tyr Gly Pro His Thr Leu Ser Gly Asp Asp Pro Thr Arg Tyr Arg Ser
            260                 265                 270

Lys Glu Thr Asp Glu Leu Trp Gln Lys Arg Asp Pro Leu Ile Arg Met
        275                 280                 285

Arg Asn Tyr Leu Thr Asp Lys Gly Leu Trp Ser Lys Asp Lys Glu Asp
    290                 295                 300

Ala Leu Ile Glu Lys Val Lys Asp Glu Ile Lys Asp Ala Ile Asn Lys
305                 310                 315                 320

Ala Asp Lys Ala Pro Gln Gln Thr Val Ser Arg Phe Leu Lys Asp Thr
                325                 330                 335

Tyr Glu Val Ala Pro Gln Asn Val Ala Glu Gln Leu Ala Glu Phe Gln
            340                 345                 350

Gly Lys Glu Ser Lys
        355

<210> SEQ ID NO 94
<211> LENGTH: 436
<212> TYPE: PRT
<213> ORGANISM: Lactobacillus rhamnosus

<400> SEQUENCE: 94

Ser Val Leu Asn Ile Asn Gly Gly Asn Leu Thr Leu Thr Asp Asp Gly
1               5                   10                  15

Val Ser Ala Gly Thr Leu Thr Gly Gly Gly Phe Leu Asn Ile Ser Gly
            20                  25                  30

Gly Val Leu Asp Ile Thr Gly Gly Asn His Thr Phe Ala Val Ser Thr
        35                  40                  45

Ile Ile Ala Lys Asp Ala Thr Val Arg Met Asn Asp Val Ser Gly Leu
    50                  55                  60

Gly Thr Gly Asn Ile Ser Asn Ala Gly Thr Leu Ser Leu Thr His Ala
65                  70                  75                  80

Ser Gly Leu Leu Ser Asn Asn Leu Ser Gly Ser Gly Thr Val Ser Leu
                85                  90                  95

Ile Asn Ser Asp Thr Gln Ile Ser Gly Asn Ser Asn Tyr Ser Gly
            100                 105                 110

Leu Phe Val Val Asp Thr Ser Ser Gln Leu Thr Ala Thr Gly Ala Gln
        115                 120                 125

Asn Leu Gly Ile Ala Ser Val Ser Asn Arg Gly Ile Leu Gln Leu Asn
    130                 135                 140

Asn Thr Thr Asp Trp Gln Leu Ile Asn Asn Val Thr Gly Thr Gly Asn
145                 150                 155                 160

Val Arg Lys Thr Gly Ser Gly Ser Leu Thr Val Arg Ser Asn Ala Ala
                165                 170                 175

Trp Ser Gly Gln Thr Asp Ile Asp Asp Gly Ser Leu Ile Leu Gly Gln
            180                 185                 190

Ser Asp Ala Pro Val Met Leu Ala Ser Ser Leu Val Asn Ile Ala Lys
        195                 200                 205

Asn Gly Lys Leu Thr Gly Phe Gly Gly Val Val Gly Asn Val Thr Asn
```

-continued

```
                210                 215                 220
    Ser Gly Ser Leu Asp Leu Arg Ser Ala Ala Pro Gly Asn Ile Leu Thr
    225                 230                 235                 240

Ile Gly Gly Asn Tyr Thr Gly Asn Asn Gly Thr Leu Leu Ile Asn Thr
                        245                 250                 255

Val Leu Asp Asp Ser Ser Ser Ala Thr Asp Lys Leu Val Ile Lys Gly
                    260                 265                 270

Asp Ala Ser Gly Lys Thr Arg Val Ala Val Thr Asn Val Gly Gly Ser
                275                 280                 285

Gly Ala Asn Thr Leu Asn Ser Ile Glu Val Ile His Val Asp Gly Asn
                290                 295                 300

Ala Ala Asn Ala Glu Phe Ile Gln Ala Gly Arg Ile Ala Ala Gly Ala
    305                 310                 315                 320

Tyr Asp Tyr Thr Leu Gly Arg Gly Pro Gly Ser Asn Tyr Gly Asn Trp
                        325                 330                 335

Tyr Leu Ser Ser Ser Lys Asn Thr Pro Glu Pro Arg Pro Asp Pro Glu
                    340                 345                 350

Pro Thr Pro Glu Gly His Asp Asn Asn Leu Arg Pro Glu Ala Ser Ser
                355                 360                 365

Tyr Thr Ala Asn Ile Ala Ala Ala Asn Thr Met Phe Val Thr Arg Leu
                370                 375                 380

His Glu Arg Leu Gly Gln Thr Gln Tyr Val Asp Ala Ile Thr Gly Glu
    385                 390                 395                 400

Pro Lys Ala Thr Ser Met Trp Met Arg His Glu Gly Gly His Asn Arg
                        405                 410                 415

Trp Arg Asp Gly Ser Gly Gln Leu Lys Thr Gln Ser Asn Arg Tyr Val
                    420                 425                 430

Ile Gln Leu Gly
                435

<210> SEQ ID NO 95
<211> LENGTH: 215
<212> TYPE: PRT
<213> ORGANISM: Lactobacillus rhamnosus

<400> SEQUENCE: 95

Met Lys Ile Leu Ile Thr Gly Ala Gln Gly Gln Leu Gly Thr Glu Leu
 1               5                  10                  15

Arg His Leu Leu Asp Ala Arg Gly Ile Thr Tyr Arg Ala Thr Asp Ala
                20                  25                  30

Lys Asp Leu Asp Ile Thr Asp Glu Ala Ala Val Asn Gln Tyr Phe Ala
            35                  40                  45

Asp Tyr Gln Pro Asp Val Val Tyr His Cys Ala Ala Tyr Thr Ala Val
        50                  55                  60

Asp Lys Ala Glu Asp Glu Ala Lys Ala Leu Asn Gln Leu Val Asn Val
65                  70                  75                  80

Asp Gly Thr Arg Asn Leu Ala Lys Ala Ala Lys Val Asp Ala Thr
                85                  90                  95

Leu Val Tyr Ile Ser Thr Asp Tyr Val Phe Asp Gly Asp Ser Lys Glu
                    100                 105                 110

Ile Tyr Thr Val Asp Asp Gln Pro Ala Pro Arg Asn Glu Tyr Gly Arg
            115                 120                 125

Ala Lys Tyr Glu Gly Glu Gln Gln Val Gln Lys Tyr Leu Lys Lys Tyr
        130                 135                 140
```

-continued

```
Tyr Ile Ile Arg Thr Ser Trp Val Phe Gly Glu Tyr Gly His Asn Phe
145                 150                 155                 160

Val Tyr Thr Met Leu Asn Leu Ala Lys Thr His Lys Glu Leu Thr Val
                165                 170                 175

Val Asp Asp His Gln Glu Ser Phe Ser Val Ser Ser Arg Thr Phe
            180                 185                 190

Val Lys Tyr Gln His Glu His Leu Ile Tyr Ser Arg Pro Val Pro Tyr
            195                 200                 205

Arg Pro His Leu Pro Gly Ile
            210                 215
```

<210> SEQ ID NO 96
<211> LENGTH: 640
<212> TYPE: PRT
<213> ORGANISM: Lactobacillus rhamnosus
<220> FEATURE:
<221> NAME/KEY: VARIANT
<222> LOCATION: (1)...(640)
<223> OTHER INFORMATION: Xaa = Any Amino Acid

<400> SEQUENCE: 96

```
Met Leu Gly Gly Lys Gln Met Pro Glu Val Lys Phe Glu Ala Gly
1               5                   10                  15

Thr Tyr Asp Val Ile Val Val Gly Ala Gly His Ala Gly Xaa Val Lys
                20                  25                  30

Pro Ala Leu Ala Ala Ala Arg Met Gly Glu Lys Thr Leu Leu Leu Thr
            35                  40                  45

Ile Ser Leu Glu Met Leu Ala Phe Met Pro Cys Asn Pro Ser Leu Gly
        50                  55                  60

Gly Pro Ala Lys Gly Ile Val Val Arg Glu Ile Asp Ala Leu Gly Gly
65                  70                  75                  80

Glu Met Gly Lys Asn Ile Asp Arg Thr Tyr Ile Gln Met Arg Met Leu
                85                  90                  95

Asn Thr Gly Lys Gly Pro Ala Val Arg Ala Leu Arg Ala Gln Ala Asp
                100                 105                 110

Lys Ala Ala Tyr His Arg Ser Met Lys His Val Ile Glu Asp Thr Pro
            115                 120                 125

His Leu Asp Leu Arg Gln Gly Leu Ala Thr Glu Val Leu Val Glu Asp
        130                 135                 140

Gly Lys Ala Val Gly Ile Val Ala Ala Thr Gly Ala Ile Tyr Arg Ala
145                 150                 155                 160

Lys Ser Ile Val Leu Thr Ala Gly Thr Ser Ser Arg Gly Lys Ile Ile
                165                 170                 175

Ile Gly Glu Leu Met Tyr Ser Ser Gly Pro Asn Asn Ser Leu Pro Ser
                180                 185                 190

Ile Lys Leu Ser Glu Asn Leu Glu Gln Leu Gly Phe Lys Leu Arg Arg
            195                 200                 205

Phe Lys Thr Gly Thr Pro Pro Arg Val Asn Gly Asn Thr Ile Asp Phe
        210                 215                 220

Ser Lys Thr Glu Glu Gln Pro Gly Asp Lys Thr Pro Asn His Phe Ser
225                 230                 235                 240

Phe Thr Thr Pro Asp Ser Val Tyr Leu Lys Asp Gln Leu Ser Cys Trp
                245                 250                 255

Met Thr Tyr Thr Asn Ala Thr Thr His Gln Ile Ile Arg Glu Asn Leu
                260                 265                 270

Asp Arg Ala Pro Met Phe Ser Gly Val Ile Lys Gly Val Gly Pro Arg
```

```
                    275                 280                 285
Tyr Cys Pro Ser Ile Glu Asp Lys Ile Val Arg Phe Ala Asp Lys Pro
    290                 295                 300
Arg His Gln Leu Phe Leu Glu Pro Gly Arg Asp Thr Ser Glu Tyr
305                 310                 315                 320
Tyr Val Gly Asp Phe Ser Thr Ser Met Pro Glu Ile Gln Leu Lys
                325                 330                 335
Met Leu His Ser Val Ala Gly Leu Glu His Ala Glu Leu Met Arg Ala
                340                 345                 350
Gly Tyr Ala Ile Glu Tyr Asp Val Ile Glu Pro Trp Gln Leu Lys Ala
            355                 360                 365
Thr Leu Glu Thr Lys Val Val Glu Asn Leu Tyr Thr Ala Gly Gln Met
370                 375                 380
Asn Gly Thr Ser Gly Tyr Glu Glu Ala Ala Gly Gln Gly Ile Val Ala
385                 390                 395                 400
Gly Ile Asn Ala Ala Arg Arg Ala Gln Gly Lys Gly Pro Phe Thr Leu
                405                 410                 415
Lys Arg Ser Asp Ala Tyr Ile Gly Val Met Ile Asp Asp Leu Val Thr
                420                 425                 430
Lys Gly Thr Asn Glu Pro Tyr Arg Leu Leu Thr Ser Arg Ala Glu Tyr
            435                 440                 445
Arg Leu Leu Arg His Asp Asn Ala Asp Leu Arg Leu Thr Pro Met
450                 455                 460
Gly His Glu Leu Gly Leu Ile Ser Asp Gln Arg Tyr Ala Val Phe Leu
465                 470                 475                 480
Ala Lys Arg Gln Ala Ile Thr Asp Glu Leu Ala Arg Leu Glu His Thr
                485                 490                 495
Arg Leu Lys Pro Lys Asp Val Asn Pro Trp Leu Glu Ala His His Phe
                500                 505                 510
Ala Ser Leu Lys Asp Gly Val Leu Ala Ser Asp Phe Leu Lys Arg Pro
            515                 520                 525
Glu Ile Asn Tyr Gln Thr Leu Glu Gln Phe Leu Pro Glu Asn Pro Thr
530                 535                 540
Leu Asp His Arg Val Ile Glu Gln Val Glu Ile Gln Ile Lys Tyr Ala
545                 550                 555                 560
Gly Tyr Ile Ala Lys Glu Glu Xaa Gln Cys Ala Lys Leu Lys Arg Leu
                565                 570                 575
Glu Gly Lys Lys Ile Pro Ala Arg Ile Asn Tyr Glu Ala Ile Asn Gly
            580                 585                 590
Leu Ala Thr Glu Ala Arg Gln Lys Leu Val Lys Ile Gln Pro Glu Thr
            595                 600                 605
Ile Ala Gln Ala Ser Arg Ile Ser Gly Val Asn Pro Ala Asp Val Ala
        610                 615                 620
Ile Leu Ser Val Tyr Ile Glu Gln Gly Arg Ile Ser Lys Val Ala Gln
625                 630                 635                 640

<210> SEQ ID NO 97
<211> LENGTH: 254
<212> TYPE: PRT
<213> ORGANISM: Lactobacillus rhamnosus

<400> SEQUENCE: 97

Pro Leu Ser Thr Met Met Leu Ala Gly Ile Arg Asp Ile Leu Val Ile
1               5                   10                  15
```

```
Ser Thr Pro Arg Asp Ile Asp Arg Phe Gln Asp Leu Leu Lys Asp Gly
             20                  25                  30

Lys Gln Leu Gly Leu Asn Ile Ser Tyr Lys Ile Gln Glu Lys Pro Asn
         35                  40                  45

Gly Leu Ala Glu Ala Phe Ile Val Gly Ala Asp Phe Ile Gly Asp Asp
    50                  55                  60

Ser Val Cys Leu Ile Leu Gly Asp Asn Ile Phe Tyr Gly Ser Gly Leu
65                  70                  75                  80

Ser Lys Leu Val Gln Arg Ser Ala Ala Lys Thr Thr Gly Ala Thr Val
                85                  90                  95

Phe Gly Tyr Gln Val Asn Asp Pro Glu Arg Phe Gly Val Val Ala Phe
            100                 105                 110

Asp Glu Gln His His Val Gln Ser Ile Val Glu Lys Pro Glu His Pro
            115                 120                 125

Glu Ser Asn Phe Ala Val Thr Gly Met Tyr Phe Tyr Asp Asn Gln Val
    130                 135                 140

Val Asp Ile Ala Lys Asn Leu Lys Pro Ser Pro Arg Gly Glu Leu Glu
145                 150                 155                 160

Ile Thr Asp Val Asn Lys Ala Tyr Leu Glu Arg Gly Gln Leu Asp Val
                165                 170                 175

Glu Leu Leu Gly Arg Gly Phe Ala Trp Leu Asp Thr Gly Thr His Glu
            180                 185                 190

Ser Leu His Glu Ala Ala Ser Phe Ile Glu Thr Val Gln Lys Arg Gln
    195                 200                 205

Asn Leu Lys Ile Ala Cys Leu Glu Glu Val Ala Tyr Arg Met Gly Tyr
    210                 215                 220

Ile Asp Arg Asp Gln Leu Arg Lys Leu Ala Gln Pro Leu Lys Lys Asn
225                 230                 235                 240

Asp Tyr Gly Gln Tyr Ile Leu Arg Leu Ala Asp Glu Glu Asp
                245                 250

<210> SEQ ID NO 98
<211> LENGTH: 312
<212> TYPE: PRT
<213> ORGANISM: Lactobacillus rhamnosus

<400> SEQUENCE: 98

Met Ala Ile Asn Leu Val Gly Ile Asn Asp Ala Asn Leu Thr Leu Ile
1               5                   10                  15

Glu Glu Gly Leu Asn Val Arg Ile Ser Pro Phe Gly Asp Glu Leu Arg
            20                  25                  30

Ile Ser Gly Glu Thr Glu Ala Val Ser Leu Thr Leu Gln Leu Leu Glu
        35                  40                  45

Ala Ala Thr Lys Leu Leu Ala Gln Gly Ile Lys Leu Ser Pro Gln Asp
    50                  55                  60

Ile Ala Ser Ala Val Ala Met Ala Lys Arg Gly Thr Leu Glu Tyr Phe
65                  70                  75                  80

Ala Asp Met Tyr Ser Glu Thr Leu Leu Arg Asp Ala Lys Gly Gln Pro
                85                  90                  95

Ile Arg Ile Lys Asn Phe Gly Gln Arg Gln Tyr Val Asp Ala Ile Lys
            100                 105                 110

His Asn Asp Ile Thr Phe Gly Ile Gly Pro Ala Gly Thr Gly Lys Thr
            115                 120                 125

Phe Leu Ala Val Val Met Ala Val Ala Ala Met Lys Ala Gly Gln Val
    130                 135                 140
```

```
Glu Arg Ile Ile Leu Thr Arg Pro Ala Val Glu Ala Gly Glu Ser Leu
145                 150                 155                 160

Gly Phe Leu Pro Gly Asp Leu Lys Glu Lys Val Asp Pro Tyr Leu Arg
                165                 170                 175

Pro Val Tyr Asp Ala Leu Tyr Ala Val Leu Gly Lys Glu His Thr Asp
            180                 185                 190

Arg Leu Met Asp Arg Gly Val Ile Glu Ile Ala Pro Leu Ala Tyr Met
        195                 200                 205

Arg Gly Arg Thr Leu Asp Asn Ala Phe Ala Ile Leu Asp Glu Ala Gln
    210                 215                 220

Asn Thr Thr Gln Ala Gln Met Lys Met Phe Leu Thr Arg Leu Gly Phe
225                 230                 235                 240

Gly Ser Lys Met Ile Val Asn Gly Asp Val Thr Gln Ile Asp Leu Pro
                245                 250                 255

His Asn Ala Lys Ser Gly Leu Leu Gln Ala Glu Gln Leu Leu Lys Gly
            260                 265                 270

Ile Ser His Ile Ala Phe Thr Gln Phe Ser Ala Gln Asp Val Val Arg
        275                 280                 285

His Pro Val Ala Lys Ile Ile Glu Ala Tyr Gly Lys His Asp Leu
    290                 295                 300

Gln Leu Gln Lys Gln Thr Lys Glu
305                 310

<210> SEQ ID NO 99
<211> LENGTH: 280
<212> TYPE: PRT
<213> ORGANISM: Lactobacillus rhamnosus

<400> SEQUENCE: 99

Met Lys Lys Phe Asp Lys Met Met Asp Trp Leu Ala Asp Val Tyr Val
 1               5                  10                  15

Asn Ala Leu Asn Val Ile His Tyr Met His Asp Lys Tyr Tyr Tyr Glu
                20                  25                  30

Ala Ala Gln Leu Ala Leu Lys Asp Thr Arg Leu Asn Arg Thr Phe Ala
            35                  40                  45

Thr Gly Ile Ser Gly Leu Ser His Ala Val Asp Ser Ile Ser Ala Ile
        50                  55                  60

Lys Tyr Gly His Val Lys Ala Ile Arg Asp Glu Asn Gly Val Ala Ile
65                  70                  75                  80

Asp Phe Val Ala Asp Asn Asp Tyr Pro Arg Tyr Gly Asn Asn Asp
                85                  90                  95

Asp Arg Ala Asp Asn Ile Ala Lys Trp Leu Val Lys Thr Phe Tyr Asn
            100                 105                 110

Lys Met Asn Thr His His Leu Tyr Arg Gly Ala Lys Leu Ser Thr Ser
        115                 120                 125

Val Leu Thr Ile Thr Ser Asn Val Val Tyr Gly Lys Asn Thr Gly Thr
    130                 135                 140

Thr Pro Asn Gly Arg Gln Lys Gly Glu Pro Phe Ser Pro Gly Ala Asn
145                 150                 155                 160

Pro Ala Tyr Gly Ala Glu Lys Asn Gly Ala Leu Ala Ser Leu Met Ser
                165                 170                 175

Thr Ala Lys Ile Pro Tyr His Tyr Ala Thr Asp Gly Ile Ser Asn Thr
            180                 185                 190

Phe Gly Val Thr Pro Asn Thr Leu Gly His Asp Asp Glu Thr Arg Lys
```

```
            195                 200                 205
Asp Thr Leu Val His Met Val Asp Gly Tyr Met Glu Asn Ser Gly Met
    210                 215                 220

His Leu Asn Ile Asn Val Phe Asn Lys Glu Thr Leu Ile Asp Ala Gln
225                 230                 235                 240

Lys His Pro Glu Glu Tyr Pro Thr Leu Thr Val Arg Val Ser Gly Tyr
                245                 250                 255

Cys Val Tyr Phe Ala Asp Leu Thr Lys Glu Gln Gln Asp Asp Val Ile
                260                 265                 270

Ala Arg Thr Phe Phe Asp Glu Met
            275                 280

<210> SEQ ID NO 100
<211> LENGTH: 447
<212> TYPE: PRT
<213> ORGANISM: Lactobacillus rhamnosus

<400> SEQUENCE: 100

Met Ala Phe Ser Lys Glu Thr Arg Thr Gln Thr Ile Asp Gln Leu Lys
1               5                   10                  15

Gln Thr Glu Leu Asp Leu Leu Ile Val Gly Gly Ile Thr Gly Ala
            20                  25                  30

Gly Val Ala Ile Gln Ala Ala Ser Gly Leu Lys Thr Gly Leu Ile
        35                  40                  45

Glu Met Gln Asp Phe Ala Glu Gly Thr Ser Ser Arg Ser Thr Lys Leu
    50                  55                  60

Val His Gly Gly Ile Arg Tyr Leu Lys Thr Phe Asp Val Gly Val Val
65                  70                  75                  80

Ala Asp Thr Val Lys Glu Arg Ala Val Gln Gly Ile Ala Pro His
                85                  90                  95

Ile Pro Arg Pro Phe Pro Met Leu Leu Pro Ile Tyr Gln Glu Ala Gly
                100                 105                 110

Ser Thr Phe Asp Met Phe Ser Ile Lys Ile Ala Met Asp Leu Tyr Asp
                115                 120                 125

Arg Leu Ala Asn Val Glu Gly Ser Gln Tyr Ala Asn Tyr Thr Val Thr
    130                 135                 140

Lys Asp Glu Ile Leu Gln Arg Glu Pro His Leu Ala Ser Asp Gly Leu
145                 150                 155                 160

Gln Gly Gly Gly Val Tyr Leu Asp Phe Val Asn Asn Asp Ala Arg Leu
                165                 170                 175

Val Ile Glu Asn Ile Lys Glu Ala Ala Glu Leu Gly Gly Leu Met Ala
                180                 185                 190

Ser Arg Val Gln Ala Ile Gly Val Leu His Asp Asp Ala Gly Gln Val
    195                 200                 205

Asn Gly Leu Gln Val Lys Asp Leu Leu Asp Gly Ser Val Phe Asp Ile
    210                 215                 220

His Ala Lys Leu Val Ile Asn Thr Thr Gly Pro Trp Ser Asp Lys Phe
225                 230                 235                 240

Lys Ala Leu Asp Gln Ala Glu Asp Gln Thr Pro Thr Leu Arg Pro Thr
                245                 250                 255

Lys Gly Val His Leu Val Val Asp Gly Ser Arg Leu Pro Val Pro Gln
                260                 265                 270

Pro Thr Tyr Met Asp Thr Gly Leu Asn Asp Gly Arg Met Phe Phe Val
                275                 280                 285
```

```
Val Pro Arg Glu Gly Lys Thr Tyr Phe Gly Thr Thr Asp Thr Asp Tyr
    290                 295                 300

His Gly Asp Phe Asn His Pro Gln Val Glu Gln Ala Asp Val Asp Tyr
305                 310                 315                 320

Leu Leu Lys Val Ile Asn Lys Arg Tyr Pro Gln Ser His Ile Thr Leu
                325                 330                 335

Asp Asp Ile Glu Ala Ser Trp Ala Gly Leu Arg Pro Leu Ile Ala Asn
            340                 345                 350

Asn Gly Ser Ser Asp Tyr Asn Gly Gly Ala Asn Thr Gly Lys Val
        355                 360                 365

Ser Asp Asp Ser Phe Glu Ala Leu Ile Arg Val Val Asp Asp Tyr Glu
    370                 375                 380

Asp Asn Gln Ala Thr Arg Ala Asp Val Glu His Ala Ile Ser Lys Leu
385                 390                 395                 400

Glu Thr Ala His Ala Glu Ala Ala Leu Ser Pro Ser Gln Val Ser Arg
                405                 410                 415

Gly Ser Ser Leu Arg Gln Ala Asp Asp Gly Met Ile Thr Leu Ser Gly
            420                 425                 430

Gly Lys Ile Thr Asp Tyr Arg Lys Met Ala Ala Gly Ala Leu Ala
        435                 440                 445

<210> SEQ ID NO 101
<211> LENGTH: 242
<212> TYPE: PRT
<213> ORGANISM: Lactobacillus rhamnosus

<400> SEQUENCE: 101

Asp Leu Phe Cys Pro Asp Ile Thr Ala Asp Ile Leu Thr Arg Lys Asp
1               5                   10                  15

Asp Leu Gly Ser Asp Lys Pro Ile Val Asp Ile Leu Asp Arg Ala
            20                  25                  30

Gly Asn Lys Gly Thr Gly Lys Trp Ser Ser Gln Ser Ala Leu Glu Leu
        35                  40                  45

Gly Val Pro Gln Ser Val Ile Thr Glu Ser Val Tyr Ala Arg Tyr Ile
    50                  55                  60

Ser Ala Met Lys Gln Glu Arg Val Ala Ala Ser Lys Val Leu Pro Lys
65                  70                  75                  80

Pro Val Gly Asn Val Thr Ile Asp Lys Lys Glu Ala Ile Glu Met Ile
                85                  90                  95

Arg Lys Ala Leu Tyr Phe Ser Lys Leu Met Ser Tyr Ala Gln Gly Phe
            100                 105                 110

Glu Gln Met Arg Val Ala Ser Asp Asn Tyr Asp Trp Asn Leu Gln Tyr
        115                 120                 125

Gly Glu Leu Ala Lys Ile Trp Arg Ala Gly Cys Ile Ile Arg Ala Arg
    130                 135                 140

Phe Leu Gln Asn Ile Thr Asp Ala Tyr Asp Lys Lys Pro Asp Leu Gln
145                 150                 155                 160

Asn Leu Leu Leu Asp Asp Tyr Phe Leu Asn Ile Ala Lys Asn Tyr Gln
                165                 170                 175

Glu Ser Val Arg Asp Leu Val Gly Leu Ala Val Lys Ala Gly Val Pro
            180                 185                 190

Val Pro Gly Phe Ser Ala Ala Ile Ser Tyr Tyr Asp Ser Tyr Arg Ala
        195                 200                 205

Pro Val Leu Pro Ala Asn Leu Thr Gln Ala Gln Arg Asp Tyr Phe Gly
    210                 215                 220
```

-continued

```
Ala His Thr Tyr Glu Arg Thr Asp Arg Asp Gly Ile Phe His Tyr Thr
225                 230                 235                 240

Trp Tyr

<210> SEQ ID NO 102
<211> LENGTH: 323
<212> TYPE: PRT
<213> ORGANISM: Lactobacillus rhamnosus

<400> SEQUENCE: 102

Glu Asp Phe Phe Ile Gln Ile Ser Ala Thr Gln His His Ile Pro Asp
  1               5                  10                  15

Cys Cys Asp Gln Ile Pro Thr Gly Asp Phe Ser Phe Phe Asp Asn Thr
             20                  25                  30

Leu Asp Val Ala Asn Leu Leu Asn Ile Val Pro Lys Arg Tyr Gln Asp
         35                  40                  45

Leu Asn Leu Ser Pro Leu Asp Thr Tyr Phe Ala Gln Ala Arg Gly Tyr
 50                  55                  60

Gln Gly Glu Ala Gly Asp Val Lys Ala Leu Ala Met Lys Lys Trp Phe
 65                  70                  75                  80

Asn Thr Asn Tyr His Tyr Leu Val Pro Glu Phe Asp Arg Asp Thr Lys
                 85                  90                  95

Ile Gln Val Thr Asp Trp Gln Leu Phe Val Gln Phe Glu Glu Ala Lys
            100                 105                 110

Ala Leu Gly Ile Asn Gly Arg Pro Thr Leu Ile Gly Pro Tyr Thr Leu
        115                 120                 125

Leu Lys Leu Ser Arg Phe Ile Asp Val Val Pro Asp Asp Phe Val Ala
130                 135                 140

Asp Leu Ile Ser Ala Tyr Thr Thr Ile Ile Asp Arg Leu His Asp Ala
145                 150                 155                 160

Gly Ala Asp Trp Val Gln Leu Asp Glu Pro Ala Leu Val Tyr Asp Gln
                165                 170                 175

Thr Asp Ala Asp Leu Ala Leu Phe Glu Arg Leu Tyr Thr Pro Ile Leu
            180                 185                 190

Thr Gln Lys Lys Ala Ala Lys Ile Leu Val Gln Thr Tyr Phe Gly Asp
        195                 200                 205

Leu Thr Asp Ser Phe Asp Arg Ile Gln Lys Leu Pro Phe Asp Gly Phe
210                 215                 220

Gly Leu Asp Phe Val Glu Gly Tyr Ala Asn Leu Asp Leu Leu Lys Gln
225                 230                 235                 240

His Gly Phe Pro Ala His Ala Thr Leu Phe Ala Gly Ile Val Asn Gly
                245                 250                 255

Lys Asn Ile Trp Arg Thr His Tyr Ala Asp Ala Leu Ala Thr Ile Lys
            260                 265                 270

Gln Leu Ala Thr Ile Thr Asp Lys Leu Val Leu Ser Thr Ser Thr Ser
        275                 280                 285

Leu Leu His Val Pro Tyr Thr Leu Arg Asn Glu Thr His Leu Lys Pro
290                 295                 300

Glu Glu Lys Gln Tyr Leu Ala Phe Ala Glu Glu Lys Leu Asn Glu Leu
305                 310                 315                 320

His Glu Leu

<210> SEQ ID NO 103
<211> LENGTH: 296
```

```
<212> TYPE: PRT
<213> ORGANISM: Lactobacillus rhamnosus

<400> SEQUENCE: 103

Gly Pro Ala Ile Phe Gly Phe Ile Pro Met Gln Asp Gly Ser Pro Ala
 1               5                  10                  15

Pro Gly Leu Ser Asn Ile Thr Ala Glu Gly Trp Phe Pro His Gly Gly
                20                  25                  30

Leu Pro Ile Leu Met Thr Met Val Ala Val Asn Phe Ala Phe Ser Gly
            35                  40                  45

Thr Glu Leu Ile Gly Ile Ala Ala Gly Glu Thr Glu Asn Pro Arg Lys
 50                  55                  60

Val Ile Pro Val Ala Ile Arg Thr Thr Ile Ala Arg Leu Ile Ile Phe
65                  70                  75                  80

Phe Ile Gly Thr Val Phe Val Leu Ala Ala Leu Ile Pro Met Gln Gln
                85                  90                  95

Val Gly Val Glu Lys Ser Pro Phe Val Leu Val Phe Glu Lys Val Gly
                100                 105                 110

Ile Pro Tyr Ala Ala Asp Ile Phe Asn Phe Val Ile Leu Thr Ala Ile
            115                 120                 125

Leu Cys Ala Ala Asn Ser Gly Leu Tyr Ala Ser Gly Arg Met Leu Trp
130                 135                 140

Ser Leu Ser Asn Glu Arg Thr Leu Pro Ala Cys Phe Ala Arg Val Thr
145                 150                 155                 160

Lys Asn Gly Val Pro Leu Thr Ala Leu Ser Val Ser Met Leu Gly Gly
                165                 170                 175

Val Leu Ala Leu Phe Ser Ser Val Val Ala Pro Asn Thr Val Phe Val
            180                 185                 190

Ala Leu Ser Ala Ile Ser Gly Phe Ala Val Val Ala Val Trp Leu Ser
            195                 200                 205

Ile Cys Ala Ser His Phe Val Phe Arg Arg His Leu Gln Gln Gly
210                 215                 220

Lys Ala Leu Ser Glu Leu His Tyr Arg Ala Pro Trp Tyr Pro Leu Val
225                 230                 235                 240

Pro Val Leu Gly Phe Val Leu Cys Leu Ala Cys Val Gly Leu Ala
                245                 250                 255

Phe Asp Pro Ala Gln Arg Ile Ala Leu Trp Cys Gly Leu Pro Phe Val
            260                 265                 270

Ala Leu Cys Tyr Gly Ala Tyr Phe Leu Thr Gln Pro Arg Asn Ala Lys
            275                 280                 285

Gln Glu Pro Glu His Val Ala Glu
    290                 295

<210> SEQ ID NO 104
<211> LENGTH: 474
<212> TYPE: PRT
<213> ORGANISM: Lactobacillus rhamnosus

<400> SEQUENCE: 104

Met Arg Lys Gln Leu Pro Lys Asp Phe Val Ile Gly Gly Ala Thr Ala
 1               5                  10                  15

Ala Tyr Gln Val Glu Gly Ala Thr Lys Glu Asp Gly Lys Gly Arg Val
                20                  25                  30

Leu Trp Asp Asp Phe Leu Glu Lys Gln Gly Arg Phe Ser Pro Asp Pro
            35                  40                  45
```

-continued

```
Ala Ala Asp Phe Tyr His Arg Tyr Asp Glu Asp Leu Ala Leu Ala Glu
     50                  55                  60

Ala Tyr Gly His Gln Val Ile Arg Leu Ser Ile Ala Trp Ser Arg Ile
 65                  70                  75                  80

Phe Ser Asp Gly Ala Gly Ala Val Glu Ser Arg Gly Val Ala Phe Tyr
                 85                  90                  95

His Arg Leu Phe Ala Ala Cys Ala Lys His His Leu Ile Pro Phe Val
                100                 105                 110

Thr Leu His His Phe Asp Thr Pro Glu Arg Leu His Glu Ile Gly Asp
            115                 120                 125

Trp Leu Ser Gln Glu Met Leu Glu Asp Phe Val Glu Tyr Ala Arg Phe
        130                 135                 140

Cys Phe Glu Glu Phe Pro Glu Ile Lys His Trp Ile Thr Ile Asn Glu
145                 150                 155                 160

Pro Thr Ser Met Ala Val Gln Gln Tyr Thr Ser Gly Thr Phe Pro Pro
                165                 170                 175

Ala Glu Thr Gly His Phe Asp Lys Thr Phe Gln Ala Glu His Asn Gln
            180                 185                 190

Ile Val Ala His Ala Arg Ile Val Asn Leu Tyr Lys Ser Met Gly Leu
        195                 200                 205

Asp Gly Glu Ile Gly Ile Val His Ala Leu Gln Thr Pro Tyr Pro Tyr
    210                 215                 220

Ser Asp Ser Ser Glu Asp Gln His Ala Ala Asp Leu Gln Asp Ala Leu
225                 230                 235                 240

Glu Asn Arg Leu Tyr Leu Asp Gly Thr Leu Ala Gly Asp Tyr Ala Pro
                245                 250                 255

Lys Thr Leu Ala Leu Ile Lys Glu Ile Leu Ala Ala Asn Gln Gln Pro
            260                 265                 270

Met Phe Lys Tyr Thr Asp Glu Glu Met Ala Ala Ile Lys Lys Ala Ala
        275                 280                 285

His Gln Leu Asp Phe Val Gly Val Asn Asn Tyr Phe Ser Lys Trp Leu
    290                 295                 300

Arg Ala Tyr His Gly Lys Ser Glu Thr Ile His Asn Gly Asp Gly Ser
305                 310                 315                 320

Lys Gly Ser Ser Val Ala Arg Leu His Gly Ile Gly Glu Glu Lys Lys
                325                 330                 335

Pro Ala Gly Ile Glu Thr Thr Asp Trp Asp Trp Ser Ile Tyr Pro Arg
            340                 345                 350

Gly Met Tyr Asp Met Leu Met Arg Ile His Gln Asp Tyr Pro Leu Val
        355                 360                 365

Pro Ala Ile Tyr Val Thr Glu Asn Gly Ile Gly Leu Lys Glu Ser Leu
    370                 375                 380

Pro Ala Glu Val Thr Pro Asn Thr Val Ile Ala Asp Pro Lys Arg Ile
385                 390                 395                 400

Asp Tyr Leu Lys Lys Tyr Leu Ser Ala Ile Ala Asp Ala Ile Gln Ala
                405                 410                 415

Gly Ala Asn Val Lys Gly Tyr Phe Val Trp Ser Leu Gln Asp Gln Phe
            420                 425                 430

Ser Trp Thr Asn Gly Tyr Ser Lys Arg Tyr Gly Leu Phe Phe Val Asp
        435                 440                 445

Phe Pro Thr Gln Lys Arg Tyr Val Lys Gln Ser Ala Glu Trp Leu Lys
450                 455                 460

Gln Val Ser Gln Thr His Val Ile Pro Glu
```

-continued 465        470

<210> SEQ ID NO 105
<211> LENGTH: 258
<212> TYPE: PRT
<213> ORGANISM: Lactobacillus rhamnosus

<400> SEQUENCE: 105

Met Thr Thr Leu Lys Ser Phe Arg Val Ile Asn Lys Val Asp Leu Pro
 1               5                  10                  15

Ser Ala Gln Pro Asp Val Val Lys Glu Glu Ile Glu Glu Met Ile Gly
            20                  25                  30

Leu Asp Ala Ser Asp Ala Ile Leu Ala Ser Gly Lys Thr Gly Leu Gly
        35                  40                  45

Val Pro Glu Ile Leu Glu Arg Ile Val Ser Asp Ile Pro Ala Pro Ser
    50                  55                  60

Gly Asp Val Asn Ala Pro Leu Gln Ala Leu Ile Phe Asp Ser Val Tyr
65                  70                  75                  80

Asp Asp Tyr Arg Gly Val Val Leu Asp Val Arg Val Lys Glu Gly Gln
                85                  90                  95

Val Lys Val Gly Asp Thr Ile Gln Leu Met Ser Asn Gly Lys Gln Phe
            100                 105                 110

Gln Val Thr Glu Val Gly Val Met Ser Pro Lys Ala Val Lys Arg Asp
        115                 120                 125

Phe Leu Met Val Gly Asp Val Gly Tyr Ile Thr Ala Ser Ile Lys Thr
    130                 135                 140

Ile Gln Asp Thr Arg Val Gly Asp Thr Val Thr Leu Ala Asp Arg Pro
145                 150                 155                 160

Ala Ala Ala Pro Leu Lys Gly Tyr Arg Lys Ile Thr Pro Met Val Tyr
                165                 170                 175

Ser Gly Leu Phe Pro Val Asp Asn Ala Lys Phe Asn Asp Leu Arg Glu
            180                 185                 190

Ala Leu Glu Lys Leu Gln Leu Asn Asp Ala Ala Leu Glu Phe Glu Pro
        195                 200                 205

Glu Thr Ser Gln Ala Leu Gly Phe Gly Phe Arg Cys Gly Phe Leu Gly
    210                 215                 220

Leu Leu His Met Asp Val Val Gln Glu Arg Leu Glu Arg Asp Tyr Gly
225                 230                 235                 240

Leu Asp Leu Ile Met Thr Ala Pro Ser Val Asp Tyr Gln Val Ala Leu
                245                 250                 255

Thr Asp

<210> SEQ ID NO 106
<211> LENGTH: 418
<212> TYPE: PRT
<213> ORGANISM: Lactobacillus rhamnosus

<400> SEQUENCE: 106

Met Asp Val Thr Thr Ile Asp Leu Glu Gln Met Gly Arg Ala Ala Lys
 1               5                  10                  15

Ala Ala Ala Thr Val Leu Ser Gln Leu Thr Thr Ala Gln Lys Asn Ala
            20                  25                  30

Gly Leu Leu Ala Met Val Thr Ala Leu Glu Thr His Thr Glu Thr Ile
        35                  40                  45

Leu Gly Ala Asn His Glu Asp Leu Lys Ala Ala Ala Ser Leu Pro Ala
    50                  55                  60

Lys Phe Thr Asp Arg Leu Val Leu Thr Ala Glu Arg Ile Ala Asp Met
65                  70                  75                  80

Ala Ala Gly Val Arg Gln Val Ala Ala Leu Pro Asp Pro Thr Ala Gln
            85                  90                  95

Thr Asp Lys Ala Trp Val Asn His Ala Gly Leu Asn Ile Ala Gln Lys
            100                 105                 110

Arg Val Pro Leu Gly Val Gly Met Ile Tyr Glu Ala Arg Pro Asn
            115                 120                 125

Val Thr Val Asp Ala Ala Leu Thr Phe Lys Ser Gly Asn Ala Val
130                 135                 140

Ile Leu Arg Gly Gly Lys Glu Ala Leu His Ser Asn Leu Ala Leu Ala
145                 150                 155                 160

Thr Val Leu Gln Ala Ala Leu Thr Ala Gln Gly Leu Pro Lys Asp Ala
            165                 170                 175

Ile Gln Leu Ile Thr Asp Pro Lys Arg Glu Val Ala Asn Gln Met Met
            180                 185                 190

His Leu Asn Gly Tyr Ile Asp Val Leu Ile Pro Arg Gly Gly Arg Gly
            195                 200                 205

Leu Ile Lys Ala Val Val Glu Gln Ala Thr Val Pro Val Ile Glu Thr
210                 215                 220

Gly Ala Gly Asn Cys His Ile Tyr Val Asp Ala Tyr Ala Gln Ala Gln
225                 230                 235                 240

Met Ala Ile Asp Ile Val Val Asn Ala Lys Val Gln Arg Pro Ser Val
            245                 250                 255

Cys Asn Ala Ala Glu Lys Leu Leu Ile His Ala Asp Val Ala Asn Ala
            260                 265                 270

Gln Leu Pro Leu Ile Ala Ala Leu Gln Ala His Gly Val Glu Leu
            275                 280                 285

Arg Gly Asp Glu Arg Ala Arg Ala Ile Val Pro Asn Met Gln Ile Ala
290                 295                 300

Thr Glu Glu Asp Trp Asp Thr Glu Tyr Asn Asp Leu Ile Met Ala Val
305                 310                 315                 320

Lys Val Val Asp Ser Glu Glu Ala Ile Ala His Ile Asn Ala His
            325                 330                 335

Asn Thr Lys His Ser Glu Ala Ile Ile Thr Asp Asn Tyr Gln Asn Ser
            340                 345                 350

Gln Gln Phe Leu Gln Gln Val Asp Ala Ala Val Val Tyr Val Asn Ala
            355                 360                 365

Ser Thr Arg Phe Thr Asp Gly Phe Glu Phe Gly Phe Ala Glu Ile
370                 375                 380

Gly Ile Ser Thr Gln Lys Leu His Ala Arg Gly Pro Met Gly Leu Ala
385                 390                 395                 400

Ala Leu Thr Thr Ile Lys Tyr Gln Val Leu Gly Asn Gly Gln Val Arg
            405                 410                 415

Glu Gly

<210> SEQ ID NO 107
<211> LENGTH: 163
<212> TYPE: PRT
<213> ORGANISM: Lactobacillus rhamnosus

<400> SEQUENCE: 107

Met Thr Ala Phe Leu Trp Ala Gln Asp Arg Asp Gly Leu Ile Gly Lys
1               5                   10                  15

```
Asp Gly His Leu Pro Trp His Leu Pro Asp Leu His Tyr Phe Arg
            20                  25                  30

Ala Gln Thr Val Gly Lys Ile Met Val Val Gly Arg Arg Thr Tyr Glu
            35                  40                  45

Ser Phe Pro Lys Arg Pro Leu Pro Glu Arg Thr Asn Val Val Leu Thr
 50                      55                  60

His Gln Glu Asp Tyr Gln Ala Pro Gly Ala Val Val His Asp Val
 65                  70                  75                  80

Ala Ala Val Phe Ala Tyr Ala Lys Gln His Pro Asp Gln Glu Leu Val
                85                  90                  95

Ile Ala Gly Gly Ala Gln Val Phe Thr Ala Phe Lys Asp Asp Val Asp
            100                 105                 110

Thr Leu Leu Val Thr Arg Leu Ala Gly Ser Phe Glu Gly Asp Thr Lys
                115                 120                 125

Met Ile Pro Leu Asn Trp Asp Asp Phe Thr Lys Val Ser Ser Arg Thr
            130                 135                 140

Val Glu Asp Thr Asn Pro Ala Leu Thr His Thr Tyr Glu Val Trp Gln
145                 150                 155                 160

Lys Lys Ala

<210> SEQ ID NO 108
<211> LENGTH: 95
<212> TYPE: PRT
<213> ORGANISM: Lactobacillus rhamnosus

<400> SEQUENCE: 108

Gln Gly Cys Asn Leu Tyr Gly Ile Ala Thr Ala Leu Ala Arg Ile Ser
 1               5                  10                  15

Lys Ala Ile Leu Asn Asp Glu Asn Ala Val Leu Pro Leu Ser Val Tyr
            20                  25                  30

Met Asp Gly Gln Tyr Gly Leu Asn Asp Ile Tyr Ile Gly Thr Pro Ala
            35                  40                  45

Val Ile Asn Arg Asn Gly Ile Gln Asn Ile Leu Glu Ile Pro Leu Thr
 50                  55                      60

Asp His Glu Glu Ser Met Gln Lys Ser Ala Ser Gln Leu Lys Lys
 65                  70                  75                  80

Val Leu Thr Asp Ala Phe Ala Lys Asn Asp Ile Glu Thr Arg Gln
                85                  90                  95

<210> SEQ ID NO 109
<211> LENGTH: 323
<212> TYPE: PRT
<213> ORGANISM: Lactobacillus rhamnosus

<400> SEQUENCE: 109

Met Leu Thr Lys Arg Gln Leu Leu Val Leu Lys Glu Ile Ile Arg Leu
 1               5                  10                  15

Phe Thr Glu Ser Gly Gln Pro Val Gly Ser Lys Thr Leu Met Gln Glu
            20                  25                  30

Leu Pro Val His Val Ser Ser Ala Thr Ile Arg Asn Asp Met Ala Ser
            35                  40                  45

Leu Glu Asp Ala Gly Leu Ile Thr Lys Thr His Ser Ser Ser Gly Arg
 50                  55                      60

Val Pro Ser Thr Gln Gly Tyr Arg Tyr Leu Asp His Leu Val Glu
 65                  70                  75                  80
```

```
Pro Val Arg Val Ser His Arg Glu Leu Ala Thr Ile Lys Gln Ala Phe
                85                  90                  95

Gly Gln Arg Tyr Asn Lys Met Asp Glu Ile Val Ala Gln Ser Ala Gln
            100                 105                 110

Ile Leu Ser Asn Leu Thr Ser Tyr Thr Ala Ile Ser Leu Gly Pro Glu
            115                 120                 125

Val Asn Asn Ile Lys Leu Thr Gly Phe Arg Leu Val Pro Leu Gly Asn
    130                 135                 140

His Gln Val Met Ala Ile Leu Val Thr Asn Asn Gly Asn Val Glu Asn
145                 150                 155                 160

Gln Val Phe Thr Val Pro Glu Ser Ile Ser Ser Asp Glu Leu Glu Lys
                165                 170                 175

Ala Ile Arg Ile Val Asn Asp Gln Leu Val Gly Leu Pro Leu Ile Gln
            180                 185                 190

Val Ala Gln Arg Leu Lys Thr Asp Val Pro Ser Met Leu Met Gln Tyr
        195                 200                 205

Leu Thr Ser Pro Glu Gly Phe Leu Asp Ile Phe Gly Asn Val Leu Lys
    210                 215                 220

Ser Ala Ala Ser Glu Arg Phe Tyr Val Gly Gly Arg Leu Asn Leu Met
225                 230                 235                 240

Asp Tyr Leu Gly Asp Ser Asp Ile His Glu Leu Lys Lys Ile Met Ser
                245                 250                 255

Leu Ile Asp Ala Asp His Gly Asp Leu Thr Glu Leu Leu Gly Gly Pro
            260                 265                 270

Val Arg Gln Thr Pro Val Thr Val Arg Leu Gly Pro Glu Leu Lys Pro
        275                 280                 285

Ile Asp Leu Ala Asn Leu Lys Leu Ile Thr Ala Ser Tyr Asp Val Gly
    290                 295                 300

Asp His Gly Thr Gly Met Ile Ala Leu Leu Gly Pro Thr Gln Met Pro
305                 310                 315                 320

Phe Ser Lys

<210> SEQ ID NO 110
<211> LENGTH: 306
<212> TYPE: PRT
<213> ORGANISM: Lactobacillus rhamnosus

<400> SEQUENCE: 110

Met Phe Glu His Gly Phe Ile Glu Val His Asp Ala Asn Gln Asn Asn
 1               5                  10                  15

Leu Gln His Val Asn Val Lys Ile Pro Lys Asp Ala Ile Thr Val Phe
            20                  25                  30

Val Gly Arg Ser Gly Ser Gly Lys Ser Ser Leu Val Phe Asp Thr Ile
        35                  40                  45

Ala Ala Glu Ser Arg Arg Glu Leu Asn Glu Thr Phe Pro Ser Phe Thr
    50                  55                  60

Gln Gln Tyr Leu Pro Lys Tyr Gly Gln Pro Asp Val Gly Ser Ile Asp
65                  70                  75                  80

His Leu Pro Val Ala Ile Val Glu Gln Lys Arg Ile Gly Lys Asn
                85                  90                  95

Ala Arg Ser Thr Leu Ala Thr Tyr Thr Gly Ile Tyr Ser Leu Leu Arg
            100                 105                 110

Leu Leu Phe Ser Arg Ala Gly Lys Pro Phe Ile Gly Tyr Ser Asp Thr
        115                 120                 125
```

-continued

```
Phe Ser Phe Asn Leu Pro Gln Gly Met Cys Pro Thr Cys Gln Gly Leu
    130                 135                 140

Gly Tyr Val Asp Asp Ile Asp Val Ser Lys Leu Ile Asp Pro Asn Lys
145                 150                 155                 160

Ser Leu Asn Gln Glu Ala Ile Thr Phe Val Ser Phe Gly Pro Asp Thr
                165                 170                 175

Trp Arg Trp Arg Arg Tyr Ala Tyr Ser Gly Leu Phe Asp Asn Asp Lys
            180                 185                 190

Pro Leu Arg Asp Tyr Thr Pro Glu Glu Met Lys Leu Leu Leu Tyr Ala
        195                 200                 205

Pro Gln Gln Thr Leu Lys His Ala Pro Ala Lys Trp Pro Arg Thr Ala
    210                 215                 220

Leu Tyr Glu Gly Val Val Pro Arg Ile Lys Arg Ser Ile Ile Gly Lys
225                 230                 235                 240

Lys Glu Ala Glu His His Lys Ala Ala Leu Ala Glu Ile Val Thr Arg
                245                 250                 255

Lys Pro Cys Pro Asp Cys Gln Gly Thr Arg Leu Arg Pro Glu Val Leu
            260                 265                 270

Thr Cys Leu Ile Asn Gln Thr Asn Ile Ala Gln Val Leu Gln Met Asp
        275                 280                 285

Leu Val Asn Val Arg His Phe Leu Lys Asn Ile Gln Val Pro Leu Val
    290                 295                 300

Gln Asp
305

<210> SEQ ID NO 111
<211> LENGTH: 253
<212> TYPE: PRT
<213> ORGANISM: Lactobacillus rhamnosus

<400> SEQUENCE: 111

Met Thr Gln Ser Ala Asp Pro His Ala Pro Pro Leu Leu Ala Lys Trp
  1                 5                  10                 15

Arg Gln Trp Asp Thr Asp Arg His Lys Ser Ser Pro Phe Glu His Pro
             20                  25                  30

Asn Pro Glu Val Pro Gly Ala Ser Asp Arg Leu Leu Thr Glu Glu Ile
         35                  40                  45

Ala Gly Ile Phe Ile Leu Gly Thr Asn Gly Glu Ser Tyr Val Leu Ala
     50                  55                  60

Glu Asp Glu Lys Leu Ala Phe Val Glu His Val Ile Asp Tyr Val His
 65                  70                  75                  80

Gly Arg Thr Lys Val Leu Val Gly Thr Gly Leu Asn Gly Thr Ala Glu
                 85                  90                  95

Thr Ile Arg Phe Ser Gln Lys Val Ala Ser Leu Lys Pro Asp Ala Ile
            100                 105                 110

Thr Leu Val Ala Pro Ser Phe Val Ala Pro Ser Gln Gln Glu Leu Val
        115                 120                 125

Asp His Val Ala Ala Ile Ile His Ala Asp Ile Pro Val Leu Leu
    130                 135                 140

Tyr Asn Met Pro Ala Lys Thr Gly Ile Asn Ile Glu Pro Ala Ser Leu
145                 150                 155                 160

Lys Gln Leu Ser Lys Tyr Glu Asn Leu Ile Gly Ile Lys Asp Ser Ser
                165                 170                 175

Gly Lys Trp Glu Asn Phe Asp Gly Tyr Leu Ala Asn Arg Pro Glu Arg
```

```
              180                 185                 190
Pro Phe Ser Val Ile Met Gly Ser Asp Gly Arg Ile Leu Glu Ser Phe
        195                 200                 205

Gln His Gly Gly Asn Ala Ala Ile Ala Ser Thr Ala Asn Leu Leu Thr
        210                 215                 220

Ala Asn Asn Val Ala Leu Tyr Gln Ala Phe Val Asn Asp Asn Ile Glu
225                 230                 235                 240

Lys Ala Gln Lys Phe Gln Asp Arg Ile Gln Pro Leu Arg
            245                 250

<210> SEQ ID NO 112
<211> LENGTH: 217
<212> TYPE: PRT
<213> ORGANISM: Lactobacillus rhamnosus

<400> SEQUENCE: 112

Met Ala Met Ser Pro Ile Asn Ala Pro Thr Ile Lys Gly Thr Ser Lys
1               5                   10                  15

Ala Thr Asp Gln Gly Val Asp Trp Ser Arg Tyr Gln Gly Asp Asn Gly
            20                  25                  30

Val Phe Gly Tyr Ser Thr Asp Lys Phe Gly Ile Ser Gln Ile Gly Gly
        35                  40                  45

Tyr Ser Gly Tyr Gly Thr Tyr Glu Gln Thr Thr Tyr Lys Thr Gln Val
50                  55                  60

Ala Ser Leu Ile Ala Ala Gly Lys Arg Ala His Thr Tyr Ile Trp Trp
65                  70                  75                  80

Gln Asn Ile Asp Asn Thr Asn Phe Ala Lys Gln Val Leu Asp His Phe
                85                  90                  95

Leu Pro Glu Ile Gln Thr Pro Lys Gly Ser Ile Val Ala Leu Asp Tyr
            100                 105                 110

Glu Ala Gly Ser Thr Asn Thr Ala Thr Leu Leu Trp Ala Leu Asp Tyr
        115                 120                 125

Ile Arg Asp Ala Gly Tyr Thr Pro Met Leu Tyr Gly Tyr Lys Ser Phe
130                 135                 140

Leu Met Ser His Ile Asp Leu Ser Gln Ile Ala Ser Arg Tyr Gln Leu
145                 150                 155                 160

Trp Leu Ala Glu Tyr Pro Asp Tyr Asn Val Thr Thr Val Pro Asn Tyr
                165                 170                 175

Gly Tyr Phe Pro Ser Phe Asp Asn Val Gly Ile Phe Gln Phe Thr Ser
            180                 185                 190

Thr Tyr Arg Ala Gly Gly Leu Asp Gly Asn Val Asp Arg Ser Pro Arg
        195                 200                 205

Thr Leu Thr Lys Pro Arg Cys Cys Gln
            210                 215

<210> SEQ ID NO 113
<211> LENGTH: 282
<212> TYPE: PRT
<213> ORGANISM: Lactobacillus rhamnosus

<400> SEQUENCE: 113

Met Ala Thr Ser His Phe Lys Ala Ser Lys Gln Leu Cys Tyr Tyr Leu
1               5                   10                  15

Leu Gly Val Leu Gly Ile Ala Val Val Phe Gly Leu Gly Leu Phe Gly
            20                  25                  30

Gly Tyr Phe Val Ser Ile Ile Asp Ala Thr Pro Ile Pro Thr Glu Thr
```

-continued

```
                35                  40                  45
Ala Met Lys Ala Thr Leu Ser Asn Thr Ser Arg Thr Ser Ser Met Tyr
     50                  55                  60
Phe Ala His Asn Val Lys Leu Ser Asp Val Lys Ser Asp Leu Tyr Ser
 65                  70                  75                  80
Thr Lys Val Asn Leu Asn Glu Met Ser Pro Trp Leu Thr Lys Ala Ile
                 85                  90                  95
Ile Ala Thr Glu Asp Glu Asp Phe Tyr Arg His Asn Gly Ile Val Pro
                100                 105                 110
Lys Ala Val Ile Arg Ala Phe Phe Ser Asp Leu Thr Gly Met Gly Ser
                115                 120                 125
Gln Thr Gly Gly Ser Thr Leu Thr Gln Gln Val Val Lys Met Met Phe
    130                 135                 140
Leu Asn Ser Glu Thr Thr Phe Lys Arg Lys Ala Ala Glu Ile Met Leu
145                 150                 155                 160
Ala Arg Arg Leu Asn Asn His Phe Ser Lys Asn Thr Ile Leu Ala Thr
                165                 170                 175
Tyr Leu Asn Val Ala Thr Leu Gly Arg Asn Asn Lys Gly Gln Asn Ile
                180                 185                 190
Ala Gly Val Glu Ala Ala Gln Gly Leu Phe Gly Val Ser Ala Lys
                195                 200                 205
Glu Val Asn Leu Pro Glu Ala Ala Phe Ile Ala Gly Leu Pro Gln Ser
    210                 215                 220
Pro Phe Val Tyr Thr Pro Tyr Thr Ala Asp Gly Lys Leu Lys Thr Ser
225                 230                 235                 240
Leu Lys Ala Gly Ile Asn Arg Gln Gln Thr Val Leu Phe Arg Met Tyr
                245                 250                 255
Arg Ala Gly Val Ile Ser His Arg Gln Tyr Val Ala Ala Lys Ser Phe
                260                 265                 270
Asp Pro Leu Val Ser Thr Cys Arg Arg Ala
                275                 280

<210> SEQ ID NO 114
<211> LENGTH: 418
<212> TYPE: PRT
<213> ORGANISM: Lactobacillus rhamnosus

<400> SEQUENCE: 114

Met Thr Thr Val Gly His Ile Arg Asn Glu Leu Leu Ala Thr Phe Arg
 1               5                  10                  15
Lys Asn Pro Asn Ile Asp Tyr Ser Val Gln Thr Leu Ser Arg Ala Leu
                20                  25                  30
Lys Leu Ser Glu Gly Gly Asp Phe Lys Val Leu Val Gln Ala Leu Asn
    35                  40                  45
Gly Met Glu Asn Asp Asn Leu Ile His Ala Asn His Glu Gly Arg Tyr
     50                  55                  60
Ala Leu Gly Gly Ala Pro Lys Val Leu Thr Gly Thr Phe Arg Gly Asn
 65                  70                  75                  80
Glu Lys Gly Phe Gly Phe Val Ala Val Glu Gly Leu Asp Asn Asp Val
                 85                  90                  95
Tyr Val Pro Ala Met Asn Thr Asp Phe Ala Leu Asp Gly Asp Thr Val
                100                 105                 110
Glu Val Arg Ile Val Arg Glu Ala Arg Pro Asn Asp Ser Arg Gly Pro
                115                 120                 125
```

-continued

Glu Gly Glu Ile Thr Lys Ile Val Gln Arg Ser Leu Thr Thr Leu Val
    130                 135                 140

Gly Glu Phe Lys Pro Phe Ser Asp Lys Asp Arg Ala Lys Ser Gly Phe
145                 150                 155                 160

Ile Gly Met Val Val Ser His Glu Lys Lys Leu Lys Asn Phe Pro Val
                165                 170                 175

Tyr Val Lys Asp Thr Gly Asn Ile Pro Gln Leu Gly Asp Met Thr Val
            180                 185                 190

Thr Glu Ile Thr Glu Phe Pro Thr Glu Tyr His Pro Lys Leu Met Tyr
        195                 200                 205

Gly Ile Val Val Glu Thr Leu Gly Asn Lys Asn Asp Pro Gly Val Asp
    210                 215                 220

Ile Met Ser Leu Val Met Gln Asn His Ile Lys Thr Glu Phe Pro Asp
225                 230                 235                 240

Glu Val Met Asp Gln Thr Asn Ala Ile Pro Asp His Val Thr Pro Glu
                245                 250                 255

Glu Arg Val Gly Arg Lys Asp Ile Thr Asp Gln Ala Val Val Thr Ile
            260                 265                 270

Asp Gly Asp Asp Ser Lys Asp Phe Asp Ala Val Val Val Trp Lys
    275                 280                 285

Leu Pro Asn Gly Asn Phe His Leu Gly Val His Ile Ala Asp Val Ser
290                 295                 300

His Tyr Val Thr Glu Gly Ser Ala Leu Asp Gln Glu Ala Phe Asp Arg
305                 310                 315                 320

Gly Thr Ser Thr Tyr Leu Val Asp Arg Val Ile Pro Met Leu Pro Phe
                325                 330                 335

Arg Leu Ser Asn Gly Ile Cys Ser Leu Asn Pro Gly Val Asp Arg Leu
            340                 345                 350

Ala Met Ser Cys Asp Met Glu Ile Asp His Asp Gly His Val Val Asn
        355                 360                 365

His Glu Ile Tyr Gln Ser Val Ile Lys Ser His Ala Arg Met Thr Tyr
    370                 375                 380

Asn Asn Val Asn Lys Ile Val Thr Asp Pro Asp Pro Glu Val Met Ala
385                 390                 395                 400

Glu Tyr Gln Glu Leu Val Pro Met Phe Glu Asp Met Val Glu Leu His
                405                 410                 415

Gln Ile

<210> SEQ ID NO 115
<211> LENGTH: 295
<212> TYPE: PRT
<213> ORGANISM: Lactobacillus rhamnosus

<400> SEQUENCE: 115

Tyr Glu Asn Glu Ile Ile Thr Ile Arg Ala Gly Arg Lys Asn His
  1               5                  10                  15

Pro Leu Leu Leu Ser Ala Asn Pro Gln Tyr Ala Arg Val Gln Ile Thr
                 20                  25                  30

His Ile Pro Phe Thr Asn Pro Asp Val Pro Ala Thr Phe Thr Met Thr
            35                  40                  45

Leu Arg Lys Tyr Phe Asn Ala Ala Thr Leu Thr Glu Ile His Gln Val
        50                  55                  60

Gln Asn Asp Arg Val Leu His Phe Glu Phe Ser Thr Arg Asp Glu Leu
65                  70                  75                  80

```
Gly Asp Glu Leu Gly Leu Arg Leu Ile Ile Glu Met Met Gly Arg His
                 85                  90                  95

Ser Asn Ile Phe Leu Val Ser Lys Arg Thr Gly Lys Ile Ile Asp Leu
            100                 105                 110

Ile Arg His Val Ser Ala Asp Gln Asn Arg Tyr Arg Pro Leu Met Pro
            115                 120                 125

Gly Ala Pro Tyr Val Glu Pro Pro Lys Gln Asp Lys Val Asp Pro Phe
            130                 135                 140

His Asp Ser Glu Arg Ile Tyr His Glu Leu Glu Arg Gln Val Thr Pro
145                 150                 155                 160

Ser Leu Ser Arg Ala Ala Leu Leu Gln Gln His Tyr Gln Gly Leu Ala
                165                 170                 175

Lys Asp Ser Ala Ala Glu Leu Ala Leu Arg Leu Asn Gln Gly Asp Ala
            180                 185                 190

Gly Trp Asp Ser Phe Phe Ala Ala Leu Ala Thr Pro Glu Pro Thr Ile
            195                 200                 205

Thr Thr Gln Gly Lys Lys Ala Val Phe Thr Ala Ile Pro Tyr Gln Ser
210                 215                 220

Leu Thr Gly Glu Gln Gln His Phe Pro Thr Leu Ser Ala Met Leu Asp
225                 230                 235                 240

Ala Tyr Tyr Ala Gln Lys Ala Glu His Asp Arg Val Leu Gln Gln Gly
                245                 250                 255

Gly Asn Leu Ile His Val Ile Lys Asn Val Ile Asp Lys Asp Arg Lys
            260                 265                 270

Lys Gln Arg Lys Leu Lys Arg Thr Leu Glu Glu Thr Glu Lys Ala Asp
            275                 280                 285

Asp Tyr Arg Ile Arg Phe Lys
            290                 295

<210> SEQ ID NO 116
<211> LENGTH: 231
<212> TYPE: PRT
<213> ORGANISM: Lactobacillus rhamnosus

<400> SEQUENCE: 116

Met Trp His Leu Pro Ile Thr Gly Tyr Thr Phe Tyr Arg Ser Asp Met
1               5                   10                  15

Met Pro Val Lys Lys Thr Asn Ala Val Asn Leu Ser Leu Phe Ile Leu
            20                  25                  30

Leu Leu Thr Leu Glu Ile Ser Phe Ser His Ala Val Ser Leu Asn Val
        35                  40                  45

Ala Leu Ile Gly Leu Ala Ser Gly Phe Leu Ile Trp Arg Arg Ala Phe
    50                  55                  60

Lys Ser Leu Val Val Leu Ala Leu Leu Pro Leu Ile Pro Ala Ala Ser
65                  70                  75                  80

Thr Tyr Trp Ala Ile Thr Leu His Gly Thr Asp Thr Thr Tyr Ala Leu
                85                  90                  95

Leu Leu Trp Val Arg Thr Tyr Ala Phe Thr Ala Leu Gly Leu Val Phe
            100                 105                 110

Leu Ile Gly Val Asp Leu Glu Thr Leu Leu Leu Trp Leu Glu Gln His
            115                 120                 125

Lys Leu Ser Pro Asn Phe Val Tyr Gly Leu Leu Val Val Ile His Ala
            130                 135                 140

Leu Pro Gln Ile Met His Glu Val Ala Ala Ile Arg Glu Ala Ser Leu
145                 150                 155                 160
```

```
Leu Arg Gly Gln Lys Leu His Ala Trp Ser Pro Met Ile Tyr Val Lys
            165                 170                 175

Val Ile Phe Val Ala Met Ser Trp Gln Asp Gln Tyr Val Lys Ala Met
        180                 185                 190

Tyr Ala His Gly Tyr Thr Glu Gly Ala Ala Arg Thr Val His Gln Thr
    195                 200                 205

Ile Arg Ser Ser Trp Arg Gly Leu Ile Ala Met Val Gly Gly Phe Val
    210                 215                 220

Leu Leu Asn Leu Ile Asp Arg
225                 230

<210> SEQ ID NO 117
<211> LENGTH: 225
<212> TYPE: PRT
<213> ORGANISM: Lactobacillus rhamnosus

<400> SEQUENCE: 117

Met Met Ala Lys Ile Leu Ile Val Glu Asp His Arg Ile Ser Arg His
 1               5                  10                  15

Leu Leu Lys Asp Val Leu Thr Pro Thr Tyr Thr Val Thr Gln Ala Tyr
            20                  25                  30

Asp Gly Ile Gln Ala Leu Thr Ala Phe His Arg Glu Gln Pro Asp Leu
        35                  40                  45

Ile Ile Leu Asp Leu Met Leu Pro Asn Val Thr Gly Glu Ser Val Leu
    50                  55                  60

Thr Thr Ile Arg Lys Thr Ser Gln Val Pro Val Leu Val Leu Thr Ala
65                  70                  75                  80

Ile Gln Glu Lys Ala Lys Thr Val Ala Leu Leu Gln Gln Gly Ala Asn
                85                  90                  95

Asp Tyr Leu Thr Lys Pro Phe Asp Ile Asp Glu Leu Leu Ala Arg Ile
            100                 105                 110

Gln Val Gln Leu Arg Gln Val Ser Gly Gln Pro Ile Thr Thr Asn Asp
        115                 120                 125

Gln Leu Lys Val Gly Glu Ile Gln Leu Asp Pro Lys Arg His Val Val
    130                 135                 140

Thr Val Asn Gln Gln Thr Leu Thr Leu Pro Lys Lys Glu Tyr Asp Met
145                 150                 155                 160

Leu Ala Leu Met Met Arg Asp Pro His Gln Val Phe Asp Lys Ser Gln
                165                 170                 175

Leu Tyr Glu His Val Trp Gly Glu Pro Phe Leu Asn Ala Asp Asn Thr
            180                 185                 190

Leu Asn Val His Ile Ser Asn Leu Arg Thr Lys Ile Asn Glu Leu Ala
        195                 200                 205

His Asp Pro Lys Tyr Ile Ile Ser Ile Trp Gly Ile Gly Val Arg Leu
    210                 215                 220

Ile
225

<210> SEQ ID NO 118
<211> LENGTH: 259
<212> TYPE: PRT
<213> ORGANISM: Lactobacillus rhamnosus

<400> SEQUENCE: 118

Arg Phe Ala Ser Val Pro Gln Asp Pro Asp Asn Leu Ala Gly Ile Asp
 1               5                  10                  15
```

-continued

Ser Asn Arg Ile Ala Lys Tyr Gln Glu Ala Phe Ala Lys Ala Tyr Lys
                20                  25                  30

Arg Leu Met Glu Ala Ile Ser Ser Met Ser Ile Ser Trp Thr Ile Ile
            35                  40                  45

Gly Ala Ala Ser Pro Arg Trp Ala Gln Lys Val Phe Pro Asp Ala Ala
        50                  55                  60

Thr Pro Glu Glu Ala Thr Glu Leu Leu Trp Glu Ala Ile Phe Lys Thr
65                  70                  75                  80

Thr Arg Ile Asp Gln Pro Asp Pro Glu Ala Ala Trp Lys Ala His Asp
                85                  90                  95

Gln Lys Leu Arg Glu Lys Ala Ala Trp Leu Asn Asn Glu Gln Phe Asp
            100                 105                 110

Gln Leu His Tyr Met Ala Pro Gly Thr Asp Leu Val Val Gly Leu Pro
        115                 120                 125

Lys Asn His Ile Trp Glu Gly Ala Gly Ala Phe Asn Pro Arg Gly Glu
    130                 135                 140

Glu Phe Met Ala Asn Met Pro Thr Glu Glu Val Phe Thr Ala Pro Asp
145                 150                 155                 160

Phe Arg Arg Ile Asp Gly Thr Val Ala Ser Thr Lys Pro Leu Ser Tyr
                165                 170                 175

Gly Gly Asn Ile Leu Glu Asp Met His Phe Thr Phe Lys Asp Gly Gln
            180                 185                 190

Ile Val Glu Ala His Ala Lys Gln Gly Asp Asp Val Leu Gln Asn Leu
        195                 200                 205

Leu Lys Thr Pro Gly Ala Arg Ser Leu Gly Glu Val Ser Leu Val Pro
    210                 215                 220

Asp Pro Ser Ser Ile Ser Gln Ser Gly Leu Ile Phe Phe Asn Thr Leu
225                 230                 235                 240

Val Asp Glu Asn Ala Ser Asp His Met Ala Leu Gly Gln Ala Tyr Pro
                245                 250                 255

Phe Ser Val

<210> SEQ ID NO 119
<211> LENGTH: 438
<212> TYPE: PRT
<213> ORGANISM: Lactobacillus rhamnosus

<400> SEQUENCE: 119

Val Lys Arg Ala Leu Leu Ser Val Ser Asp Lys Thr Gly Leu Val Pro
1               5                   10                  15

Phe Ala Lys Gly Leu Val Glu Arg Gly Phe Glu Leu Ile Ser Thr Gly
                20                  25                  30

Gly Thr His Arg Ala Leu Ala Glu Ala Gly Val Ala Val Thr Gly Val
            35                  40                  45

Glu Ala Val Thr Gly Phe Pro Glu Met Leu Asp Gly Arg Val Lys Thr
        50                  55                  60

Leu His Pro Lys Ile His Ala Gly Ile Leu Ala Arg Arg Asp Pro
65                  70                  75                  80

Ala His Met Gln Ala Leu Ala Asp His Asp Ile Gln Pro Ile Asp Val
                85                  90                  95

Val Cys Val Asn Leu Tyr Pro Phe Ala Ala Thr Ile Gln Arg Ala Gly
            100                 105                 110

Val Thr Arg Ala Glu Ala Ile Glu Gln Ile Asp Ile Gly Gly Pro Ser
        115                 120                 125

```
Ala Leu Arg Ala Ala Ala Lys Asn Ser Asp Ser Val Trp Ala Val Val
        130                 135                 140

Asp Pro Ala Asp Tyr Ala Asp Val Leu Ala Gly Leu Asp Gln Asn Asp
145                 150                 155                 160

Ala Asp Leu Arg Gln Arg Leu Ala Ala Lys Val Phe Ser Ala Thr Ala
                165                 170                 175

Ala Tyr Asp Ala Gln Ile Ala His Tyr Leu Asp Pro Glu Pro Phe Pro
            180                 185                 190

Glu Gln Phe Thr Pro Thr Tyr His Lys Arg Gln Asp Leu Arg Tyr Gly
        195                 200                 205

Glu Asn Ser His Gln Gln Ala Ala Phe Tyr Val Glu Pro Asn Pro Asp
    210                 215                 220

Pro Thr Ser Leu Ala Ala Lys Gln Leu His Gly Lys Glu Leu Ser
225                 230                 235                 240

Tyr Asn Asn Ile Lys Asp Ala Asp Ala Ala Leu Ala Met Leu Arg Glu
                245                 250                 255

Phe Lys Gln Pro Ala Ala Val Ala Val Lys His Met Asn Pro Cys Gly
            260                 265                 270

Ile Gly Leu Gly Asp Thr Leu Glu Ala Ala Trp Asp Lys Ala Tyr Ala
        275                 280                 285

Ala Asp Pro Met Ser Ile Phe Gly Gly Ile Ile Ala Leu Asn Arg Arg
290                 295                 300

Val Asp Leu Ala Thr Ala Glu Lys Met His Lys Leu Phe Leu Glu Ile
305                 310                 315                 320

Ile Met Ala Pro Ala Phe Asp Asp Ala Tyr Glu Ile Leu Ala Lys
                325                 330                 335

Lys Lys Asn Val Arg Leu Leu Thr Ile Asn Thr Ala Asp Thr Pro Glu
                340                 345                 350

Glu Leu Gly Thr Glu Thr Thr Ser Ile Tyr Gly Gly Leu Leu Ile Gln
            355                 360                 365

Thr Arg Asp Asp Lys Ala Glu Thr Pro Ala Asp Met Thr Val Val Thr
370                 375                 380

Glu Val Lys Pro Thr Glu Ala Gln Leu Lys Ala Leu Ala Phe Ala Gln
385                 390                 395                 400

Thr Val Val Lys His Val Lys Ser Asn Ala Ile Val Val Ala Gln Ala
                405                 410                 415

Asp Gln Thr Leu Gly Ile Gly Ala Gly Gln Met Asn Arg Ile Gly Ser
            420                 425                 430

Val Glu Leu Ala Leu Thr
        435

<210> SEQ ID NO 120
<211> LENGTH: 279
<212> TYPE: PRT
<213> ORGANISM: Lactobacillus rhamnosus

<400> SEQUENCE: 120

Met Val Lys Arg Asn Pro Asn Gly Thr Arg Phe Ile Thr Leu Pro Asn
1               5                   10                  15

Gly Tyr His Leu Trp Thr Gln Thr Leu Ala Ala Ala Asp Ser Leu Leu
            20                  25                  30

Thr Leu His Gly Gly Pro Gly Gly Thr Asn Glu Val Phe Glu Asn Phe
        35                  40                  45

Ala Thr Glu Leu Ala Ser Phe Gly Val Arg Val Ser Arg Tyr Asp Gln
```

```
                50                  55                  60
Leu Gly Ser Phe Phe Ser Asp Gln Pro Asp Phe Ser Asp Pro Ala Asn
 65                  70                  75                  80

Gln Lys Arg Phe Leu Asn Ile Ala Tyr Tyr Val Asp Glu Val Glu Asn
                 85                  90                  95

Val Arg Gln Gln Leu Gly Leu Asp His Phe Tyr Leu Leu Gly Gln Ser
            100                 105                 110

Trp Gly Gly Val Leu Ala Ile Glu Tyr Gly Leu Lys Tyr Ser Gln His
            115                 120                 125

Leu Lys Gly Leu Ile Leu Ser Ser Met Ile Asp Asn Leu Asp Glu Tyr
130                 135                 140

Leu Val Asn Ile Asn Lys Ile Arg Glu Thr Met Phe Ser Ser Asp Asp
145                 150                 155                 160

Val Ala Tyr Met Gln Arg Ile Glu Ala Gln His Ala Phe Thr Asp Ala
                165                 170                 175

Lys Tyr Gln Gln Leu Val Arg Glu Leu Gly Glu Gln Tyr Leu His His
            180                 185                 190

Ala Lys Asp Pro Gln Pro Arg His Leu Ile Ser Thr Leu Ala Thr Pro
            195                 200                 205

Val Tyr His His Phe Gln Gly Asp Asn Glu Phe Val Met Val Gly Ala
            210                 215                 220

Leu Arg Asp Trp Asp Arg Arg Ala Asp Ile His Arg Leu Thr Met Pro
225                 230                 235                 240

Thr Tyr Leu Thr Phe Gly Gly His Glu Thr Met Pro Leu Ser Ala Ala
                245                 250                 255

Lys Arg Met Ala Arg Thr Ile Pro Asn Ala Thr Leu His Val Thr Pro
            260                 265                 270

Asn Ala Gly His Gly Gln Met
            275

<210> SEQ ID NO 121
<211> LENGTH: 317
<212> TYPE: PRT
<213> ORGANISM: Lactobacillus rhamnosus

<400> SEQUENCE: 121

Met Ser Arg Arg Tyr Arg Gln Phe Asp Ala Asn Arg Ala Gly Ser Arg
  1               5                  10                  15

Ser Arg Gly Gly Leu Asn Leu Ile Ser Leu Gly Ile Tyr Glu Lys Ala
             20                  25                  30

Leu Pro Arg Thr Glu Ser Trp Val Glu Arg Leu Lys Met Val Arg Asp
         35                  40                  45

Leu Gly Phe Asn Phe Leu Glu Leu Ser Val Asp Glu Ser Asp Glu Arg
 50                  55                  60

Leu Ala Arg Leu Asp Trp Thr Ala Ala Lys Arg Ala Lys Val Arg Asp
 65                  70                  75                  80

Ala Cys Trp Gln Thr Gly Val Arg Ile His Thr Leu Met Leu Ser Gly
                 85                  90                  95

His Arg Arg Phe Pro Leu Gly Ser Ala Asp Pro Ala Ile Arg Glu Lys
            100                 105                 110

Ser Leu Thr Met Leu Cys Lys Ala Ile Asp Leu Ala Ser Asp Leu Gly
            115                 120                 125

Val Arg Asn Val Gln Leu Ala Gly Tyr Asp Val Tyr Tyr Glu Pro Lys
            130                 135                 140
```

-continued

```
Thr Leu Ala Ser Arg Glu Tyr Phe Ile Glu Asn Leu Lys Arg Gly Val
145                 150                 155                 160

Ala Tyr Ala Ala Ala Lys Glu Val Met Leu Ala Ile Glu Thr Met Asp
            165                 170                 175

Asp Pro Phe Leu Asn Ser Leu Ser Lys Ile Lys Thr Ile Lys Asp Glu
        180                 185                 190

Ile Pro Ser Pro Trp Leu Gln Ala Tyr Pro Asp Leu Gly Asn Leu Ser
    195                 200                 205

Ala Trp Pro Glu Asn Asn Val Gly Arg Glu Leu Glu Leu Gly Ile Ala
    210                 215                 220

Asn Ile Val Ser Val His Leu Lys Asp Thr Gln Ala Val Thr Val Lys
225                 230                 235                 240

Ser Lys Gly Gln Phe Arg Asp Val Pro Phe Gly Ala Gly Val Val Asp
            245                 250                 255

Phe Ser Gly Cys Leu Arg Thr Leu Lys Arg Leu Asp Tyr Ser Gly Ala
            260                 265                 270

Phe Thr Ile Glu Met Trp Thr Glu Lys Ala Ala Asp Pro Ile Gln Glu
        275                 280                 285

Val Lys Gln Ala Lys Asp Phe Phe Asp Pro Leu Phe Val Gln Ala Gly
    290                 295                 300

Phe Val Gln Glu Pro Val Ala Lys Thr Asn Val Pro Ser
305                 310                 315

<210> SEQ ID NO 122
<211> LENGTH: 310
<212> TYPE: PRT
<213> ORGANISM: Lactobacillus rhamnosus

<400> SEQUENCE: 122

Met Thr Asp Pro Ile Ala Phe Leu Gln Lys Leu Ile Gln Ile Asp Ser
1               5                   10                  15

Ala Asn Gly Asn Glu Leu Ala Val Ala Arg Val Leu Gln Ala Glu Leu
            20                  25                  30

Glu Ala Ala Asp Ile Pro Thr Lys Leu Ile Pro Tyr Lys Asp Asp Arg
        35                  40                  45

Val Asn Leu Val Ala Gln Leu Asn His Gly Asp Arg Val Leu Gly Phe
    50                  55                  60

Thr Gly His Glu Asp Val Val Ser Pro Gly Asp Glu Asn Ala Trp Thr
65                  70                  75                  80

Tyr Pro Pro Phe Ser Gly Lys Ile Val Asn Asn Thr Met Tyr Gly Arg
                85                  90                  95

Gly Thr Asp Asp Met Lys Ser Gly Leu Ala Ala Met Thr Leu Ala Leu
            100                 105                 110

Ile His Leu Lys Gln Ser Gly Phe Ala His Pro Leu Arg Phe Met Ala
        115                 120                 125

Thr Val Gly Glu Glu Phe Gly Ala Met Gly Ala Arg Gln Leu Thr Glu
    130                 135                 140

Gln Gly Tyr Ala Asp Asp Leu Thr Gly Leu Val Val Gly Glu Pro Thr
145                 150                 155                 160

Asn Lys Leu Leu Lys Tyr Ala His Gly Gly Thr Val Asn Tyr Glu Ile
                165                 170                 175

Asp Ser Glu Gly Val Ser Val His Ser Ser Arg Pro Glu Lys Gly Val
            180                 185                 190

Asn Ala Ile Glu Gly Leu Val Ala Phe Ser Thr Pro Glu Pro His Ala
        195                 200                 205
```

```
Phe Asp Gln Ala Pro Asp Asp Pro Asp Leu Gly Pro Phe Arg His Ser
    210                 215                 220
Ile Thr Val Ile Lys Gly Gly Asp Gln Val Asn Thr Ile Pro Ala His
225                 230                 235                 240
Ala Tyr Leu Arg Gly Asn Leu Arg Pro Thr Pro Ala Ala Asn Ile Glu
                245                 250                 255
Leu Val Val Gly Leu Leu Glu Lys Leu Val Asp Gln Ala Asn Lys Ala
                260                 265                 270
Thr Ala Ala Asn Leu Thr Leu Asn Val Leu His Arg Phe Leu Pro Val
            275                 280                 285
His Ser Asp Lys Asn Gly His Leu Val Thr Thr Ala Asn Glu Ala Ile
        290                 295                 300
Ala Ala Val Thr Gly Lys
305                 310

<210> SEQ ID NO 123
<211> LENGTH: 246
<212> TYPE: PRT
<213> ORGANISM: Lactobacillus rhamnosus

<400> SEQUENCE: 123

Met Lys Ile Asp Ile Asp Lys Thr Ser Met Ile Pro Val Tyr Glu Gln
1               5                   10                  15
Ile Ala Asn Ser Leu Arg Asp Met Met Tyr Gly Gly Ser Leu Gln Asp
                20                  25                  30
Gly Asp Arg Leu Asp Ser Glu Gln Lys Met Cys Arg Asn Leu Asn Val
            35                  40                  45
Ser Arg Gly Thr Val Arg Lys Ala Ile Asp Ile Leu Leu Lys Glu Gly
        50                  55                  60
Met Val Lys Lys Ile His Gly Lys Gly Thr Phe Val Ser Asn Pro Asn
65                  70                  75                  80
Val Glu Tyr Ser Leu Asn Asp Gln Leu Met Ser Phe Ala Glu Ser Leu
                85                  90                  95
Asp Asn Gln His Leu Ser Tyr Thr Thr Gln Val Ile Gln Gln Glu Leu
                100                 105                 110
Arg Pro Ala Thr Ala Lys Ile Ala Asp Met Leu Lys Ile Pro Ile Asp
            115                 120                 125
Ser Gln Tyr Leu Tyr Leu Glu Arg Leu Arg Ser Val Ala Asp Asp Lys
        130                 135                 140
Leu Met Leu Ile Glu Asn Arg Ile Asn Ile Thr Leu Cys Pro Gly Ile
145                 150                 155                 160
Glu Lys Val Asn Phe Asn Asn Ile Ser Leu Phe Asn Glu Ile Glu Glu
                165                 170                 175
Leu Ala Lys Arg Lys Ile Ser Phe Ala Arg Ser Thr Tyr Glu Ala Leu
                180                 185                 190
Thr Ile Gly Thr Glu Arg Gly Lys Leu Leu Glu Leu Pro Ser Ser Thr
            195                 200                 205
Pro Ala Leu Lys Met Gln Gln Thr Val Tyr Leu Ser Glu Lys Glu Pro
        210                 215                 220
Val Glu Tyr Gly Ser Val Trp Leu Lys Gly Asn Lys Tyr Phe Leu Thr
225                 230                 235                 240
Thr Thr Leu Gln Arg Arg
                245
```

-continued

```
<210> SEQ ID NO 124
<211> LENGTH: 520
<212> TYPE: PRT
<213> ORGANISM: Lactobacillus rhamnosus

<400> SEQUENCE: 124
```

| | | | | | | | | | | | | | | | |
|---|---|---|---|---|---|---|---|---|---|---|---|---|---|---|---|
| Leu | Val | Asp | Pro | Phe | Leu | Phe | Thr | Pro | Gln | Leu | Thr | Ile | Glu | Glu | Val |
| 1 | | | | 5 | | | | | 10 | | | | | 15 | |
| Lys | Lys | Ala | Gly | Trp | Ala | Tyr | Pro | Val | Phe | Gly | Tyr | Leu | Asp | His | Glu |
| | | | 20 | | | | | 25 | | | | | 30 | | |
| Asp | Pro | Phe | Ala | Lys | Leu | Ala | Ser | His | Ile | Lys | Thr | Val | Asn | Pro | Asn |
| | | | 35 | | | | | 40 | | | | | 45 | | |
| Pro | Thr | Lys | Trp | Ala | Ile | Glu | Lys | Asp | Asn | Leu | Ala | Val | Phe | Lys | Phe |
| | 50 | | | | | 55 | | | | | 60 | | | | |
| Glu | Ala | Ile | Met | Lys | Gln | Phe | Pro | Asp | Ala | Thr | Phe | Pro | Ile | Asp | Ala |
| 65 | | | | | 70 | | | | | 75 | | | | | 80 |
| Ser | Arg | Phe | Ile | Glu | Lys | Gln | Arg | Leu | Ile | Lys | Thr | Ala | Ser | Glu | Ile |
| | | | | 85 | | | | | 90 | | | | | 95 | |
| Lys | Gln | Met | Glu | Ala | Ala | Gly | Ala | Gln | Ala | Asp | Arg | Ala | Phe | Gln | Ala |
| | | | 100 | | | | | 105 | | | | | 110 | | |
| Gly | Phe | Asn | Ala | Ile | Lys | Ala | Gly | Ala | Thr | Glu | Gln | Glu | Val | Ala | Ala |
| | | | 115 | | | | | 120 | | | | | 125 | | |
| Glu | Ile | Asp | Tyr | Ala | Met | Met | Lys | Glu | Gly | Val | Met | His | Met | Ser | Phe |
| | | | 130 | | | | | 135 | | | | | 140 | | |
| Gly | Thr | Ile | Val | Gln | Ala | Gly | Val | Asp | Ala | Ala | Asn | Pro | His | Gly | Glu |
| 145 | | | | | 150 | | | | | 155 | | | | | 160 |
| Pro | Met | Gly | Thr | Lys | Leu | Ala | Pro | Asn | Glu | Leu | Val | Leu | Phe | Asp | Leu |
| | | | | 165 | | | | | 170 | | | | | 175 | |
| Gly | Thr | Asp | Asn | His | Gly | Tyr | Met | Ser | Asp | Ala | Thr | Arg | Thr | Val | Ala |
| | | | 180 | | | | | 185 | | | | | 190 | | |
| Phe | Gly | Gln | Val | Thr | Gly | Lys | Pro | Arg | Glu | Ile | Phe | Asp | Ile | Cys | Leu |
| | | | 195 | | | | | 200 | | | | | 205 | | |
| Glu | Ala | Asn | Leu | Thr | Ala | Met | Asp | Ala | Val | Lys | Pro | Gly | Leu | Lys | Ala |
| | 210 | | | | | 215 | | | | | 220 | | | | |
| Ser | Glu | Leu | Asp | Lys | Ile | Ala | Arg | Asp | Ile | Ile | Thr | Lys | Ala | Gly | Tyr |
| 225 | | | | | 230 | | | | | 235 | | | | | 240 |
| Gly | Glu | Tyr | Phe | Asn | His | Arg | Leu | Gly | His | Gly | Ile | Gly | Met | Ser | Thr |
| | | | | 245 | | | | | 250 | | | | | 255 | |
| His | Glu | Phe | Pro | Ser | Ile | Met | Glu | Gly | Asn | Asp | Met | Ile | Val | Gly | Glu |
| | | | 260 | | | | | 265 | | | | | 270 | | |
| Asp | Phe | Gly | Met | Arg | Val | Ser | Val | Leu | Ala | Ser | Ser | Ser | Ser | Gly | Asn |
| | | | 275 | | | | | 280 | | | | | 285 | | |
| Ala | Thr | Tyr | Ile | Glu | Thr | Pro | Gly | His | Lys | Val | Leu | Val | Asp | Ala | Gly |
| | 290 | | | | | 295 | | | | | 300 | | | | |
| Leu | Ser | Gly | Lys | Lys | Ile | Glu | Ala | Leu | Met | Lys | Ser | Ile | Gly | Arg | Asp |
| 305 | | | | | 310 | | | | | 315 | | | | | 320 |
| Leu | Thr | Asp | Val | Asp | Ser | Val | Phe | Ile | Thr | His | Glu | His | Ser | Asp | His |
| | | | | 325 | | | | | 330 | | | | | 335 | |
| Val | Arg | Gly | Val | Gly | Val | Leu | Ala | Arg | Arg | Tyr | Pro | Gln | Leu | Asn | Val |
| | | | 340 | | | | | 345 | | | | | 350 | | |
| Tyr | Ala | Asn | Ala | Lys | Thr | Phe | Ala | Ala | Leu | Pro | Lys | Ser | Val | Gly | Lys |
| | | | 355 | | | | | 360 | | | | | 365 | | |
| Ile | Pro | Glu | Ala | Gln | Leu | Arg | Leu | Phe | Asp | Met | Gly | Thr | Thr | Leu | Thr |
| | 370 | | | | | 375 | | | | | 380 | | | | |

-continued

```
Leu Gly Asp Leu Asp Val Glu Ser Phe Gly Val Ser His Asp Ala Ala
385                 390                 395                 400

Ala Pro Gln Phe Tyr Gln Phe His His Asp Gly Lys Ala Phe Thr Ile
                405                 410                 415

Leu Thr Asp Thr Gly Tyr Val Ser Asp Arg Val Ala Gly Thr Ile Arg
            420                 425                 430

Asp Ala Asp Ala Tyr Val Met Glu Cys Asn His Asp Leu Glu Met Leu
            435                 440                 445

Arg Thr Gly Pro Tyr Pro Trp Pro Leu Lys Gln Arg Ile Leu Ser Asp
        450                 455                 460

Gln Gly His Leu Ser Asn Glu Asp Gly Ala Asp Ala Leu Met Asp Val
465                 470                 475                 480

Ile Gly Leu Arg Thr Lys Arg Ile Tyr Leu Gly His Leu Ser Pro His
                485                 490                 495

Asn Asn Asn Lys Ala Thr Gly Ala Phe Asn Arg Gly Val Val Val Gly
                500                 505                 510

Thr Thr Arg Ser Gly Gly Gly Ser
            515                 520
```